US007683084B2

(12) United States Patent
Faghih et al.

(10) Patent No.: US 7,683,084 B2
(45) Date of Patent: Mar. 23, 2010

(54) THIAZOLINE AND OXAZOLINE DERIVATIVES AND THEIR METHODS OF USE

(75) Inventors: Ramin Faghih, Lake Forest, IL (US); Gregory A. Gfesser, Lindenhurst, IL (US); Christopher L. Lynch, Trevor, WI (US); Murali Gopalakrishnan, Libertyville, IL (US); Sujatha Gopalakrishnan, Libertyville, IL (US); John Malysz, Round Lake, IL (US); Earl J. Gubbins, Libertyville, IL (US); Rachid El Kouhen, Libertyville, IL (US); Jinhe Li, Long Grove, IL (US); Kathy A. Sarris, Deerfield, IL (US); Melissa J. Michmerhuizen, Beach Park, IL (US); Ying Wang, Lake Villa, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 11/769,241

(22) Filed: Jun. 27, 2007

(65) Prior Publication Data

US 2008/0070929 A1 Mar. 20, 2008

Related U.S. Application Data

(60) Provisional application No. 60/816,822, filed on Jun. 27, 2006.

(51) Int. Cl.
*A61K 31/427* (2006.01)
*A61K 31/343* (2006.01)
*A61K 31/4025* (2006.01)
*C07D 317/06* (2006.01)
*C07D 277/18* (2006.01)
*C07D 407/14* (2006.01)

(52) U.S. Cl. ............... 514/370; 514/422; 514/423; 514/465; 548/184; 548/517; 548/518; 549/435

(58) Field of Classification Search ............ 514/255.05, 514/307, 311, 318, 377, 370; 544/405; 546/139, 546/152; 548/190, 233
See application file for complete search history.

(56) References Cited

U.S. PATENT DOCUMENTS

| 3,427,205 | A |  | 2/1969 | Plitt et al. |  |
|---|---|---|---|---|---|
| 5,244,863 | A |  | 9/1993 | Kawamura et al. |  |
| 5,508,415 | A |  | 4/1996 | Kawamura et al. |  |
| 5,935,990 | A |  | 8/1999 | Khanna et al. |  |
| 6,165,943 | A | * | 12/2000 | Mayer et al. | 504/266 |
| 2005/0065178 | A1 |  | 3/2005 | Basha et al. |  |
| 2005/0137204 | A1 |  | 6/2005 | Ji et al. |  |
| 2005/0245531 | A1 |  | 11/2005 | Ji et al. |  |

FOREIGN PATENT DOCUMENTS

| EP | 1277743 | 3/2001 |
|---|---|---|
| GB | 1263940 | 7/1969 |
| WO | 9842703 | 10/1998 |
| WO | 0110853 | 2/2001 |
| WO | 2004009558 | 1/2004 |
| WO | 2004029053 | 4/2004 |

OTHER PUBLICATIONS

Adler et al., Schizophrenia Bull. 24: 189-202 (1998).
Albuquerque et al., "Modulation of nicotinic receptor activity in the central nervous system: a novel approach to the treatment of Alzheimer disease," Alzheimer Dis. Assoc. Disord. 15 Suppl 1: S19-25 (2001).
Alkondon et al., "The nicotinic acetylcholine receptor subtypes and their function in the hippocampus and cerebral cortex," Prog. Brain Res. 145: 109-120 (2004).
Cordero-Erausquin et al., PNAS 98: 2803-2807 (2001).
Couturier et al., "A neuronal nicotinic acetylcholine receptor subunit (alpha 7) is developmentally regulated and forms a homo-oligomeric channel blocked by alpha blocked by alpha-BTX," Neuron 5: 847-856 (1990).
D'Andrea et al., "Targeting the alpha 7 nicotinic acetylcholine receptor to reduce amyloid accumulation in Alzheimer's disease pyramidal neurons," Curr. Pharm. Des. 12: 677-684 (2006).
Dajas-Bailador et al., "Nicotinic acetylcholine receptors and the regulation of neuronal signalling," Trends Pharmacol. Sci. 25: 317-324 (2004).
Friedman et al., Biol. Psychiatry 51: 349-357 (2002).
Furniss et al., "Vogel's Textbook of Practical Organic Chemistry," 5th edition, Longman Scientific & Technical, Essex CM20 2JE, England (Table of Contents).
Gotti, et al, "Brain neuronal nicotinic receptors as new targets for drug discovery," Curr. Pharm. Des. 12: 407-428 (2006).
Hajos et al., "The selective alpha7 nicotinic acetylcholine receptor agonist PNU-282987 [N-{(3R)-1-Azabicyclo {2.2.2} oct-3-yl}-4-chlorobenzamide hydrochloride} enhances GABAergic synaptic activity in brain slices and restores auditory gating deficits in anesthetized rats," J. Pharm. Exp. Ther. 312: 1213-1222 (2005).
Heeschen et al., J. Clin. Invest. 110: 527-536 (2002).
Heeschen et al., Nature Medicine 7: 833-839 (2001).
Hevers et al., "The diversity of $GABA_A$ receptors. Pharmacological and electrophysiological properties of $GABA_A$ channel subtypes," Mol. Neurobiol. 18: 35-86 (1998).
Hogg et al., "Nicotinic acetylcholine receptors: From structure to brain function," Rev. Physiol Biochem. Pharmacol. 147: 1-46 (2003).
Hunter et al., "A novel nicotinic against facilitates induction of long-term potentiation in the rat hippocampus," Neurosci. Lett. 168: 130-134 (1994).
Hurst et al., A novel positive allosteric modulator of the alpha7 neuronal nicotinic acetylcholine receptor: in vitro and in vivo characterization, J. Neurosci. 25(17): 4396-4405 (2005).
IUPAC 1974 Recommendations for Section E, Fundamental Stereochemistry, Pure Appl. Chem., 45: 13-30 (1976).

(Continued)

*Primary Examiner*—Yong Chu
(74) *Attorney, Agent, or Firm*—Antonia M. Holland

(57) ABSTRACT

The invention relates to a series of thiazoline and oxazoline derivatives, compositions thereof, and methods of treating conditions and disorders using such compounds.

6 Claims, 4 Drawing Sheets

OTHER PUBLICATIONS

Jonnala et al., Neurosci. Res. 66: 565-575 (2001).
Keller et al., "Performance of alpha7 nicotinic receptor null mutants is impaired in appetitive learning measured in a signaled nose poke task," Behav. Brain Res., 162: 143-152 (2005).
Kihara et al., J. Biol. Chem. 276: 13541-13546 (2001).
Leonard, S., Eur. J. Pharmacol. 393: 237-242 (2000).
Levin, E.D., J. Neurobiol. 53: 633-640 (2002).
Liu et al., PNAS 98: 4734-4739 (2001).
Martin et al., "SSR180711, Alpha-7 nicotinic receptor agonists: potential new candidates for the treatment of schizophrenia," Psychopharmacology (Berl) 174: 54-64 (2004).
Paterson et al., "Neuronal nicotinic receptors in the human brain," Prog. Neurobiol. 61: 75-111 (2000).
Pichat et al., "A novel selective alpha7 nicotinic receptor partial agonist III effects in models predictive of therapeutic activity on cognitive symptoms of schizophrenia," Neuroscience Abstract 583.3 (2004).
Roche, E.B., ed, Bioreversible Carriers in Drug Design, (Table of Contents) American Pharmaceutical Association and Pergamon Press; (1987).
Rowley et al., J. Med. Chem. 44: 477-501 (2001).
Shimohama et al., Brain Res. 779: 359-363 (1998).
Son et al., Biol. Reproduct. 68: 1348-1353 (2003).
Stevens et al., Psychopharmacology 136: 320-327 (1998).
T. Higuchi and V. Stella, Pro-drugs as Novel Delivery Systems, V. 14 of the A.C.S. Symposium Series (Table of Contents).
Ulloa et al., "The vagus nerve and the nicotinic anti-inflammatory pathway," Drug Discov. 4: 673-684 (2005).
Van Kampen et al., "AR-R 17779 improves social recognition in rats by activation of nicotinic alpha7 receptors," Psychopharmacology (Berl) 172: 375-383 (2004).
Wang et al., "Nicotinic acetylcholine receptor alpha7 subunit is an essential regulator of inflammation," Nature 421 (6921): 384-388 (2003).

* cited by examiner

THIAZOLINE AND OXAZOLINE DERIVATIVES AND THEIR METHODS OF USE

This application claims the benefit of U.S. Patent Application No. 60/816,822, filed Jun. 27, 2006, which is hereby incorporated by reference in its entirety.

BACKGROUND OF THE INVENTION

1. Technical Field

The invention relates to thiazoline and oxazoline derivative compounds, compositions comprising the same, and methods for using such compounds and compositions.

2. Description of Related Technology

Neuronal nicotinic acetylcholine receptors (nAChRs) are neurotransmitter receptors that are widely distributed throughout the central nervous system (CNS) and the peripheral nervous system (PNS) and are widely understood to play an important role in regulating CNS function. Primarily, nAChRs are a significant part of regulating the release of many neurotransmitters, for example acetylcholine (ACh), norepinephrine, dopamine, serotonin, and GABA, among others. Consequently, nAChRs mediate a wide range of physiological effects.

Twelve protein subunits of neuronal nicotinic receptors have been reported to date (Paterson, D. and Nordberg, A.: Neuronal nicotinic receptors in the human brain. Prog Neurobiol. 2000; 61: 75-111; Hogg, R. C., Raggenbass, M. and Bertrand, D.: Nicotinic acetylcholine receptors: From structure to brain function, Rev. Physiol., Biochem. Pharmacol. 2003; 147: 1-46). These subunits are identified as $\alpha 2$, $\alpha 3$, $\alpha 4$, $\alpha 5$, $\alpha 6$, $\alpha 7$, $\alpha \alpha 8$, $\alpha 9$, $\alpha 10$; $\beta 2$, $\beta 3$, and $\beta 4$. Of these subunits, nine subunits, $\alpha 2$ through $\alpha 7$ and $\beta 2$ through $\beta 4$, prominently exist in the mammalian brain. Multiple functionally distinct nAChR complexes also exist, for example five $\alpha 7$ subunits can form a receptor as a homomeric functional pentamer or combinations of different subunits can complex together as in case of $\alpha 4\beta 2$ and $\alpha 3\beta 4$ receptors. In the mammalian brain, $\alpha 4\beta 2$ and $\alpha 7$ nAChRs are prominently found.

The role of $\alpha 7$ nAChR in neuronal signaling in the CNS also has been actively investigated. (Couturier, S., Bertrand, D., Matter, J. M., Hernandez, M. C., Bertrand, S., Millar, N., Valera, S., Barkas, T., Ballivet, M. A neuronal nicotinic acetylcholine receptor subunit (alpha 7) is developmentally regulated and forms a homo-oligomeric channel blocked by alpha-BTX. Neuron 1990; 5: 847-56). The $\alpha 7$ nAChRs have been demonstrated to regulate interneuron excitability, modulate the release of excitatory and inhibitory neurotransmitters, and lead to neuroprotective effects in experimental in vitro models of cellular damage (Alkondon, M., Albuquerque, E. X. The nicotinic acetylcholine receptor subtypes and their function in the hippocampus and cerebral cortex. Prog. Brain Res. 2004; 145: 109-20). Also, studies support that $\alpha 7$ nAChRs are involved in various cognitive functions, including memory, attention, and in schizophrenia (Keller, J. J., Keller, A. B., Bowers, B. J., Wehner, J. M. Performance of alpha 7 nicotinic receptor null mutants is impaired in appetitive learning measured in a signaled nose poke task. Behav. Brain Res. 2005; 162: 143-52). Biophysical studies have shown that $\alpha 7$ subunits, when expressed in heterologous expression systems, activate and desensitize rapidly, and furthermore, exhibit relatively higher calcium permeability compared to other nAChR combinations (Dajas-Bailador, F., Wonnacott, S. Nicotinic acetylcholine receptors and the regulation of neuronal signalling. Trends Pharmacol. Sci. 2004; 25: 317-24).

As such, modulating, or modifying, the activity of $\alpha 7$ nAChRs demonstrates promising potential to prevent or treat a variety of diseases with an underlying pathology that involves cognitive function including, for example, aspects of learning, memory, and attention, as well as schizophrenia and neurodegeneration, such as in Alzheimer's disease (AD) and other dementias (reviewed in Gotti, C., Riganti, L., Vailati, S., Clementi, F. Brain neuronal nicotinic receptors as new targets for drug discovery. Curr. Pharm. Des. 2006; 12: 407-428.). More particularly, the $\alpha 7$ nAChRs have been linked to conditions and disorders related to attention deficit disorder, attention deficit hyperactivity disorder (ADHD), Alzheimer's disease (AD), mild cognitive impairment (MCI), senile dementia, dementia associated with Lewy bodies, dementia associated with Down's syndrome, AIDS dementia, Pick's disease, as well as cognitive deficits associated with schizophrenia, among other systemic activities (for example, Martin, L. F., Kem, W. R., Freedman, R. Alpha-7 nicotinic receptor agonists: potential new candidates for the treatment of schizophrenia. Psychopharmacology (Berl). 2004; 174: 54-64). The $\alpha 7$ nAChRs have also been reported to slow disease progression in Alzheimer's disease (D'Andrea, M. R., Nagele, R. G. Targeting the alpha 7 nicotinic acetylcholine receptor to reduce amyloid accumulation in Alzheimer's disease pyramidal neurons. Curr. Pharm. Des. 2006; 12: 677-84). Additionally, recent studies indicate that $\alpha 7$ nAChR are involved in non-neuronal cell function, which supports that compounds targeting $\alpha 7$ nAChRs are useful for treating or preventing inflammation and inflammatory pain, septic shock, wound healing, tumor growth inhibition, angiogenesis and skin disorders as well (Ulloa, L. The vagus nerve and the nicotinic anti-inflammatory pathway. Nat. Rev. Drug Discov. 2005; 4:673-84; Wang, H., Yu, M., Ochani, M., Amella, C. A., Tanovic, M., Susarla, S., Li, J. H., Wang, H., Yang, H., Ulloa, L., Al-Abed, Y., Czura, C. J., Tracey, K. J. Nicotinic acetylcholine receptor alpha7 subunit is an essential regulator of inflammation. Nature. 2003; 421(6921): 384-8).

One well-known compound, nicotine, is known to provide enhanced attention and cognitive performance, reduced anxiety, enhanced sensory gating, and analgesia and neuroprotective effects when administered. Such effects are mediated by the non-selective effect of nicotine at a variety of nicotinic receptor subtypes. However, nicotine also produces adverse consequences, such as cardiovascular and gastrointestinal problems. Accordingly there is a need to identify subtype-selective compounds that embrace the beneficial effects of nicotine, or a nAChR ligand, while eliminating or decreasing adverse effects.

Examples of reported nAChR ligands are $\alpha 7$ nAChR agonists, such as PNU-282987 (Hajos, M., Hurst, R. S., Hoffmann, W. E., Krause, M., Wall, T. M., Higdon, N. R., Groppi, V. E. The selective alpha7 nicotinic acetylcholine receptor agonist PNU-282987 [N-[(3R)-1-Azabicyclo[2.2.2]oct-3-yl]-4-chlorobenzamide hydrochloride] enhances GABAergic synaptic activity in brain slices and restores auditory gating deficits in anesthetized rats. J. Pharmacol. Exp. Ther. 2005; 312: 1213-22). Another compound is SSR180711A (Pichat, P., Bergins, O. E., Terranova, J., Santucci, V., Gueudet, C., Francon, D., Voltz, C., Steinberg, R., Griebel, G., Scatton, B., Avenet, P., Oury-Donat, F., Soubri, P. (2004) SSR180711A, A novel selective alpha7 nicotinic receptor partial agonist III effects in models predictive of therapeutic activity on cognitive symptoms of schizophrenia. Society for Neuroscience Abstract number 583.3). Yet another compound, AR-R17779 (Van Kampen, M., Selbach, K., Schneider, R., Schiegel, E., Boess, F., Schreiber, R. AR-R 17779 improves social recognition in rats by activation of nicotinic alpha7 receptors. Psychopharmacology (Berl) 2004; 172: 375-83), has been reported to improve performance of rats in social recognition, water maze, or inhibitory avoidance models of cognitive domains. AR-R17779 also reportedly facilitates the induction of hippocampal long term potentiation (LTP) in a proposed cellular model for learning and memory in rats (Hunter, B. E., De Fiebre, C. M., Papke, R. L., Kem, W. R., Meyer, E. M. A novel nicotinic agonist facilitates induction of long-term potentiation in the rat hippocampus. Neurosci. Lett. 1994; 168: 130-4).

Despite the beneficial effects of nAChR ligands, it remains uncertain whether chronic treatment with agonists affecting nAChRs may provide suboptimal benefit due to sustained activation and desensitization of the nAChR. In contrast to agonists, administering a nicotinic positive allosteric modulator can reinforce endogenous cholinergic transmission without directly simulating the target receptor (Albuquerque, E. X., Santos, M. D., Alkondon, M., Pereira, E. F., Maelicke, A. Modulation of nicotinic receptor activity in the central nervous system: a novel approach to the treatment of Alzheimer disease. Alzheimer Dis. Assoc. Disord. 2001; 15 Suppl 1: S19-25). Accordingly, it would be beneficial to target $\alpha 7$ nAChR function by enhancing effects of the endogenous neurotransmitter acetylcholine via positive allosteric modulators that can reinforce the endogenous cholinergic neurotransmission (ACh) without directly activating $\alpha 7$ nAChRs like agonists. Indeed, allosteric modulators for enhancing channel activity have been proven clinically successful for $GABA_A$ receptors where benzodiazepines, barbiturates, and neurosteroids behave as allosteric positive modulators acting at distinct sites (Hevers, W., Luddens, H. The diversity of $GABA_A$ receptors. Pharmacological and electrophysiological properties of $GABA_A$ channel subtypes. Mol. Neurobiol. 1998; 18: 35-86).

To date, only a few nAChR allosteric modulators are known, including: 5-hydroxyindole (5-HI), ivermectin, galantamine, bovine serum albumin, and SLURP-1, a peptide derived from acetylcholinesterase (AChE). Recently, genistein, a kinase inhibitor was reported to increase $\alpha 7$ responses, and PNU-120596, a urea analog, was reported to increase the potency and maximal efficacy of ACh as well as improve auditory gating deficits induced by amphetamine in rats (Hurst, R. S., Hajos, M., Raggenbass, M., Wall, T. M., Higdon, N. R., Lawson, J. A., Rutherford-Root, K. L., Berkenpas, M. B., Hoffmann, W. E., Piotrowski, D. W., Groppi, V. E., Allaman, G., Ogier, R., Bertrand, S., Bertrand, D., Americ, S. P. A novel positive allosteric modulator of the alpha7 neuronal nicotinic acetylcholine receptor: in vitro and in vivo characterization. J. Neurosci. 2005; 25: 4396-4405). However, positive allosteric modulator compounds presently known generally demonstrate weak activity, have a range of non-specific effects, or can only achieve limited access to the central nervous system where $\alpha 7$ nAChRs are abundantly expressed.

Accordingly, it would be beneficial to identify and provide new positive allosteric modulator compounds and compositions for treating or preventing conditions associated with $\alpha 7$ nAChRs. It would further be particularly beneficial if such compounds can provide improved efficacy of treatment while reducing adverse effects associated with compounds targeting neuronal nicotinic receptors by selectively modulating $\alpha 7$ nAChRs.

BRIEF DESCRIPTION OF THE DRAWINGS

FIG. 1 demonstrates that when an $\alpha 7$ nAChR positive allosteric modulator and a known $\alpha 7$ nAChR agonist are applied together in the assay, a positive calcium response is triggered.

In FIG. 2, the Y-axis is the normalized change in fluorescence and the X-axis represents increasing concentrations of the modulator.

In FIG. 3, the Y-axis is the normalized change in fluorescence and the X-axis represents increasing concentrations of the agonist.

In FIG. 4, the Y-axis is the normalized change in phospho-ERK1/2 to total ERK ratio and the X-axis represents increasing concentrations of an allosteric modulator.

SUMMARY OF THE INVENTION

Figure 1:
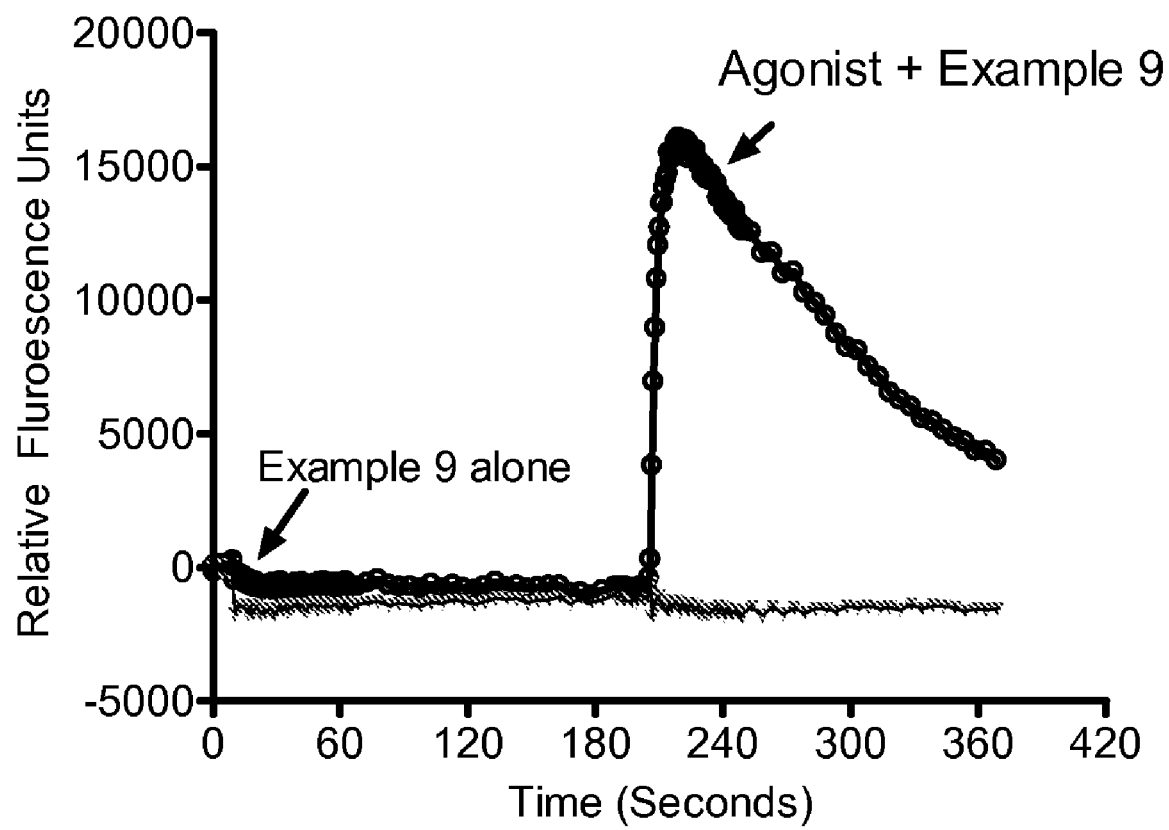
FIG. 1 is a graphical representation of relative fluorescence measured in relative fluorescence units represented as a function of time (in seconds) obtained by assaying a compound, Example 9, in the presence of selective $\alpha 7$ nAChR agonists in cells natively expressing $\alpha 7$ nAChRs, for example the IMR-32 cell line.

In one embodiment, the invention relates to compounds of formula (I) selected from compounds of formulas:

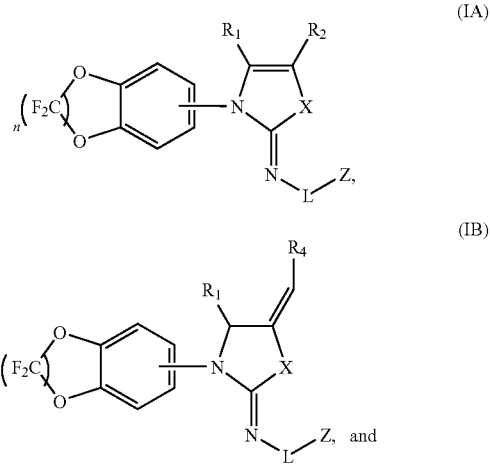

(IA)

(IB)

and

-continued

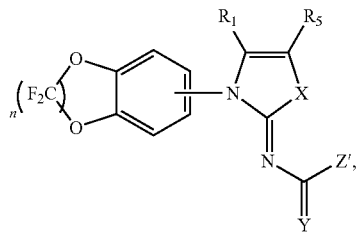

(IC)

or a pharmaceutically acceptable salt, ester, or amide thereof, wherein n is 1 or 2;

$R_1$ is hydrogen, alkyl, alkenyl, alkynyl, aryl, or heteroaryl, wherein the alkyl group, alkenyl, alkynyl, aryl, and heteroaryl groups are each substituted with 0, 1, 2 or 3 substituents independently selected from the group consisting of alkoxy, alkoxycarbonyl, carboxy, cyano, haloalkoxy, halo, hydroxyl, nitro, and $R_aR_bN$—;

$R_2$ is alkyl, alkenyl, formyl, cyano, heteroaryl(hydroxyl) alkyl, or —CH=N—$(CH_2)_h$—$OR_g$, wherein the alkyl group and the alkenyl group is substituted with 1, 2, or 3 substituents independently selected from the group consisting of alkoxycarbonyl, alkylcarbonyloxy, aryl, aryloxy, arylalkoxy, carboxy, cyano, cycloalkyl, haloalkoxy, heteroaryl, heterocycle, hydroxyl, nitro, and $R_cR_dN$—, wherein the group represented by $R_2$ can be further substituted with 0, 1, or 2 groups selected from halo and alkoxy;

h is 0, 2, or 3;

L is C(O), C(S), S(O), or $S(O)_2$;

X is O or S;

Y is O or S;

Z is aryl, cycloalkyl, heteroaryl, heterocycle, $R_eR_fN$—, —$R_3$ or —$OR_3$;

Z' is $R_eR_hN$— or $R_iR_jN$—;

$R_a$ and $R_b$ are each independently hydrogen, alkyl, alkylcarbonyl, arylalkyl, and heteroaryl;

$R_c$ and $R_d$ are each independently hydrogen, alkyl, aryl, arylalkyl, heteroaryl, heteroarylalkyl, heterocycle, and heterocyclealkyl;

$R_e$ and $R_f$ are each independently hydrogen, alkyl, alkylcarbonyl, alkenyl, alkynyl, aryl, arylalkyl, aryl(hydroxyl)alkyl, cycloalkyl, cycloalkylalkyl, heterocycle, heterocyclealkyl, heteroaryl, heteroarylalkyl, or hydroxyalkyl, wherein the alkyl group and the alkyl of alkylcarbonyl is substituted with 0, 1, 2, or 3 substituents selected from alkoxy, cyano, or halo;

$R_g$ is hydrogen or alkyl;

$R_h$ is heterocycle, arylalkyl, heterocyclealkyl, heteroarylalkyl, aryl(hydroxyl)alkyl, cycloalkyl, and heteroaryl(hydroxyl)alkyl;

$R_i$ and $R_j$ taken together with the nitrogen atom to which each is attached form a 4-, 5-, or 6-membered heterocycle fused to a monocyclic aromatic ring; or $R_i$ and $R_j$ taken together with the nitrogen atom to which each is attached form a monocyclic heterocycle substituted with 1, 2, or 3 substituents selected from halo, hydroxyl, aryl, and heteroaryl;

$R_3$ is alkyl, alkenyl, alkynyl, arylalkyl, haloalkyl, haloalkenyl, or haloalkynyl;

$R_4$ is hydrogen or alkyl; and $R_5$ is alkyl or alkenyl, wherein the alkyl group and the alkenyl group is substituted with 0, 1, 2 substituents independently selected from alkoxy and halo.

In another embodiment, the invention relates to a method of using compounds of formula (II) selected from the group consisting of compounds of formulas:

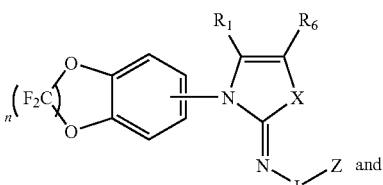

(IIA)

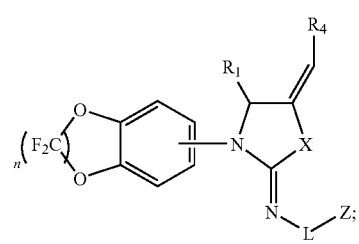

(IIB)

or a pharmaceutically acceptable salt, ester or amide thereof, wherein n is 1 or 2;

$R_1$ is hydrogen, alkyl, alkenyl, alkynyl, aryl, or heteroaryl, wherein the alkyl group, alkenyl, alkynyl, aryl, and heteroaryl groups are each substituted with 0, 1, 2 or 3 substituents independently selected from the group consisting of alkoxy, alkoxycarbonyl, carboxy, cyano, haloalkoxy, halo, hydroxyl, nitro, and $R_aR_bN$—;

L is C(O), C(S), S(O), or $S(O)_2$;

X is O or S;

Z is aryl, cycloalkyl, heteroaryl, heterocycle, $R_eR_fN$—, —$R_3$ or —$OR_3$;

$R_a$ and $R_b$ are each independently hydrogen, alkyl, alkylcarbonyl, arylalkyl, and heteroaryl;

$R_c$ and $R_d$ are each independently hydrogen, alkyl, aryl, arylalkyl, heteroaryl, heteroarylalkyl, heterocycle, and heterocyclealkyl;

$R_e$ and $R_f$ are each independently hydrogen, alkyl, alkylcarbonyl, alkenyl, alkynyl, aryl, arylalkyl, aryl(hydroxyl)alkyl, cycloalkyl, cycloalkylalkyl, heterocycle, heterocyclealkyl, heteroaryl, heteroarylalkyl, or hydroxyalkyl, wherein the alkyl group and the alkyl of alkylcarbonyl is substituted with 0, 1, 2, or 3 substituents selected from alkoxy, cyano, or halo;

$R_3$ is alkyl, alkenyl, alkynyl, arylalkyl, haloalkyl, haloalkenyl, or haloalkynyl;

$R_4$ is hydrogen or alkyl; and $R_6$ is alkyl, alkenyl, formyl, cyano, heteroaryl(hydroxyl) alkyl, or —CH=N—$(CH_2)_h$—$OR_g$, wherein the alkyl group and the alkenyl group is substituted with 0, 1, 2, or 3 substituents independently selected from the group consisting of alkoxy, alkoxycarbonyl, alkylcarbonyloxy, aryl, aryloxy, arylalkoxy, carboxy, cyano, cycloalkyl, halo, haloalkoxy, heteroaryl, heterocycle, hydroxyl, nitro, and $R_cR_dN$—;

h is 0, 2, or 3; and $R_g$ is hydrogen or alkyl; for preventing or treating, or both, a disease or condition mediated by nicotinic acetylcholine receptors.

The invention also is directed to the methods of treating conditions and disorders that are regulated by the nicotinic acetylcholine receptors (nAChR) using compounds of formula (I) or formula (II) or therapeutically acceptable compositions of compounds of formula (I) or (II).

Such compositions containing compounds of formula (I) or (II) can be administered in accordance with described methods, typically as part of a therapeutic regimen for treatment or prevention of conditions and disorders related to nAChR activity, and more particularly allosteric modulation of nAChR activity.

Compounds of formula (I) or (II) can be used in a method for treating or preventing conditions and disorders related to nAChR modulation in mammals. More particularly, the method is useful for conditions and disorders related to attention deficit disorder, attention deficit hyperactivity disorder (ADHD), Alzheimer's disease (AD), mild cognitive impairment (MCI), schizophrenia, senile dementia, AIDS dementia, Pick's Disease, dementia associated with Lewy bodies, dementia associated with Down's syndrome, amyotrophic lateral sclerosis, Huntington's disease, diminished CNS function associated with traumatic brain injury, acute pain, post-surgical pain, chronic pain, inflammation, inflammatory pain, neuropathic pain, infertility, need for new blood vessel growth associated with wound healing, need for new blood vessel growth associated with vascularization of skin grafts, and lack of circulation, rheumatoid arthritis, Crohn's disease, ulcerative colitis, inflammatory bowel disease, organ transplant rejection, acute immune disease associated with organ transplantation, chronic immune disease associated with organ transplantation, septic shock, toxic shock syndrome, sepsis syndrome, depression, and rheumatoid spondylitis, and various other conditions modulated by $\alpha 7$ nAChRs.

In another embodiment, the invention relates to a method of identifying a positive $\alpha 7$ allosteric modulator comprising the steps of allowing a compound to interact with cells or cell lines endogenously expressing $\alpha 7$ nAChRs or cells expressing recombinant $\alpha 7$ nAChRs in a fluorescent medium and measuring changes in such fluorescence. In one aspect, the positive $\alpha 7$ allosteric modulator is identified by measuring changes in fluorescence related to calcium ion flux or cell membrane potential. In another aspect, the positive $\alpha 7$ allosteric modulator identified by measuring the changes in fluorescence related to phosphorylation of ERK.

Another embodiment of the invention relates to a method of assessing or diagnosing conditions or disorders related to $\alpha 7$ receptor activity comprising allowing isotope-labelled forms of compounds of formula (I) or (II) to interact with cells expressing endogenous $\alpha 7$ nAChRs or cells expressing recombinant $\alpha 7$ nAChRs and measuring the effects of such isotope-labelled forms of compounds on such cells.

Another method of the invention relates to identifying an $\alpha 7$ nAChR agonist comprising the steps of allowing a compound to interact with cells or cell lines endogenously expressing $\alpha 7$ nAChRs or cells expressing recombinant $\alpha 7$ nAChRs in a fluorescent medium and measuring changes in such fluorescence.

Accordingly, various aspects of the invention also describe the use of nAChR ligands, and particularly allosteric modulator compounds, to identify other useful target compounds for treating or preventing, or both, diseases or conditions associated with nAChR function, in cell-based assays, for example in high-throughput format, using cells or tissues that express native $\alpha 7$ receptors for the purpose of identifying novel $\alpha 7$ agonists or $\alpha 7$ allosteric modulators.

The compounds, compositions comprising the compounds, and methods for treating or preventing conditions and disorders by administering the compounds are further described herein.

DETAILED DESCRIPTION OF THE INVENTION

Definition of Terms

Certain terms as used in the specification are intended to refer to the following definitions, as detailed below.

The term "acyl", as used herein, means an alkyl group, as defined herein, appended to the parent molecular moiety through a carbonyl group, as defined herein. Representative examples of acyl include, but are not limited to, acetyl, 1-oxopropyl, 2,2-dimethyl-1-oxopropyl, 1-oxobutyl, and 1-oxopentyl.

The term "acyloxy", as used herein, means an acyl group, as defined herein, appended to the parent molecular moiety through an oxygen atom. Representative examples of acyloxy include, but are not limited to, acetyloxy, propionyloxy, and isobutyryloxy.

The term "alkenyl", as used herein, means a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkoxy", as used herein, means an alkyl group as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkoxy", as used herein, means an alkoxy group, as defined herein, appended to the parent molecular moiety through another alkoxy group, as defined herein. Representative examples of alkoxyalkoxy include, but are not limited to, tert-butoxymethoxy, 2-ethoxyethoxy, 2-methoxyethoxy, and methoxymethoxy.

The term "alkoxyalkyl", as used herein, means an alkoxy group, as defined herein, appended to the parent molecular moiety through an alkyl group, as defined herein. Representative examples of alkoxyalkyl include, but are not limited to, tert-butoxymethyl, 2-ethoxyethyl, 2-methoxyethyl, and methoxymethyl.

The term "alkoxycarbonyl", as used herein, means an alkoxy group, as defined herein, appended to the parent molecular moiety through a carbonyl group, represented by —C(O)—, as defined herein. Representative examples of alkoxycarbonyl include, but are not limited to, methoxycarbonyl, ethoxycarbonyl, and tert-butoxycarbonyl.

The term "alkoxysulfonyl", as used herein, means an alkoxy group, as defined herein, appended to the parent molecular moiety through a sulfonyl group, as defined herein. Representative examples of alkoxysulfonyl include, but are not limited to, methoxysulfonyl, ethoxysulfonyl and propoxysulfonyl.

The term "alkyl", as used herein, means a straight or branched chain hydrocarbon containing from 1 to 6 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, and n-hexyl.

The term "alkylcarbonyl", as used herein, means an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The term "alkylcarbonyloxy", as used herein, means an alkylcarbonyl group, as defined herein, appended to the parent molecular moiety through an oxygen atom. Representative examples of alkylcarbonyloxy include, but are not limited to, acetyloxy, ethylcarbonyloxy, and tert-butylcarbonyloxy.

The term "alkylsulfonyl", as used herein, means an alkyl group, as defined herein, appended to the parent molecular moiety through a sulfonyl group, as defined herein. Representative examples of alkylsulfonyl include, but are not limited to, methylsulfonyl and ethylsulfonyl.

The term "alkynyl", as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "aryl", as used herein, means a monocyclic or bicyclic aromatic ring system. Representative examples of aryl include, but are not limited to, phenyl and naphthyl.

The aryl groups of this invention are substituted with 0, 1, 2, 3, 4, or 5 substituents independently selected from acyl, acyloxy, alkenyl, alkoxy, alkoxyalkoxy, alkoxyalkyl, alkoxycarbonyl, alkoxysulfonyl, alkyl, alkylsulfonyl, alkynyl, carboxy, cyano, formyl, haloalkoxy, haloalkyl, halo, hydroxy, hydroxyalkyl, mercapto, nitro, thioalkoxy, —$NR_iR_j$, ($NR_iR_j$)alkyl, ($NR_iR_j$)alkoxy, ($NR_iR_j$)carbonyl, ($NR_iR_j$)sulfonyl, —$OCH_2CH=CH_2$, —$OC_6H_5$, and pyridyl wherein $R_i$ and $R_j$ are defined herein.

The term "arylalkoxy" as used herein, means an aryl group, as defined herein, appended to the parent molecular moiety through an alkoxy group, as defined herein. Representative examples of arylalkoxy include, but are not limited to, 2-phenylethoxy, 3-naphth-2-ylpropoxy, and 5-phenylpentyloxy.

The term "arylalkyl" as used herein, means an aryl group, as defined herein, appended to the parent molecular moiety through an alkyl group, as defined herein. Representative examples of arylalkyl include, but are not limited to, benzyl, 2-phenylethyl, 3-phenylpropyl, and 2-naphth-2-ylethyl.

The term "aryl(hydroxyl)alkyl", as used herein, means an arylalkyl, as defined herein, substituted with 1, 2, or 3 hydroxyl groups on the alkyl portion wherein each hydroxyl group is a substituent on a separate carbon. One hydroxyl group is preferred. Representative examples of aryl(hydroxyl)alkyl include, but are not limited to, 2-hydroxy-1-pheylethyl.

The term "aryloxy" as used herein, means an aryl group, as defined herein, appended to the parent molecular moiety through an oxygen atom. Representative examples of aryloxy include, but are not limited to, phenoxy, naphthyloxy, 3-bromophenoxy, 4-chlorophenoxy, 4-methylphenoxy, and 3,5-dimethoxyphenoxy.

The term "carbonyl", as used herein, means a —C(O)— group.

The term "carboxy", as used herein, means a —$CO_2H$ group.

The term "cyano", as used herein, means a —CN group.

The term "cyanoalkyl" as used herein, means a cyano group, as defined herein, appended to the parent molecular moiety through an alkylene group, as defined herein. Representative examples of cyanoalkyl include, but are not limited to, cyanomethyl, 2-cyanoethyl, and 3-cyanopropyl.

The term "cycloalkyl" as used herein, means a monocyclic, bicyclic, or tricyclic ring system. Monocyclic ring systems are exemplified by a saturated cyclic hydrocarbon group containing from 3 to 8 carbon atoms. Examples of monocyclic ring systems include cyclopropyl, cyclobutyl, cyclopentyl, cyclohexyl, cycloheptyl, and cyclooctyl. Bicyclic ring systems are exemplified by a bridged monocyclic ring system in which two non-adjacent carbon atoms of the monocyclic ring are linked by an alkylene bridge of between one and three additional carbon atoms. Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. Bicyclic ring systems are also exemplified by a monocyclic ring system fused to a phenyl or heteroaryl ring. Representative examples of bicyclic ring systems include, but are not limited to, 1,2,3,4-tetrahydronaphthalene, indane, and 6,7-dihydro-5H-cyclopenta[c]pyridine. Tricyclic ring systems are exemplified by a bicyclic ring system in which two non-adjacent carbon atoms of the bicyclic ring are linked by a bond or an alkylene bridge of between one and three carbon atoms. Representative examples of tricyclic-ring systems include, but are not limited to, tricyclo[3.3.1.0$^{3,7}$]nonane and tricyclo[3.3.1.1$^{3,7}$]decane (adamantane).

The cycoalkyl groups of the present invention are optionally substituted with 1, 2, 3, or 4 substituents selected from the group consisting of acyl, acyloxy, alkenyl, alkoxy, alkoxyalkoxy, alkoxyalkyl, alkoxycarbonyl, alkoxysulfonyl, alkyl, alkylsulfonyl, alkynyl, aryl, carboxy, cyano, formyl, haloalkoxy, haloalkyl, halo, hydroxy, hydroxyalkyl, mercapto, nitro, thioalkoxy, —$NR_iR_j$, ($NR_iR_j$)alkyl, ($NR_iR_j$)alkoxy, ($NR_iR_j$)carbonyl, and ($NR_iR_j$)sulfonyl, wherein $R_i$ and $R_j$ are as defined in the Definition of Terms herein.

The term "cycloalkylalkyl," as used herein, means a cycloalkyl group appended to the parent molecular moiety through an alkyl group, as defined herein.

The term "formyl", as used herein, means a —CHO group.

The term "halo" or "halogen", as used herein, means —Cl, —Br, —I or —F.

The term "haloalkoxy", as used herein, means at least one halogen, as defined herein, appended to the parent molecular moiety through an alkoxy group, as defined herein. Representative examples of haloalkoxy include, but are not limited to, chloromethoxy, 2-fluoroethoxy, trifluoromethoxy, and pentafluoroethoxy.

The term "haloalkenyl," as used herein, means alkenyl wherein one or more of the hydrogens thereof are replaced by independently selected F, Cl or Br.

The term "haloalkyl", as used herein, means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "haloalkynyl," as used herein, means alkynyl wherein one or more of the hydrogens thereof are replaced by independently selected F, Cl, or Br.

The term "heteroaryl," as used herein, means a monocyclic heteroaryl or a bicyclic heteroaryl. The monocyclic heteroaryl is a 5 or 6 membered ring containing at least one heteroatom independently selected from the group consisting of O, N, and S. The 5 or 6 membered heteroaryl is connected to the parent molecular moiety through any carbon atom or any nitrogen atom contained within the heteroaryl. Representative examples of monocyclic heteroaryl include, but are not limited to, furyl, imidazolyl, imidazolium, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The bicyclic heteroaryl consists of a monocyclic heteroaryl fused to a phenyl, or a monocyclic heteroaryl fused to a cycloalkyl, or a monocyclic heteroaryl fused to a cycloalkenyl, or a monocyclic heteroaryl fused to a monocyclic heteroaryl, or a monocyclic heteroaryl fused to a monocyclic heterocycle. The bicyclic heteroaryl is connected to the parent molecular moiety through any carbon atom or any substitutable nitrogen atom contained within the bicyclic heteroaryl. Representative examples of bicyclic heteroaryl include, but are not limited to, benzimidazolyl, benzofuranyl, benzothienyl, benzoxadiazolyl, cinnolinyl, dihydroquinolinyl, dihydroisoquinolinyl, furopyridinyl, indazolyl, indolyl, isoquinolinyl, naphthyridinyl, quinolinyl, tetrahydroquinolinyl, and thienopyridinyl.

The heteroaryl groups of the invention are substituted with 0, 1, 2, or 3 substituents independently selected from acyl, acyloxy, alkenyl, alkoxy, alkoxyalkoxy, alkoxyalkyl, alkoxycarbonyl, alkoxysulfonyl, alkyl, alkylsulfonyl, alkynyl, carboxy, cyano, formyl, haloalkoxy, haloalkyl, halo, hydroxy, hydroxyalkyl, mercapto, nitro, thioalkoxy, —$NR_iR_j$, ($NR_iR_j$)alkyl, ($NR_iR_j$)alkoxy, ($NR_iR_j$)carbonyl, and ($NR_iR_j$)sulfonyl, wherein $R_i$ and $R_j$ are defined in the Definitions of Terms herein.

The term "heteroarylalkyl" as used herein, means a heteroaryl, as defined herein, appended to the parent molecular moiety through an alkyl group, as defined herein. Representative examples of heteroarylalkyl include, but are not limited to, fur-3-ylmethyl, 1H-imidazol-2-ylmethyl, 1H-imidazol-4-ylmethyl, 1-(pyridin-4-yl)ethyl, pyridin-3-ylmethyl, 6-chloropyridin-3-ylmethyl, pyridin-4-ylmethyl, (6-(trifluoromethyl)pyridin-3-yl)methyl, (6-(cyano)pyridin-3-yl)methyl, (2-(cyano)pyridin-4-yl)methyl, (5-(cyano)pyridin-2-yl)methyl, (2-(chloro)pyridin-4-yl)methyl, pyrimidin-5-ylmethyl, 2-(pyrimidin-2-yl)propyl, thien-2-ylmethyl, and thien-3-ylmethyl.

The term "heteroaryl(hydroxyl)alkyl", as used herein, means an heteroarylalkyl, as defined herein, substituted with 1, 2, or 3 hydroxyl groups on the alkyl portion wherein each hydroxyl group is a substituent on a separate carbon. One hydroxyl group is preferred. Representative examples of heteroaryl(hydroxyl)alkyl include, but are not limited to, 2-hydroxy-1-pyrid-2-ylethyl.

The term "heterocycle" or "heterocyclic" as used herein, means a monocyclic heterocycle or a bicyclic heterocycle. The monocyclic heterocycle is a 3, 4, 5, 6 or 7 membered ring containing at least one heteroatom independently selected from the group consisting of O, N, and S. The monocyclic heterocycle is connected to the parent molecular moiety through any carbon atom or any nitrogen atom contained within the monocyclic heterocycle. Representative examples of monocyclic heterocycle include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, or a monocyclic heterocycle fused to a cycloalkyl, or a monocyclic heterocycle fused to a cycloalkenyl, or a monocyclic heterocycle fused to a monocyclic heterocycle. The bicyclic heterocycle is connected to the parent molecular moiety through any carbon atom or any nitrogen atom contained within the monocyclic heterocycle. Representative examples of bicyclic heterocycle include, but are not limited to, 1,3-benzodioxolyl, 1,3-benzodithiolyl, 2,3-dihydro-1,4-benzodioxinyl, 2,3-dihydro-1-benzofuranyl, 2,3-dihydro-1-benzothienyl, 2,3-dihydro-1H-indolyl, and 1,2,3,4-tetrahydroquinolinyl.

The heterocycles of this invention are optionally substituted with 1, 2, or 3 substituents independently selected from the group consisting of acyl, acyloxy, alkenyl, alkoxy, alkoxyalkoxy, alkoxyalkyl, alkoxycarbonyl, alkoxysulfonyl, alkyl, alkylsulfonyl, alkynyl, carboxy, cyano, formyl, haloalkoxy, haloalkyl, halo, hydroxy, hydroxyalkyl, mercapto, nitro, thioalkoxy, —$NR_iR_j$, ($NR_iR_j$)alkyl, ($NR_iR_j$)alkoxy, ($NR_iR_j$)carbonyl, and ($NR_iR_j$)sulfonyl, wherein $R_i$ and $R_j$ are defined in the Definition of Terms herein.

The term "heterocyclealkyl," as used herein, means a heterocycle group appended to the parent molecular moiety through an alkyl group, as defined herein.

The term "hydroxy" or "hydroxyl", as used herein, means an —OH group.

The term "hydroxyalkyl", as used herein, means at least one hydroxy group, as defined herein, is appended to the parent molecular moiety through an alkyl group, as defined herein. Representative examples of hydroxyalkyl include, but are not limited to, hydroxymethyl, 2-hydroxyethyl, 3-hydroxypropyl, 2,3-dihydroxypentyl, and 2-ethyl-4-hydroxyheptyl.

The term "mercapto", as used herein, means a —SH group.

The term "nitro", as used herein, means a —$NO_2$ group.

The term "—$NR_iR_j$", as used herein, means two groups, $R_i$ and $R_j$, which are appended to the parent molecular moiety through a nitrogen atom. $R_i$ and $R_j$ are each independently hydrogen, alkyl, alkylcarbonyl, or formyl. In addition, $R_i$ and $R_j$ taken together with the nitrogen atom to which they are attached, may form a 5, 6 or 7 membered heterocyclic ring. Representative examples of —$NR_iR_j$ include, but are not limited to, amino, methylamino, acetylamino, and acetylmethylamino.

The term "($NR_iR_j$)alkyl", as used herein, means a —$NR_iR_j$ group, as defined herein, appended to the parent molecular moiety through an alkyl group, as defined herein. Representative examples of ($NR_iR_j$)alkyl include, but are not limited to, (amino)methyl, (dimethylamino)methyl, and (ethylamino)methyl.

The term "($NR_iR_j$)alkoxy", as used herein, means a —$NR_iR_j$ group, as defined herein, appended to the parent molecular moiety through an alkoxy group, as defined herein. Representative examples of ($NR_iR_j$)alkoxy include, but are not limited to, (amino)methoxy, (dimethylamino)methoxy, and (diethylamino)ethoxy.

The term "($NR_iR_j$)carbonyl", as used herein, means a —$NR_iR_j$ group, as defined herein, appended to the parent molecular moiety through a carbonyl group, as defined herein. Representative examples of ($NR_iR_j$)carbonyl include, but are not limited to, aminocarbonyl, (methylamino)carbonyl, (dimethylamino)carbonyl, and (ethylmethylamino)carbonyl.

The term "($NR_iR_j$)sulfonyl", as used herein, means a —$NR_iR_j$ group, as defined herein, appended to the parent molecular moiety through a sulfonyl group, as defined herein. Representative examples of ($NR_iR_j$)sulfonyl include, but are not limited to, aminosulfonyl, (methylamino)sulfonyl, (dimethylamino)sulfonyl, and (ethylmethylamino)sulfonyl.

The term "sulfonyl", as used herein, means a —$S(O)_2$— group.

The term "thioalkoxy", as used herein, means an alkyl group, as defined herein, appended to the parent molecular moiety through a sulfur atom. Representative examples of thioalkoxy include, but are no limited to, methylthio, ethylthio, and propylthio.

The term "Positive Allosteric Modulator," as used herein, means a compound that enhances activity of an endogenous ligand, such as but not limited to ACh, or an exogenously administered agonist.

Although typically it may be recognized that an asterisk is used to indicate that the exact subunit composition of a receptor is uncertain, for example α3β4* indicates a receptor that contains the α3 and α4 proteins in combination with other subunits, the term α7 as used herein is intended to include receptors wherein the exact subunit composition is both certain and uncertain. For example, as used herein α7 includes homomeric (α7)$_5$ receptors and α7* receptors, which denote a nAChR containing at least one α7 subunit.

Compounds of the Invention

Compounds of the invention can have the formula (I), or more particularly (IA), (IB), or (IC), as described above. In addition, certain embodiments described compounds of formula (I) wherein R$_1$ is hydrogen; and X is S. Furthermore, compounds of formula (I), particularly compounds of formula (IA) are disclosed wherein R$_2$ is alkyl, wherein the alkyl group is substituted with 1, 2, or 3 substituents selected from hydroxyl, cyano, nitro, and R$_c$R$_d$N— groups. The preferred group for R$_2$ in such embodiment is hydroxyalkyl, wherein the alkyl portion is substituted with one or two hydroxyl groups.

In another embodiment, certain embodiments describe compounds of formula (I) wherein R$_1$ is hydrogen; and L is C(O). More particularly, in such embodiment, it is preferred that R$_1$ is hydrogen; L is C(O); and R$_2$ is alkyl substituted with 1, 2, or 3 hydroxyl groups.

The heteroaryl and heterocycle groups represented by Z in compounds of formula (I) can be represented by the formula R$_k$R$_l$N—, wherein R$_k$ and R$_l$ taken together with the nitrogen atom to which each is attached form a monocyclic heterocycle, a bicyclic heterocycle, a monocyclic heteroaryl, or a bicyclic heteroaryl, wherein each group is substituted with 0, 1, 2, or 3 substituents selected from halo, hydroxyl, aryl, and heteroaryl. More particularly, Z can be a monocyclic heterocycle.

Preferably, in such embodiments, Z is unsubstituted pyrrolidine or pyrrolidine substituted with halo, for example fluoro. Other compounds of formula (I) are those wherein Z is —NR$_e$R$_f$; and R$_e$ and R$_f$ are each independently selected from hydrogen, alkyl, aryl, aryl(hydroxyl)alkyl, arylalkyl, heterocycle, heterocyclealkyl, heteroaryl, heteroaryl(hydroxyl)alkyl, and heteroarylalkyl. In such embodiments, it is preferred that R$_e$ is hydrogen or alkyl; and R$_f$ is arylalkyl, heterocyclealkyl, or heteroarylalkyl.

In another embodiment, compounds of formula (I) wherein X is O are disclosed.

In another embodiment, compounds of formula (I) wherein L is C(O) are disclosed.

In another embodiment, compounds of formula (I) wherein X is S; L is C(O); and Z is R$_i$R$_j$N— wherein R$_i$ and R$_j$ are taken together to form a 4-, 5-, or 6-membered heterocycle fused to an aromatic ring, are disclosed. In such embodiments, it is preferred that Z is a pyrrolidine ring fused to phenyl. Alternatively, compounds of formula (I) are those wherein X is S; L is C(O); R$_e$ is hydrogen or alkyl; and R$_h$ is arylalkyl, heterocyclealkyl, or heteroarylalkyl.

In yet another embodiment, compounds of formula (I) wherein X is S; L is C(O); and Z is R$_i$R$_j$N— wherein R$_i$ and R$_j$ are taken together to form a heterocycle substituted with hydroxyl or pyridyl.

In other embodiments there is described a method for treating disorders or conditions, comprising administration of a therapeutically effective amount of a compound of formula (II), wherein the compounds are positive allosteric nicotinic acetylcholine receptors (nAChR) modulators. Particularly useful compounds are described wherein R$_1$ is hydrogen, X is S, and L is C(O). Furthermore, certain embodiments are described wherein Z is a ring such as aryl, cycloalkyl, heterocycle or heteroaryl, as defined herein. The heteroaryl and heterocyclic groups useful within the scope of compounds of formula (II) can be mono or bicyclic. In certain preferred embodiments the heterocycles are monocyclic, for example as in unsubstituted and substituted pyrrolidinyl, such as fluoropyrrolidinyl and hydroxypyrrolidinyl. In certain other embodiments, there are described compounds of formula (II), wherein Z is a group R$_e$R$_f$N—, wherein R$_e$ is hydrogen or alkyl, and R$_f$ is selected from the group consisting of heterocycle, heterocyclealkyl, arylalkyl, and heteroarylalkyl.

Specific embodiments contemplated as part of the invention include, but are not limited to, compounds of formula (I), for example:

ethyl(2Z)-3-(2,2-difluoro-1,3-benzodioxol-5-yl)-5-methylene-1,3-thiazolidin-2-ylidenecarbamate;

N-[(2Z)-3-(2,2-difluoro-1,3-benzodioxol-5-yl)-5-methylene-1,3-thiazolidin-2-ylidene]acetamide;

N'-[(2Z)-3-(2,2-difluoro-1,3-benzodioxol-5-yl)-5-methylene-1,3-thiazolidin-2-ylidene]-N,N-dimethylurea;

N'-[(2Z)-3-(2,2-difluoro-1,3-benzodioxol-5-yl)-5-methyl-1,3-oxazol-2(3H)-ylidene]-N,N-dimethylurea;

N'-[(2Z)-3-(2,2-difluoro-1,3-benzodioxol-5-yl)-5-methyl-1,3-oxazol-2(3H)-ylidene]-N,N-dimethylthiourea;

N-[(2Z)-5-methylene-3-(2,2,3,3-tetrafluoro-2,3-dihydro-1,4-benzodioxin-6-yl)-1,3-thiazolidin-2-ylidene]pyrrolidine-1-carboxamide;

N-[(2Z)-3-(2,2-difluoro-1,3-benzodioxol-5-yl)-5-(pyrrolidin-1-ylmethyl)-1,3-thiazol-2(3H)-ylidene]acetamide;

N-[(2Z)-5-(hydroxymethyl)-3-(2,2,3,3-tetrafluoro-2,3-dihydro-1,4-benzodioxin-6-yl)-1,3-thiazol-2(3H)-ylidene]pyrrolidine-1-carboxamide;

N'-[(2Z)-3-(2,2-difluoro-1,3-benzodioxol-5-yl)-5-methyl-1,3-thiazol-2(3H)-ylidene]-N-(1,3-dioxolan-2-ylmethyl)-N-methylurea;

N-benzyl-N'-[(2Z)-3-(2,2-difluoro-1,3-benzodioxol-5-yl)-5-methyl-1,3-thiazol-2(3H)-ylidene]-N-ethylurea;

N-benzyl-N'-[(2Z)-3-(2,2-difluoro-1,3-benzodioxol-5-yl)-5-methyl-1,3-thiazol-2(3H)-ylidene]-N-isopropylurea;

N-benzyl-N-butyl-N'-[(2Z)-3-(2,2-difluoro-1,3-benzodioxol-5-yl)-5-methyl-1,3-thiazol-2(3H)-ylidene]urea;

N-benzyl-N'-[(2Z)-3-(2,2-difluoro-1,3-benzodioxol-5-yl)-5-methyl-1,3-thiazol-2(3H)-ylidene]-N-(2-hydroxyethyl)urea;

N-[(2Z)-3-(2,2-difluoro-1,3-benzodioxol-5-yl)-5-methyl-1,3-thiazol-2(3H)-ylidene]-N'-(1,1,3,3-tetramethylbutyl)urea;

N-[(2Z)-3-(2,2-difluoro-1,3-benzodioxol-5-yl)-5-methyl-1,3-thiazol-2(3H)-ylidene]-N'-[(1R)-2-hydroxy-1-phenylethyl]urea;

N-[(2Z)-3-(2,2-difluoro-1,3-benzodioxol-5-yl)-5-methyl-1,3-thiazol-2(3H)-ylidene]-N'-[(1S)-2-hydroxy-1-phenylethyl]urea;

N-[(2Z)-3-(2,2-difluoro-1,3-benzodioxol-5-yl)-5-methyl-1,3-thiazol-2(3H)-ylidene]-N'-[(1S)-1-phenylethyl]urea;

N-[(2Z)-3-(2,2-difluoro-1,3-benzodioxol-5-yl)-5-methyl-1,3-thiazol-2(3H)-ylidene]-N'-[(1R)-1-phenylethyl]urea;

N-benzyl-N-(tert-butyl)-N'-[(2Z)-3-(2,2-difluoro-1,3-benzodioxol-5-yl)-5-methyl-1,3-thiazol-2(3H)-ylidene]urea;

N-benzyl-N'-[(2Z)-3-(2,2-difluoro-1,3-benzodioxol-5-yl)-5-methyl-1,3-thiazol-2(3H)-ylidene]-N-methylurea;

N-benzyl-N-(2-cyanoethyl)-N'-[(2Z)-3-(2,2-difluoro-1,3-benzodioxol-5-yl)-5-methyl-1,3-thiazol-2(3H)-ylidene]urea;

N-(3-chlorobenzyl)-N'-[(2Z)-3-(2,2-difluoro-1,3-benzodioxol-5-yl)-5-methyl-1,3-thiazol-2(3H)-ylidene]-N-methylurea;

N'-[(2Z)-3-(2,2-difluoro-1,3-benzodioxol-5-yl)-5-methyl-1,3-thiazol-2(3H)-ylidene]-N-(2-methoxybenzyl)-N-methylurea;

N'-[(2Z)-3-(2,2-difluoro-1,3-benzodioxol-5-yl)-5-methyl-1,3-thiazol-2(3H)-ylidene]-N-(3-methoxybenzyl)-N-methylurea;

N-[(2Z)-3-(2,2-difluoro-1,3-benzodioxol-5-yl)-5-methyl-1,3-thiazol-2(3H)-ylidene]-1,3-dihydro-2H-isoindole-2-carboxamide;

N-[(2Z)-3-(2,2-difluoro-1,3-benzodioxol-5-yl)-5-methyl-1,3-thiazol-2(3H)-ylidene]-3,4-dihydroisoquinoline-2(1H)-carboxamide;

N'-[(2Z)-3-(2,2-difluoro-1,3-benzodioxol-5-yl)-5-methyl-1,3-thiazol-2(3H)-ylidene]-N-ethyl-N-(pyridin-4-ylmethyl)urea;

N-[(2Z)-3-(2,2-difluoro-1,3-benzodioxol-5-yl)-5-methyl-1,3-thiazol-2(3H)-ylidene]-N'-(1-phenylpropyl)urea;

N-[(2Z)-3-(2,2-difluoro-1,3-benzodioxol-5-yl)-5-methyl-1,3-thiazol-2(3H)-ylidene]-N'-2,3-dihydro-1H-inden-1-ylurea;

N-(5-fluoro-2-phenoxybenzyl)-N-methyl-N'-[(2Z)-5-methyl-3-(2,2,3,3-tetrafluoro-2,3-dihydro-1,4-benzodioxin-6-yl)-1,3-thiazol-2(3H)-ylidene]urea;

N-(2-chloro-6-fluorobenzyl)-N-ethyl-N'-[(2Z)-5-methyl-3-(2,2,3,3-tetrafluoro-2,3-dihydro-1,4-benzodioxin-6-yl)-1,3-thiazol-2(3H)-ylidene]urea;

N-benzyl-N'-[(2Z)-5-methyl-3-(2,2,3,3-tetrafluoro-2,3-dihydro-1,4-benzodioxin-6-yl)-1,3-thiazol-2(3H)-ylidene]-N-prop-2-ynylurea;

N-[4-(allyloxy)benzyl]-N-methyl-N'-[(2Z)-5-methyl-3-(2,2,3,3-tetrafluoro-2,3-dihydro-1,4-benzodioxin-6-yl)-1,3-thiazol-2(3H)-ylidene]urea;

N-[(2Z)-3-(2,2-difluoro-1,3-benzodioxol-5-yl)-5-formyl-1,3-thiazol-2(3H)-ylidene]pyrrolidine-1-carboxamide;

N-[(2Z)-3-(2,2-difluoro-1,3-benzodioxol-5-yl)-5-[(Z)-(hydroxyimino)methyl]-1,3-thiazol-2(3H)-ylidene]pyrrolidine-1-carboxamide;

N'-[(2Z)-3-(2,2-difluoro-1,3-benzodioxol-5-yl)-5-(fluoromethyl)-1,3-thiazol-2(3H)-ylidene]-N,N-dimethylurea;

N'-[(2Z)-3-(2,2-difluoro-1,3-benzodioxol-5-yl)-5-formyl-1,3-thiazol-2(3H)-ylidene]-N,N-dimethylurea;

(3R)-3-fluoro-N-[(2Z)-5-methylene-3-(2,2,3,3-tetrafluoro-2,3-dihydro-1,4-benzodioxin-6-yl)-1,3-thiazolidin-2-ylidene]pyrrolidine-1-carboxamide;

(3S)-3-fluoro-N-[(2Z)-5-methylene-3-(2,2,3,3-tetrafluoro-2,3-dihydro-1,4-benzodioxin-6-yl)-1,3-thiazolidin-2-ylidene]pyrrolidine-1-carboxamide;

(3R)-3-fluoro-N-[(2Z)-5-(hydroxymethyl)-3-(2,2,3,3-tetrafluoro-2,3-dihydro-1,4-benzodioxin-6-yl)-1,3-thiazol-2(3H)-ylidene]pyrrolidine-1-carboxamide;

(3S)-3-fluoro-N-[(2Z)-5-(hydroxymethyl)-3-(2,2,3,3-tetrafluoro-2,3-dihydro-1,4-benzodioxin-6-yl)-1,3-thiazol-2(3H)-ylidene]pyrrolidine-1-carboxamide;

N-[4-(difluoromethoxy)benzyl]-N-methyl-N'-[(2Z)-5-methyl-3-(2,2,3,3-tetrafluoro-2,3-dihydro-1,4-benzodioxin-6-yl)-1,3-thiazol-2(3H)-ylidene]urea;

N-[1-(4-ethoxyphenyl)ethyl]-N-methyl-N'-[(2Z)-5-methyl-3-(2,2,3,3-tetrafluoro-2,3-dihydro-1,4-benzodioxin-6-yl)-1,3-thiazol-2(3H)-ylidene]urea;

N-methyl-N-[(6-methylpyridin-2-yl)methyl]-N'-[(2Z)-5-methyl-3-(2,2,3,3-tetrafluoro-2,3-dihydro-1,4-benzodioxin-6-yl)-1,3-thiazol-2(3H)-ylidene]urea;

N-benzyl-N-but-2-ynyl-N'-[(2Z)-5-methyl-3-(2,2,3,3-tetrafluoro-2,3-dihydro-1,4-benzodioxin-6-yl)-1,3-thiazol-2(3H)-ylidene]urea;

N-(1-methyl-1-phenylethyl)-N'-[(2Z)-5-methyl-3-(2,2,3,3-tetrafluoro-2,3-dihydro-1,4-benzodioxin-6-yl)-1,3-thiazol-2(3H)-ylidene]urea;

N-(2-chlorobenzyl)-N-methyl-N'-[(2Z)-5-methyl-3-(2,2,3,3-tetrafluoro-2,3-dihydro-1,4-benzodioxin-6-yl)-1,3-thiazol-2(3H)-ylidene]urea;

N-methyl-N'-[(2Z)-5-methyl-3-(2,2,3,3-tetrafluoro-2,3-dihydro-1,4-benzodioxin-6-yl)-1,3-thiazol-2(3H)-ylidene]-N-(thien-2-ylmethyl)urea;

N-(4-chlorobenzyl)-N-methyl-N'-[(2Z)-5-methyl-3-(2,2,3,3-tetrafluoro-2,3-dihydro-1,4-benzodioxin-6-yl)-1,3-thiazol-2(3H)-ylidene]urea;

N-(3-chlorobenzyl)-N-methyl-N'-[(2Z)-5-methyl-3-(2,2,3,3-tetrafluoro-2,3-dihydro-1,4-benzodioxin-6-yl)-1,3-thiazol-2(3H)-ylidene]urea;

N-cyclopentyl-N-(4-fluorobenzyl)-N'-[(2Z)-5-methyl-3-(2,2,3,3-tetrafluoro-2,3-dihydro-1,4-benzodioxin-6-yl)-1,3-thiazol-2(3H)-ylidene]urea;

N-[(1S)-2-hydroxy-1-phenylethyl]-N'-[(2Z)-5-methyl-3-(2,2,3,3-tetrafluoro-2,3-dihydro-1,4-benzodioxin-6-yl)-1,3-thiazol-2(3H)-ylidene]urea;

N-[(2Z)-5-methyl-3-(2,2,3,3-tetrafluoro-2,3-dihydro-1,4-benzodioxin-6-yl)-1,3-thiazol-2(3H)-ylidene]-N'-[(1R)-1-phenylethyl]urea;

N-[(2Z)-5-methyl-3-(2,2,3,3-tetrafluoro-2,3-dihydro-1,4-benzodioxin-6-yl)-1,3-thiazol-2(3H)-ylidene]-N'-[(1S)-1-phenylethyl]urea;

(3R)-3-hydroxy-N-[(2Z)-5-methyl-3-(2,2,3,3-tetrafluoro-2,3-dihydro-1,4-benzodioxin-6-yl)-1,3-thiazol-2(3H)-ylidene]pyrrolidine-1-carboxamide;

N-methyl-N-[(1-methyl-1H-pyrazol-4-yl)methyl]-N'-[(2Z)-5-methyl-3-(2,2,3,3-tetrafluoro-2,3-dihydro-1,4-benzodioxin-6-yl)-1,3-thiazol-2(3H)-ylidene]urea;

N-methyl-N'-[(2Z)-5-methyl-3-(2,2,3,3-tetrafluoro-2,3-dihydro-1,4-benzodioxin-6-yl)-1,3-thiazol-2(3H)-ylidene]-N-(pyrazin-2-ylmethyl)urea;

N-[(2Z)-3-(2,2-difluoro-1,3-benzodioxol-5-yl)-5-methylene-1,3-thiazolidin-2-ylidene]-1H-imidazole-1-carboxamide;

N-[(2Z)-3-(2,2-difluoro-1,3-benzodioxol-5-yl)-5-methylene-1,3-thiazolidin-2-ylidene]-2-methylpyrrolidine-1-carboxamide;

N-[(2Z)-3-(2,2-difluoro-1,3-benzodioxol-5-yl)-5-methylene-1,3-thiazolidin-2-ylidene]pyrrolidine-1-carboxamide;

N-[(2Z)-4-amino-3-(2,2-difluoro-1,3-benzodioxol-5-yl)-5-methylene-1,3-thiazolidin-2-ylidene]pyrrolidine-1-carboxamide;

N-[(2Z)-3-(2,2-difluoro-1,3-benzodioxol-5-yl)-5-(hydroxymethyl)-1,3-thiazol-2(3H)-ylidene]pyrrolidine-1-carboxamide;

N-[(2Z)-3-(2,2-difluoro-1,3-benzodioxol-5-yl)-5-{[(4-fluorophenyl)amino]methyl}-1,3-thiazol-2(3H)-ylidene]pyrrolidine-1-carboxamide;

N-[(2Z)-3-(2,2-difluoro-1,3-benzodioxol-5-yl)-5-{[(4-fluorophenyl)(methyl)amino]methyl}-1,3-thiazol-2(3H)-ylidene]pyrrolidine-1-carboxamide;

N-[(2Z)-3-(2,2-difluoro-1,3-benzodioxol-5-yl)-5-methylene-4-(pyridin-3-ylamino)-1,3-thiazolidin-2-ylidene]pyrrolidine-1-carboxamide;

N-[(2Z)-3-(2,2-difluoro-1,3-benzodioxol-5-yl)-5-methyl-1,3-thiazol-2(3H)-ylidene]-N'-2,3-dihydro-1H-inden-2-ylurea;

N-[(2Z)-3-(2,2-difluoro-1,3-benzodioxol-5-yl)-5-methyl-1,3-thiazol-2(3H)-ylidene]-N'-(1-methyl-1-phenylethyl)urea;

N-cyclopropyl-N'-[(2Z)-3-(2,2-difluoro-1,3-benzodioxol-5-yl)-5-methyl-1,3-thiazol-2(3H)-ylidene]-N-(2-fluorobenzyl)urea;

N-(2-chlorobenzyl)-N'-[(2Z)-3-(2,2-difluoro-1,3-benzodioxol-5-yl)-5-methyl-1,3-thiazol-2(3H)-ylidene]-N-methylurea;

N-(4-chlorobenzyl)-N'-[(2Z)-3-(2,2-difluoro-1,3-benzodioxol-5-yl)-5-methyl-1,3-thiazol-2(3H)-ylidene]-N-methylurea;

N'-[(2Z)-3-(2,2-difluoro-1,3-benzodioxol-5-yl)-5-methyl-1,3-thiazol-2(3H)-ylidene]-N-(4-methoxybenzyl)-N-methylurea;

N'-[(2Z)-3-(2,2-difluoro-1,3-benzodioxol-5-yl)-5-methyl-1,3-thiazol-2(3H)-ylidene]-N-methyl-N-(pyridin-2-ylmethyl)urea;

N'-[(2Z)-3-(2,2-difluoro-1,3-benzodioxol-5-yl)-5-methyl-1,3-thiazol-2(3H)-ylidene]-N-methyl-N-(pyridin-3-ylmethyl)urea;

N'-[(2Z)-3-(2,2-difluoro-1,3-benzodioxol-5-yl)-5-methyl-1,3-thiazol-2(3H)-ylidene]-N-ethyl-N-(pyridin-3-ylmethyl)urea;

N'-[(2Z)-3-(2,2-difluoro-1,3-benzodioxol-5-yl)-5-methyl-1,3-thiazol-2(3H)-ylidene]-N-methyl-N-(pyridin-4-ylmethyl)urea;

N'-[(2Z)-3-(2,2-difluoro-1,3-benzodioxol-5-yl)-5-methyl-1,3-thiazol-2(3H)-ylidene]-N-methyl-N-(pyrazin-2-ylmethyl)urea;

N-methyl-N'-[(2Z)-5-methyl-3-(2,2,3,3-tetrafluoro-2,3-dihydro-1,4-benzodioxin-6-yl)-1,3-thiazol-2(3H)-ylidene]-N-(pyridin-3-ylmethyl)urea;

N-[(2Z)-5-(hydroxymethyl)-3-(2,2,3,3-tetrafluoro-2,3-dihydro-1,4-benzodioxin-6-yl)-1,3-thiazol-2(3H)-ylidene]acetamide;

2-methyl-N-[(2Z)-5-methyl-3-(2,2,3,3-tetrafluoro-2,3-dihydro-1,4-benzodioxin-6-yl)-1,3-thiazol-2(3H)-ylidene]indoline-1-carboxamide;

5-bromo-N-[(2Z)-5-methyl-3-(2,2,3,3-tetrafluoro-2,3-dihydro-1,4-benzodioxin-6-yl)-1,3-thiazol-2(3H)-ylidene]indoline-1-carboxamide;

N-methyl-N-[(1-methyl-1H-indol-5-yl)methyl]-N'-[(2Z)-5-methyl-3-(2,2,3,3-tetrafluoro-2,3-dihydro-1,4-benzodioxin-6-yl)-1,3-thiazol-2(3H)-ylidene]urea;

N-methyl-N'-[(2Z)-5-methyl-3-(2,2,3,3-tetrafluoro-2,3-dihydro-1,4-benzodioxin-6-yl)-1,3-thiazol-2(3H)-ylidene]-N-(4-pyridin-4-ylbenzyl)urea;

N-methyl-N'-[(2Z)-5-methyl-3-(2,2,3,3-tetrafluoro-2,3-dihydro-1,4-benzodioxin-6-yl)-1,3-thiazol-2(3H)-ylidene]-N-[(1R)-1-phenylethyl]urea;

2-(4-fluorophenyl)-N-[(2Z)-5-methyl-3-(2,2,3,3-tetrafluoro-2,3-dihydro-1,4-benzodioxin-6-yl)-1,3-thiazol-2(3H)-ylidene]indoline-1-carboxamide;

N-ethyl-N'-[(2Z)-5-methyl-3-(2,2,3,3-tetrafluoro-2,3-dihydro-1,4-benzodioxin-6-yl)-1,3-thiazol-2(3H)-ylidene]-N-(thien-2-ylmethyl)urea;

N-methyl-N-[(3-methylpyridin-2-yl)methyl]-N'-[(2Z)-5-methyl-3-(2,2,3,3-tetrafluoro-2,3-dihydro-1,4-benzodioxin-6-yl)-1,3-thiazol-2(3H)-ylidene]urea;

N-methyl-N-[(3-methylpyridin-4-yl)methyl]-N'-[(2Z)-5-methyl-3-(2,2,3,3-tetrafluoro-2,3-dihydro-1,4-benzodioxin-6-yl)-1,3-thiazol-2(3H)-ylidene]urea;

N-[(2Z)-5-methyl-3-(2,2,3,3-tetrafluoro-2,3-dihydro-1,4-benzodioxin-6-yl)-1,3-thiazol-2(3H)-ylidene]-2-pyridin-3-ylpyrrolidine-1-carboxamide;

N-(4-ethylbenzyl)-N-methyl-N'-[(2Z)-5-methyl-3-(2,2,3,3-tetrafluoro-2,3-dihydro-1,4-benzodioxin-6-yl)-1,3-thiazol-2(3H)-ylidene]urea;

N-ethyl-N'-[(2Z)-5-methyl-3-(2,2,3,3-tetrafluoro-2,3-dihydro-1,4-benzodioxin-6-yl)-1,3-thiazol-2(3H)-ylidene]-N-(pyridin-4-ylmethyl)urea;

N-(4-ethoxybenzyl)-N-methyl-N'-[(2Z)-5-methyl-3-(2,2,3,3-tetrafluoro-2,3-dihydro-1,4-benzodioxin-6-yl)-1,3-thiazol-2(3H)-ylidene]urea;

N-methyl-N-(4-methylbenzyl)-N'-[(2Z)-5-methyl-3-(2,2,3,3-tetrafluoro-2,3-dihydro-1,4-benzodioxin-6-yl)-1,3-thiazol-2(3H)-ylidene]urea;

N-(4-bromobenzyl)-N-methyl-N'-[(2Z)-5-methyl-3-(2,2,3,3-tetrafluoro-2,3-dihydro-1,4-benzodioxin-6-yl)-1,3-thiazol-2(3H)-ylidene]urea;

N-(4-tert-butylbenzyl)-N-methyl-N'-[(2E)-5-methyl-3-(2,2,3,3-tetrafluoro-2,3-dihydro-1,4-benzodioxin-6-yl)-1,3-thiazol-2(3H)-ylidene]urea;

N-(4-isopropylbenzyl)-N-methyl-N'-[(2Z)-5-methyl-3-(2,2,3,3-tetrafluoro-2,3-dihydro-1,4-benzodioxin-6-yl)-1,3-thiazol-2(3H)-ylidene]urea;

N-(3,4-dichlorobenzyl)-N-methyl-N'-[(2Z)-5-methyl-3-(2,2,3,3-tetrafluoro-2,3-dihydro-1,4-benzodioxin-6-yl)-1,3-thiazol-2(3H)-ylidene]urea;

N-(2,4-dichlorobenzyl)-N-methyl-N'-[(2Z)-5-methyl-3-(2,2,3,3-tetrafluoro-2,3-dihydro-1,4-benzodioxin-6-yl)-1,3-thiazol-2(3H)-ylidene]urea;

N-(4-fluorobenzyl)-N-methyl-N'-[(2Z)-5-methyl-3-(2,2,3,3-tetrafluoro-2,3-dihydro-1,4-benzodioxin-6-yl)-1,3-thiazol-2(3H)-ylidene]urea;

N-(4-methoxybenzyl)-N-methyl-N'-[(2Z)-5-methyl-3-(2,2,3,3-tetrafluoro-2,3-dihydro-1,4-benzodioxin-6-yl)-1,3-thiazol-2(3H)-ylidene]urea;

N-methyl-N'-[(2Z)-5-methyl-3-(2,2,3,3-tetrafluoro-2,3-dihydro-1,4-benzodioxin-6-yl)-1,3-thiazol-2(3H)-ylidene]-N-(quinolin-6-ylmethyl)urea;

N-(3-bromobenzyl)-N-methyl-N'-[(2Z)-5-methyl-3-(2,2,3,3-tetrafluoro-2,3-dihydro-1,4-benzodioxin-6-yl)-1,3-thiazol-2(3H)-ylidene]urea;

N-(2-bromobenzyl)-N-methyl-N'-[(2Z)-5-methyl-3-(2,2,3,3-tetrafluoro-2,3-dihydro-1,4-benzodioxin-6-yl)-1,3-thiazol-2(3H)-ylidene]urea;

N-[(2Z)-3-(2,2-difluoro-1,3-benzodioxol-5-yl)-5-[(pyridin-3-ylamino)methyl]-1,3-thiazol-2(3H)-ylidene]pyrrolidine-1-carboxamide;

N-[(2Z)-5-[(benzyloxy)methyl]-3-(2,2-difluoro-1,3-benzodioxol-5-yl)-1,3-thiazol-2(3H)-ylidene]pyrrolidine-1-carboxamide;

N-[(2Z)-5-methylene-3-(2,2,3,3-tetrafluoro-2,3-dihydro-1,4-benzodioxin-6-yl)-1,3-thiazolidin-2-ylidene]-1H-imidazole-1-carboxamide;

N-[(2Z)-5-methylene-3-(2,2,3,3-tetrafluoro-2,3-dihydro-1,4-benzodioxin-6-yl)-1,3-thiazolidin-2-ylidene]-2,5-dihydro-1H-pyrrole-1-carboxamide;

(2S)-2-methyl-N-[(2Z)-5-methylene-3-(2,2,3,3-tetrafluoro-2,3-dihydro-1,4-benzodioxin-6-yl)-1,3-thiazolidin-2-ylidene]pyrrolidine-1-carboxamide;

N-(1-cyclopropyl-1-methylethyl)-N'-[(2Z)-5-methyl-3-(2,2,3,3-tetrafluoro-2,3-dihydro-1,4-benzodioxin-6-yl)-1,3-thiazol-2(3H)-ylidene]urea;

N-(1,3-dioxolan-2-ylmethyl)-N-methyl-N'-[(2Z)-5-methyl-3-(2,2,3,3-tetrafluoro-2,3-dihydro-1,4-benzodioxin-6-yl)-1,3-thiazol-2(3H)-ylidene]urea;

N-[(1,3-dimethyl-1H-pyrazol-4-yl)methyl]-N-methyl-N'-[(2Z)-5-methyl-3-(2,2,3,3-tetrafluoro-2,3-dihydro-1,4-benzodioxin-6-yl)-1,3-thiazol-2(3H)-ylidene]urea;

N-[(2Z)-5-cyano-3-(2,2-difluoro-1,3-benzodioxol-5-yl)-1,3-thiazol-2(3H)-ylidene]pyrrolidine-1-carboxamide;

N'-[(2Z)-3-(2,2-difluoro-1,3-benzodioxol-5-yl)-5-(1-hydroxyethyl)-1,3-thiazol-2(3H)-ylidene]-N,N-dimethylurea;

N'-[(2Z)-3-(2,2-difluoro-1,3-benzodioxol-5-yl)-5-(1-hydroxybutyl)-1,3-thiazol-2(3H)-ylidene]-N,N-dimethylurea;

N'-[(2Z)-3-(2,2-difluoro-1,3-benzodioxol-5-yl)-5-(1-hydroxy-2-methylpropyl)-1,3-thiazol-2(3H)-ylidene]-N,N-dimethylurea;

N'-[(2Z)-3-(2,2-difluoro-1,3-benzodioxol-5-yl)-5-{(E)-[(2-hydroxyethyl)imino]methyl}-1,3-thiazol-2(3H)-ylidene]-N,N-dimethylurea;

N'-[(2Z)-3-(2,2-difluoro-1,3-benzodioxol-5-yl)-5-(hydroxymethyl)-4-pyridin-2-yl-1,3-thiazol-2(3H)-ylidene]-N,N-dimethylurea compound with N'-[(2Z)-3-(2,2-difluoro-1,3-benzodioxol-5-yl)-5-[hydroxy(pyridin-2-yl)methyl]-1,3-thiazol-2(3H)-ylidene]-N,N-dimethylurea (1:1);

N-[(2Z)-3-(2,2-difluoro-1,3-benzodioxol-5-yl)-4-hydroxy-5-methylene-1,3-thiazolidin-2-ylidene]pyrrolidine-1-carboxamide;

(3S)-3-hydroxy-N-[(2Z)-5-methyl-3-(2,2,3,3-tetrafluoro-2,3-dihydro-1,4-benzodioxin-6-yl)-1,3-thiazol-2(3H)-ylidene]pyrrolidine-1-carboxamide;

N-[(2Z)-5-(cyanomethyl)-3-(2,2-difluoro-1,3-benzodioxol-5-yl)-1,3-thiazol-2(3H)-ylidene]pyrrolidine-1-carboxamide;

N-[(2Z)-5-(hydroxymethyl)-3-(2,2,3,3-tetrafluoro-2,3-dihydro-1,4-benzodioxin-6-yl)-1,3-thiazol-2(3H)-ylidene]-2,2-dimethylpropanamide;

N-[(2Z)-5-(hydroxymethyl)-3-(2,2,3,3-tetrafluoro-2,3-dihydro-1,4-benzodioxin-6-yl)-1,3-thiazol-2(3H)-ylidene]benzamide;

N-[(2Z)-5-(hydroxymethyl)-3-(2,2,3,3-tetrafluoro-2,3-dihydro-1,4-benzodioxin-6-yl)-1,3-thiazol-2(3H)-ylidene]-1H-imidazole-1-carboxamide;

N-benzyl-N-(2-hydroxyethyl)-N'-[(2Z)-5-methyl-3-(2,2,3,3-tetrafluoro-2,3-dihydro-1,4-benzodioxin-6-yl)-1,3-thiazol-2(3H)-ylidene]urea;

N-[(2Z)-5-methyl-3-(2,2,3,3-tetrafluoro-2,3-dihydro-1,4-benzodioxin-6-yl)-1,3-thiazol-2(3H)-ylidene]indoline-1-carboxamide;

N-(2-hydroxy-1,1-dimethylethyl)-N'-[(2Z)-5-methyl-3-(2,2,3,3-tetrafluoro-2,3-dihydro-1,4-benzodioxin-6-yl)-1,3-thiazol-2(3H)-ylidene]urea;

N-[(2Z)-5-methyl-3-(2,2,3,3-tetrafluoro-2,3-dihydro-1,4-benzodioxin-6-yl)-1,3-thiazol-2(3H)-ylidene]-N'-(1,1,3,3-tetramethylbutyl)urea;

N-methyl-N'-[(2Z)-5-methyl-3-(2,2,3,3-tetrafluoro-2,3-dihydro-1,4-benzodioxin-6-yl)-1,3-thiazol-2(3H)-ylidene]-N-(thieno[2,3-b]pyridin-2-ylmethyl)urea;

N-[(1R)-2-hydroxy-1-phenylethyl]-N'-[(2Z)-5-methyl-3-(2,2,3,3-tetrafluoro-2,3-dihydro-1,4-benzodioxin-6-yl)-1,3-thiazol-2(3H)-ylidene]urea;

N-benzyl-N-methyl-N'-[(2Z)-5-methyl-3-(2,2,3,3-tetrafluoro-2,3-dihydro-1,4-benzodioxin-6-yl)-1,3-thiazol-2(3H)-ylidene]urea;

N-benzyl-N-isopropyl-N'-[(2Z)-5-methyl-3-(2,2,3,3-tetrafluoro-2,3-dihydro-1,4-benzodioxin-6-yl)-1,3-thiazol-2(3H)-ylidene]urea;

N-benzyl-N-ethyl-N'-[(2Z)-5-methyl-3-(2,2,3,3-tetrafluoro-2,3-dihydro-1,4-benzodioxin-6-yl)-1,3-thiazol-2(3H)-ylidene]urea; and N-benzyl-N-butyl-N'-[(2Z)-5-methyl-3-(2,2,3,3-tetrafluoro-2,3-dihydro-1,4-benzodioxin-6-yl)-1,3-thiazol-2(3H)-ylidene]urea; or salts thereof.

In other embodiments there is described a method for treating disorders or conditions, comprising administration of a therapeutically effective amount of a compound of formula (II), wherein the compounds are positive allosteric nicotinic acetylcholine receptors (nAChR) modulators. Particularly useful compounds are described wherein $R_1$ is hydrogen, $R_4$ is hydrogen, X is S, and Y is C(O). Furthermore, certain embodiments are described wherein Z is ring such as aryl, cycloalkyl, heterocycle or heteroaryl, as defined herein. The heteroaryl and heterocyclic groups useful within the scope of compounds of formula (II) may be mono or bicyclic. In certain other embodiments, there is described compounds of formula (II), wherein Z is —$R_3$, wherein $R_3$ is alkyl and wherein Z is —$NR_eR_f$, wherein $R_e$ and $R_f$ are each independently hydrogen, alkyl, alkoxyalkyl, alkylcarbonyl, alkenyl, alkynyl, aryl, arylalkyl, cyanoalkyl, cycloalkyl, cycloalkylalkyl, heterocyclealkyl, heteroarylalkyl, or hydroxyalkyl, wherein the alkyl group and the alkyl of alkylcarbonyl are optionally substituted with 1, 2 or 3 substituents selected from alkoxy, cyano, and halo.

Specific embodiments contemplated as part of the invention include, but are not limited to compounds of formula (II), for example:

ethyl(2Z)-3-(2,2-difluoro-1,3-benzodioxol-5-yl)-5-methylene-1,3-thiazolidin-2-ylidenecarbamate;

ethyl(2Z)-3-(2,2-difluoro-1,3-benzodioxol-5-yl)-5-methyl-1,3-thiazol-2(3H)-ylidenecarbamate;

methyl(2Z)-3-(2,2-difluoro-1,3-benzodioxol-5-yl)-5-methyl-1,3-thiazol-2(3H)-ylidenecarbamate;

N-[(2Z)-3-(2,2-difluoro-1,3-benzodioxol-5-yl)-5-methylene-1,3-thiazolidin-2-ylidene]acetamide;

N'-[(2Z)-3-(2,2-difluoro-1,3-benzodioxol-5-yl)-5-methylene-1,3-thiazolidin-2-ylidene]-N,N-dimethylurea;

N-[(2Z)-3-(2,2-difluoro-1,3-benzodioxol-5-yl)-5-methyl-1,3-thiazol-2(3H)-ylidene]acetamide;

N'-[(2Z)-3-(2,2-difluoro-1,3-benzodioxol-5-yl)-5-methyl-1,3-thiazol-2(3H)-ylidene]-N,N-dimethylurea;

N'-[(2Z)-3-(2,2-difluoro-1,3-benzodioxol-5-yl)-5-methyl-1,3-thiazol-2(3H)-ylidene]-N,N-diethylurea;

N'-[(2Z)-3-(2,2-difluoro-1,3-benzodioxol-5-yl)-5-methyl-1,3-thiazol-2(3H)-ylidene]-N,N-diisopropylurea;

N-[(2Z)-3-(2,2-difluoro-1,3-benzodioxol-5-yl)-5-methyl-1,3-thiazol-2(3H)-ylidene]pyrrolidine-1-carboxamide;

N-[(2Z)-3-(2,2-difluoro-1,3-benzodioxol-5-yl)-5-methyl-1,3-thiazol-2(3H)-ylidene]piperidine-1-carboxamide;

N-[(2Z)-3-(2,2-difluoro-1,3-benzodioxol-5-yl)-5-methyl-1,3-thiazol-2(3H)-ylidene]cyclobutanecarboxamide;

N-[(2Z)-3-(2,2-difluoro-1,3-benzodioxol-5-yl)-5-methyl-1,3-thiazol-2(3H)-ylidene]-2,2-dimethylpropanamide;

N-[(2Z)-3-(2,2-difluoro-1,3-benzodioxol-5-yl)-5-methyl-1,3-thiazol-2(3H)-ylidene]benzamide;

4-chloro-N-[(2Z)-3-(2,2-difluoro-1,3-benzodioxol-5-yl)-5-methyl-1,3-thiazol-2(3H)-ylidene]benzamide;

N'-[(2Z)-3-(2,2-difluoro-1,3-benzodioxol-5-yl)-5-methyl-1,3-oxazol-2(3H)-ylidene]-N,N-dimethylurea;

N'-[(2Z)-3-(2,2-difluoro-1,3-benzodioxol-5-yl)-5-methyl-1,3-oxazol-2(3H)-ylidene]-N,N-dimethylthiourea;

N-[(2Z)-5-methylene-3-(2,2,3,3-tetrafluoro-2,3-dihydro-1,4-benzodioxin-6-yl)-1,3-thiazolidin-2-ylidene]pyrrolidine-1-carboxamide;

N-[(2Z)-5-methyl-3-(2,2,3,3-tetrafluoro-2,3-dihydro-1,4-benzodioxin-6-yl)-1,3-thiazol-2(3H)-ylidene]pyrrolidine-1-carboxamide;

N-[(2Z)-3-(2,2-difluoro-1,3-benzodioxol-5-yl)-5-(pyrrolidin-1-ylmethyl)-1,3-thiazol-2(3H)-ylidene]acetamide;

N-[(2Z)-5-(hydroxymethyl)-3-(2,2,3,3-tetrafluoro-2,3-dihydro-1,4-benzodioxin-6-yl)-1,3-thiazol-2(3H)-ylidene]pyrrolidine-1-carboxamide;

N-[(2Z)-5-methyl-3-(2,2,3,3-tetrafluoro-2,3-dihydro-1,4-benzodioxin-6-yl)-1,3-thiazol-2(3H)-ylidene]piperidine-1-carboxamide;

N,N-diethyl-N'-[(2Z)-5-methyl-3-(2,2,3,3-tetrafluoro-2,3-dihydro-1,4-benzodioxin-6-yl)-1,3-thiazol-2(3H)-ylidene]urea;

N-methyl-N'-[(2Z)-5-methyl-3-(2,2,3,3-tetrafluoro-2,3-dihydro-1,4-benzodioxin-6-yl)-1,3-thiazol-2(3H)-ylidene]-N-phenylurea;

N,N-dimethyl-N'-[(2Z)-5-methyl-3-(2,2,3,3-tetrafluoro-2,3-dihydro-1,4-benzodioxin-6-yl)-1,3-thiazol-2(3H)-ylidene]urea;

N-[(2Z)-5-methyl-3-(2,2,3,3-tetrafluoro-2,3-dihydro-1,4-benzodioxin-6-yl)-1,3-thiazol-2(3H)-ylidene]cyclobutanecarboxamide;

N-[(2Z)-5-methyl-3-(2,2,3,3-tetrafluoro-2,3-dihydro-1,4-benzodioxin-6-yl)-1,3-thiazol-2(3H)-ylidene]cyclopropanecarboxamide;

N-[(2Z)-5-methyl-3-(2,2,3,3-tetrafluoro-2,3-dihydro-1,4-benzodioxin-6-yl)-1,3-thiazol-2(3H)-ylidene]methanesulfonamide;

N-[(2Z)-5-methyl-3-(2,2,3,3-tetrafluoro-2,3-dihydro-1,4-benzodioxin-6-yl)-1,3-thiazol-2(3H)-ylidene]ethanesulfonamide;

N-[(2Z)-5-methyl-3-(2,2,3,3-tetrafluoro-2,3-dihydro-1,4-benzodioxin-6-yl)-1,3-thiazol-2(3H)-ylidene]propane-1-sulfonamide;

N-[(2Z)-5-methyl-3-(2,2,3,3-tetrafluoro-2,3-dihydro-1,4-benzodioxin-6-yl)-1,3-thiazol-2(3H)-ylidene]benzenesulfonamide;

N-[(2Z)-5-methyl-3-(2,2,3,3-tetrafluoro-2,3-dihydro-1,4-benzodioxin-6-yl)-1,3-thiazol-2(3H)-ylidene]thiophene-2-sulfonamide;

3-cyano-N-[(2Z)-5-methyl-3-(2,2,3,3-tetrafluoro-2,3-dihydro-1,4-benzodioxin-6-yl)-1,3-thiazol-2(3H)-ylidene]benzenesulfonamide;

3-methoxy-N-[(2Z)-5-methyl-3-(2,2,3,3-tetrafluoro-2,3-dihydro-1,4-benzodioxin-6-yl)-1,3-thiazol-2(3H)-ylidene]benzenesulfonamide;

3-chloro-N-[(2Z)-5-methyl-3-(2,2,3,3-tetrafluoro-2,3-dihydro-1,4-benzodioxin-6-yl)-1,3-thiazol-2(3H)-ylidene]benzenesulfonamide;

N-[(2Z)-3-(2,2-difluoro-1,3-benzodioxol-5-yl)-5-methyl-1,3-thiazol-2(3H)-ylidene]-N'-isopropylurea;

N-(sec-butyl)-N'-[(2Z)-3-(2,2-difluoro-1,3-benzodioxol-5-yl)-5-methyl-1,3-thiazol-2(3H)-ylidene]urea;

N-(tert-butyl)-N'-[(2Z)-3-(2,2-difluoro-1,3-benzodioxol-5-yl)-5-methyl-1,3-thiazol-2(3H)-ylidene]urea;

N-[(2Z)-3-(2,2-difluoro-1,3-benzodioxol-5-yl)-5-methyl-1,3-thiazol-2(3H)-ylidene]-N'-(1-methylbutyl)urea;

N-[(2Z)-3-(2,2-difluoro-1,3-benzodioxol-5-yl)-5-methyl-1,3-thiazol-2(3H)-ylidene]-N'-(1,1-dimethylpropyl)urea;

N-[(2Z)-3-(2,2-difluoro-1,3-benzodioxol-5-yl)-5-methyl-1,3-thiazol-2(3H)-ylidene]-N'-(1,2-dimethylpropyl)urea;

N-[(2Z)-3-(2,2-difluoro-1,3-benzodioxol-5-yl)-5-methyl-1,3-thiazol-2(3H)-ylidene]-N'-(1-ethylpropyl)urea;

N-[(2Z)-3-(2,2-difluoro-1,3-benzodioxol-5-yl)-5-methyl-1,3-thiazol-2(3H)-ylidene]-N'-(2-methoxy-1-methylethyl)urea;

N-cyclopentyl-N'-[(2Z)-3-(2,2-difluoro-1,3-benzodioxol-5-yl)-5-methyl-1,3-thiazol-2(3H)-ylidene]urea;

N'-[(2Z)-3-(2,2-difluoro-1,3-benzodioxol-5-yl)-5-methyl-1,3-thiazol-2(3H)-ylidene]-N-ethyl-N-methylurea;

N'-[(2Z)-3-(2,2-difluoro-1,3-benzodioxol-5-yl)-5-methyl-1,3-thiazol-2(3H)-ylidene]-N-isopropyl-N-methylurea;

N-butyl-N'-[(2Z)-3-(2,2-difluoro-1,3-benzodioxol-5-yl)-5-methyl-1,3-thiazol-2(3H)-ylidene]-N-methylurea;

N'-[(2Z)-3-(2,2-difluoro-1,3-benzodioxol-5-yl)-5-methyl-1,3-thiazol-2(3H)-ylidene]-N-isobutyl-N-methylurea;

N'-[(2Z)-3-(2,2-difluoro-1,3-benzodioxol-5-yl)-5-methyl-1,3-thiazol-2(3H)-ylidene]-N-(1,3-dioxolan-2-ylmethyl)-N-methylurea;

N'-[(2Z)-3-(2,2-difluoro-1,3-benzodioxol-5-yl)-5-methyl-1,3-thiazol-2(3H)-ylidene]-N-methyl-N-(3-methylbutyl)urea;

N-butyl-N'-[(2Z)-3-(2,2-difluoro-1,3-benzodioxol-5-yl)-5-methyl-1,3-thiazol-2(3H)-ylidene]-N-ethylurea;

N'-[(2Z)-3-(2,2-difluoro-1,3-benzodioxol-5-yl)-5-methyl-1,3-thiazol-2(3H)-ylidene]-N,N-dipropylurea;

N,N-dibutyl-N'-[(2Z)-3-(2,2-difluoro-1,3-benzodioxol-5-yl)-5-methyl-1,3-thiazol-2(3H)-ylidene]urea;

N-[(2Z)-3-(2,2-difluoro-1,3-benzodioxol-5-yl)-5-methyl-1,3-thiazol-2(3H)-ylidene]-2,5-dimethylpyrrolidine-1-carboxamide;

N-[(2Z)-3-(2,2-difluoro-1,3-benzodioxol-5-yl)-5-methyl-1,3-thiazol-2(3H)-ylidene]-2-methylpiperidine-1-carboxamide;

N'-[(2Z)-3-(2,2-difluoro-1,3-benzodioxol-5-yl)-5-methyl-1,3-thiazol-2(3H)-ylidene]-N-(2-methoxyethyl)-N-methylurea;

N-benzyl-N'-[(2Z)-3-(2,2-difluoro-1,3-benzodioxol-5-yl)-5-methyl-1,3-thiazol-2(3H)-ylidene]-N-ethylurea;

N-benzyl-N'-[(2Z)-3-(2,2-difluoro-1,3-benzodioxol-5-yl)-5-methyl-1,3-thiazol-2(3H)-ylidene]-N-isopropylurea;

N-benzyl-N-butyl-N'-[(2Z)-3-(2,2-difluoro-1,3-benzodioxol-5-yl)-5-methyl-1,3-thiazol-2(3H)-ylidene]urea;

N-benzyl-N'-[(2Z)-3-(2,2-difluoro-1,3-benzodioxol-5-yl)-5-methyl-1,3-thiazol-2(3H)-ylidene]-N-(2-hydroxyethyl)urea;

N-[(2Z)-3-(2,2-difluoro-1,3-benzodioxol-5-yl)-5-methyl-1,3-thiazol-2(3H)-ylidene]-N'-(1,1,3,3-tetramfethylbutyl)urea;

N-[(2Z)-3-(2,2-difluoro-1,3-benzodioxol-5-yl)-5-methyl-1,3-thiazol-2(3H)-ylidene]-N'-[(1R)-2-hydroxy-1-phenylethyl]urea;

N-[(2Z)-3-(2,2-difluoro-1,3-benzodioxol-5-yl)-5-methyl-1,3-thiazol-2(3H)-ylidene]-N'-[(1S)-2-hydroxy-1-phenylethyl]urea;

N-[(2Z)-3-(2,2-difluoro-1,3-benzodioxol-5-yl)-5-methyl-1,3-thiazol-2(3H)-ylidene]-N'-[(1S)-1-phenylethyl]urea;

N-[(2Z)-3-(2,2-difluoro-1,3-benzodioxol-5-yl)-5-methyl-1,3-thiazol-2(3H)-ylidene]-N'-[(1R)-1-phenylethyl]urea;

N-benzyl-N-(tert-butyl)-N'-[(2Z)-3-(2,2-difluoro-1,3-benzodioxol-5-yl)-5-methyl-1,3-thiazol-2(3H)-ylidene]urea;

N-benzyl-N'-[(2Z)-3-(2,2-difluoro-1,3-benzodioxol-5-yl)-5-methyl-1,3-thiazol-2(3H)-ylidene]-N-methylurea;

N-benzyl-N-(2-cyanoethyl)-N'-[(2Z)-3-(2,2-difluoro-1,3-benzodioxol-5-yl)-5-methyl-1,3-thiazol-2(3H)-ylidene]urea;

N-(3-chlorobenzyl)-N'-[(2Z)-3-(2,2-difluoro-1,3-benzodioxol-5-yl)-5-methyl-1,3-thiazol-2(3H)-ylidene]-N-methylurea;

N'-[(2Z)-3-(2,2-difluoro-1,3-benzodioxol-5-yl)-5-methyl-1,3-thiazol-2(3H)-ylidene]-N-(2-methoxybenzyl)-N-methylurea;

N'-[(2Z)-3-(2,2-difluoro-1,3-benzodioxol-5-yl)-5-methyl-1,3-thiazol-2(3H)-ylidene]-N-(3-methoxybenzyl)-N-methylurea;

N-[(2Z)-3-(2,2-difluoro-1,3-benzodioxol-5-yl)-5-methyl-1,3-thiazol-2(3H)-ylidene]-1,3-dihydro-2H-isoindole-2-carboxamide;

N-[(2Z)-3-(2,2-difluoro-1,3-benzodioxol-5-yl)-5-methyl-1,3-thiazol-2(3H)-ylidene]-3,4-dihydroisoquinoline-2(1H)-carboxamide;

N'-[(2Z)-3-(2,2-difluoro-1,3-benzodioxol-5-yl)-5-methyl-1,3-thiazol-2(3H)-ylidene]-N-ethyl-N-(pyridin-4-ylmethyl)urea;

N-[(2Z)-3-(2,2-difluoro-1,3-benzodioxol-5-yl)-5-methyl-1,3-thiazol-2(3H)-ylidene]-N'-(1-phenylpropyl)urea;

N-[(2Z)-3-(2,2-difluoro-1,3-benzodioxol-5-yl)-5-methyl-1,3-thiazol-2(3H)-ylidene]-N'-2,3-dihydro-1H-inden-1-ylurea;

N-(5-fluoro-2-phenoxybenzyl)-N-methyl-N'-[(2Z)-5-methyl-3-(2,2,3,3-tetrafluoro-2,3-dihydro-1,4-benzodioxin-6-yl)-1,3-thiazol-2(3H)-ylidene]urea;

N-(2-chloro-6-fluorobenzyl)-N-ethyl-N'-[(2Z)-5-methyl-3-(2,2,3,3-tetrafluoro-2,3-dihydro-1,4-benzodioxin-6-yl)-1,3-thiazol-2(3H)-ylidene]urea;

N-benzyl-N'-[(2Z)-5-methyl-3-(2,2,3,3-tetrafluoro-2,3-dihydro-1,4-benzodioxin-6-yl)-1,3-thiazol-2(3H)-ylidene]-N-prop-2-ynylurea;

N-[4-(allyloxy)benzyl]-N-methyl-N'-[(2Z)-5-methyl-3-(2,2,3,3-tetrafluoro-2,3-dihydro-1,4-benzodioxin-6-yl)-1,3-thiazol-2(3H)-ylidene]urea;

N-[(2Z)-3-(2,2-difluoro-1,3-benzodioxol-5-yl)-5-formyl-1,3-thiazol-2(3H)-ylidene]pyrrolidine-1-carboxamide;

N-[(2Z)-3-(2,2-difluoro-1,3-benzodioxol-5-yl)-5-[(Z)-(hydroxyimino)methyl]-1,3-thiazol-2(3H)-ylidene]pyrrolidine-1-carboxamide;

N'-[(2Z)-3-(2,2-difluoro-1,3-benzodioxol-5-yl)-5-(hydroxymethyl)-1,3-thiazol-2(3H)-ylidene]-N,N-dimethylurea;

N'-[(2Z)-3-(2,2-difluoro-1,3-benzodioxol-5-yl)-5-(fluoromethyl)-1,3-thiazol-2(3H)-ylidene]-N,N-dimethylurea;

N'-[(2Z)-3-(2,2-difluoro-1,3-benzodioxol-5-yl)-5-formyl-1,3-thiazol-2(3H)-ylidene]-N,N-dimethylurea;

(3R)-3-fluoro-N-[(2Z)-5-methylene-3-(2,2,3,3-tetrafluoro-2,3-dihydro-1,4-benzodioxin-6-yl)-1,3-thiazolidin-2-ylidene]pyrrolidine-1-carboxamide;

(3S)-3-fluoro-N-[(2Z)-5-methylene-3-(2,2,3,3-tetrafluoro-2,3-dihydro-1,4-benzodioxin-6-yl)-1,3-thiazolidin-2-ylidene]pyrrolidine-1-carboxamide;

(3R)-3-fluoro-N-[(2Z)-5-(hydroxymethyl)-3-(2,2,3,3-tetrafluoro-2,3-dihydro-1 4-benzodioxin-6-yl)-1,3-thiazol-2(3H)-ylidene]pyrrolidine-1-carboxamide;

(3S)-3-fluoro-N-[(2Z)-5-(hydroxymethyl)-3-(2,2,3,3-tetrafluoro-2,3-dihydro-1,4-benzodioxin-6-yl)-1,3-thiazol-2(3H)-ylidene]pyrrolidine-1-carboxamide;

N-[4-(difluoromethoxy)benzyl]-N-methyl-N'-[(2Z)-5-methyl-3-(2,2,3,3-tetrafluoro-2,3-dihydro-1,4-benzodioxin-6-yl)-1,3-thiazol-2(3H)-ylidene]urea;

N-[1-(4-ethoxyphenyl)ethyl]-N-methyl-N'-[(2Z)-5-methyl-3-(2,2,3,3-tetrafluoro-2,3-dihydro-1,4-benzodioxin-6-yl)-1,3-thiazol-2(3H)-ylidene]urea;

N-methyl-N-[(6-methylpyridin-2-yl)methyl]-N'-[(2Z)-5-methyl-3-(2,2,3,3-tetrafluoro-2,3-dihydro-1,4-benzodioxin-6-yl)-1,3-thiazol-2(3H)-ylidene]urea;

N-benzyl-N-but-2-ynyl-N'-[(2Z)-5-methyl-3-(2,2,3,3-tetrafluoro-2,3-dihydro-1,4-benzodioxin-6-yl)-1,3-thiazol-2(3H)-ylidene]urea;

N-(1-methyl-1-phenylethyl)-N'-[(2Z)-5-methyl-3-(2,2,3,3-tetrafluoro-2,3-dihydro-1,4-benzodioxin-6-yl)-1,3-thiazol-2(3H)-ylidene]urea;

N-(2-chlorobenzyl)-N-methyl-N'-[(2Z)-5-methyl-3-(2,2,3,3-tetrafluoro-2,3-dihydro-1,4-benzodioxin-6-yl)-1,3-thiazol-2(3H)-ylidene]urea;

N-methyl-N'-[(2Z)-5-methyl-3-(2,2,3,3-tetrafluoro-2,3-dihydro-1,4-benzodioxin-6-yl)-1,3-thiazol-2(3H)-ylidene]-N-(thien-2-ylmethyl)urea;

N-(4-chlorobenzyl)-N-methyl-N'-[(2Z)-5-methyl-3-(2,2,3,3-tetrafluoro-2,3-dihydro-1,4-benzodioxin-6-yl)-1,3-thiazol-2(3H)-ylidene]urea;

N-(3-chlorobenzyl)-N-methyl-N'-[(2Z)-5-methyl-3-(2,2,3,3-tetrafluoro-2,3-dihydro-1,4-benzodioxin-6-yl)-1,3-thiazol-2(3H)-ylidene]urea;

N-[1-(methoxymethyl)propyl]-N'-[(2Z)-5-methyl-3-(2,2,3,3-tetrafluoro-2,3-dihydro-1,4-benzodioxin-6-yl)-1,3-thiazol-2(3H)-ylidene]urea;

N-cyclopentyl-N-(4-fluorobenzyl)-N'-[(2Z)-5-methyl-3-(2,2,3,3-tetrafluoro-2,3-dihydro-1,4-benzodioxin-6-yl)-1,3-thiazol-2(3H)-ylidene]urea;

N-[(1S)-2-hydroxy-1-phenylethyl]-N'-[(2Z)-5-methyl-3-(2,2,3,3-tetrafluoro-2,3-dihydro-1,4-benzodioxin-6-yl)-1,3-thiazol-2(3H)-ylidene]urea;

N-[(2Z)-5-methyl-3-(2,2,3,3-tetrafluoro-2,3-dihydro-1,4-benzodioxin-6-yl)-1,3-thiazol-2(3H)-ylidene]-N'-[(1R)-1-phenylethyl]urea;

N-[(2Z)-5-methyl-3-(2,2,3,3-tetrafluoro-2,3-dihydro-1,4-benzodioxin-6-yl)-1,3-thiazol-2(3H)-ylidene]-N'-[(1S)-1-phenylethyl]urea;

(3R)-3-hydroxy-N-[(2Z)-5-methyl-3-(2,2,3,3-tetrafluoro-2,3-dihydro-1,4-benzodioxin-6-yl)-1,3-thiazol-2(3H)-ylidene]pyrrolidine-1-carboxamide;

N-methyl-N-[(1-methyl-1H-pyrazol-4-yl)methyl]-N'-[(2Z)-5-methyl-3-(2,2,3,3-tetrafluoro-2,3-dihydro-1,4-benzodioxin-6-yl)-1,3-thiazol-2(3H)-ylidene]urea;

N-methyl-N'-[(2Z)-5-methyl-3-(2,2,3,3-tetrafluoro-2,3-dihydro-1,4-benzodioxin-6-yl)-1,3-thiazol-2(3H)-ylidene]-N-(pyrazin-2-ylmethyl)urea;

N-[(2Z)-5-(methoxymethyl)-3-(2,2,3,3-tetrafluoro-2,3-dihydro-1,4-benzodioxin-6-yl)-1,3-thiazol-2(3H)-ylidene]pyrrolidine-1-carboxamide;

N-[(2Z)-5-(ethoxymethyl)-3-(2,2,3,3-tetrafluoro-2,3-dihydro-1,4-benzodioxin-6-yl)-1,3-thiazol-2(3H)-ylidene]pyrrolidine-1-carboxamide;

N-[(2Z)-3-(2,2-difluoro-1,3-benzodioxol-5-yl)-5-methylene-1,3-thiazolidin-2-ylidene]-1H-imidazole-1-carboxamide;

N-[(2Z)-3-(2,2-difluoro-1,3-benzodioxol-5-yl)-5-methylene-1,3-thiazolidin-2-ylidene]-2-methylpyrrolidine-1-carboxamide;

N-[(2Z)-3-(2,2-difluoro-1,3-benzodioxol-5-yl)-5-methylene-1,3-thiazolidin-2-ylidene]pyrrolidine-1-carboxamide;

N-[(2Z)-4-amino-3-(2,2-difluoro-1,3-benzodioxol-5-yl)-5-methylene-1,3-thiazolidin-2-ylidene]pyrrolidine-1-carboxamide;

N-[(2Z)-3-(2,2-difluoro-1,3-benzodioxol-5-yl)-5-(hydroxymethyl)-1,3-thiazol-2(3H)-ylidene]pyrrolidine-1-carboxamide;

N-[(2Z)-3-(2,2-difluoro-1,3-benzodioxol-5-yl)-5-(ethoxymethyl)-1,3-thiazol-2(3H)-ylidene]pyrrolidine-1-carboxamide;

N-[(2Z)-3-(2,2-difluoro-1,3-benzodioxol-5-yl)-5-{[(4-fluorophenyl)amino]methyl}-1,3-thiazol-2(3H)-ylidene]pyrrolidine-1-carboxamide;

N-[(2Z)-3-(2,2-difluoro-1,3-benzodioxol-5-yl)-5-{[(4-fluorophenyl)(methyl)amino]methyl}-1,3-thiazol-2(3H)-ylidene]pyrrolidine-1-carboxamide;

N-[(2Z)-3-(2,2-difluoro-1,3-benzodioxol-5-yl)-5-methylene-4-(pyridin-3-ylamino)-1,3-thiazolidin-2-ylidene]pyrrolidine-1-carboxamide;

N-[(2Z)-3-(2,2-difluoro-1,3-benzodioxol-5-yl)-5-methyl-1,3-thiazol-2(3H)-ylidene]-N'-2,3-dihydro-1H-inden-2-ylurea;

N-[(2Z)-5-methyl-3-(2,2,3,3-tetrafluoro-2,3-dihydro-1,4-benzodioxin-6-yl)-1,3-thiazol-2(3H)-ylidene]-1H-imidazole-1-carboxamide;

N-[(2Z)-3-(2,2-difluoro-1,3-benzodioxol-5-yl)-5-methyl-1,3-thiazol-2(3H)-ylidene]-N'-[1-(methoxymethyl)propyl]urea;

N'-[(2Z)-3-(2,2-difluoro-1,3-benzodioxol-5-yl)-5-methyl-1,3-thiazol-2(3H)-ylidene]-N-isobutyl-N-prop-2-ynylurea;

N-[(2Z)-3-(2,2-difluoro-1,3-benzodioxol-5-yl)-5-methyl-1,3-thiazol-2(3H)-ylidene]azetidine-1-carboxamide;

N-[(2Z)-3-(2,2-difluoro-1,3-benzodioxol-5-yl)-5-methyl-1,3-thiazol-2(3H)-ylidene]-N'-(1-methyl-1-phenylethyl)urea;

N-cyclopropyl-N'-[(2Z)-3-(2,2-difluoro-1,3-benzodioxol-5-yl)-5-methyl-1,3-thiazol-2(3H)-ylidene]-N-(2-fluorobenzyl)urea;

N-(2-chlorobenzyl)-N'-[(2Z)-3-(2,2-difluoro-1,3-benzodioxol-5-yl)-5-methyl-1,3-thiazol-2(3H)-ylidene]-N-methylurea;

N-(4-chlorobenzyl)-N'-[(2Z)-3-(2,2-difluoro-1,3-benzodioxol-5-yl)-5-methyl-1,3-thiazol-2(3H)-ylidene]-N-methylurea;

N'-[(2Z)-3-(2,2-difluoro-1,3-benzodioxol-5-yl)-5-methyl-1,3-thiazol-2(3H)-ylidene]-N-(4-methoxybenzyl)-N-methylurea;

N'-[(2Z)-3-(2,2-difluoro-1,3-benzodioxol-5-yl)-5-methyl-1,3-thiazol-2(3H)-ylidene]-N-methyl-N-(pyridin-2-ylmethyl)urea;

N'-[(2Z)-3-(2,2-difluoro-1,3-benzodioxol-5-yl)-5-methyl-1,3-thiazol-2(3H)-ylidene]-N-methyl-N-(pyridin-3-ylmethyl)urea;

N'-[(2Z)-3-(2,2-difluoro-1,3-benzodioxol-5-yl)-5-methyl-1,3-thiazol-2(3H)-ylidene]-N-ethyl-N-(pyridin-3-ylmethyl)urea;

N'-[(2Z)-3-(2,2-difluoro-1,3-benzodioxol-5-yl)-5-methyl-1,3-thiazol-2(3H)-ylidene]-N-methyl-N-(pyridin-4-ylmethyl)urea;

N'-[(2Z)-3-(2,2-difluoro-1,3-benzodioxol-5-yl)-5-methyl-1,3-thiazol-2(3H)-ylidene]-N-methyl-N-(pyrazin-2-ylmethyl)urea;

N-methyl-N'-[(2Z)-5-methyl-3-(2,2,3,3-tetrafluoro-2,3-dihydro-1,4-benzodioxin-6-yl)-1,3-thiazol-2(3H)-ylidene]-N-(pyridin-3-ylmethyl)urea;

N-[(2Z)-5-(hydroxymethyl)-3-(2,2,3,3-tetrafluoro-2,3-dihydro-1,4-benzodioxin-6-yl)-1,3-thiazol-2(3H)-ylidene]acetamide;

N-[(2Z)-3-(2,2-difluoro-1,3-benzodioxol-5-yl)-5-methyl-1,3-thiazol-2(3H)-ylidene]pyrrolidine-1-carbothioamide;

2-methyl-N-[(2Z)-5-methyl-3-(2,2,3,3-tetrafluoro-2,3-dihydro-1,4-benzodioxin-6-yl)-1,3-thiazol-2(3H)-ylidene]indoline-1-carboxamide;

5-bromo-N-[(2Z)-5-methyl-3-(2,2,3,3-tetrafluoro-2,3-dihydro-1,4-benzodioxin-6-yl)-1,3-thiazol-2(3H)-ylidene]indoline-1-carboxamide;

N-methyl-N-[(1-methyl-1H-indol-5-yl)methyl]-N'-[(2Z)-5-methyl-3-(2,2,3,3-tetrafluoro-2,3-dihydro-1,4-benzodioxin-6-yl)-1,3-thiazol-2(3H)-ylidene]urea;

N-methyl-N'-[(2Z)-5-methyl-3-(2,2,3,3-tetrafluoro-2,3-dihydro-1,4-benzodioxin-6-yl)-1,3-thiazol-2(3H)-ylidene]-N-(4-pyridin-4-ylbenzyl)urea;

N-methyl-N'-[(2Z)-5-methyl-3-(2,2,3,3-tetrafluoro-2,3-dihydro-1,4-benzodioxin-6-yl)-1,3-thiazol-2(3H)-ylidene]-N-[(1R)-1-phenylethyl]urea;

2-(4-fluorophenyl)-N-[(2Z)-5-methyl-3-(2,2,3,3-tetrafluoro-2,3-dihydro-1,4-benzodioxin-6-yl)-1,3-thiazol-2(3H)-ylidene]indoline-1-carboxamide;

N-but-2-ynyl-N'-[(2Z)-5-methyl-3-(2,2,3,3-tetrafluoro-2,3-dihydro-1,4-benzodioxin-6-yl)-1,3-thiazol-2(3H)-ylidene]-N-phenylurea;

N-isobutyl-N'-[(2Z)-5-methyl-3-(2,2,3,3-tetrafluoro-2,3-dihydro-1,4-benzodioxin-6-yl)-1,3-thiazol-2(3H)-ylidene]-N-prop-2-ynylurea;

N,N-dibut-2-ynyl-N'-[(2Z)-5-methyl-3-(2,2,3,3-tetrafluoro-2,3-dihydro-1,4-benzodioxin-6-yl)-1,3-thiazol-2(3H)-ylidene]urea;

N-ethyl-N'-[(2Z)-5-methyl-3-(2,2,3,3-tetrafluoro-2,3-dihydro-1,4-benzodioxin-6-yl)-1,3-thiazol-2(3H)-ylidene]-N-(thien-2-ylmethyl)urea;

N-methyl-N-[(3-methylpyridin-2-yl)methyl]-N'-[(2Z)-5-methyl-3-(2,2,3,3-tetrafluoro-2,3-dihydro-1,4-benzodioxin-6-yl)-1,3-thiazol-2(3H)-ylidene]urea;

N-methyl-N-[(3-methylpyridin-4-yl)methyl]-N'-[(2Z)-5-methyl-3-(2,2,3,3-tetrafluoro-2,3-dihydro-1,4-benzodioxin-6-yl)-1,3-thiazol-2(3H)-ylidene]urea;

N-[(2Z)-5-methyl-3-(2,2,3,3-tetrafluoro-2,3-dihydro-1,4-benzodioxin-6-yl)-1,3-thiazol-2(3H)-ylidene]-2-pyridin-3-ylpyrrolidine-1-carboxamide;

N-(4-ethylbenzyl)-N-methyl-N'-[(2Z)-5-methyl-3-(2,2,3,3-tetrafluoro-2,3-dihydro-1,4-benzodioxin-6-yl)-1,3-thiazol-2(3H)-ylidene]urea;

N-ethyl-N'-[(2Z)-5-methyl-3-(2,2,3,3-tetrafluoro-2,3-dihydro-1,4-benzodioxin-6-yl)-1,3-thiazol-2(3H)-ylidene]-N-(pyridin-4-ylmethyl)urea;

N-(4-ethoxybenzyl)-N-methyl-N'-[(2Z)-5-methyl-3-(2,2,3,3-tetrafluoro-2,3-dihydro-1,4-benzodioxin-6-yl)-1,3-thiazol-2(3H)-ylidene]urea;

N-methyl-N-(4-methylbenzyl)-N'-[(2Z)-5-methyl-3-(2,2,3,3-tetrafluoro-2,3-dihydro-1,4-benzodioxin-6-yl)-1,3-thiazol-2(3H)-ylidene]urea;

N-(4-bromobenzyl)-N-methyl-N'-[(2Z)-5-methyl-3-(2,2,3,3-tetrafluoro-2,3-dihydro-1,4-benzodioxin-6-yl)-1,3-thiazol-2(3H)-ylidene]urea;

N-(4-tert-butylbenzyl)-N-methyl-N'-[(2E)-5-methyl-3-(2,2,3,3-tetrafluoro-2,3-dihydro-1,4-benzodioxin-6-yl)-1,3-thiazol-2(3H)-ylidene]urea;

N-(4-isopropylbenzyl)-N-methyl-N'-[(2Z)-5-methyl-3-(2,2,3,3-tetrafluoro-2,3-dihydro-1,4-benzodioxin-6-yl)-1,3-thiazol-2(3H)-ylidene]urea;

N-(3,4-dichlorobenzyl)-N-methyl-N'-[(2Z)-5-methyl-3-(2,2,3,3-tetrafluoro-2,3-dihydro-1,4-benzodioxin-6-yl)-1,3-thiazol-2(3H)-ylidene]urea;

N-(2,4-dichlorobenzyl)-N-methyl-N'-[(2Z)-5-methyl-3-(2,2,3,3-tetrafluoro-2,3-dihydro-1,4-benzodioxin-6-yl)-1,3-thiazol-2(3H)-ylidene]urea;

N-(4-fluorobenzyl)-N-methyl-N'-[(2Z)-5-methyl-3-(2,2,3,3-tetrafluoro-2,3-dihydro-1,4-benzodioxin-6-yl)-1,3-thiazol-2(3H)-ylidene]urea;

N-(4-methoxybenzyl)-N-methyl-N'-[(2Z)-5-methyl-3-(2,2,3,3-tetrafluoro-2,3-dihydro-1,4-benzodioxin-6-yl)-1,3-thiazol-2(3H)-ylidene]urea;

N-methyl-N'-[(2Z)-5-methyl-3-(2,2,3,3-tetrafluoro-2,3-dihydro-1,4-benzodioxin-6-yl)-1,3-thiazol-2(3H)-ylidene]-N-(quinolin-6-ylmethyl)urea;

N-(3-bromobenzyl)-N-methyl-N'-[(2Z)-5-methyl-3-(2,2,3,3-tetrafluoro-2,3-dihydro-1,4-benzodioxin-6-yl)-1,3-thiazol-2(3H)-ylidene]urea;

N-(2-bromobenzyl)-N-methyl-N'-[(2Z)-5-methyl-3-(2,2,3,3-tetrafluoro-2,3-dihydro-1,4-benzodioxin-6-yl)-1,3-thiazol-2(3H)-ylidene]urea;

N-[(2Z)-3-(2,2-difluoro-1,3-benzodioxol-5-yl)-5-[(pyridin-3-ylamino)methyl]-1,3-thiazol-2(3H)-ylidene]pyrrolidine-1-carboxamide;

N-[(2Z)-3-(2,2-difluoro-1,3-benzodioxol-5-yl)-5-(methoxymethyl)-1,3-thiazol-2(3H)-ylidene]pyrrolidine-1-carboxamide;

N-[(2Z)-3-(2,2-difluoro-1,3-benzodioxol-5-yl)-5-(isopropoxymethyl)-1,3-thiazol-2(3H)-ylidene]pyrrolidine-1-carboxamide;

N-[(2Z)-5-[(benzyloxy)methyl]-3-(2,2-difluoro-1,3-benzodioxol-5-yl)-1,3-thiazol-2(3H)-ylidene]pyrrolidine-1-carboxamide;

N-[(2Z)-5-methylene-3-(2,2,3,3-tetrafluoro-2,3-dihydro-1,4-benzodioxin-6-yl)-1,3-thiazolidin-2-ylidene]-1H-imidazole-1-carboxamide;

N-[(2Z)-5-methylene-3-(2,2,3,3-tetrafluoro-2,3-dihydro-1,4-benzodioxin-6-yl)-1,3-thiazolidin-2-ylidene]-2,5-dihydro-1H-pyrrole-1-carboxamide;

(2S)-2-methyl-N-[(2Z)-5-methylene-3-(2,2,3,3-tetrafluoro-2,3-dihydro-1,4-benzodioxin-6-yl)-1,3-thiazolidin-2-ylidene]pyrrolidine-1-carboxamide;

N-[(2Z)-5-methyl-3-(2,2,3,3-tetrafluoro-2,3-dihydro-1,4-benzodioxin-6-yl)-1,3-thiazol-2(3H)-ylidene]-2,5-dihydro-1H-pyrrole-1-carboxamide;

(2S)-2-methyl-N-[(2Z)-5-methyl-3-(2,2,3,3-tetrafluoro-2,3-dihydro-1,4-benzodioxin-6-yl)-1,3-thiazol-2(3H)-ylidene]pyrrolidine-1-carboxamide;

N-(1-cyclopropyl-1-methylethyl)-N'-[(2Z)-5-methyl-3-(2,2,3,3-tetrafluoro-2,3-dihydro-1,4-benzodioxin-6-yl)-1,3-thiazol-2(3H)-ylidene]urea;

N-(1,3-dioxolan-2-ylmethyl)-N-methyl-N'-[(2Z)-5-methyl-3-(2,2,3,3-tetrafluoro-2,3-dihydro-1,4-benzodioxin-6-yl)-1,3-thiazol-2(3H)-ylidene]urea;

N-methyl-N'-[(2Z)-5-methyl-3-(2,2,3,3-tetrafluoro-2,3-dihydro-1,4-benzodioxin-6-yl)-1,3-thiazol-2(3H)-ylidene]urea;

N-[(1,3-dimethyl-1H-pyrazol-4-yl)methyl]-N-methyl-N'-[(2Z)-5-methyl-3-(2,2,3,3-tetrafluoro-2,3-dihydro-1,4-benzodioxin-6-yl)-1,3-thiazol-2(3H)-ylidene]urea;

N-[(2Z)-5-cyano-3-(2,2-difluoro-1,3-benzodioxol-5-yl)-1,3-thiazol-2(3H)-ylidene]pyrrolidine-1-carboxamide;

N'-[(2Z)-3-(2,2-difluoro-1,3-benzodioxol-5-yl)-5-(1-hydroxyethyl)-1,3-thiazol-2(3H)-ylidene]-N,N-dimethylurea;

N'-[(2Z)-3-(2,2-difluoro-1,3-benzodioxol-5-yl)-5-(1-hydroxybutyl)-1,3-thiazol-2(3H)-ylidene]-N,N-dimethylurea;

N'-[(2Z)-3-(2,2-difluoro-1,3-benzodioxol-5-yl)-5-(1-hydroxy-2-methylpropyl)-1,3-thiazol-2(3H)-ylidene]-N,N-dimethylurea;

N'-[(2Z)-3-(2,2-difluoro-1,3-benzodioxol-5-yl)-5-{(E)-[(2-hydroxyethyl)imino]methyl}-1,3-thiazol-2(3H)-ylidene]-N,N-dimethylurea;

N'-[(2Z)-3-(2,2-difluoro-1,3-benzodioxol-5-yl)-5-(hydroxymethyl)-4-pyridin-2-yl-1,3-thiazol-2(3H)-ylidene]-N,N-dimethylurea compound with N'-[(2Z)-3-(2,2-difluoro-1,3-benzodioxol-5-yl)-5-[hydroxy(pyridin-2-yl)methyl]-1,3-thiazol-2(3H)-ylidene]-N,N-dimethylurea (1:1);

N'-[(2Z)-3-(2,2-difluoro-1,3-benzodioxol-5-yl)-5-(difluoromethyl)-1,3-thiazol-2(3H)-ylidene]-N,N-dimethylurea;

N-[(2Z)-3-(2,2-difluoro-1,3-benzodioxol-5-yl)-5-(fluoromethyl)-1,3-thiazol-2(3H)-ylidene]pyrrolidine-1-carboxamide;

N-[(2Z)-3-(2,2-difluoro-1,3-benzodioxol-5-yl)-4-hydroxy-5-methylene-1,3-thiazolidin-2-ylidene]pyrrolidine-1-carboxamide;

(3S)-3-hydroxy-N-[(2Z)-5-methyl-3-(2,2,3,3-tetrafluoro-2,3-dihydro-1,4-benzodioxin-6-yl)-1,3-thiazol-2(3H)-ylidene]pyrrolidine-1-carboxamide;

2,2-dimethyl-N-[(2Z)-5-methyl-3-(2,2,3,3-tetrafluoro-2,3-dihydro-1,4-benzodioxin-6-yl)-1,3-thiazol-2(3H)-ylidene]propanamide;

3,3-dimethyl-N-[(2Z)-5-methylene-3-(2,2,3,3-tetrafluoro-2,3-dihydro-1,4-benzodioxin-6-yl)-1,3-thiazolidin-2-ylidene]butanamide;

3-methyl-N-[(2Z)-5-methyl-3-(2,2,3,3-tetrafluoro-2,3-dihydro-1,4-benzodioxin-6-yl)-1,3-thiazol-2(3H)-ylidene]butanamide;

N-[(2Z)-5-(cyanomethyl)-3-(2,2-difluoro-1,3-benzodioxol-5-yl)-1,3-thiazol-2(3H)-ylidene]pyrrolidine-1-carboxamide;

(3R)-3-fluoro-N-[(2Z)-5-methyl-3-(2,2,3,3-tetrafluoro-2,3-dihydro-1,4-benzodioxin-6-yl)-1,3-thiazol-2(3H)-ylidene]pyrrolidine-1-carboxamide;

(3S)-3-fluoro-N-[(2Z)-5-methyl-3-(2,2,3,3-tetrafluoro-2,3-dihydro-1,4-benzodioxin-6-yl)-1,3-thiazol-2(3H)-ylidene]pyrrolidine-1-carboxamide;

N-[(2Z)-5-(hydroxymethyl)-3-(2,2,3,3-tetrafluoro-2,3-dihydro-1,4-benzodioxin-6-yl)-1,3-thiazol-2(3H)-ylidene]-2,2-dimethylpropanamide;

N-[(2Z)-5-(hydroxymethyl)-3-(2,2,3,3-tetrafluoro-2,3-dihydro-1,4-benzodioxin-6-yl)-1,3-thiazol-2(3H)-ylidene]benzamide;

N-[(2Z)-5-(hydroxymethyl)-3-(2,2,3,3-tetrafluoro-2,3-dihydro-1,4-benzodioxin-6-yl)-1,3-thiazol-2(3H)-ylidene]-1H-imidazole-1-carboxamide;

N-benzyl-N-(2-hydroxyethyl)-N'-[(2Z)-5-methyl-3-(2,2,3,3-tetrafluoro-2,3-dihydro-1,4-benzodioxin-6-yl)-1,3-thiazol-2(3H)-ylidene]urea;

N-[(2Z)-5-methyl-3-(2,2,3,3-tetrafluoro-2,3-dihydro-1,4-benzodioxin-6-yl)-1,3-thiazol-2(3H)-ylidene]indoline-1-carboxamide;

2-methyl-N-[(2Z)-5-methyl-3-(2,2,3,3-tetrafluoro-2,3-dihydro-1,4-benzodioxin-6-yl)-1,3-thiazol-2(3H)-ylidene]piperidine-1-carboxamide;

N-(tert-butyl)-N'-[(2Z)-5-methyl-3-(2,2,3,3-tetrafluoro-2,3-dihydro-1,4-benzodioxin-6-yl)-1,3-thiazol-2(3H)-ylidene]urea;

N-(2-hydroxy-1,1-dimethylethyl)-N'-[(2Z)-5-methyl-3-(2,2,3,3-tetrafluoro-2,3-dihydro-1,4-benzodioxin-6-yl)-1,3-thiazol-2(3H)-ylidene]urea;

N-(1,1-dimethylprop-2-ynyl)-N'-[(2Z)-5-methyl-3-(2,2,3,3-tetrafluoro-2,3-dihydro-1,4-benzodioxin-6-yl)-1,3-thiazol-2(3H)-ylidene]urea;

N-[(2Z)-5-methyl-3-(2,2,3,3-tetrafluoro-2,3-dihydro-1,4-benzodioxin-6-yl)-1,3-thiazol-2(3H)-ylidene]-N'-(1,1,3,3-tetramethylbutyl)urea;

N-(1,1-dimethylpropyl)-N'-[(2Z)-5-methyl-3-(2,2,3,3-tetrafluoro-2,3-dihydro-1,4-benzodioxin-6-yl)-1,3-thiazol-2(3H)-ylidene]urea;

N-(1-ethyl-1-methylpropyl)-N'-[(2Z)-5-methyl-3-(2,2,3,3-tetrafluoro-2,3-dihydro-1,4-benzodioxin-6-yl)-1,3-thiazol-2(3H)-ylidene]urea;

N-methyl-N'-[(2Z)-5-methyl-3-(2,2,3,3-tetrafluoro-2,3-dihydro-1,4-benzodioxin-6-yl)-1,3-thiazol-2(3H)-ylidene]-N-(thieno[2,3-b]pyridin-2-ylmethyl)urea;

N-[(1R)-2-hydroxy-1-phenylethyl]-N'-[(2Z)-5-methyl-3-(2,2,3,3-tetrafluoro-2,3-dihydro-1,4-benzodioxin-6-yl)-1,3-thiazol-2(3H)-ylidene]urea;

N-(1,2-dimethylpropyl)-N'-[(2Z)-5-methyl-3-(2,2,3,3-tetrafluoro-2,3-dihydro-1,4-benzodioxin-6-yl)-1,3-thiazol-2(3H)-ylidene]urea;

N-isopropyl-N'-[(2Z)-5-methyl-3-(2,2,3,3-tetrafluoro-2,3-dihydro-1,4-benzodioxin-6-yl)-1,3-thiazol-2(3H)-ylidene]urea;

N-(2-methoxy-1-methylethyl)-N'-[(2Z)-5-methyl-3-(2,2,3,3-tetrafluoro-2,3-dihydro-1,4-benzodioxin-6-yl)-1,3-thiazol-2(3H)-ylidene]urea;

N-(sec-butyl)-N'-[(2Z)-5-methyl-3-(2,2,3,3-tetrafluoro-2,3-dihydro-1,4-benzodioxin-6-yl)-1,3-thiazol-2(3H)-ylidene]urea;

N-(1-ethylpropyl)-N'-[(2Z)-5-methyl-3-(2,2,3,3-tetrafluoro-2,3-dihydro-1,4-benzodioxin-6-yl)-1,3-thiazol-2(3H)-ylidene]urea;

N-(1-methylbutyl)-N'-[(2Z)-5-methyl-3-(2,2,3,3-tetrafluoro-2,3-dihydro-1,4-benzodioxin-6-yl)-1,3-thiazol-2(3H)-ylidene]urea;

N-benzyl-N-methyl-N'-[(2Z)-5-methyl-3-(2,2,3,3-tetrafluoro-2,3-dihydro-1,4-benzodioxin-6-yl)-1,3-thiazol-2(3H)-ylidene]urea;

N-methyl-N'-[(2Z)-5-methyl-3-(2,2,3,3-tetrafluoro-2,3-dihydro-1,4-benzodioxin-6-yl)-1,3-thiazol-2(3H)-ylidene]-N-prop-2-ynylurea;

N-benzyl-N-isopropyl-N'-[(2Z)-5-methyl-3-(2,2,3,3-tetrafluoro-2,3-dihydro-1,4-benzodioxin-6-yl)-1,3-thiazol-2(3H)-ylidene]urea;

N-ethyl-N-methyl-N'-[(2Z)-5-methyl-3-(2,2,3,3-tetrafluoro-2,3-dihydro-1,4-benzodioxin-6-yl)-1,3-thiazol-2(3H)-ylidene]urea;

N-benzyl-N-ethyl-N'-[(2Z)-5-methyl-3-(2,2,3,3-tetrafluoro-2,3-dihydro-1,4-benzodioxin-6-yl)-1,3-thiazol-2(3H)-ylidene]urea; and N-benzyl-N-butyl-N'-[(2Z)-5-methyl-3-(2,2,3,3-tetrafluoro-2,3-dihydro-1,4-benzodioxin-6-yl)-1,3-thiazol-2(3H)-ylidene]urea.

Compound names are assigned by using Name Pro naming software, which is provided by ACD/Labs. Alternatively, compound names are assigned using AUTONoM naming software, which is provided by MDL Information Systems GmbH (formerly known as Beilstein Informationssysteme) of Frankfurt, Germany, and is part of the CHEMDRAW® ULTRA v. 6.0.2 software suite and ISIS Draw v. 2.5. Also, compound names are assigned using Struct=Name naming algorithm, which is part of the CHEMDRAW® ULTRA v. 9.0.7 software suite.

Yet another aspect of the invention relates to radiolabelled or isotopically labelled pharmaceutical compositions. Radiolabelled or isotopically labelled forms of compounds of formula (I) or of formula (II) are provided as compositions of the invention and administered in accordance with the method of the invention. The radiolabelled or isotopically labelled forms of compounds of formula (I) or of formula (II) may be used as a pharmaceutical agent or may be useful in the discovery of other compounds which are modulators of $\alpha 7$ nAChR. In these uses, the compounds of the invention possess at least one atom of a deuterium or tritium.

The compounds, compositions comprising the compounds, processes for making the compounds, methods for treating or preventing conditions and disorders by administering the compounds, radiolabelled or isotopically labelled forms of the compounds, and compositions containing radiolabelled or isotopically labelled forms of the compounds are further described herein.

Compounds of the invention may exist as stereoisomers wherein, asymmetric or chiral centers are present. These stereoisomers are "R" or "S" depending on the configuration of substituents around the chiral element. The terms "R" and "S" used herein are configurations as defined in IUPAC 1974 Recommendations for Section E, Fundamental Stereochemistry, Pure Appl. Chem., 1976, 45: 13-30. The invention contemplates various stereoisomers and mixtures thereof and are specifically included within the scope of this invention. Stereoisomers include enantiomers and diastereomers, and mixtures of enantiomers or diastereomers. Individual stereoisomers of compounds of the invention may be prepared synthetically from commercially available starting materials which contain asymmetric or chiral centers or by preparation of racemic mixtures followed by resolution well-known to those of ordinary skill in the art. These methods of resolution are exemplified by (1) attachment of a mixture of enantiomers to a chiral auxiliary, separation of the resulting mixture of diastereomers by recrystallization or chromatography and optional liberation of the optically pure product from the auxiliary as described in Furniss, Hannaford, Smith, and Tatchell, "Vogel's Textbook of Practical Organic Chemistry", 5th edition (1989), Longman Scientific & Technical, Essex CM20 2JE, England, or (2) direct separation of the mixture of optical enantiomers on chiral chromatographic columns or (3) fractional recrystallization methods.

Compounds including geometric isomers of carbon-carbon double bonds and carbon-nitrogen double are included in the present invention. Substituents around a carbon-carbon or a carbon-nitrogen double bond are designated as being of Z or E configuration and substituents around a cycloalkyl or heterocycle are designated as being of cis or trans configuration. All geometric isomeric forms and mixtures thereof of the compounds described herein are encompassed within the scope of the present invention.

In another embodiment, compounds of formula (III),

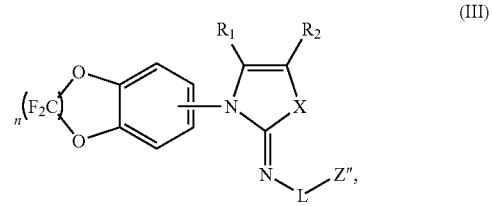

wherein n is 1 or 2;

$R_1$ is hydrogen, alkyl, alkenyl, alkynyl, aryl, or heteroaryl, wherein the alkyl alkenyl, alkynyl, aryl, or heteroaryl groups each are independently substituted with 0, 1, 2, 3, 4, or 5 substituents independently selected from the group consisting of alkoxy, alkoxycarbonyl, carboxy, cyano, haloalkoxy, halo, hydroxyl, nitro, and $R_xR_yN$—;

$R_2$ is alkyl, arylalkyl, formyl, cyano, heteroarylalkyl, or —CH=N—$(CH_2)_h$—$OR_g$, wherein the alkyl group is substituted with 0, 1, 2, or 3 substituents independently selected from alkoxy, alkoxycarbonyl, alkylcarbonyloxy, aryl, aryloxy, arylalkoxy, carboxy, cyano, cycloalkyl, haloalkoxy, halo, heteroaryl, heterocycle, hydroxyl, nitro, and $R_cR_dN$—;

X is O or S;

L is C(O), C(S), S(O), or S(O)$_2$;

Z" is imidazolide, halo, phenol, nitrophenol, or pentafluorophenol;

$R_x$ and $R_y$ are each independently hydrogen, alkyl, arylalkyl, or heteroaryl; and $R_c$ and $R_d$ are each independently hydrogen, alkyl, aryl, arylalkyl, heteroaryl, heteroarylalkyl, heterocycle, and heterocyclealkyl;

$R_g$ is hydrogen or alkyl; and h is 0, 2, or 3;

are useful in the synthesis of compounds of formula (I) or compounds of formula (II). Compounds of formula (IV)

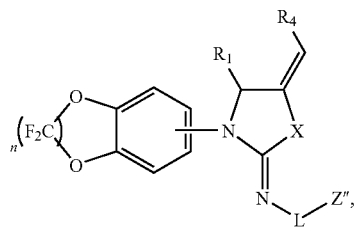

wherein n is 1 or 2;

$R_1$ is hydrogen, alkyl, alkenyl, alkynyl, aryl, heteroaryl, hydroxyl, or $R_aR_bN$—;

X is O or S;

L is C(O), C(S), S(O), or S(O)$_2$;

Z" is imidazolide, halo, phenol, nitrophenol, or pentafluorophenol;

$R_a$ and $R_b$ are each independently hydrogen, alkyl, alkylcarbonyl, arylalkyl, or heteroaryl; and $R_4$ is hydrogen or alkyl;

also are suitable in the synthesis of compounds of formula (I) or compounds of formula (II).

Methods of the Invention

Compounds and compositions of the invention are useful for modulating the effects of nAChRs, particularly by allosteric modulation. In particular, the compounds and compositions of the invention can be used for treating and preventing disorders modulated by nAChRs. Typically, such disorders can be ameliorated by modulating the nAChRs in a mammal, preferably by administering a compound or composition of the invention, either alone or in combination with another active agent, for example, as part of a therapeutic regimen.

Certain substituted thiazoline or oxazoline containing compounds of formula (I) or (II), including but not limited to those specified as compounds of the invention, demonstrate the ability to affect nAChR activity, and particularly for allosteric modulation of nAChRs. Such compounds can be useful for the treatment and prevention of a number of nAChR-mediated diseases or conditions. Substituted thiazoline or oxazoline containing compounds contemplated to demonstrate such activity have the formula (I) or (II).

Particularly preferred are compound of formula (I) as described in Detailed Description above.

Accordingly, compounds of formula (I) or (II) are useful for preventing or treating a disorder mediated by nicotinic acetylcholine receptors. Such compounds can be administered to a subject having such a disorder or susceptible to such disorders in a therapeutically effective amount. The compounds are particularly useful for a method of treating a mammal having a condition where modulation of nicotinic acetylcholine receptor activity is of therapeutic benefit, wherein the method is accomplished by administering a therapeutically effective amount of a compound of formula (I) or (II) to a subject having, or susceptible to, such a disorder.

For example, α7 nAChRs have been shown to play a significant role in enhancing cognitive function, including aspects of learning, memory and attention (Levin, E. D. J. Neurobiol. 2002; 53: 633-640). As such, α7 ligands are suitable for the treatment of cognitive disorders including, for example, attention deficit disorder, attention deficit hyperactivity disorder (ADHD), Alzheimer's disease (AD), mild cognitive impairment (MCI), senile dementia, AIDS dementia, Pick's Disease, dementia associated with Lewy bodies, and dementia associated with Down's syndrome, as well as cognitive deficits associated with schizophrenia.

In addition, α7-containing nAChRs have been shown to be involved in the neuroprotective effects of nicotine both in vitro (Jonnala, R. B., Buccafusco, J. J. J. Neurosci. Res. 2001; 66: 565-572) and in vivo (Shimohama, S. et al. Brain Res. 1998; 779: 359-363). More particularly, neurodegeneration underlies several progressive CNS disorders, including, but not limited to, Alzheimer's disease, Parkinson's disease, amyotrophic lateral sclerosis, Huntington's disease, dementia with Lewy bodies, as well as diminished CNS function resulting from traumatic brain injury. For example, the impaired function of α7 nAChRs by β-amyloid peptides linked to Alzheimer's disease has been implicated as a key factor in development of the cognitive deficits associated with the disease (Liu, Q.-S., Kawai, H., Berg, D. K. PNAS 2001; 98: 4734-4739). The activation of α7 nAChRs has been shown to block this neurotoxicity (Kihara, T. et al. J. Biol. Chem. 2001; 276: 13541-13546). As such, selective ligands that enhance α7 activity can counter the deficits of Alzheimer's and other neurodegenerative diseases.

Schizophrenia is a complex disease that is characterized by abnormalities in perception, cognition, and emotions. Significant evidence implicates the involvement of α7 nAChRs in this disease, including a measured deficit of these receptors in post-mortem patients (Leonard, S. Eur. J. Pharmacol. 2000; 393: 237-242). Deficits in sensory processing (gating) are one of the hallmarks of schizophrenia. These deficits can be normalized by nicotinic ligands that operate at the α7 nAChR (Adler, L. E. et al. Schizophrenia Bull. 1998; 24: 189-202; Stevens, K. E. et al. Psychopharmacology 1998; 136: 320-327). Thus, α7 ligands demonstrate potential in the treatment of schizophrenia.

Angiogenesis, a process involved in the growth of new blood vessels, is important in beneficial systemic functions, such as wound healing, vascularization of skin grafts, and enhancement of circulation, for example, increased circulation around a vascular occlusion. Non-selective nAChR agonists like nicotine have been shown to stimulate angiogenesis (Heeschen, C. et al. Nature Medicine 2001; 7: 833-839). Improved angiogenesis has been shown to involve activation of the α7 nAChR (Heeschen, C. et al. J. Clin. Invest. 2002; 110: 527-536). Therefore, nAChR ligands that are selective for the α7 subtype offer improved potential for stimulating angiogenesis with an improved side effect profile.

A population of α7 nAChRs in the spinal cord modulate serotonergic transmission that have been associated with the pain-relieving effects of nicotinic compounds (Cordero-Erausquin, M., Changeux, J.-P. PNAS 2001; 98: 2803-2807). The α7 nAChR ligands demonstrate therapeutic potential for the treatment of pain states, including acute pain, post-surgical pain, as well as chronic pain states including inflammatory pain and neuropathic pain. Moreover, α7 nAChRs are expressed on the surface of primary macrophages that are involved in the inflammation response, and that activation of the α7 receptor inhibits release of TNF and other cytokines that trigger the inflammation response (Wang, H. et al. Nature 2003; 421: 384-388). TNF-α plays a pathological role indiverse inflammatory diseases including arthritis and psoriasis and endometriosis. Therefore, selective α7 ligands demonstrate potential for treating conditions involving inflammation and pain. Inflammatory diseases could involve The mammalian sperm acrosome reaction is an exocytosis process important in fertilization of the ovum by sperm. Activation of an α7 nAChR on the sperm cell has been shown to be essential for the acrosome reaction (Son, J.-H., Meizel, S. Biol. Reprod. 2003; 68: 1348-1353). Consequently, selective α7 agents demonstrate utility for treating fertility disorders.

Compounds of the invention are particularly useful for treating and preventing a condition or disorder affecting cognition, neurodegeneration, and schizophrenia.

Cognitive impairment associated with schizophrenia often limits the ability of patients to function normally; a symptom not adequately treated by commonly available treatments, for example, treatment with an atypical antipsychotic. (Rowley, M. et al. J. Med. Chem. 2001; 44: 477-501). Such cognitive deficit has been linked to dysfunction of the nicotinic cholinergic system, in particular with decreased activity at α7 receptors. (Friedman, J. I. et al. Biol Psychiatry 2002; 51: 349-357). Thus, activators of α7 receptors can provide useful treatment for enhancing cognitive function in schizophrenic patients who are being treated with atypical antipsychotics. Accordingly, the combination of an α7 nAChR ligand and an atypical antipsychotic would offer improved therapeutic utility. Specific examples of suitable atypical antipsychotics include, but are not limited to, clozapine, risperidone, olanzapine, quietapine, ziprasidone, zotepine, iloperidone, and the like. Accordingly, it is contemplated that compounds of formula (I) or (II) of the invention also can be administered in combination with an atypical antipsychotic.

One of the measurable abnormalities in schizophrenic patients, is the P50 auditory gating deficit, an indication of impaired information processing and diminished ability to "filter" unimportant or repetitive sensory information. On the basis of clinical observations that these deficits are normalized by nicotine, it has been suggested that the high prevalence of smoking among patients with schizophrenia (>80%) may a form of self medication. Pharmacological studies have shown that nicotine's mechanisms of action is via α7 nAChRs. Restoration of P50 gating deficits in humans by α7 selective ligands—agonists and positive allosteric modulators—could lead to discontinuation of continous smoking. Therefore, nAChR ligands that are selective for the α7 subtype be a therapy for smoking cessation, with an improved side effect profile compared to nicotine.

Furthermore, the administration of a therapeutically effective amount of a compound of formula (I) or (II) to a mammal provides a method of treating or preventing condition or disorder selected from attention deficit disorder, attention deficit hyperactivity disorder (ADHD), Alzheimer's disease (AD), mild cognitive impairment (MCI), senile dementia, AIDS dementia, Pick's Disease, dementia associated with Lewy bodies, dementia associated with Down's syndrome, amyotrophic lateral sclerosis, Huntington's disease, diminished CNS function associated with traumatic brain injury, acute pain, post-surgical pain, chronic pain, inflammation, inflammatory pain, neuropathic pain, infertility, need for new blood vessel growth associated with wound healing, need for new blood vessel growth associated with vascularization of skin grafts, and lack of circulation, rheumatoid arthritis, Crohn's disease, ulcerative colitis, inflammatory bowel disease, organ transplant rejection, acute immune disease associated with organ transplantation, chronic immune disease associated with organ transplantation, septic shock, toxic shock syndrome, sepsis syndrome, depression, and rheumatoid spondylitis. More preferred, the administration of a therapeutically effective amount of a compound of formula (I) or (II) to a mammal provides a method of treating cognitive disorders, neurodegeneration, and schizophrenia. In addition, compounds of formula (I) or (II) can be administered in combination with a medication used in the treatment of attention deficit hyperactivity disorders and other cognitive disorders, such as Alzheimer's disease.

Actual dosage levels of active ingredients in the pharmaceutical compositions of this invention can be varied so as to obtain an amount of the active compound(s) that is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

When used in the above or other treatments, a therapeutically effective amount of one of the compounds of the invention can be employed in pure form or, where such forms exist, in pharmaceutically acceptable salt, ester, amide or prodrug form. Alternatively, the compound can be administered as a pharmaceutical composition containing the compound of interest in combination with one or more pharmaceutically acceptable carriers. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well-known in the medical arts. For example, it is well within the skill of the art to start doses of the compound at levels lower than required to achieve the desired therapeutic effect and to gradually increase the dosage until the desired effect is achieved.

The total daily dose of the compounds of this invention administered to a human or lower animal range from about 0.001 mg/kg body weight to about 1 g/kg body weight. More preferable doses can be in the range of from about 0.001 mg/kg body weight to about 100 mg/kg body weight. If desired, the effective daily dose can be divided into multiple doses for purposes of administration. Consequently, single dose compositions may contain such amounts or submultiples thereof to make up the daily dose.

Methods for Preparing Compounds of the Invention

The methods described below can entail use of various enantiomers. Where the stereochemistry is shown in the Schemes, it is intended for illustrative purposes only.

Schemes

The compounds of this invention can be prepared according to the synthetic methods described in either the Schemes or Experimentals sections. Certain groups described in the Scheme are meant to illustrate certain substituent contained within the invention and are not intended to limit the scope of the invention. Representative procedures are shown in, but are not limited to, Schemes 1-12.

Scheme 1

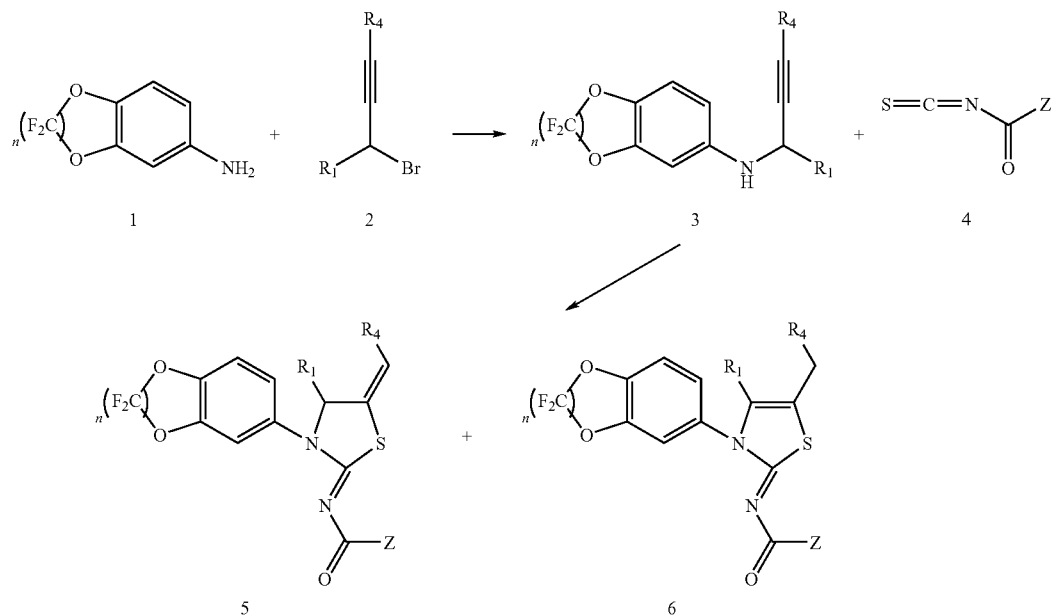

As outlined in Scheme 1, compounds of formula 5 and 6 are representative of compounds of formula (I) or formula (II), wherein X is S, $R_4$ is hydrogen or alkyl, and $R_1$ is as defined in formula (I) or formula (II), may be prepared accordingly. Compounds of formula 1, when treated with compounds of formula 2, wherein $R_4$ is hydrogen or alkyl and $R_1$ is as defined in formula (I) or (II), in the presence or absence of a base such as but not limited to diisopropylethylamine, will provide compounds of formula 3. Compounds of formula 3 when treated with an acylisothiocyanate of formula 4, wherein Z is aryl, cycloalkyl, heteroaryl, heterocycle, $R_eR_fN—$, $—R_3$, or $—OR_3$, wherein $R_e$, $R_f$ and $R_3$ are as defined in formulas (I) or (II), will provide either compounds of formula 5, compounds of formula 6, or a mixture of both. Depending on the nature of Z, compounds of formula 6 may often be separated from the mixture of both compounds using chromatographic techniques known to one skilled in the art to provide compounds of formula 6, which is representative of compounds of the present invention. Furthermore, compounds of formula 5 may be separated from the mixture and may be further treated using suitable conditions to provide compounds of formula 6 as outlined in Scheme 2.

Scheme 2

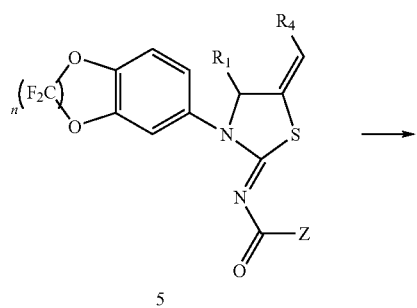

-continued

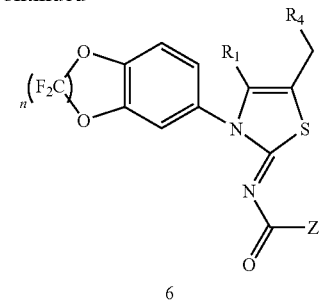

As described in Scheme 2, compounds of formula 5, wherein $R_1$ and Z are as defined in formula (I) or formula (II) and $R_4$ is hydrogen or alkyl, obtained either as the sole product from the conditions outlined in Scheme 1, or separated from the mixture of compound of formula 5 and compound of formula 6, may be converted into the compound of formula 6 by treatment with a base such as sodium methoxide in methanol or similar conditions. Alternatively, compounds of formula 5 may be converted to compounds of formula 6 by exposure to an acid such as trifluoroacetic acid in a solvent such as dichloromethane at or near room temperature over a period of 1 to 5 days.

Scheme 3

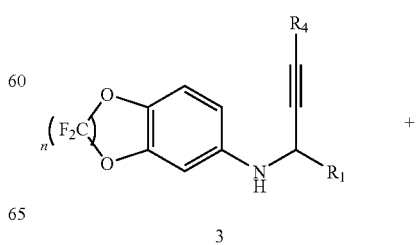

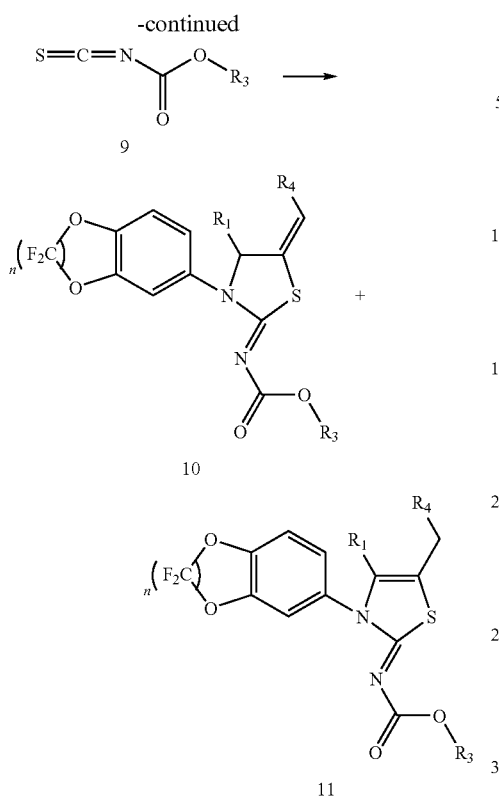

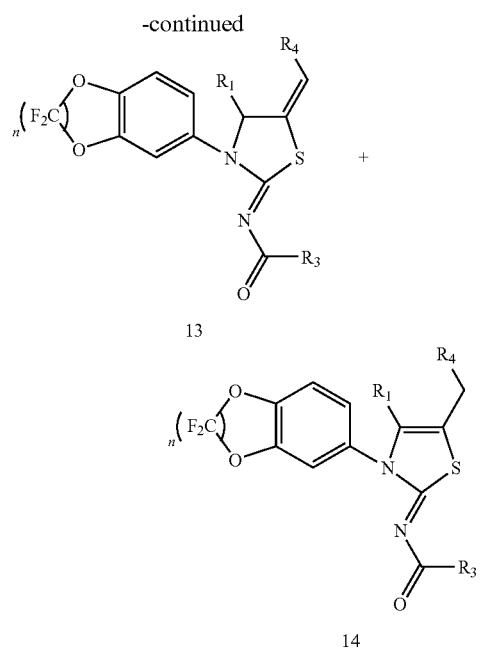

Similarly, compounds of formula 3 when treated with compounds of formula 9, wherein $R_1$ and $R_3$ are defined in compounds of formulas (I) or formula (II) and $R_4$ is hydrogen or alkyl, when treated according to conditions outlined in Scheme 1, will provide either the compound of formula 10, the compound of formula 11 or a mixture of both. The mixture when subjected to chromatographic techniques as known to one skilled in the art, may provide compounds of formula 10 or compounds of formula 11. The compounds of formula 10 obtained either directly or through separation of a mixture of a compound of formula 10 and a compound of formula 11, may be converted into the compound of formula 11 by treatment according to conditions outlined in Scheme 2. Compounds of formula 11 which are representative of compounds of formulas (I) or compounds of formula 10 which are representative of formulas (II) may be further treated using methods known to one skilled in the art to provide compounds of the present invention. Such compounds are representative of compounds of the present invention, but may also be used as intermediates when generating compounds of formula (I) or formula (II), wherein L is C(O) and Z" is —$NR_eR_f$.

Scheme 4

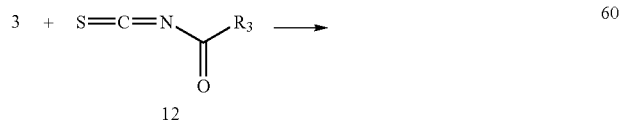

As outlined in Scheme 4, compounds of formula 3 when treated with compounds of formula 12, wherein $R_1$ and $R_3$ are defined in compounds of formula (I) or formula (II) and $R_4$ is hydrogen or alkyl, will provide either a compound of formula 13, a compound of formula 14 or a mixture of both. The mixture may be subjected to chromatographic separation to provide either the compound of formula 13 or the compound of formula 14. Additionally, a compound of formula 13 may be treated according to the conditions outlined in Scheme 2 to provide the resulting compound of formula 14, which is representative of compounds of formula (I) or compounds of formula (II).

Scheme 5

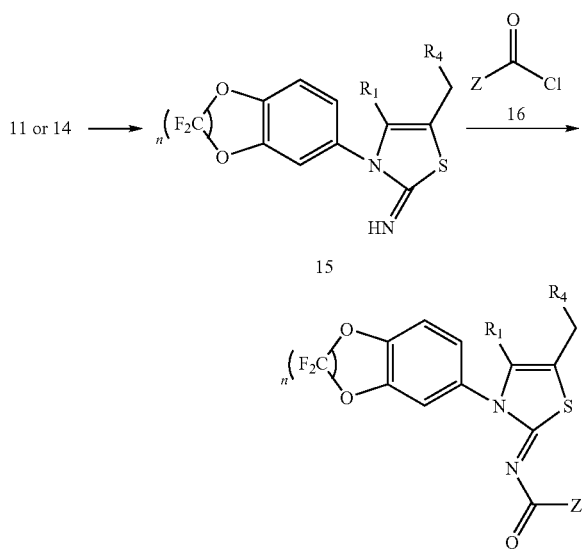

As shown in Scheme 5, compounds of formula 11 obtained from the methods described in Scheme 3 or compounds of formula 14 obtained from the methods described in Scheme 4, wherein $R_1$ is defined under formula (I) or formula (II), $R_4$ is hydrogen or alkyl, and $R_3$ is alkyl may be further treated to provide compounds of formula 6 by the stepwise deprotection of $R_3O$—C(O)— or $R_3$—C(O)— providing compounds of formula 15, followed by treatment with compounds of formula 16 wherein Z is defined in compounds of formula (I) or formula (II), to provide compounds of formula 6. This process allows the introduction of Z groups that may be sensitive to conditions used in the synthesis of the core molecule. For example, compounds of formula 11 when treated with an aqueous alkali base such as sodium, potassium or lithium hydroxide in a solvent such as but not limited to an aqueous mixture of THF or dioxane or an alcoholic solvent including methanol or ethanol will provide the compound of formula 15. Likewise, compounds of formula 14 when subjected to either an aqueous solution containing a mineral acid or an alkali base will provide the compound of formula 15. Compounds of formula 15 when treated with compounds of formula 16, wherein Z is as defined in compounds of formula (I) or formula (II), will provide compounds of formula 6, which are representative of compounds of the present invention.

As shown in Scheme 6, compounds of formula 23, which are representative of compounds of formula (I) or formula (II), wherein X is O, may be prepared accordingly. For example, the treatment of compounds of formula 1 with cyanogen bromide will provide compounds of formula 20. The treatment of compounds of formula 20 with compounds of formula 21, wherein W is chloride, bromide, iodide, mesylate or triflate and $R_2$ is as defined in compounds of formula (I) or formula (II), will provide compounds of formula 22. Compounds of formula 22 when treated with compounds of formula 16 will provide compounds of formula 23 which are representative of compounds of formula (I) or formula (II) wherein X is O.

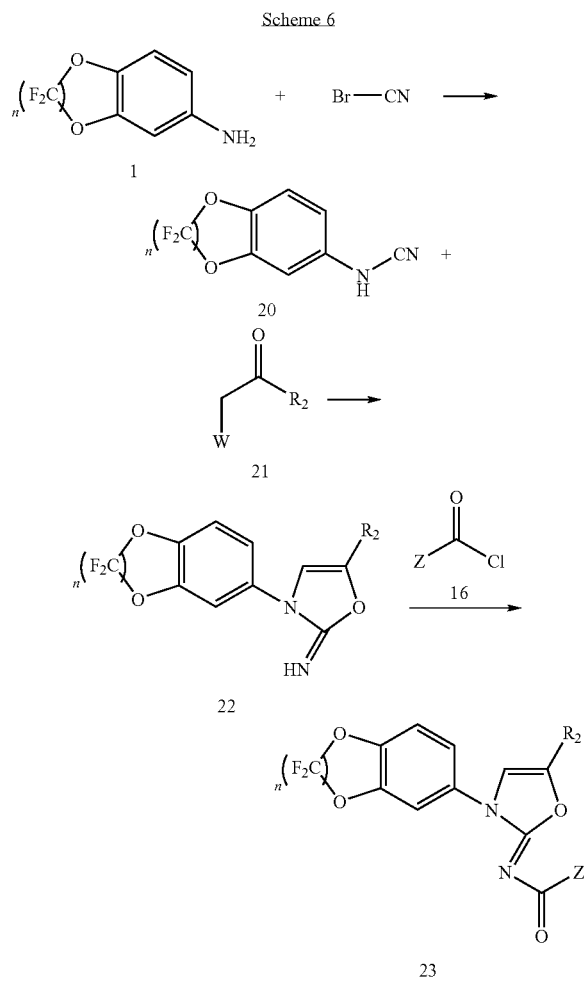

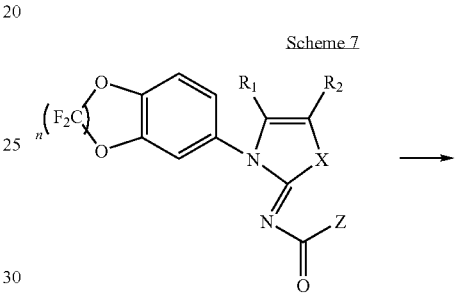

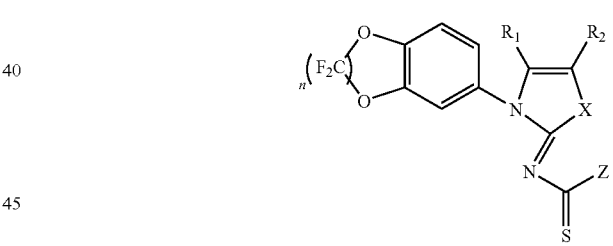

As outlined in Scheme 7, compounds of formula 25, which are representative of compounds of formula (I) or formula (II), wherein L is C(S), and $R_1$ and $R_2$ are defined in formula (I) or formula (II), may be obtained through the treatment of compounds of formula 24 with reagents such as Lawesson's reagent. For example the treatment of compounds of formula 24 with 2,4-bis(4-methoxyphenyl)-1,3-dithia-2,4-diphosphetane-2,4-disulfide, [19172-47-5], (Lawesson's reagent, available from Aldrich Chemical Co. Milwaukee Wis.), in a solvent such as toluene under heated conditions, will provide compounds of formula 25 which is representative of compounds of formula (I) or formula (II), wherein Y is C(S).

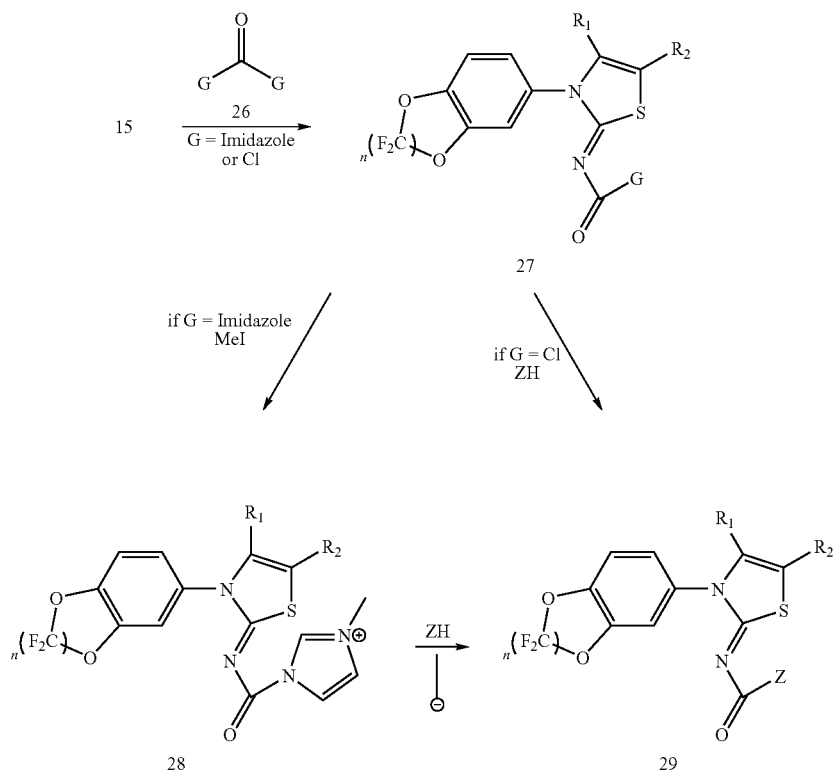

As outlined in Scheme 8, compounds of formula 29, which are representative of compounds of formula (I) or formula (II), wherein $R_1$, $R_2$ and Z are as outlined in the compounds of formula (I) or formula (II), may be obtained from a compound of formula 27 or formula 28 which are representative of compounds of formula (III). The treatment of compounds of formula 15 which is obtained as outlined in Scheme 5, with a reagent of formula 26, wherein G is imidazole or halogen such as but not limited to chloro, will provide compounds of formula 27. Compounds of formula 27, wherein G is imidazole, when treated with methyl iodide will provide compounds of formula 28. Treatment of compounds of formula 28 with Z-H, wherein Z is a heterocycle, —$NR_aR_b$, or —$OR_3$ and H is hydrogen, will provide compounds of formula 29. Alternatively, compounds of formula 27, wherein G is chloro, when treated with Z-H, wherein Z is a heterocycle, —$NR_aR_b$, or —$OR_3$ and H is hydrogen, will also provide compounds of formula 29.

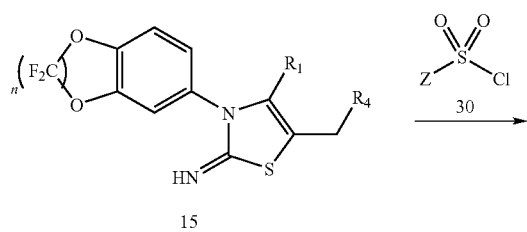

-continued

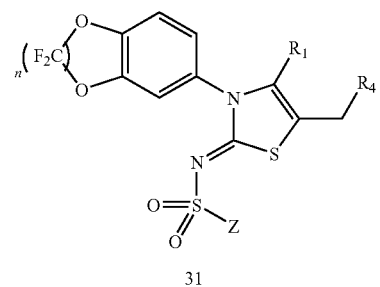

As outlined in Scheme 9, compounds of formula 31, which are representative of compounds of formula (I) and formula (II), wherein L is $S(O)_2$, Z is alkyl, aryl, heteroaryl, or heterocycle, $R_4$ is hydrogen or alkyl, and $R_1$ is defined in formula (I) and formula (II), may be prepared accordingly. For example, the treatment of compounds of formula 15 with a sulfonyl chloride such as methanesulfonyl chloride or benzenesulfonyl chloride in the presence of a base such as diisopropylethylamine in a solvent such as dichloromethane at or near ambient temperature over a period of 2 to 24 hours which will provide compounds of formula 31 which are representative of compounds of formula (I) or formula (II).

Scheme 10

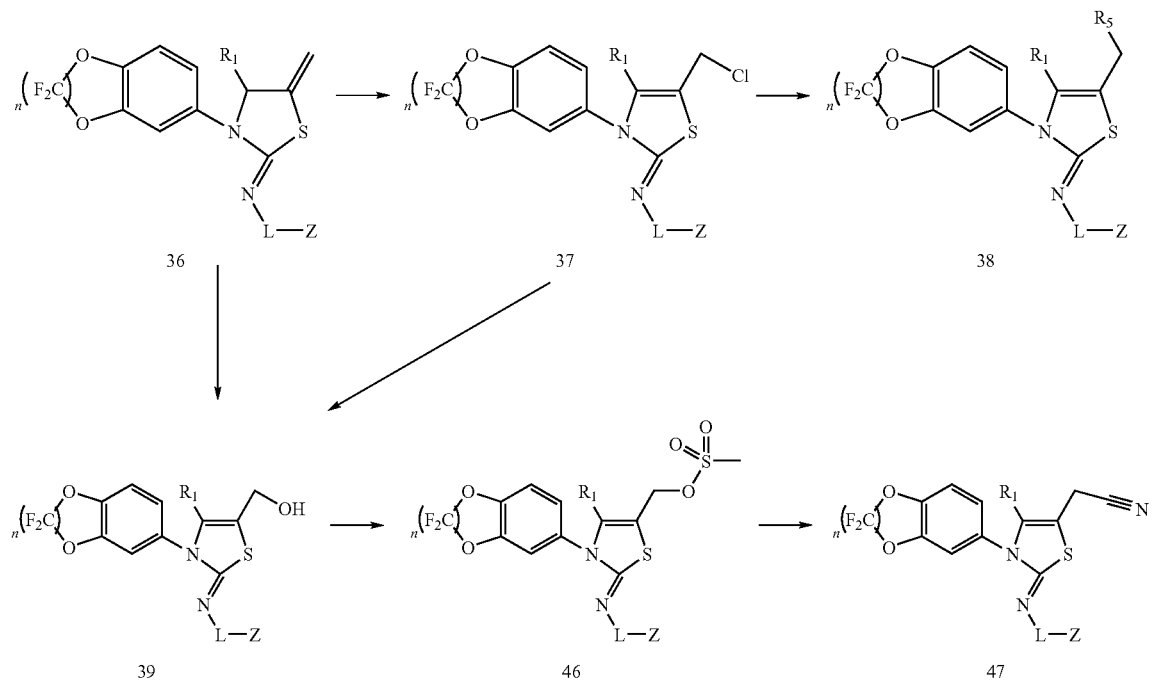

As outlined in Scheme 10, compounds of formula 38 wherein $R_5$ is heterocycle or $-NR_cR_d$, and compounds of formula 39 wherein $R_2$ is $-CH_2OH$, may be prepared accordingly. Compounds of formula 36, when treated with a solution of iodine monochloride and a base such as but not limited to cesium carbonate, will provide compounds of formula 37. An additive such as but not limited to tetrabutylammonium chloride may also be employed. Compounds of formula 37, when treated with an amine, will provide compounds of formula 38. Compounds of formula 37 when treated with a base such as but not limited to cesium carbonate in water and an optional solvent such as but not limited to methanol or tetrahydrofuran may be converted to compounds of formula 39. Alternatively, compounds of formula 36 may be converted to compounds of formula 39 using benzyltrimethylammonium tribromide followed by sodium sulfite in a solvent such as but not limited to acetonitrile, followed in turn by the addition of water. Also, compounds of formula 39 can be converted to compounds of formula 46 which in turn can be converted to compounds of formula 47. Treatment of compounds of formula 39 with methanesulfonyl chloride in the presence of a base such as triethylamine in a solvent such as dichloromethane initially in an ice bath with gradual warming to ambient temperature and continued reaction for 1 to 8 hours furnishes compounds of formula 46. Compounds of formula 46 upon treatment for 1 to 24 hours with a nucleophile such as tetraethylammonium cyanide in a solvent such as dimethyl sulfoxide at ambient temperature yield compounds of formula 47.

Scheme 11

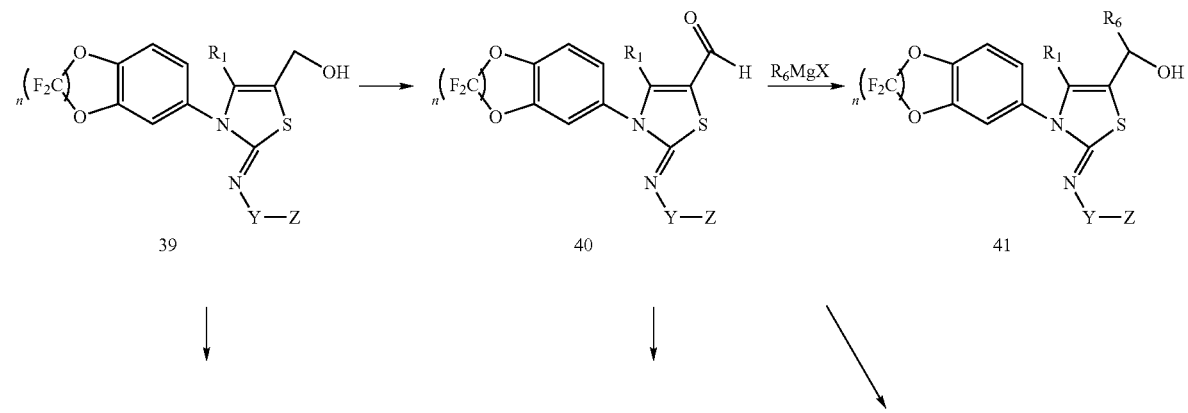

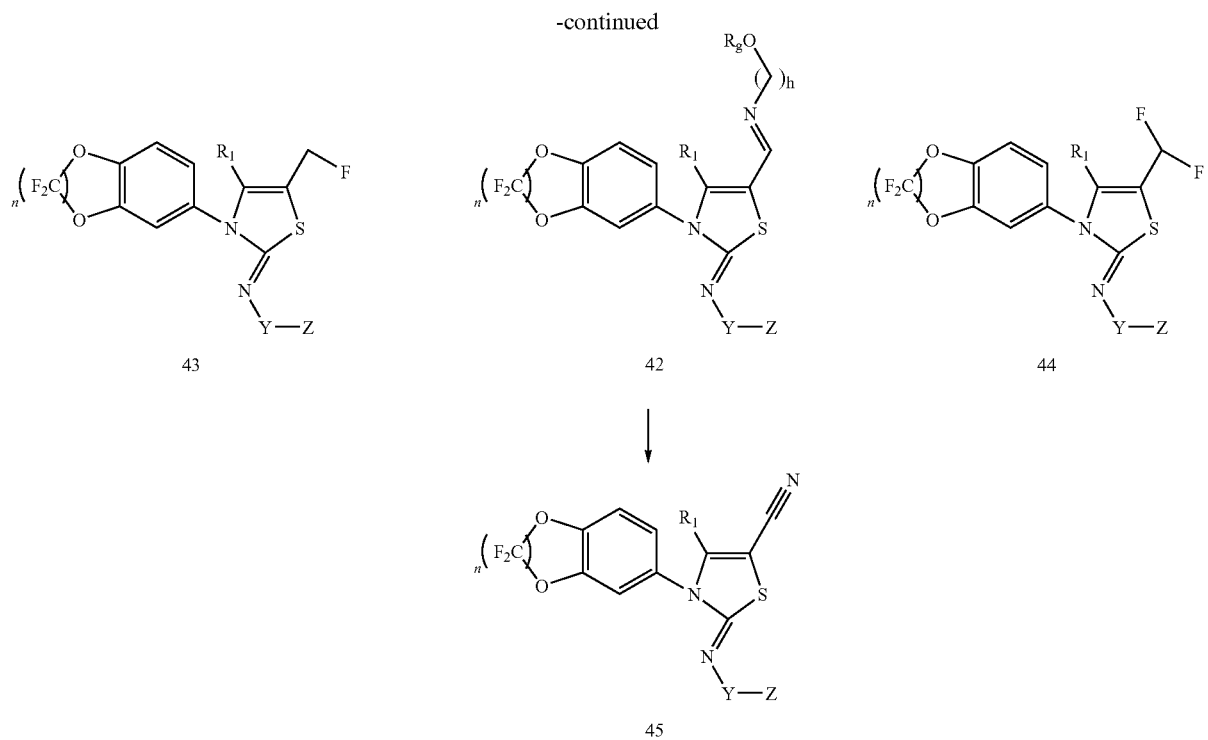

As shown in Scheme 11, compounds of formula 41 wherein $R_6$ in Scheme 11 is alkyl, aryl, heteroaryl, or heterocycle, and compounds of formula 42 wherein $R_2$ is —CH=N—$(CH_2)_h OR_g$ and h is 0, 2, or 3; may be prepared accordingly. Compounds of formula 39, which can be prepared as described in Scheme 10, can be converted to compounds of formula 40 under typical Dess-Martin oxidation conditions known to those skilled in the art and readily available in the literature. Compounds of formula 40 can be converted to compounds of Formula 41 using $R_6$MgX, wherein X is halo and $R_6$ is as defined above for Scheme 11, under typical Grignard reaction conditions known to those skilled in the art and readily available in the literature. Compounds of formula 40 can also be converted to compounds of formula 42 using a hydroxylamine or alkoxyalkylamine in a solvent such as but not limited to ethanol, acetonitrile, DMF or mixtures thereof. Compounds of formula 42, wherein h is 0 and $R_g$ is hydrogen, can be converted to compounds of formula 45 using a dehydrating agent such as 2,4,6-trichlorotriazine in a solvent such as dimethylformamide over a period of 1 to 24 hours at or near ambient temperature. Compounds of formula 39 can be converted to compounds of formula 43 upon treatment with reagents such as bis(2-methoxyethyl)aminosulfur trifluoride or diethylaminosulfur trifluoride in a solvent such as dichloromethane at temperatures starting at −78° C. and warming gradually to ambient temperature or proceeding entirely at ambient temperature over a period of 2 to 24 hours. Similarly, compounds of formula 40 can be converted to compounds of formula 44 with treatment with bis(2-methoxyethyl)aminosulfur trifluoride in a solvent such as dichloromethane at ambient temperature over a period of 1 to 7 days.

Scheme 12

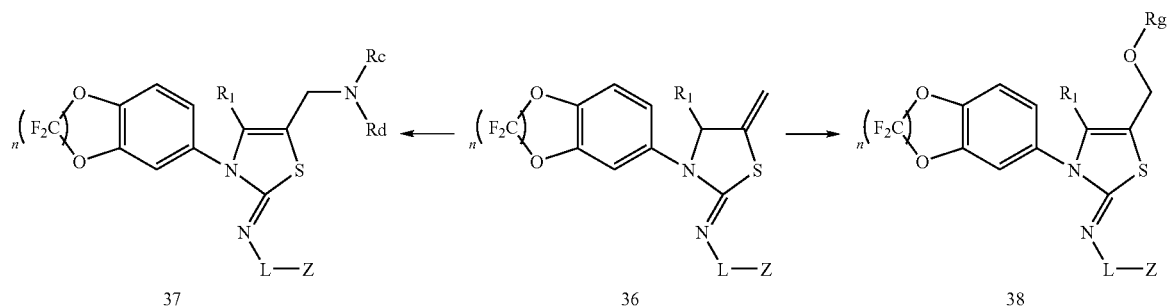

As outlined in Scheme 12, compounds of formula 37, wherein $R_c$ and $R_d$ are hydrogen, alkyl, aryl, arylalkyl, heteroaryl, heteroarylalkyl, heterocycle, or heterocyclealkyl can be prepared accordingly. Compounds of formula 36, which can be prepared analogously to compounds of formula 5 as described in Scheme 1 or compounds of formula 10 in Scheme 3 or compounds of formula 13 in Scheme 4, when treated with $CuBr_2$ followed by $R_cR_dNH$ in a solvent such as but not limited to acetonitrile, methylene chloride or mixtures thereof, will provide compounds of formula 37. Similarly, compounds of formula 36, when treated with $CuBr_2$ followed by $R_gOH$ in a solvent such as but not limited to acetonitrile or a mixture of acetonitrile with methylene chloride, will provide compounds of formula 37.

In addition, nitrogen protecting groups can be used for protecting amine groups during the synthesis of compounds of formula (I) or formula (II). Such methods, and some suitable nitrogen protecting groups, are described in Greene and Wuts (Protective Groups In Organic Synthesis, Wiley and Sons, 1999). For example, suitable nitrogen protecting groups include, but are not limited to, tert-butoxycarbonyl (Boc), benzyloxycarbonyl (Cbz), benzyl (Bn), acetyl, and trifluoroacetyl. More particularly, the Boc protecting group may be removed by treatment with an acid such as trifluoroacetic acid or hydrochloric acid. The Cbz and Bn protecting groups may be removed by catalytic hydrogenation and acetyl and trifluoroacetyl protecting groups may be removed by variety of conditions including the use of sodium, potassium or lithium hydroxide in aqueous organic or alcoholic solvents.

The compounds and intermediates of the invention may be isolated and purified by methods well-known to those skilled in the art of organic synthesis. Examples of conventional methods for isolating and purifying compounds can include, but are not limited to, chromatography on solid supports such as silica gel, alumina, or silica derivatized with alkylsilane groups, by recrystallization at high or low temperature with an optional pretreatment with activated carbon, thin-layer chromatography, distillation at various pressures, sublimation under vacuum, and trituration, as described for instance in "Vogel's Textbook of Practical Organic Chemistry", 5th edition (1989), by Furniss, Hannaford, Smith, and Tatchell, pub. Longman Scientific & Technical, Essex CM20 2JE, England.

Some compounds of the invention have at least one basic site whereby the compound can be treated with an acid to form a desired salt. For example, a compound may be reacted with an acid at or above room temperature to provide the desired salt, which is deposited, and collected by filtration after cooling. Examples of acids suitable for the reaction include, but are not limited to tartaric acid, lactic acid, succinic acid, as well as mandelic, atrolactic, methanesulfonic, ethanesulfonic, toluenesulfonic, naphthalenesulfonic, carbonic, fumaric, gluconic, acetic, propionic, salicylic, hydrochloric, hydrobromic, phosphoric, sulfuric, citric, or hydroxybutyric acid, camphorsulfonic, malic, phenylacetic, aspartic, glutamic, and the like.

Compositions of the Invention

The invention also provides pharmaceutical compositions comprising a therapeutically effective amount of a compound of formula (I) or (II) in combination with a pharmaceutically acceptable carrier. The compositions comprise compounds of the invention formulated together with one or more non-toxic pharmaceutically acceptable carriers. The pharmaceutical compositions can be formulated for oral administration in solid or liquid form, for parenteral injection or for rectal administration.

The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; cocoa butter and suppository waxes; oils such as peanut oil, cottonseed oil, safflower oil, sesame oil, olive oil, corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of one skilled in the art of formulations.

The pharmaceutical compositions of this invention can be administered to humans and other mammals orally, rectally, parenterally, intracisternally, intravaginally, intraperitoneally, topically (as by powders, ointments or drops), bucally or as an oral or nasal spray. The term "parenterally," as used herein, refers to modes of administration, including intravenous, intramuscular, intraperitoneal, intrasternal, subcutaneous, intraarticular injection and infusion.

Pharmaceutical compositions for parenteral injection comprise pharmaceutically acceptable sterile aqueous or non-aqueous solutions, dispersions, suspensions or emulsions and sterile powders for reconstitution into sterile injectable solutions or dispersions. Examples of suitable aqueous and non-aqueous carriers, diluents, solvents or vehicles include water, ethanol, polyols (propylene glycol, polyethylene glycol, glycerol, and the like, and suitable mixtures thereof), vegetable oils (such as olive oil) and injectable organic esters such as ethyl oleate, or suitable mixtures thereof. Suitable fluidity of the composition may be maintained, for example, by the use of a coating such as lecithin, by the maintenance of the required particle size in the case of dispersions, and by the use of surfactants.

These compositions can also contain adjuvants such as preservative agents, wetting agents, emulsifying agents, and dispersing agents. Prevention of the action of microorganisms can be ensured by various antibacterial and antifungal agents, for example, parabens, chlorobutanol, phenol, sorbic acid, and the like. It also can be desirable to include isotonic agents, for example, sugars, sodium chloride and the like. Prolonged absorption of the injectable pharmaceutical form can be brought about by the use of agents delaying absorption, for example, aluminum monostearate and gelatin.

In some cases, in order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug can depend upon its rate of dissolution, which, in turn, may depend upon crystal size and crystalline form. Alternatively, a parenterally administered drug form can be administered by dissolving or suspending the drug in an oil vehicle.

Suspensions, in addition to the active compounds, can contain suspending agents, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

If desired, and for more effective distribution, the compounds of the invention can be incorporated into slow-release or targeted-delivery systems such as polymer matrices, liposomes, and microspheres. They may be sterilized, for example, by filtration through a bacteria-retaining filter or by incorporation of sterilizing agents in the form of sterile solid compositions, which may be dissolved in sterile water or some other sterile injectable medium immediately before use.

Injectable depot forms are made by forming microencapsulated matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides) Depot injectable formulations also are prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Injectable preparations, for example, sterile injectable aqueous or oleaginous suspensions can be formulated according to the known art using suitable dispersing or wetting agents and suspending agents. The sterile injectable preparation also can be a sterile injectable solution, suspension or emulsion in a nontoxic, parenterally acceptable diluent or solvent such as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Solid dosage forms for oral administration include capsules, tablets, pills, powders, and granules. In such solid dosage forms, one or more compounds of the invention is mixed with at least one inert pharmaceutically acceptable carrier such as sodium citrate or dicalcium phosphate and/or a) fillers or extenders such as starches, lactose, sucrose, glucose, mannitol, and salicylic acid; b) binders such as carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using lactose or milk sugar as well as high molecular weight polyethylene glycols.

The solid dosage forms of tablets, dragees, capsules, pills, and granules can be prepared with coatings and shells such as enteric coatings and other coatings well-known in the pharmaceutical formulating art. They can optionally contain opacifying agents and can also be of a composition that they release the active ingredient(s) only, or preferentially, in a certain part of the intestinal tract in a delayed manner. Examples of materials useful for delaying release of the active agent can include polymeric substances and waxes.

Compositions for rectal or vaginal administration are preferably suppositories which can be prepared by mixing the compounds of this invention with suitable non-irritating carriers such as cocoa butter, polyethylene glycol or a suppository wax which are solid at ambient temperature but liquid at body temperature and therefore melt in the rectum or vaginal cavity and release the active compound.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Dosage forms for topical or transdermal administration of a compound of this invention include ointments, pastes, creams, lotions, gels, powders, solutions, sprays, inhalants or patches. A desired compound of the invention is admixed under sterile conditions with a pharmaceutically acceptable carrier and any needed preservatives or buffers as may be required. Ophthalmic formulation, eardrops, eye ointments, powders and solutions are also contemplated as being within the scope of this invention.

The ointments, pastes, creams and gels may contain, in addition to an active compound of this invention, animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, lactose, talc, silicic acid, aluminum hydroxide, calcium silicates and polyamide powder, or mixtures of these substances. Sprays can additionally contain customary propellants such as chlorofluorohydrocarbons.

Compounds of the invention also can be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes may be used. The present compositions in liposome form may contain, in addition to the compounds of the invention, stabilizers, preservatives, and the like. The preferred lipids are the natural and synthetic phospholipids and phosphatidylcholines (lecithins) used separately or together.

Methods to form liposomes are known in the art. See, for example, Prescott, Ed., Methods in Cell Biology, Volume XIV, Academic Press, New York, N.Y., (1976), p 33 et seq.

Dosage forms for topical administration of a compound of this invention include powders, sprays, ointments and inhalants. The active compound is mixed under sterile conditions with a pharmaceutically acceptable carrier and any needed preservatives, buffers or propellants. Ophthalmic formulations, eye ointments, powders and solutions are also contemplated as being within the scope of this invention. Aqueous liquid compositions of the invention also are particularly useful.

The compounds of the invention can be used in the form of pharmaceutically acceptable salts, esters, or amides derived from inorganic or organic acids. The term "pharmaceutically acceptable salts, esters and amides," as used herein, include salts, zwitterions, esters and amides of compounds of formula (I) or (II) which are, within the scope of sound medical judgment, suitable for use in contact with the tissues of humans and lower animals without undue toxicity, irritation, allergic response, and the like, are commensurate with a reasonable benefit/risk ratio, and are effective for their intended use.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well-known in the art. The salts can be prepared in situ during the final isolation and purification of the compounds of the invention or separately by reacting a free base function with a suitable organic acid.

Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, phosphate, glutamate, bicarbonate, p-toluenesulfonate and undecanoate.

Also, the basic nitrogen-containing groups can be quaternized with such agents as lower alkyl halides such as methyl, ethyl, propyl, and butyl chlorides, bromides and iodides; dialkyl sulfates such as dimethyl, diethyl, dibutyl and diamyl sulfates; long chain halides such as decyl, lauryl, myristyl and stearyl chlorides, bromides and iodides; arylalkyl halides such as benzyl and phenethyl bromides and others. Water or oil-soluble or dispersible products are thereby obtained.

Examples of acids which can be employed to form pharmaceutically acceptable acid addition salts include such inorganic acids as hydrochloric acid, hydrobromic acid, sulfuric acid and phosphoric acid and such organic acids as oxalic acid, maleic acid, succinic acid, and citric acid.

Basic addition salts can be prepared in situ during the final isolation and purification of compounds of this invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium, and aluminum salts, and the like, and nontoxic quaternary ammonia and amine cations including ammonium, tetramethylammonium, tetraethylammonium, methylammonium, dimethylammonium, trimethylammonium, triethylammonium, diethylammonium, ethylammonium and the like. Other representative organic amines useful for the formation of base addition salts include ethylenediammonium, ethanolammonium, diethanolammonium, piperidinium, and piperazinium.

The term "pharmaceutically acceptable ester," as used herein, refers to esters of compounds of the invention which hydrolyze in vivo and include those that break down readily in the human body to leave the parent compound or a salt thereof. Examples of pharmaceutically acceptable, non-toxic esters of the invention include $C_1$-to-$C_6$ alkyl esters and $C_5$-to-$C_7$ cycloalkyl esters, although $C_1$-to-$C_4$ alkyl esters are preferred. Esters of the compounds of formula (I) or (II) can be prepared according to conventional methods. Pharmaceutically acceptable esters can be appended onto hydroxy groups by reaction of the compound that contains the hydroxy group with acid and an alkylcarboxylic acid such as acetic acid, or with acid and an arylcarboxylic acid such as benzoic acid. In the case of compounds containing carboxylic acid groups, the pharmaceutically acceptable esters are prepared from compounds containing the carboxylic acid groups by reaction of the compound with base such as triethylamine and an alkyl halide, for example with methyl iodide, benzyl iodide, cyclopentyl iodide or alkyl triflate. They also can be prepared by reaction of the compound with an acid such as hydrochloric acid and an alcohol such as ethanol or methanol.

The term "pharmaceutically acceptable amide," as used herein, refers to non-toxic amides of the invention derived from ammonia, primary $C_1$-to-$C_6$ alkyl amines and secondary $C_1$-to-$C_6$ dialkyl amines. In the case of secondary amines, the amine can also be in the form of a 5- or 6-membered heterocycle containing one nitrogen atom. Amides derived from ammonia, $C_1$-to-$C_3$ alkyl primary amides and $C_1$-to-$C_2$ dialkyl secondary amides are preferred. Amides of the compounds of formula (I) or (II) can be prepared according to conventional methods. Pharmaceutically acceptable amides can be prepared from compounds containing primary or secondary amine groups by reaction of the compound that contains the amino group with an alkyl anhydride, aryl anhydride, acyl halide, or aroyl halide. In the case of compounds containing carboxylic acid groups, the pharmaceutically acceptable esters are prepared from compounds containing the carboxylic acid groups by reaction of the compound with base such as triethylamine, a dehydrating agent such as dicyclohexyl carbodiimide or carbonyl diimidazole, and an alkyl amine, dialkylamine, for example with methylamine, diethylamine, and piperidine. They also can be prepared by reaction of the compound with an acid such as sulfuric acid and an alkylcarboxylic acid such as acetic acid, or with acid and an arylcarboxylic acid such as benzoic acid under dehydrating conditions such as with molecular sieves added. The composition can contain a compound of the invention in the form of a pharmaceutically acceptable prodrug.

The term "pharmaceutically acceptable prodrug" or "prodrug," as used herein, represents those prodrugs of the compounds of the invention which are, within the scope of sound medical judgment, suitable for use in contact with the tissues of humans and lower animals without undue toxicity, irritation, allergic response, and the like, commensurate with a reasonable benefit/risk ratio, and effective for their intended use. Prodrugs of the invention can be rapidly transformed in vivo to a parent compound of formula (I) or (II), for example, by hydrolysis in blood. A thorough discussion is provided in T. Higuchi and V. Stella, Pro-drugs as Novel Delivery Systems, V. 14 of the A.C.S. Symposium Series, and in Edward B. Roche, ed., Bioreversible Carriers in Drug Design, American Pharmaceutical Association and Pergamon Press (1987).

The invention contemplates pharmaceutically active compounds either chemically synthesized or formed by in vivo biotransformation to compounds of formula (I) or (II).

The compounds, compositions, and methods of the invention will be better understood by reference to the following examples and reference examples, which are intended as an illustration of and not a limitation upon the scope of the invention.

EXAMPLES

Abbreviations

EtOAc for Ethyl acetate, DMF for N,N-dimethylformamide, hex for hexane, DMSO for dimethylsulfoxide, DCM for dichloromethane, Et$_2$O for ethyl ether, EtOH for ethanol, MeCN for acetonitrile, THF for tetrahydrofuran, TEA for triethylamine, p-TSA for p-toluenesulfonic acid, DMAP for 4-dimethylaminopyridine, PBS for phosphate buffered saline, PC for potassium carbonate, IPA for isopropyl alcohol and MeOH for methanol.

Example 1

N-(2,2-difluoro-1,3-benzodioxol-5-yl)-N-prop-2-ynylamine

To a stirred solution of 5-amino-2,2-difluorobenzo-1,3-dioxole (2.8 g, 16.17 mmmol) in 25 mL of anhydrous toluene was dropwise added propargyl bromide (0.99 mL, 11 mmol). The mixture was heated to 80° C. overnight after which it was allowed to cool to ambient temperature and filtered. The filtrate was concentrated under reduced pressure and purified by column chromatography using DCM as eluant to provide the titled compound. $^1$H NMR (CDCl$_3$) δ ppm 2.22 (1H), 3.85 (2H), 6.30-6.85 (3H); MS (ESI) 212 (M+H).

Example 2 ethyl(2Z)-3-(2,2-difluoro-1,3-benzodioxol-5-yl)-5-methylene-1,3-thiazolidin-2-ylidenecarbamate A solution of Example 1 (0.22 g, 1.05 mmol) and ethyl isothiocyanatoformate (0.11 mL, 1.05 mmol) in dry THF was stirred at room temperature for 3 hours. The mixture was concentrated under reduced pressure and the residue purified by column chromatography using DCM as eluant to provide the titled compound. $^1$H NMR (CDCl$_3$) δ ppm 1.32 (3H), 4.27 (2H), 4.70 (2H), 5.30 (2H), 7.00-7.25 (3H); MS (ESI) 343 (M+H).

Example 3 ethyl(2Z)-3-(2,2-difluoro-1,3-benzodioxol-5-yl)-5-methyl-1,3-thiazol-2(3H)-ylidenecarbamate A solution of Example 2 (0.35 g, 1.023 mmol) and sodium methoxide (25% wt/wt, 5.11 mmol) in methanol (10 mL) was heated to 50° C. for 2 hours. The mixture was concentrated to dryness under reduced pressure, taken up in DCM (100 mL), washed with water and brine. The organic phase was dried over sodium sulfate, filtered and concentrated to dryness under reduced pressure. The residue was purified by column chromatography using DCM as eluant to provide the titled compound. $^1$H NMR (CDCl$_3$) δ ppm 1.31 (3H), 2.2 (3H), 4.27 (2H), 6.65 (1H), 7.05-7.25 (3H); MS (ESI) 343 (M+H).

Example 4 methyl(2Z)-3-(2,2-difluoro-1,3-benzodioxol-5-yl)-5-methyl-1,3-thiazol-2(3H)-ylidenecarbamate The titled compound was obtained as another product from Example 3. $^1$H NMR (CDCl$_3$) δ ppm 2.30 (3H), 3.67 (3H), 6.65 (1H), 7.00-7.32 (3H); MS (ESI) 329 (M+H).

Example 5

N-[(2Z)-3-(2,2-difluoro-1,3-benzodioxol-5-yl)-5-methylene-1,3-thiazolidin-2-ylidene]acetamide A solution of Example 1 (1.4 g, 6.63 mmol) and acetyl isothiocyanate (0.60 mL, 6.63 mmol) in dry THF (25 mL) was stirred at room temperature for 3 hours. The solvent was removed under reduced pressure and the residue purified by column chromatography using DCM as eluant to provide the titled compound. $^1$H NMR (CDCl$_3$) δ ppm 2.20 (3H), 3.73 (2H), 4.85-5.00 (2H), 7.00-7.25 (3H); MS (ESI) 313 (M+H).

Example 6

N'-[(2Z)-3-(2,2-difluoro-1,3-benzodioxol-5-yl)-5-methylene-1,3-thiazolidin-2-ylidene]-N,N-dimethylurea The titled compound was obtained according to the procedure outlined in Example 5 substituting dimethylcarbamoyl isothiocyanate for acetyl isothiocyanate. $^1$H NMR (CDCl$_3$) δ ppm 3.00 (6H), 3.70 (2H), 4.85-5.05 (2H), 7.00-7.25 (3H); MS (DCI) 342 (M+H).

Example 7

N-[(2Z)-3-(2,2-difluoro-1,3-benzodioxol-5-yl)-5-methyl-1,3-thiazol-2(3H)-ylidene]acetamide A solution of Example 5 (2.0 g, 6.4 mmol) and sodium methoxide (25% wt/wt, 32.02 mmol) in methanol (25 mL) was heated to 50° C. for two hours. The mixture was concentrated to dryness under reduced pressure, diluted with DCM (300 mL), and washed with water (200 mL) and brine (200 mL). The organic phase was dried over sodium sulfate, filtered and concentrated to dryness under reduced pressure. The residue was purified by column chromatography using mixture DCM-MeOH (95:5) as eluant to provide the titled compound. $^1$H NMR (CDCl$_3$) δ ppm 2.24 (3H), 2.32 (3H), 6.75 (1H), 7.05-7.35 (3H); MS (ESI) 313 (M+H).

Example 8

3-(2,2-difluoro-1,3-benzodioxol-5-yl)-5-methyl-1,3-thiazol-2(3H)-imine

A mixture of Example 5 (1.8 g, 5.76 mmol) and hydrochloric acid (38%, 4.76 mL) in 40 mL of ethanol-water (1:1) was refluxed for 15 hours. Then the solvent was removed under reduced pressure, and the residue was carried on to the next step. $^1$H NMR (CD$_3$OD) δ ppm 2.28 (3H), 7.15 (1H), 7.40-7.65 (3H); MS (ESI) 271 (M+H).

General Procedure for Preparation of Thiazoline Ureas and Amides

Examples 9-17

A mixture of Example 8, TEA (3×), and a reagent selected from a carbamyl chloride, an acyl chloride or an isocyanate (1.5×) in acetonitrile was heated to 70° C. for 15 hours followed by concentration under reduced pressure. The residue was extracted with DCM (3×20 mL), the combined organic layers were washed with an aqueous saturated solution of sodium bicarbonate, water and then brine.

The organic solution was dried over sodium sulfate, filtered, and concentrated under reduced pressure. The residue was purified by column chromatography using a mixture of DCM-MeOH (95:5) as eluant to provide the titled compound.

Example 9

N'-[(2Z)-3-(2,2-difluoro-1,3-benzodioxol-5-yl)-5-methyl-1,3-thiazol-2(3H)-ylidene]-N,N-dimethylurea The titled compound was obtained according to the procedure outlined in the General Procedure for Preparation of Thiazoline Ureas and Amides using N-dimethyl carbamoyl chloride. $^1$H NMR (CDCl$_3$) δ ppm 2.25 (3H), 2.98 (6H), 6.60 (1H), 7.10-7.35 (3H); MS (ESI) 342 (M+H).

Example 10

N'-[(2Z)-3-(2,2-difluoro-1,3-benzodioxol-5-yl)-5-methyl-1,3-thiazol-2(3H)-ylidene]-N,N-diethylurea The titled compound was obtained according to the procedure outlined in the General Procedure for Preparation of Thiazoline Ureas and Amides using N,N-diethyl carbamoyl chloride. $^1$H NMR (CDCl$_3$) δ ppm 1.05 (6H), 3.40 (4H), 6.60 (1H), 7.10-7.45 (3H); MS (ESI) 370 (M+H).

Example 11

N'-[(2Z)-3-(2,2-difluoro-1,3-benzodioxol-5-yl)-5-methyl-1,3-thiazol-2(3H)-ylidene]-N,N-diisopropylurea The titled compound was obtained according to the procedure outlined in the General Procedure for Preparation of Thiazoline Ureas and Amides using N,N-diisopropyl carbamyl chloride. $^1$H NMR (CDCl$_3$) δ ppm 1.25 (12H), 3.90 (2H), 6.55 (1H), 7.10-7.45 (3H); MS (ESI) 398 (M+H).

Example 12

N-[(2Z)-3-(2,2-difluoro-1,3-benzodioxol-5-yl)-5-methyl-1,3-thiazol-2(3H)-ylidene]pyrrolidine-1-carboxamide The titled compound was obtained according to the procedure outlined in the General Procedure for Preparation of Thiazoline Ureas and Amides using 1-pyrrolidinecarbonyl chloride. $^1$H NMR (CDCl$_3$) δ ppm 1.83 (4H), 2.21 (3H), 3.40 (4H), 6.60 (1H), 7.10-7.45 (3H); MS (ESI) 368 (M+H).

Example 13

N-[(2Z)-3-(2,2-difluoro-1,3-benzodioxol-5-yl)-5-methyl-1,3-thiazol-2(3H)-ylidene]piperidine-1-carboxamide The titled compound was obtained according to the procedure outlined in the General Procedure for Preparation of Thiazoline Ureas and Amides using 1-piperidinecarbonyl chloride. $^1$H NMR (CDCl$_3$) δ ppm 1.50 (6H), 2.20 (3H), 3.20 (2H), 3.44 (2H), 6.58 (1H), 7.10-7.35 (3H); MS (ESI) 382 (M+H).

Example 14

N-[(2Z)-3-(2,2-difluoro-1,3-benzodioxol-5-yl)-5-methyl-1,3-thiazol-2(3H)-ylidene]cyclobutanecarboxamide The titled compound was obtained according to the procedure outlined in the General Procedure for Preparation of Thiazoline Ureas and Amides using cyclobutane carbonyl chloride. $^1$H NMR (CDCl$_3$) δ ppm 1.99 (2H), 2.25 (7H), 3.20 (1H), 6.80 (1H), 7.15-7.38 (3H); MS (DCI) 353 (M+H).

Example 15

N-[(2Z)-3-(2,2-difluoro-1,3-benzodioxol-5-yl)-5-methyl-1,3-thiazol-2(3H)-ylidene]-2,2-dimethylpropanamide The titled compound was obtained according to the procedure outlined in the General Procedure for Preparation of Thiazoline Ureas and Amides using trimethylacetyl chloride. $^1$H NMR (CDCl$_3$) δ ppm 1.19 (9H), 2.25 (3H), 6.75 (1H), 7.15-7.38 (3H); MS (DCI) 355 (M+H).

Example 16

N-[(2Z)-3-(2,2-difluoro-1,3-benzodioxol-5-yl)-5-methyl-1,3-thiazol-2(3H)-ylidene]benzamide The titled compound was obtained according to the procedure outlined in the General Procedure for Preparation of Thiazoline Ureas and Amides using benzoyl chloride. $^1$H NMR (CDCl$_3$) δ ppm 2.20 (3H), 6.80 (1H), 7.15-8.10 (8H); MS (DCI) 375 (M+H).

Example 17

4-chloro-N-[(2Z)-3-(2,2-difluoro-1,3-benzodioxol-5-yl)-5-methyl-1,3-thiazol-2(3H)-ylidene]benzamide The titled compound was obtained according to the procedure outlined in the General Procedure for Preparation of Thiazoline Ureas and Amides using 4-chlorobenzoyl chloride. $^1$HNMR(CDCl$_3$) δ ppm 2.38 (3H), 6.82 (1H), 7.15-8.10 (7H); MS (DCI) 409 (M+H).

Example 18

2,2-difluoro-1,3-benzodioxol-5-ylcyanamide

To a mixture of 2,2-difluorobenzo[d][1,3]dioxol-5-amine (1.0 g, 5.77 mmol) in anhydrous DCM (15 mL) cyanogen bromide (3M, 1.55 mL) was added dropwise; after 16 hours the mixture was diluted with 150 mL of DCM and filtered. The organic phase was evaporated under vacuum and the residue purified by column chromatography using a mixture of DCM-MeOH (95:5) as eluant to provide the titled compound. $^1$H NMR (CDCl$_3$) δ ppm 5.82 (1H), 6.65-7.25 (3H); MS (DCI) 216 (M+NH$_4^+$).

Example 19

(2Z)-3-(2,2-difluoro-1,3-benzodioxol-5-yl)-5-methyl-1,3-oxazol-2(3H)-imine

To an ice cold mixture of Example 18 (0.3 g, 1.51 mmol) and potassium carbonate (0.2 g, 1.51 mmol) in DMF (10 mL), chloroacetone (0.13 mL, 1.51 mmol) was added. After stirring the mixture at room temperature for 16 hours, the reaction mixture was diluted with 50 mL of DCM and washed with water and brine. The organic phase was dried over sodium sulfate and then evaporated after filtration under vacuum. The residue purified by column chromatography using a mixture of DCM-MeOH (95:5) as eluant to provide the titled compound. $^1$H NMR (CDCl$_3$) δ ppm 2.10 (3H), 6.40 (1H), 7.05-7.65 (3H); MS (DCI) 255 (M+H).

Example 20

N'-[(2Z)-3-(2,2-difluoro-1,3-benzodioxol-5-yl)-5-methyl-1,3-oxazol-2(3H)-ylidene]-N,N-dimethylurea The titled compound was obtained according to the procedure outlined in the General procedure for preparation of thiazoline ureas and amides substituting Example 19 for Example 8 and using N-dimethyl carbamoyl chloride. $^1$H NMR (CDCl$_3$) δ ppm 2.20 (3H), 3.00 (6H), 6.45 (1H), 7.10-7.55 (3H); MS (DCI) 326 (M+H)

Example 21

N'-[(2Z)-3-(2,2-difluoro-1,3-benzodioxol-5-yl)-5-methyl-1,3-oxazol-2(3H)-ylidene]-N,N-dimethylthiourea A solution of Example 20 (14 mg, 0.043 mmol) and [2,4-bis(4-methoxyphenyl)-1,3-dithia-2,4-diphosphetane-2,4-disulfide] (Lawesson's reagent, Aldrich, 17 mg, 0.043 mmol) in anhydrous toluene (0.25 mL) was heated at 100° C. for 1 hour. The mixture was cooled and applied directly to a silica column. The product was eluted with 0-1% methanol in dichloromethane to provide the title compound. 1H NMR (300 MHz, CDCl$_3$) δ ppm 2.27 (3H) 3.17 (3H) 3.47 (3H) 6.57 (1H) 7.09 (1H) 7.17 (1H) 7.45 (1H); MS (ESI) m/z 342.0 (M+H)+.

Example 22

N-[(2Z)-5-methylene-3-(2,2,3,3-tetrafluoro-2,3-dihydro-1,4-benzodioxin-6-yl)-1,3-thiazolidin-2-ylidene] pyrrolidine-1-carboxamide

Example 22A

Prop-2-ynyl-(2,2,3,3-tetrafluoro-2,3-dihydro-benzo[1,4]dioxin-6-yl)-amine 2,2,3,3-Tetrafluoro-6-aminobenzodioxane (6.694 g, 30.0 mmol) and Aldrich basic alumina (activated, Brockmann 1, 150 mesh, CAS #1344-28-1) (51 g) were mixed in fluorobenzene (100 mL) and then treated with 80% propargyl bromide in toluene (2.56 mL, 23.0 mmol). The resulting mixture was thoroughly stirred and heated at 50° C. for 17 hours. The mixture was cooled to ambient temperature and filtered. The alumina was rinsed thoroughly with dichloromethane (150 mL), the filtrate was reduced in volume under reduced pressure, washed with concentrated aqueous NH$_4$OH (5 mL), dried (Na$_2$SO$_4$), concentrated and chromatographed on silica eluting with 0-10% EtOAc/hexanes to provide the titled compound. $^1$H NMR (CDCl$_3$) δ ppm 2.24 (t, 1H), 3.92 (m, 2H), 3.96 (m, 1H), 6.43 (d, 1H), 6.45 (dd, 1H), 6.96 (d, 1H); MS (DCI) 262 (M+H).

Another method to prepare the titled compound is as follows. 2,2,3,3-Tetrafluoro-6-aminobenzodioxane (50.2 g, 225 mmol) and potassium carbonate (43.54 g, 315 mmol) were suspended into acetonitrile (250 mL), stirred in a 1-liter three-necked flask equipped with an overhead mechanical stirrer, and treated with ~80% propargyl bromide in toluene (33.5 g, ~225 mmol). The mixture was slowly heated to 65-70° C. over about three hours. Stirring was continued at that temperature for 24 hours, at which time the heat was turned off and the mixture was permitted to cool to room temperature. The mixture was filtered through a glass fritted funnel, and the solids were rinsed with acetonitrile (300 mL). The filtrate was concentrated, reconcentrated thrice from hexanes, and chromatographed on silica (0 to 1 to 2 to 4% EtOAc/hexanes) to give the titled compound.

Example 22B

N-[5-Methylene-3-(2,2,3,3-tetrafluoro-2,3-dihydrobenzo[1,4]dioxin-6-yl)-thiazolidin-2-ylidene]-acetamide Example 22A (1.98 g, 7.6 mmol) was dissolved into THF (30 mL) and treated with acetyl isothiocyanate (670 µL, 7.62 mmol). The mixture was stirred for 19 hours at ambient temperature, heated to 65° C. for 3 hours, and then stirred at ambient temperature for 72 hours. The mixture was concentrated under reduced pressure, passed through neutral alumina (activated, Brockmann 1, ~150 mesh, CAS #1344-28-1) with 2:1 CH$_2$Cl$_2$/hexanes, followed by a CH$_2$Cl$_2$ wash. The combined filtrate was concentrated under reduced pressure to furnish the titled compound. $^1$H NMR (CDCl$_3$) δ ppm 2.26 (s, 3H), 4.71 (m, 2H), 5.35 (m, 1H), 5.38 (m, 1H), 7.22 (d, 1H), 7.30 (dd, 1H), 7.42 (d, 1H); MS (DCI) 363 (M+H).

An alternative procedure to prepare the titled compound follows. The propargylaniline (Example 22A, 31.08 g, ~119 mmol) was dissolved into THF (300 mL) and treated with acetylisothiocyanate (11.5 mL, 131 mmol). After being stirred at room temperature briefly, it was heated to approximately 55° C. overnight, and at 60-65° C. for another 6 days. Then the mixture was concentrated and reconcentrated from CH$_2$Cl$_2$/hexanes to give a semi-solid which was mixed into 3:1 Et$_2$O/hexanes and chromatographed on neutral alumina (40% Et$_2$O/hexanes then 40% Et$_2$O/CH$_2$Cl$_2$) to give the titled compound.

Example 22C

5-Methylene-3-(2,2,3,3-tetrafluoro-2,3-dihydrobenzo[b][1,4]dioxin-6-yl)thiazolidin-2-imine The mixture of Example 22B (160 mg, 0.44 mmol) and sodium perborate (123 mg, 1.5 mmol) in acetic acid (1.5 mL) was stirred at room temperature for 1.5 hours, concentrated under reduced pressure, dissolved in EtOAc and concentrated under reduced pressure, partitioned between 1:1 EtOAc/hexanes (10 mL) and pH 12½ potassium phosphate buffer (10 mL). The aqueous phase was separated and reextracted with more 1:1 EtOAc/hexanes (4 mL). The combined organic phases were washed with brine, dried (Na$_2$SO$_4$), and concentrated under reduced pressure. The residue was chromatographed through Alltech silica eluting with 0-3% EtOAc/CH$_2$Cl$_2$, and concentrated to supply the titled compound. $^1$H NMR (CDCl$_3$) δ ppm 4.70 (m, 2H), 5.14 (m, 1H), 5.27 (m, 1H), 7.14 (d, 1H), 7.30 (dd, 1H), 7.53 (m, 1H); MS (ESI) 321 (M+H).

An alternative procedure for the preparation of the titled compound follows. The acetyl-imine (Example 22B, 725 mg, 2.0 mmol) was dissolved into acetic acid (5 mL) and treated with a solution of methylboronic acid (180 mg, 3.0 mmol) in acetic acid (2 mL). After the solution was stirred for 5 minutes, it was further treated with solid sodium perborate (491 mg, 6.0 mmol). The mixture was stirred at room temperature overnight, and then more sodium perborate (163 mg, 2.0 mmol) was added. After 2 hours, the solution was concentrated thrice from EtOAc (3×15 mL), partitioned between 2:1 EtOAc/hexanes (15 mL) and water (5 mL) with enough concentrated NH$_4$OH to bring the aqueous pH to 8. The aqueous phase was separated and extracted with more 2:1 solution, and the combined organic phases were twice washed with a mixture of water (2 mL) and concentrated NH$_4$OH (0.5 mL), washed with brine, dried (Na$_2$SO$_4$), concentrated, and chromatographed on silica (50% CH$_2$Cl$_2$/hexanes, then 0 to 4% EtOAc/CH$_2$Cl$_2$) to give the titled compound.

Example 22D

N-[(2Z)-5-methylene-3-(2,2,3,3-tetrafluoro-2,3-dihydro-1,4-benzodioxin-6-yl)-1,3-thiazolidin-2-ylidene]pyrrolidine-1-carboxamide Example 22C (32 mg, 0.10 mmol) was dissolved into CH$_2$Cl$_2$ (2.0 mL) and cooled in a –45° C. bath. To the solution was added 20% phosgene in toluene (80 µL, 150 µmol) followed by addition of diisopropylethylamine (35 µL, 200 µmol). The mixture was stirred another 10 minutes at –45° C., followed by the dropwise addition of pyrrolidine (25 µL, 300 µmol). The mixture was stirred for 5 minutes, allowed to warm to ambient temperature, and diluted with concentrated aqueous NH$_4$OH (500 µL). To the mixture was added EtOAc (200 µL), and the aqueous phase was separated and extracted with CH$_2$Cl$_2$. The combined organic phases were washed with concentrated aqueous NH$_4$OH (500 µL). The aqueous phase was separated and extracted with additional CH$_2$Cl$_2$. The combined organic phases were dried (Na$_2$SO$_4$), concentrated under reduced pressure and chromatographed through Alltech silica eluting with 0-10% EtOAc/CH$_2$Cl$_2$ to provide the titled compound. $^1$H NMR (CDCl$_3$) δ ppm 1.87 (m, 4H), 3.45 (m, 4H), 4.65 (m, 2H), 5.26 (m, 1H), 5.30 (m, 1H), 7.16 (d, 1H), 7.34 (dd, 1H), 7.58 (d, 1H); MS (ESI) 418 (M+H).

Example 23

N-[(2Z)-5-methyl-3-(2,2,3,3-tetrafluoro-2,3-dihydro-1,4-benzodioxin-6-yl)-1,3-thiazol-2(3H)-ylidene]pyrrolidine-1-carboxamide A solution of Example 22C (290 mg, 0.90 mmol) in CH$_2$Cl$_2$ (4.0 mL, 0.2 M) was added dropwise over 17 minutes to a –78° C. solution of 20% phosgene/toluene (630 µL, 1.2 mmol) in CH$_2$Cl$_2$ (5.0 mL, 0.2M). The mixture was stirred cold for 10 minutes after which diisopropylethylamine (140 µL, 0.80 mmol) was added dropwise over 3 minutes. The mixture was stirred cold for 45 minutes and allowed to warm to –20° C. over 1 hour; then allowed to warm to ambient temperature. After 1 hour at ambient temperature, pyrrolidine (135 µL, 1.6 mmol) was added and the mixture was stirred for 16 hours. To the solution was added more pyrrolidine (90 µL, 1.1 mmol), the mixture was stirred for 20 minutes, diluted with concentrated aqueous NH$_4$OH (2 mL) and stirred for 5 minutes. The aqueous phase was separated and extracted with CH$_2$Cl$_2$ (3×). The combined organic phases were dried with Na$_2$SO$_4$, concentrated under reduced pressure, and chromatographed on Alltech silica eluting with 0-10% Et$_2$O in 1:1 CH$_2$Cl$_2$/hexanes to provide the titled compound. $^1$H NMR (CD$_2$Cl$_2$) δ ppm 1.83 (m, 4H), 2.24 (d, 3H), 3.36 (m, 2H), 3.40 (m, 2H), 6.66 (d, 1H), 7.25 (d, 1H), 7.42 (dd, 1H), 7.54 (d, 1H); MS (ESI) 418 (M+H).

Example 24

N-[(2Z)-3-(2,2-difluoro-1,3-benzodioxol-5-yl)-5-(pyrrolidin-1-ylmethyl)-1,3-thiazol-2(3H)-ylidene]acetamide

Example 24A (Z)-N-(5-(chloromethyl)-3-(2,2-difluorobenzo[d][1,3]dioxol-5-yl)thiazol-2(3H)-ylidene)acetamide Example 5 (32 mg, 0.10 mmol) was dissolved into acetic acid (300 µL, 0.3 M) and treated with 1 M iodine monochloride (200 µL, 0.20 mmol, methylene chloride). After 15 minutes, cesium carbonate (~65 mg, 0.20 mmol) was added. After another 10 minutes, solid NaHSO$_3$ (31 mg, 0.3 mmol) was added, and the resulting suspension was thoroughly stirred until the orange color of the solution had disappeared (~10 minutes). The suspension was diluted with CH$_2$Cl$_2$ and filtered through a glass-fritted funnel with a CH$_2$Cl$_2$ rinse. The filtrate was concentrated, concentrated twice from EtOAc, dissolved into 20% EtOAc/CH$_2$Cl$_2$, and filtered through a pad of Aldrich basic alumina (activated, Brockmann 1, ~150 mesh, CAS #1344-28-1) with a 20% EtOAc/CH$_2$Cl$_2$ rinse. The filtrate was concentrated and chromatographed through silica (10 to 20% diethyl ether/20% CH$_2$Cl$_2$/70 to 60% hexanes) to give the titled compound. 1H NMR (300 MHz, CDCl$_3$) δ ppm 2.25 (3H), 4.62 (2H), 7.07 (1H), 7.18 (2H), 7.33 (1H); MS (DCI) m/z 347 (M+H)$^+$.

Example 24B

N-[(2Z)-3-(2,2-difluoro-1,3-benzodioxol-5-yl)-5-(pyrrolidin-1-ylmethyl)-1,3-thiazol-2(3H)-ylidene]acetamide The allyl chloride (Example 24A, 16 mg, 46 µmol) was dissolved into pyrrolidine (200 µL) and stirred 10 minutes. Then the mixture was twice diluted with and concentrated from EtOAc, and partitioned between 2:1 EtOAc/hexanes (1.5 mL) and water (1 mL). The organic phase was separated and washed with water, dried (Na$_2$SO$_4$), and chromatographed on silica (2 to 5% MeOH/CH$_2$Cl$_2$) to give the titled compound. $^1$H NMR (300 MHz, CDCl$_3$) δ ppm 1.81 (4H), 2.22 (3H), 2.60 (4H), 3.66 (2H), 6.91 (1H), 7.17 (2H), 7.36 (1H); MS (ESI) 382 (M+H)$^+$.

Example 25

N-[(2Z)-5-(hydroxymethyl)-3-(2,2,3,3-tetrafluoro-2,3-dihydro-1,4-benzodioxin-6-yl)-1,3-thiazol-2(3H)-ylidene]pyrrolidine-1-carboxamide The alkene (Example 22D, 23 mg, 55 µmol) and tetrabutylammonium chloride (1.2 mg, 4 µmol) were dissolved into acetic acid (500 µL) and treated with 1 M iodine monochloride (110 µL, 110 µmol) in CH$_2$Cl$_2$, dropwise over 1 minute. After 15 minutes, cesium carbonate (18 mg, 55 µmol) was added. After another 10 minutes, solid NaHSO$_3$ (16 mg, 150 µmol) was added, and the resulting suspension was thoroughly stirred until the deep iodine color had changed to a light orange (15 minutes). The suspension was diluted with CH$_2$Cl$_2$, stirred for 2 minutes, and filtered through a glass-fritted funnel with a CH$_2$Cl$_2$ rinse. The filtrate was concentrated, concentrated twice from EtOAc, dissolved into 20% EtOAc/CH$_2$Cl$_2$, and filtered through a pad of Aldrich basic alumina (activated, Brockmann 1, ~150 mesh, CAS #1344-

28-1) with a 20→50% EtOAc/CH$_2$Cl$_2$ rinse. The intermediate mixture was concentrated to 13 mg, dissolved into MeOH (500 µL), and treated with 1 M aqueous Cs$_2$CO$_3$ (30 µL). After ~15 minutes, the mixture was concentrated and partitioned between CH$_2$Cl$_2$ and pH 7 potassium phosphate buffer. The aqueous phase was separated and extracted with CH$_2$Cl$_2$, and the combined organic phases were dried (Na$_2$SO$_4$), concentrated, and chromatographed through silica (20% EtOAc/CH$_2$Cl$_2$, then 5% MeOH/CH$_2$Cl$_2$) to give the title compound. $^1$H NMR (300 MHz, CDCl$_3$) δ ppm 1.86 (4H), 3.44 (4H), 4.65 (2H), 6.89 (1H), 7.23 (1H), 7.37 (1H), 7.48 (1H); MS (ESI) m/z 434 (M+H)$^+$.

Example 26

N-[(2Z)-5-methyl-3-(2,2,3,3-tetrafluoro-2,3-dihydro-1,4-benzodioxin-6-yl)-1,3-thiazol-2(3H)-ylidene]piperidine-1-carboxamide Example 26A 5-methyl-3-(2,2,3,3-tetrafluoro-2,3-dihydrobenzo[b][1,4]dioxin-6-yl)thiazol-2(3H)-imine Example 22B (11.1 g) was suspended in MeOH (60 mL) and concentrated aqueous HCl (40 mL), and heated at 60° C. for three days. The mixture was brought to room temperature and concentrated to the aqueous phase. The aqueous mixture was combined with CH$_2$Cl$_2$ (150 mL) and treated with enough concentrated NH$_4$OH (30 mL) to make the solution basic to litmus. The aqueous phase was separated and extracted with CH$_2$Cl$_2$. The combined organic phases were dried (Na$_2$SO$_4$), concentrated, mixed with a little 10% EtOAc/CH$_2$Cl$_2$, filtered, and chromatographed on silica (0 to 3% MeOH/10% EtOAc/CH$_2$Cl$_2$) to give the titled compound. $^1$H NMR (300 MHz, CDCl$_3$) δ ppm 2.09 (3H), 6.27 (1H), 7.19 (1H), 7.30 (1H), 7.39 (1H); MS (ESI) m/z 321 (M+H)$^+$.

Example 26B

N-[(2Z)-5-methyl-3-(2,2,3,3-tetrafluoro-2,3-dihydro-1,4-benzodioxin-6-yl)-1,3-thiazol-2(3H)-ylidene]piperidine-1-carboxamide The imine (Example 26A, 30 mg, 0.09 mmol) was dissolved in acetonitrile (1.5 mL). Triethylamine (19 µl, 0.18 mmol) was added followed by the 1-piperidinecarbonyl chloride (0.11 mmol). The reaction was heated at 65° C. overnight. The reaction mixture was cooled down and passed through a Si-amine cartridge (1 g, 1.6 mmol/g) to remove the excess carbamyl chloride eluting with additional acetonitrile. The resulting solution was dried and purified by reverse phase HPLC to supply the titled compound. $^1$H NMR (500 MHz, DMSO-d$_6$) δ ppm 1.40 (4H), 1.53 (2H), 2.20 (3H), 3.43 (4H), 7.24 (1H), 7.63 (2H), 7.83 (1H); MS (ESI) m/z 432.2 (M+H)$^+$.

Example 27

N,N-diethyl-N'-[(2Z)-5-methyl-3-(2,2,3,3-tetrafluoro-2,3-dihydro-1,4-benzodioxin-6-yl)-1,3-thiazol-2(3H)-ylidene]urea The titled compound was prepared using the procedure described in Example 26B substituting diethylcarbamyl chloride for 1-piperidinecarbonyl chloride.
The titled compound was also prepared as described in Example 97 substituting diethylamine for N-benzylbut-2-yn-1-amine. $^1$H NMR (300 MHz, DMSO-d$_6$/D$_2$O) δ ppm 1.04 (6H) 2.21-2.27 (3H) 3.32 (4H) 7.01-7.11 (1H) 7.48-7.54 (2H) 7.72-7.78 (1H); MS (ESI+) m/z 420 (M+H)$^+$.

Example 28

N-methyl-N'-[(2Z)-5-methyl-3-(2,2,3,3-tetrafluoro-2,3-dihydro-1,4-benzodioxin-6-yl)-1,3-thiazol-2(3H)-ylidene]-N-phenylurea The titled compound was prepared using the procedure described in Example 26B substituting N-methyl-N-phenylcarbamoyl chloride for 1-piperidinecarbonyl chloride. $^1$H NMR(500 MHz, DMSO-d$_6$) δ ppm 2.22 (3H), 3.27 (3H), 7.10 (1H), 7.25 (5H), 7.46 (2H), 7.67 (1H); MS (ESI) m/z 454.0 (M+H)$^+$.

Example 29

N,N-dimethyl-N'-[(2Z)-5-methyl-3-(2,2,3,3-tetrafluoro-2,3-dihydro-1,4-benzodioxin-6-yl)-1,3-thiazol-2(3H)-ylidene]urea The titled compound was prepared using the procedure described in Example 26B substituting dimethylcarbamyl chloride for 1-piperidinecarbonyl chloride. $^1$H NMR (500 MHz, DMSO-d$_6$) δ ppm 2.20 (3H), 2.86 (3H), 2.89 (3H), 7.24 (1H), 7.64 (2H), 7.86 (1H); MS (ESI) m/z 391.9 (M+H)$^+$.

Example 30

N-[(2Z)-5-methyl-3-(2,2,3,3-tetrafluoro-2,3-dihydro-1,4-benzodioxin-6-yl)-1,3-thiazol-2(3H)-ylidene]cyclobutanecarboxamide The imine (Example 26A, 30 mg, 0.09 mmol) was dissolved in 1.5 ml acetonitrile (1.5 mL). Triethylamine (19 µl, 0.18 mmol) was added followed by the cyclobutanecarbonyl chloride (0.11 mmol). The reaction was heated at 65° C. overnight. The reaction mixture was cooled down and passed through a Si-amine cartridge (1 g, 1.6 mmol/g) to remove the excess carbonyl chloride eluting with additional acetonitrile. The resulting solution was dried and purified by reverse phase HPLC. $^1$H NMR (500 MHz, DMSO-d$_6$) δ ppm 1.75 (1H), 1.88 (1H), 2.10 (4H), 2.26 (3H), 3.15 (1H), 7.44 (1H), 7.63 (1H), 7.68 (1H), 7.90 (1H); MS (ESI) m/z 403.0 (M+H)$^+$.

Example 31

N-[(2Z)-5-methyl-3-(2,2,3,3-tetrafluoro-2,3-dihydro-1,4-benzodioxin-6-yl)-1,3-thiazol-2(3H)-ylidene]cyclopropanecarboxamide The titled compound was prepared using the procedure described in Example 30 substituting cyclopropanecarbonyl chloride for cyclobutanecarbonyl chloride. $^1$H NMR (500 MHz, DMSO-d$_6$) δ ppm 0.78 (4H), 1.67 (1H), 2.26 (3H), 7.40 (1H), 7.62 (1H), 7.68 (1H), 7.89 (1H); MS (ESI) m/z 388.9 (M+H)$^+$.

Example 32

N-[(2Z)-5-methyl-3-(2,2,3,3-tetrafluoro-2,3-dihydro-1,4-benzodioxin-6-yl)-1,3-thiazol-2(3H)-ylidene]methanesulfonamide The imine (Example 26A, 30 mg, 0.09 mmol) was dissolved in dichloromethane (1.5 mL). Diisopropylethylamine (31 µl, 0.18 mmol, 2 equiv.) was added followed by the methanesulfonyl chloride (0.1 mmol, 1.1 equiv.). The reaction was stirred at room temperature for 4 hours. The reaction mixture was passed through a Si-amine cartridge (1 g, 1.6 mmol/g) to remove the excess sulfonyl chloride and washed with additional dichloromethane. The resulting solution was dried, concentrated, and purified by reverse phase HPLC. $^1$H NMR (500 MHz, DMSO-$d_6$) δ ppm 2.24 (3H), 2.90-2.96 (3H), 7.31 (1H), 7.56 (1H), 7.68 (1H), 7.8 (1H); MS (ESI) m/z 398.9 (M+H)$^+$.

Example 33

N-[(2Z)-5-methyl-3-(2,2,3,3-tetrafluoro-2,3-dihydro-1,4-benzodioxin-6-yl)-1,3-thiazol-2(3H)-ylidene]ethanesulfonamide The titled compound was prepared using the procedure described for Example 32 substituting ethanesulfonyl chloride for methanesulfonyl chloride. $^1$H NMR (500 MHz, DMSO-$d_6$) δ ppm 1.16 (3H), 2.23 (3H), 3.01 (2H), 7.31 (1H), 7.56 (1H), 7.68 (1H), 7.83 (1H); MS (ESI) m/z 412.9 (M+H)$^+$.

Example 34

N-[(2Z)-5-methyl-3-(2,2,3,3-tetrafluoro-2,3-dihydro-1,4-benzodioxin-6-yl)-1,3-thiazol-2(3H)-ylidene]propane-1-sulfonamide The titled compound was prepared using the procedure described for Example 32 substituting 1-propanesulfonyl chloride for methanesulfonyl chloride. $^1$H NMR (500 MHz, DMSO-$d_6$) δ ppm 0.93 (3H), 1.64 (2H), 2.24 (3H), 3.0 (2H), 7.31 (1H), 7.56 (1H), 7.68 (1H), 7.83 (1H); MS (ESI) m/z 426.9 (M+H)$^+$.

Example 35

N-[(2Z)-5-methyl-3-(2,2,3,3-tetrafluoro-2,3-dihydro-1,4-benzodioxin-6-yl)-1,3-thiazol-2(3H)-ylidene]benzenesulfonamide The titled compound was prepared using the procedure described for Example 32 substituting benzenesulfonyl chloride for methanesulfonyl chloride. $^1$H NMR (500 MHz, DMSO-$d_6$) δ ppm 2.23 (3H), 7.35 (1H), 7.47 (1H), 7.55 (2H), 7.62 (1H), 7.68 (1H), 7.75 (1H), 7.78 (2H); MS (ESI) m/z 460.9 (M+H)$^+$.

Example 36

N-[(2Z)-5-methyl-3-(2,2,3,3-tetrafluoro-2,3-dihydro-1,4-benzodioxin-6-yl)-1,3-thiazol-2(3H)-ylidene]thiophene-2-sulfonamide The titled compound was prepared using the procedure described for Example 32 substituting 2-thiophenesulfonyl chloride for methanesulfonyl chloride. $^1$H NMR (500 MHz, DMSO-$d_6$) δ ppm 2.25 (3H), 7.13 (1H), 7.40 (1H), 7.47 (1H), 7.60 (m, 1H), 7.70 (1H), 7.75 (1H), 7.88 (1H); MS (ESI) m/z 466.9 (M+H)$^+$.

Example 37

3-cyano-N-[(2Z)-5-methyl-3-(2,2,3,3-tetrafluoro-2,3-dihydro-1,4-benzodioxin-6-yl)-1,3-thiazol-2(3H)-ylidene]benzenesulfonamide The titled compound was prepared using the procedure described for Example 32 substituting 3-cyanobenzenesulfonyl chloride for methanesulfonyl chloride. $^1$H NMR (500 MHz, DMSO-$d_6$) δ ppm 2.26 (3H), 7.40 (1H), 7.51 (1H), 7.68 (1H), 7.75 (2H), 8.09 (2H), 8.19 (1H); MS (ESI) m/z 485.9 (M+H)$^-$.

Example 38

3-methoxy-N-[(2Z)-5-methyl-3-(2,2,3,3-tetrafluoro-2,3-dihydro-1,4-benzodioxin-6-yl)-1,3-thiazol-2(3H)-ylidene]benzenesulfonamide The titled compound was prepared using the procedure described for Example 32 substituting 3-methoxybenzenesulfonyl chloride for methanesulfonyl chloride. $^1$H NMR (500 MHz, DMSO-$d_6$) δ ppm 2.25 (3H), 7.18 (1H), 7.23 (1H), 7.35 (2H), 7.47 (2H), 7.68 (1H), 7.75 (1H); MS (ESI) m/z 490.9 (M+H)$^-$.

Example 39

3-chloro-N-[(2Z)-5-methyl-3-(2,2,3,3-tetrafluoro-2,3-dihydro-1,4-benzodioxin-6-yl)-1,3-thiazol-2(3H)-ylidene]benzenesulfonamide The titled compound was prepared using the procedure described for Example 32 substituting 3-chlorobenzenesulfonyl chloride for methanesulfonyl chloride. $^1$H NMR (500 MHz, DMSO-$d_6$) δ ppm 2.25 (3H), 7.38 (1H), 7.50 (1H), 7.58 (m, 1H), 7.69 (2H), 7.75 (3H); MS (ESI) m/z 494.9 (M+H)$^+$.

Example 40

N-[(2Z)-3-(2,2-difluoro-1,3-benzodioxol-5-yl)-5-methyl-1,3-thiazol-2(3H)-ylidene]-N'-isopropylurea Example 40A N-[(2Z)-3-(2,2-difluoro-1,3-benzodioxol-5-yl)-5-methyl-1,3-thiazol-2(3H)-ylidene]-1H-imidazole-1-carboxamide Example 8 was treated as described in Example 126 to supply the titled compound.

Example 40B (Z)-1-(3-(2,2-difluorobenzo[d][1,3]dioxol-5-yl)-5-methylthiazol-2(3H)-ylidenecarbamoyl)-3-methyl-1H-imidazol-3-ium iodide Example 40A was treated as described in Example 81A to supply the titled compound.

Example 40C

N-[(2Z)-3-(2,2-difluoro-1,3-benzodioxol-5-yl)-5-methyl-1,3-thiazol-2(3H)-ylidene]-N'-isopropylurea Into a 20 mL vial, a solution of (Z)-1-(3-(2,2-difluorobenzo[d][1,3]dioxol-5-yl)-5-methylthiazol-2(3H)-ylidenecarbamoyl)-3-methyl-1H-imidazol-3-ium iodide (Example 40B, 48 mg, 0.09 mmol) dissolved in acetonitrile (0.5 mL) was added followed by the addition of diisopropylethylamine (21 μL, 0.12 mmol) dissolved in acetonitrile(0.5 mL). Then, to the solution was added propan-2-amine (5.9 mg, 0.10 mmol) dissolved in acetonitrile (0.5 mL). The vial was capped and shaken overnight at room temperature. The reaction was checked by LC/MS and concentrated to dryness. The residue was dissolved in 1:1 DMSO/MeOH and purified by reverse phase HPLC (acetonitrile/water 0.1% TFA gradient elution method) to supply the titled compound. $^1$H NMR (500 MHz, DMSO-d$_6$/D$_2$O) δ ppm 1.07 (6H) 2.22 (3H) 3.65-3.83 (1H) 6.99 (1H) 7.32 (1H) 7.43 (1H) 7.61 (1H); MS (ESI) m/z 356 (M+H)$^+$

Example 41

N-(sec-butyl)-N'-[(2Z)-3-(2,2-difluoro-1,3-benzodioxol-5-yl)-5-methyl-1,3-thiazol-2(3H)-ylidene]urea The titled compound was prepared as described in Example 40C substituting butan-2-amine for propan-2-amine. $^1$H NMR (500 MHz, DMSO-d$_6$/D$_2$O) δ ppm 0.84 (3H) 1.06 (3H) 1.31-1.54 (2H) 2.24 (3H) 3.52-3.68 (1H) 6.99 (1H), 7.35 (1H), 7.46 (1H) 7.65 (1H); MS (ESI) m/z 370 (M+H)$^+$.

Example 42

N-(tert-butyl)-N'-[(2Z)-3-(2,2-difluoro-1,3-benzodioxol-5-yl)-5-methyl-1,3-thiazol-2(3H)-ylidene]urea The titled compound was prepared as described in Example 40C substituting 2-methylpropan-2-amine for propan-2-amine. $^1$H NMR (500 MHz, DMSO-d$_6$/D$_2$O) δ ppm 1.19-1.30 (9H) 2.19-2.25 (3H) 6.91-7.05 (1H) 7.31 (1H) 7.44 (1H), 7.60 (1H); MS (ESI) m/z 370 (M+H)$^+$.

Example 43

N-[(2Z)-3-(2,2-difluoro-1,3-benzodioxol-5-yl)-5-methyl-1,3-thiazol-2(3H)-ylidene]-N'-(1-methylbutyl)urea The titled compound was prepared as described in Example 40C substituting pentan-2-amine for propan-2-amine. $^1$H NMR (500 MHz, DMSO-d$_6$/D$_2$O) δ ppm 0.79-0.89 (3H) 1.00-1.08 (3H) 1.17-1.50 (4H) 2.18-2.24 (3H) 3.56-3.72 (1H) 6.92-6.98 (1H) 7.27-7.35 (1H) 7.39-7.47 (1H) 7.60 (1H); MS (ESI) m/z 384 (M+H)$^+$.

Example 44

N-[(2Z)-3-(2,2-difluoro-1,3-benzodioxol-5-yl)-5-methyl-1,3-thiazol-2(3H)-ylidene]-N'-(1-dimethylpropyl)urea The titled compound was prepared as described in Example 40C substituting 2-methylbutan-2-amine for propan-2-amine. $^1$H NMR (500 MHz, DMSO-d$_6$/D$_2$O) δ ppm 0.76 (3H) 1.19-1.21 (6H) 1.63 (2H) 2.22 (3H) 6.94-6.99 (1H) 7.32 (1H) 7.44 (1H) 7.60 (1H); MS (ESI) m/z 384 (M+H)$^+$.

Example 45

N-[(2Z)-3-(2,2-difluoro-1,3-benzodioxol-5-yl)-5-methyl-1,3-thiazol-2(3H)-ylidene]-N'-(1,2-dimethylpropyl)urea The titled compound was prepared as described in Example 40C substituting 3-methylbutan-2-amine for propan-2-amine. $^1$H NMR (500 MHz, DMSO-d$_6$/D$_2$O) δ ppm 0.82 (6H) 0.99 (3H) 1.56-1.78 (1H) 2.22 (3H) 3.44-3.57 (1H) 6.98 (1H) 7.33 (1H) 7.43 (1H) 7.62 (1H); MS (ESI) m/z 384 (M+H)$^+$.

Example 46

N-[(2Z)-3-(2,2-difluoro-1,3-benzodioxol-5-yl)-5-methyl-1,3-thiazol-2(3H)-ylidene]-N'-(1-ethylpropyl)urea The titled compound was prepared as described in Example 40C substituting pentan-3-amine for propan-2-amine. $^1$H NMR (500 MHz, DMSO-d$_6$/D$_2$O) δ ppm 0.80 (6H) 1.21-1.59 (4H) 2.22 (3H) 3.30-3.49 (1H) 7.00 (1H) 7.33 (1H) 7.44 (1H) 7.63 (1H); MS (ESI) m/z 384 (M+H)$^+$.

Example 47

N-[(2Z)-3-(2,2-difluoro-1,3-benzodioxol-5-yl)-5-methyl-1,3-thiazol-2(3H)-ylidene]-N'-(2-methoxy-1-methylethyl)urea The titled compound was prepared as described in Example 40C substituting 1-methoxypropan-2-amine for propan-2-amine. $^1$H NMR (500 MHz, DMSO-d$_6$/D$_2$O) δ ppm 1.05 (3H) 2.22 (3H) 3.18-3.35 (5H) 3.74-3.93 (1H) 6.98 (1H) 7.31 (1H) 7.43 (1H) 7.61 (1H); MS (ESI) m/z 386 (M+H)$^+$.

Example 48

N-cyclopentyl-N'-[(2Z)-3-(2,2-difluoro-1,3-benzodioxol-5-yl)-5-methyl-1,3-thiazol-2(3H)-ylidene]urea The titled compound was prepared as described in Example 40C substituting cyclopentanamine for propan-2-amine. $^1$H NMR (500 MHz, DMSO-d$_6$/D$_2$O) δ ppm 1.25-1.90 (8H) 2.19-2.24 (3H) 3.83-4.00 (1H) 6.95-7.02 (1H) 7.28-7.37 (1H) 7.39-7.49 (1H) 7.58-7.64 (1H); MS (ESI) m/z 382 (M+H)$^+$.

Example 49

N'-[(2Z)-3-(2,2-difluoro-1,3-benzodioxol-5-yl)-5-methyl-1,3-thiazol-2(3H)-ylidene]-N-ethyl-N-methylurea The titled compound was prepared as described in Example 40C substituting N-methylethanamine for propan-2-amine. $^1$H NMR (500 MHz, DMSO-D$_6$/D$_2$O) δ ppm 0.98 (3H) 2.20 (3H) 2.82-2.84 (3H) 3.31 (2H) 6.98 (1H) 7.35 (1H) 7.43 (1H) 7.60 (1H); MS (ESI) m/z 356 (M+H)$^+$.

Example 50

N'-[(2Z)-3-(2,2-difluoro-1,3-benzodioxol-5-yl)-5-methyl-1,3-thiazol-2(3H)-ylidene]-N-isopropyl-N-methylurea The titled compound was prepared as described in Example 40C substituting N-methylpropan-2-amine for propan-2-amine. $^1$H NMR (500 MHz, DMSO-d$_6$/D$_2$O) δ ppm 0.98-1.05 (6H) 2.17-2.22 (3H) 2.67-2.74 (3H) 4.34-4.53 (1H) 6.92-7.04 (1H) 7.29-7.48 (2H) 7.56-7.63 (1H); MS (ESI) m/z 370 (M+H)$^+$.

Example 51

N-butyl-N'-[(2Z)-3-(2,2-difluoro-1,3-benzodioxol-5-yl)-5-methyl-1,3-thiazol-2(3H)-ylidene]-N-methylurea The titled compound was prepared as described in Example 40C substituting N-methylbutan-1-amine for propan-2-amine. $^1$H NMR (500 MHz, DMSO-$d_6$/$D_2O$) δ ppm 0.78 (3H) 1.04-1.25 (2H) 1.29-1.48 (2H) 2.17-2.22 (3H) 2.80-2.85 (3H) 3.18-3.31 (2H) 6.92-6.99 (1H) 7.26-7.34 (1H) 7.37-7.45 (1H) 7.56-7.63 (1H); MS (ESI) m/z 384 (M+H)$^+$.

Example 52

N'-[(2Z)-3-(2,2-difluoro-1,3-benzodioxol-5-yl)-5-methyl-1,3-thiazol-2(3H)-ylidene]-N-isobutyl-N-methylurea The titled compound was prepared as described in Example 40C substituting N,2-dimethylpropan-1-amine for propan-2-amine. $^1$H NMR (500 MHz, DMSO-$d_6$/$D_2O$) δ ppm 0.72 (6H) 1.71-1.93 (1H) 2.20 (3H) 2.81-2.88 (3H) 3.05-3.07 (2H) 6.93-7.04 (1H) 7.31 (1H) 7.44 (1H) 7.58 (1H); MS (ESI) m/z 384 (M+H)$^+$.

Example 53

N'-[(2Z)-3-(2,2-difluoro-1,3-benzodioxol-5-yl)-5-methyl-1,3-thiazol-2(3H)-ylidene]-N-(1,3-dioxolan-2-ylmethyl)-N-methylurea The titled compound was prepared as described in Example 40C substituting 1-(1,3-dioxolan-2-yl)-N-methylmethanamine for propan-2-amine. $^1$H NMR (500 MHz, DMSO-$d_6$/$D_2O$) δ ppm 2.21 (3H) 2.88-2.92 (3H) 3.39 (2H) 3.68-3.87 (4H) 4.87 (1H) 7.00 (1H) 7.32 (1H) 7.41 (1H) 7.61 (1H); MS (ESI) m/z 414 (M+H)$^+$.

Example 54

N'-[(2Z)-3-(2,2-difluoro-1,3-benzodioxol-5-yl)-5-methyl-1,3-thiazol-2(3H)-ylidene]-N-methyl-N-(3-methylbutyl)urea The titled compound was prepared as described in Example 40C substituting N,3-dimethylbutan-1-amine for propan-2-amine. $^1$H NMR (500 MHz, DMSO-$d_6$/$D_2O$) δ ppm 0.71-0.79 (6H) 1.23-1.30 (2H) 2.20 (3H) 2.80-2.84 (3H) 3.20-3.30 (2H) 6.94-6.97 (1H) 7.25-7.34 (1H) 7.41 (1H) 7.58 (1H); MS (ESI) m/z 398 (M+H)$^+$.

Example 55

N-butyl-N'-[(2Z)-3-(2,2-difluoro-1,3-benzodioxol-5-yl)-5-methyl-1,3-thiazol-2(3H)-ylidene]-N-ethylurea The titled compound was prepared as described in Example 40C substituting N-ethylbutan-1-amine for propan-2-amine. $^1$H NMR (500 MHz, DMSO-$d_6$/$D_2O$) δ ppm 0.78 (3H) 0.99 (3H) 1.08-1.26 (2H) 1.28-1.46 (2H) 2.20 (3H) 3.17-3.32 (4H) 6.94-7.00 (1H) 7.29 (1H) 7.41 (1H) 7.57 (1H); MS (ESI) m/z 398 (M+H)$^+$.

Example 56

N'-[(2Z)-3-(2,2-difluoro-1,3-benzodioxol-5-yl)-5-methyl-1,3-thiazol-2(3H)-ylidene]-N,N-dipropylurea The titled compound was prepared as described in Example 40C substituting dipropylamine for propan-2-amine. $^1$H NMR (500 MHz, DMSO-$d_6$/$D_2O$) δ ppm 0.73 (6H) 1.35-1.52 (4H) 2.20 (3H) 3.14-3.22 (4H) 6.91-7.00 (1H) 7.29 (1H) 7.42 (1H) 7.59 (1H); MS (ESI) m/z 398 (M+H)$^+$.

Example 57

N,N-dibutyl-N'-[(2Z)-3-(2,2-difluoro-1,3-benzodioxol-5-yl)-5-methyl-1,3-thiazol-2(3H)-ylidene]urea The titled compound was prepared as described in Example 40C substituting dibutylamine for propan-2-amine. $^1$H NMR (500 MHz, DMSO-$d_6$/$D_2O$) δ ppm 0.82 (t, 6H) 1.08-1.31 (m, 4H) 1.34-1.51 (m, 4H) 2.20-2.25 (m, 3H) 3.24 (t, 4H) 6.96-7.00 (m, 1H) 7.31 (dd, 1H) 7.43 (d, 1H) 7.59 (d, 1H); MS (ESI) m/z 426 (M+H)$^+$.

Example 58

N-[(2Z)-3-(2,2-difluoro-1,3-benzodioxol-5-yl)-5-methyl-1,3-thiazol-2(3H)-ylidene]-2,5-dimethylpyrrolidine-1-carboxamide The titled compound was prepared as described in Example 40C substituting 2,5-dimethylpyrrolidine for propan-2-amine. $^1$H NMR (500 MHz, DMSO-$d_6$/$D_2O$) δ ppm 1.11 (6H) 1.44-1.64 (2H) 1.80-1.97 (2H) 2.21 (3H) 3.76-3.99 (2H) 6.95-7.03 (1H) 7.32 (1H) 7.42 (1H) 7.61 (1H); MS (ESI) m/z 396 (M+H)$^+$.

Example 59

N-[(2Z)-3-(2,2-difluoro-1,3-benzodioxol-5-yl)-5-methyl-1,3-thiazol-2(3H)-ylidene]-2-methylpiperidine-1-carboxamide The titled compound was prepared as described in Example 40C substituting 2-methylpiperidine for propan-2-amine. $^1$H NMR (500 MHz, DMSO-$d_6$/$D_2O$) δ ppm 1.04 (3H) 1.12-1.63 (6H) 2.19 (3H) 2.77 (1H) 4.07 (1H) 4.46-4.62 (1H) 6.98 (1H) 7.34 (1H) 7.43 (1H) 7.58 (1H); MS (ESI) m/z 396 (M+H)$^+$.

Example 60

N'-[(2Z)-3-(2,2-difluoro-1,3-benzodioxol-5-yl)-5-methyl-1,3-thiazol-2(3H)-ylidene]-N-(2-methoxyethyl)-N-methylurea The titled compound was prepared as described in Example 40C substituting 2-methoxy-N-methylethanamine for propan-2-amine. $^1$H NMR (500 MHz, DMSO-$d_6$/$D_2O$) δ ppm 2.21 (3H) 2.86-2.90 (3H) 3.15-3.21 (3H) 3.33-3.46 (4H) 6.98 (1H) 7.33 (1H) 7.42 (1H) 7.60 (1H); MS (ESI) m/z 386 (M+H)$^+$.

Example 61

N-benzyl-N'-[(2Z)-3-(2,2-difluoro-1,3-benzodioxol-5-yl)-5-methyl-1,3-thiazol-2(3H)-ylidene]-N-ethylurea The titled compound was prepared as described in Example 40C substituting N-benzylethanamine for propan-2-amine. $^1$H NMR (500 MHz, DMSO-$d_6$/$D_2O$) δ ppm 0.96 (3H) 2.21 (3H) 3.30 (2H) 4.45-4.50 (2H) 6.96-7.01 (1H) 7.08-7.30 (6H) 7.34 (1H) 7.45-7.55 (1H); MS (ESI) m/z 432 (M+H)$^+$.

Example 62

N-benzyl-N'-[(2Z)-3-(2,2-difluoro-1,3-benzodioxol-5-yl)-5-methyl-1,3-thiazol-2(3H)-ylidene]-N-isopropylurea The titled compound was prepared as described in Example 40C substituting N-benzylpropan-2-amine for propan-2-amine. $^1$H NMR (500 MHz, DMSO-d$_6$/D$_2$O) δ ppm 1.02 (6H) 2.21 (3H) 4.30-4.41 (1H) 4.42-4.46 (2H) 6.90-7.01 (1H) 7.05 -7.32 (7H) 7.32-7.44 (1H); MS (ESI) m/z 446 (M+H)$^+$.

Example 63

N-benzyl-N-butyl-N'-[(2Z)-3-(2,2-difluoro-1,3-benzodioxol-5-yl)-5-methyl-1,3-thiazol-2(3H)-ylidene]urea The titled compound was prepared as described in Example 40C substituting N-benzylbutan-1-amine for propan-2-amine. $^1$H NMR (500 MHz, DMSO-d$_6$/D$_2$O) δ ppm 0.73 (3H) 1.02-1.20 (2H) 1.28-1.47 (2H) 2.22 (3H) 3.23 (2H) 4.44-4.52 (2H) 6.94-7.01 (1H) 7.08-7.29 (6H) 7.35 (1H) 7.45-7.56 (1H); MS (ESI) m/z 460 (M+H)$^+$.

Example 64

N-benzyl-N'-[(2Z)-3-(2,2-difluoro-1,3-benzodioxol-5-yl)-5-methyl-1,3-thiazol-2(3H)-ylidene]-N-(2-hydroxyethyl)urea The titled compound was prepared as described in Example 40C substituting 2-(benzylamino)ethanol for propan-2-amine. $^1$H NMR (500 MHz, DMSO-d$_6$/D$_2$O) δ ppm 2.21 (3H) 3.30-3.41 (2H) 3.42-3.52 (2H) 4.50-4.57 (2H) 6.96-7.02 (1H) 7.06-7.29 (6H) 7.34 (1H) 7.43-7.53 (1H); MS (ESI) m/z 448 (M+H)$^+$.

Example 65

N-[(2Z)-3-(2,2-difluoro-1,3-benzodioxol-5-yl)-5-methyl-1,3-thiazol-2(3H)-ylidene]-N'-(1,1,3,3-tetramethylbutyl)urea The titled compound was prepared as described in Example 40C substituting 2,4,4-trimethylpentan-2-amine for propan-2-amine. $^1$H NMR (500 MHz, DMSO-d$_6$/D$_2$O) δ ppm 0.88-0.95 (9H) 1.26-1.33 (6H) 1.64-1.72 (2H) 2.21 (3H) 6.89-6.97 (1H) 7.29 (1H) 7.42 (1H) 7.57 (1H); MS (ESI) m/z 426 (M+H)$^+$.

Example 66

N-[(2Z)-3-(2,2-difluoro-1,3-benzodioxol-5-yl)-5-methyl-1,3-thiazol-2(3H)-ylidene]-N'-[(1R)-2-hydroxy-1-phenylethyl]urea The titled compound was prepared as described in Example 40C substituting (R)-2-amino-2-phenylethanol for propan-2-amine. $^1$H NMR (500 MHz, DMSO-d$_6$/D$_2$O) δ ppm 2.18 (3H) 3.58-3.63 (2H) 4.75 (1H) 6.96 (1H) 7.12-7.32 (6H) 7.42 (1H) 7.51-7.65 (1H); MS (ESI) m/z 434 (M+H)$^+$.

Example 67

N-[(2Z)-3-(2,2-difluoro-1,3-benzodioxol-5-yl)-5-methyl-1,3-thiazol-2(3H)-ylidene]-N'-[(1S)-2-hydroxy-1-phenylethyl]urea The titled compound was prepared as described in Example 40C substituting (S)-2-amino-2-phenylethanol for propan-2-amine. $^1$H NMR (500 MHz, DMSO-d$_6$/D$_2$O) δ ppm 2.19 (3H) 3.57-3.65 (2H) 4.71 (1H) 6.96 (1H) 7.12-7.33 (6H) 7.41 (1H) 7.52-7.61 (1H); MS (ESI) m/z 434 (M+H)$^+$.

Example 68

N-[(2Z)-3-(2,2-difluoro-1,3-benzodioxol-5-yl)-5-methyl-1,3-thiazol-2(3H)-ylidene]-N'-[(1S)-1-phenylethyl]urea The titled compound was prepared as described in Example 40C substituting (S)-1-phenylethanamine for propan-2-amine. $^1$H NMR (500 MHz, DMSO-d$_6$/D$_2$O) δ ppm 1.35 (3H) 2.19 (3H) 4.81 (1H) 6.92 (1H) 7.09-7.30 (6H) 7.42 (1H) 7.53-7.59 (1H); MS (ESI) m/z 418 (M+H)$^+$.

Example 69

N-[(2Z)-3-(2,2-difluoro-1,3-benzodioxol-5-yl)-5-methyl-1,3-thiazol-2(3H)-ylidene]-N'-[(1R)-1-phenylethyl]urea The titled compound was prepared as described in Example 40C substituting (R)-1-phenylethanamine for propan-2-amine. $^1$H NMR (500 MHz, DMSO-d$_6$/D$_2$O) δ ppm 1.35 (3H) 2.17 (3H) 4.80 (1H) 6.92 (1H) 7.07-7.34 (6H) 7.39 (1H) 7.53-7.59 (1H); MS (ESI) m/z 418 (M+H)$^+$.

Example 70

N-benzyl-N-(tert-butyl)-N'-[(2Z)-3-(2,2-difluoro-1,3-benzodioxol-5-yl)-5-methyl-1,3-thiazol-2(3H)-ylidene]urea The titled compound was prepared as described in Example 40C substituting N-benzyl-2-methylpropan-2-amine for propan-2-amine. $^1$H NMR (500 MHz, DMSO-d$_6$/D$_2$O) δ ppm 1.33-1.35 (9H) 2.21 (3H) 4.62-4.66 (2H) 6.90-6.96 (1H) 7.02-7.22 (7H) 7.26-7.32 (1H); MS (ESI) m/z 460 (M+H)$^+$.

Example 71

N-benzyl-N'-[(2Z)-3-(2,2-difluoro-1,3-benzodioxol-5-yl)-5-methyl-1,3-thiazol-2(3H)-ylidene]-N-methylurea The titled compound was prepared as described in Example 40C substituting N-methyl-1-phenylmethanamine for propan-2-amine. $^1$H NMR (500 MHz, DMSO-d$_6$/D$_2$O) δ ppm 2.22 (3H) 2.85-2.87 (3H) 4.46-4.49 (2H) 6.99 (1H) 7.04-7.32 (6H) 7.35 (1H) 7.46-7.59 (1H); MS (ESI) m/z 418 (M+H)$^+$.

Example 72

N-benzyl-N-(2-cyanoethyl)-N'-[(2Z)-3-(2,2-difluoro-1,3-benzodioxol-5-yl)-5-methyl-1,3-thiazol-2(3H)-ylidene]urea The titled compound was prepared as described in Example 40C substituting 3-(benzylamino)propanenitrile for propan-2-amine. $^1$H NMR (500 MHz, DMSO-d$_6$/D$_2$O) δ ppm 2.23 (3H) 2.53-2.60 (2H) 3.51 (2H) 4.51-4.56 (2H) 7.02 (1H) 7.11-7.41 (7H) 7.47-7.54 (1H); MS (ESI) m/z 457 (M+H)$^+$.

Example 73

N-(3-chlorobenzyl)-N'-[(2Z)-3-(2,2-difluoro-1,3-benzodioxol-5-yl)-5-methyl-1,3-thiazol-2(3H)-ylidene]-N-methylurea The titled compound was prepared as described in Example 40C substituting 1-(3-chlorophenyl)-N-methylmethanamine for propan-2-amine. $^1$H NMR (500 MHz, DMSO-d$_6$/D$_2$O) δ ppm 2.22 (3H) 2.85-2.90 (3H) 4.43-4.50 (2H) 6.99 (1H) 7.04-7.15 (2H) 7.17-7.41 (4H) 7.47-7.55 (1H); MS (ESI) m/z 452 (M+H)$^+$.

Example 74

N'-[(2Z)-3-(2,2-difluoro-1,3-benzodioxol-5-yl)-5-methyl-1,3-thiazol-2(3H)-ylidene]-N-(2-methoxybenzyl)-N-methylurea The titled compound was prepared as described in Example 40C substituting 1-(2-methoxyphenyl)-N-methylmethanamine for propan-2-amine. $^1$H NMR (500 MHz, DMSO-d$_6$/D$_2$O) δ ppm 2.21 (3H) 2.82-2.89 (3H) 3.67-3.82 (3H) 4.43-4.53 (2H) 6.74-7.04 (4H) 7.12-7.39 (3H) 7.41-7.54 (1H); MS (ESI) m/z 448 (M+H)$^+$.

Example 75

N'-[(2Z)-3-(2,2-difluoro-1,3-benzodioxol-5-yl)-5-methyl-1,3-thiazol-2(3H)-ylidene]-N-(3-methoxybenzyl)-N-methylurea The titled compound was prepared as described in Example 40C substituting 1-(3-methoxyphenyl)-N-methylmethanamine for propan-2-amine. $^1$H NMR (500 MHz, DMSO-d$_6$/D$_2$O) δ ppm 2.22 (3H) 2.81-2.89 (3H) 3.65-3.74 (3H) 4.40-4.50 (2H) 6.62-6.83 (3H) 6.95-7.03 (1H) 7.16 (1H) 7.24-7.40 (2H) 7.47-7.56 (1H); MS (ESI) m/z 448 (M+H)$^+$.

Example 76

N-[(2Z)-3-(2,2-difluoro-1,3-benzodioxol-5-yl)-5-methyl-1,3-thiazol-2(3H)-ylidene]-1,3-dihydro-2H-isoindole-2-carboxamide The titled compound was prepared as described in Example 40C substituting isoindoline for propan-2-amine. $^1$H NMR (500 MHz, DMSO-D$_6$/D$_2$O) δ ppm 2.23 (3H) 4.61-4.65 (4H) 7.01-7.07 (1H) 7.19-7.30 (4H) 7.44-7.47 (2H) 7.65-7.71 (1H); MS (ESI) m/z 416 (M+H)$^+$.

Example 77

N-[(2Z)-3-(2,2-difluoro-1,3-benzodioxol-5-yl)-5-methyl-1,3-thiazol-2(3H)-ylidene]-3,4-dihydroisoquinoline-2(1H)-carboxamide The titled compound was prepared as described in Example 40C substituting 1,2,3,4-tetrahydroisoquinoline for propan-2-amine. $^1$H NMR (500 MHz, DMSO-d$_6$/D$_2$O) δ ppm 2.22 (3H) 2.75 (2H) 3.66 (2H) 4.54-4.62 (2H) 6.97-7.06 (1H) 7.08-7.17 (4H) 7.38 (1H) 7.47 (1H) 7.60-7.64 (1H); MS (ESI) m/z 430 (M+H)$^+$.

Example 78

N'-[(2Z)-3-(2,2-difluoro-1,3-benzodioxol-5-yl)-5-methyl-1,3-thiazol-2(3H)-ylidene]-N-ethyl-N-(pyridin-4-ylmethyl)urea The titled compound was prepared as described in Example 40C substituting N-(pyridin-4-ylmethyl)ethanamine for propan-2-amine. $^1$H NMR (500 MHz, DMSO-d$_6$/D$_2$O) δ ppm 1.00 (3H) 2.21 (3H) 3.38 (2H) 4.49-4.59 (2H) 6.94-7.02 (1H) 7.12-7.70 (5H) 8.47 (2H); MS (ESI) m/z 433 (M+H)$^+$.

Example 79

N-[(2Z)-3-(2,2-difluoro-1,3-benzodioxol-5-yl)-5-methyl-1,3-thiazol-2(3H)-ylidene]-N'-(1-phenylpropyl)urea The titled compound was prepared as described in Example 40C substituting 1-phenylpropan-1-amine for propan-2-amine. $^1$H NMR (500 MHz, DMSO-d$_6$/D$_2$O) δ ppm 0.80 (3H) 1.59-1.86 (2H) 2.18 (3H) 4.56 (1H) 6.87-7.01 (1H) 7.08-7.34 (6H) 7.41 (1H) 7.52-7.62 (1H); MS (ESI) m/z 432 (M+H)$^+$

Example 80

N-[(2Z)-3-(2,2-difluoro-1,3-benzodioxol-5-yl)-5-methyl-1,3-thiazol-2(3H)-ylidene]-N'-2,3-dihydro-1H-inden-1-ylurea The titled compound was prepared as described in Example 40C substituting 2,3-dihydro-1H-inden-1-amine for propan-2-amine. $^1$H NMR (500 MHz, DMSO-d$_6$/D$_2$O) δ ppm 1.75-1.95 (1H) 2.22 (3H) 2.26-2.45 (1H) 2.66-2.82 (1H) 2.84-2.99 (1H) 5.16 (1H) 6.97 (1H) 7.06-7.25 (4H) 7.31 (1H) 7.39 (1H) 7.61 (1H); MS (ESI) m/z 430 (M+H)$^+$.

Example 81

N-(5-fluoro-2-phenoxybenzyl)-N-methyl-N'-[(2Z)-5-methyl-3-(2,2,3,3-tetrafluoro-2,3-dihydro-1,4-benzodioxin-6-yl)-1,3-thiazol-2(3H)-ylidene]urea

Example 81A (Z)-3-Methyl-1-(5-methyl-3-(2,2,3,3-tetrafluoro-2,3-dihydrobenzo[b][1,4]dioxin-6-yl)thiazol-2(3H)-ylidenecarbamoyl)-1H-imidazol-3-ium iodide The imidazole-urea (Example 126, 6.78 g, 16 mmol) was suspended into acetonitrile (50 mL), treated with methyl iodide (4.0 mL, 64 mmol), and stirred at room temperature for five days. More methyl iodide (1.0 mL, 16 mmol) was added, and then the mixture was stirred overnight, concentrated, and dried under vacuum to a soft solid. This material was suspended into diethyl ether (30 mL), mixed thoroughly, filtered, rinsed with more diethyl ether (20 mL), and placed under vacuum to give the titled compound that was used without further purification.

Example 81B

N-(5-fluoro-2-phenoxybenzyl)-N-methyl-N'-[(2Z)-5-methyl-3-(2,2,3,3-tetrafluoro-2,3-dihydro-1,4-benzodioxin-6-yl)-1,3-thiazol-2(3H)-ylidene]urea To a solution of Example 81A (0.1 g, 0.18 mmol) and 1-(5-fluoro-2-phenoxyphenyl)-N-methylmethanamine (0.20 mmol) in anhydrous acetonitrile (3 mL) was added Hunig's base (0.025 g), and the solution was heated at 60° C. for 3 hours. After cooling to room temperature, the reaction mixture was diluted with 50 mL of CH$_2$Cl$_2$ and washed with water and brine, dried over sodium sulfate, and concentrated under reduced pressure. The crude residue was choromatographed over silica using CH$_2$Cl$_2$ to give the titled compound. $^1$H NMR (CD$_3$OD) δ ppm 2.25 (3H), 2.90 (3H), 4.60 (2H), 6.90-7.60 (12H); MS (ESI) 578 (M+H)$^+$.

Example 82

N-(2-chloro-6-fluorobenzyl)-N-ethyl-N'-[(2Z)-5-methyl-3-(2,2,3,3-tetrafluoro-2,3-dihydro-1,4-benzodioxin-6-yl)-1,3-thiazol-2(3H)-ylidene]urea The titled compound was obtained using the procedure described in Example 81B substituting N-(2-chloro-6-fluorobenzyl)ethanamine for 1-(5-fluoro-2-phenoxyphenyl)-N-methylmethanamine. $^1$H NMR (CD$_3$OD) δ ppm: 1.25 (3H), 2.30 (3H), 3.50 (2H), 4.50 (2H), 6.90-7.60 (7H); MS (ESI) m/z 534(M+H)$^+$.

Example 83

N-benzyl-N'-[(2Z)-5-methyl-3-(2,2,3,3-tetrafluoro-2,3-dihydro-1,4-benzodioxin-6-yl)-1,3-thiazol-2(3H)-ylidene]-N-prop-2-ynylurea The titled compound was obtained using the procedure described in Example 81B substituting N-benzylprop-2-yn-1-amine for 1-(5-fluoro-2-phenoxyphenyl)-N-methylmethanamine. $^1$H NMR (CD$_3$OD) δ ppm 2.25 (3H), 2.80 (1H), 4.05 (1H), 4.20 (1H), 4.65 (2H), 7.00-7.75 (9H); MS (ESI) m/z 492(M+H)$^-$.

Example 84

N-[4-(allyloxy)benzyl]-N-methyl-N'-[(2Z)-5-methyl-3-(2,2,3,3-tetrafluoro-2,3-dihydro-1,4-benzodioxin-6-yl)-1,3-thiazol-2(3H)-ylidene]urea The titled compound was obtained using the procedure described in Example 81B substituting 1-(4-(allyloxy)phenyl)-N-methylmethanamine for 1-(5-fluoro-2-phenoxyphenyl)-N-methylmethanamine. $^1$H NMR (CD$_3$OD) δ ppm 2.25 (3H), 2.90 (3H), 4.45 (4H), 5.20 (1H), 5.35 (1H), 6.00 (1H), 6.80-7.55 (8H); MS (ESI) m/z 524 (M+H)$^+$.

Example 85

N-[(2Z)-3-(2,2-difluoro-1,3-benzodioxol-5-yl)-5-formyl-1,3-thiazol-2(3H)-ylidene]pyrrolidine-1-carboxamide Example 25 (43 mg, 0.11 mmol) was dissolved into a mixture of acetonitrile (1.0 mL), CH$_2$Cl$_2$ (0.2 mL), and DMSO (0.1 mL), then treated with Dess-Martin reagent (64 mg, 0.15 mmol). After 7 hours, the mixture was diluted with water (3 mL) and extracted twice with 9:1 CH$_2$Cl$_2$/hexanes. The combined organic phases were washed with water, dried (Na$_2$SO$_4$), and concentrated. The crude sample was passed quickly through silica (2% MeOH/78% CH$_2$Cl$_2$/20% hexanes), and the filtrate was reconcentrated to give the titled compound. $^1$H NMR (300 MHz, DMSO-d$_6$) δ ppm 1.77 (4H), 3.26 (4H), 7.54 (1H), 7.62 (1H), 7.90 (1H), 8.65 (1H), 9.75 (1H); MS (ESI+) m/z 382 (M+H)$^+$.

Example 86

N-[(2Z)-3-(2,2-difluoro-1,3-benzodioxol-5-yl)-5-[(Z)-(hydroxyimino)methyl]-1,3-thiazol-2(3H)-ylidene]pyrrolidine-1-carboxamide Example 85 (41 mg, 0.10 mmol) and hydroxylamine hydrochloride (10 mg, 0.14 mmol) were suspended into EtOH (1.0 mL) and treated with triethylamine (20 µL, 0.14 mmol). The reaction mixture was stirred at room temperature for two days. Saturated aqueous NaHCO$_3$ (50 µL) was added, and the mixture was stirred several minutes. Then the solids were collected by filtration with a 10% water/EtOH rinse. The collection flask was changed, the solids were rinsed through the fritted funnel with 20% MeOH/CH$_2$Cl$_2$ (10 mL), and the filtrate was concentrated to give the titled compound that was used without further purification. MS (ESI+) m/z 397 (M+H)$^+$.

Example 87

N'-[(2Z)-3-(2,2-difluoro-1,3-benzodioxol-5-yl)-5-(hydroxymethyl)-1,3-thiazol-2(3H)-ylidene]-N,N-dimethylurea Example 6 (1.366 g, 4.0 mmol) was dissolved into anhydrous MeCN (40 mL) and treated with benzyltrimethylammonium tribromide (1.95 g, 5.00 mmol). After the mixture was stirred 5 minutes, powdered NaHSO$_3$ (520 mg, ~5 mmol, mixture with Na$_2$S$_2$O$_5$) was added, the suspension was stirred 31 minutes, ~2 M aqueous NaHSO$_3$ (400 µL) was added, the mixture was stirred another 5 minutes, and finally water (8 mL) was added. The mixture was stirred 40 minutes and then partitioned between CH$_2$Cl$_2$ (80 mL) and water (20 mL). The aqueous phase was separated and extracted with CH$_2$Cl$_2$. The combined organic phases were washed with brine, dried (Na$_2$SO$_4$), concentrated, and chromatographed on silica (2:2:2 to 3:1:2 to 4:0:2 EtOAc/CH$_2$Cl$_2$/hexanes) to give the titled compound. $^1$H NMR (300 MHz, CD$_3$OD) δ ppm 2.95 (6H), 4.57 (2H), 7.18 (1H), 7.32 (1H), 7.34 (1H), 7.55 (1H); MS (ESI+) 358 (M+H)$^+$.

Example 88

N'-[(2Z)-3-(2,2-difluoro-1,3-benzodioxol-5-yl)-5-(fluoromethyl)-1,3-thiazol-2(3H)-ylidene]-N,N-dimethylurea A solution of N'-[(2Z)-3-(2,2-difluoro-1,3-benzodioxol-5-yl)-5-(hydroxymethyl)-1,3-thiazol-2(3H)-ylidene]-N,N-dimethylurea (Example 87, 0.2 g, 0.56 mmol) in dry CH$_2$Cl$_2$ (10 mL) was treated with bis(2-methoxyethyl)aminosulfur trifluoride (0.148 g, 0.67 mmol). After 4 hours at room temperature, the mixture was neutralized by dropwise addition of a saturated solution of sodium bicarbonate. The mixture was washed with water and brine, dried over sodium sulfate, filtered and concentrated under reduced pressure. The residue was purified over silica using CH$_2$Cl$_2$ as mobile phase. $^1$H NMR (CDCl$_3$) δ ppm 3.00 (6H), 5.20 (1H), 5.38 (1H), 7.00 (1H), 7.30 (2H), 7.38 (1H); MS (ESI) 360 (M+H)$^+$.

Example 89

N'-[(2Z)-3-(2,2-difluoro-1,3-benzodioxol-5-yl)-5-formyl-1,3-thiazol-2(3H)-ylidene]-N,N-dimethylurea Example 87 (894 mg, 2.50 mmol) and Dess-Martin reagent (1.40 g, 3.30 mmol) were dissolved into a mixture of acetonitrile (20 mL), dichloromethane (5 mL), and DMSO (2 mL) and stirred at room temperature overnight. The suspension was thoroughly mixed with 9:1 CH$_2$Cl$_2$/hexanes (100 mL) and water (70 mL), and the pH of the aqueous phase was made basic with saturated aqueous NaHCO$_3$ (10 mL). The suspension was filtered through a glass-fritted funnel with a CH$_2$Cl$_2$ rinse. The aqueous phase was separated and extracted with CH$_2$Cl$_2$. Then the combined organic phases were washed with water, dried (Na$_2$SO$_4$), concentrated, mostly dissolved into MeOH/CH$_2$Cl$_2$ and refiltered, then partially concentrated before being filtered through silica (50% EtOAc/CH$_2$Cl$_2$). The filtrate was concentrated, and the resulting residue was mixed thoroughly with MeOH (7 mL), treated with 0.2 M K$_2$HPO$_4$ (3 mL), stirred, collected by filtration, rinsed with 30% water in MeOH, and dried under vacuum to give the titled compound. (NMR suggests part of the material is the hydrate of the aldehyde.) $^1$H NMR (300 MHz, CD$_3$OD) δ ppm 2.96 (6H), 7.40 (2H), 7.62 (1H), 8.33 (1H), 9.74 (1H); MS (ESI+) m/z 356 (M+H)$^-$.

Example 90

(3R)-3-fluoro-N-[(2Z)-5-methylene-3-(2,2,3,3-tetrafluoro-2,3-dihydro-1,4-benzodioxin-6-yl)-1,3-thiazolidin-2-ylidene]pyrrolidine-1-carboxamide Example 90A 3-methyl-1-(5-methylene-3-(2,2,3,3-tetrafluoro-2,3-dihydrobenzo[b][1,4]dioxin-6-yl)thiazolidin-2-ylidenecarbamoyl)-1H-imidazol-3-ium iodide Example 174 (4.365 g, 10.5 mmol) and iodomethane (2.6 mL, 42 mmol) were stirred in anhydrous MeCN (35 mL) at room temperature in a sealed flask. After four days, more iodomethane (0.66 mL, 10.6 mmol) was added. Stirring was continued at room temperature overnight, and the mixture was concentrated and mixed into more MeCN. Crystals formed, and the mixture was reconcentrated and slurried twice with Et$_2$O, which was decanted and removed, and then slurried with a mixture of Et$_2$O and a small quantity of MeCN, which was also removed by decantation. The solids were placed under vacuum to give the crude product, which was used without further purification.

Example 90B (3R)-3-fluoro-N-[(2Z)-5-methylene-3-(2,2,3,3-tetrafluoro-2,3-dihydro-1,4-benzodioxin-6-yl)-1,3-thiazolidin-2-ylidene]pyrrolidine-1-carboxamide Example 90A (if 70% pure, then 350 mg is 0.44 mmol) and (R)-3-fluoropyrrolidine.HCl (88 mg, 0.70 mmol) were mixed as a suspension in anhydrous CH$_2$Cl$_2$ (700 μL) and then treated with diisopropylethylamine (245 μL, 1.4 mmol). After 10 minutes, the resulting solution was quenched with pH 7 potassium phosphate buffer (1.4 mL) (aqueous phase now pH 8-9) and stirred thoroughly. The aqueous phase was separated and extracted with CH$_2$Cl$_2$. Then the combined organic phases were washed with more buffer solution, the aqueous phase was back extracted with CH$_2$Cl$_2$, and the again combined organic phases were dried (Na$_2$SO$_4$) and chromatographed on silica (20 to 30% EtOAc/hexanes) to give the titled compound. $^1$H NMR (500 MHz, CD$_2$Cl$_2$) δ ppm 1.99 (1H), 2.20 (1H), 3.44-3.61 (2H), 3.64-3.80 (2H), 4.67 (2H), 5.22 (1H), 5.27 (1H), 5.33 (1H), 7.19-7.22 (1H), 7.35-7.38 (1H), 7.55-7.60 (1H); MS (ESI+) m/z 436 (M+H)$^+$.

Example 91

(3S)-3-fluoro-N-[(2Z)-5-methylene-3-(2,2,3,3-tetrafluoro-2,3-dihydro-1,4-benzodioxin-6-yl)-1,3-thiazolidin-2-ylidene]pyrrolidine-1-carboxamide Example 90A (if 70% pure, then 350 mg is 0.44 mmol) and (S)-3-fluoropyrrolidine.HCl (88 mg, 0.70 mmol) were mixed as a suspension in anhydrous CH$_2$Cl$_2$ (700 μL) and then treated with diisopropylethylamine (245 μL, 1.4 mmol). After 10 minutes, the resulting solution was quenched with pH 7 potassium phosphate buffer (1.4 mL) (aqueous phase now pH 8-9) and stirred thoroughly. The aqueous phase was separated and extracted with CH$_2$Cl$_2$. Then the combined organic phases were washed with more buffer solution, the aqueous phase was back extracted with CH$_2$Cl$_2$, and the again combined organic phases were dried (Na$_2$SO$_4$) and chromatographed on silica (20 to 30% EtOAc/hexanes) to give the titled compound. $^1$H NMR (500 MHz, CD$_2$Cl$_2$) δ ppm 1.99 (1H), 2.20 (1H), 3.44-3.61 (2H), 3.64-3.80 (2H), 4.68 (2H), 5.22 (1H), 5.27 (1H), 5.32 (1H), 7.19-7.22 (1H), 7.35-7.38 (1H), 7.55-7.60 (1H); MS (ESI+) m/z 436 (M+H)$^+$.

Example 92

(3R)-3-fluoro-N-[(2Z)-5-(hydroxymethyl)-3-(2,2,3,3-tetrafluoro-2,3-dihydro-1,4-benzodioxin-6-yl)-1,3-thiazol-2(3H)-ylidene]pyrrolidine-1-carboxamide Crude Example 90B (157 mg, <0.36 mmol) was suspended into anhydrous MeCN (3.0 mL) and treated with benzyltrimethylammonium tribromide (168 mg, 0.43 mmol). After the mixture was stirred for 7 minutes, powdered NaHSO$_3$ (45 mg, ~0.43 mmol, mixture with Na$_2$S$_2$O$_5$) was added, and the mixture was stirred another 35 minutes. ~2 M NaHSO$_3$ (35 μL) was added, and the mixture was stirred another 5 minutes, and then water (600 μL) was added. The mixture was stirred 45 minutes and then partitioned between CH$_2$Cl$_2$ (6 mL) and water (1.5 mL). The aqueous phase was separated and extracted with CH$_2$Cl$_2$. The combined organic phases were washed with brine, dried (Na$_2$SO$_4$), concentrated and chromatographed on silica (2:2:2 to 3:1:2 to 4:0:2 EtOAc/CH$_2$Cl$_2$/hexanes) to give the titled compound. $^1$H NMR (400 MHz, DMSO-d$_6$) δ ppm 1.88-2.18 (2H), 3.25-3.67 (4H), 4.44 (2H), 5.28 (1H), 5.48 (1H), 7.42 (1H), 7.61-7.70 (2H), 7.88-7.89 (1H); MS (ESI+) m/z 452 (M+H)$^+$.

Example 93

(3S)-3-fluoro-N-[(2Z)-5-(hydroxymethyl)-3-(2,2,3,3-tetrafluoro-2,3-dihydro-1,4-benzodioxin-6-yl)-1,3-thiazol-2(3H)-ylidene]pyrrolidine-1-carboxamide Crude Example 91 (157 mg, <0.36 mmol) was suspended into anhydrous MeCN (3.0 mL) and treated with benzyltrimethylammonium tribromide (168 mg, 0.43 mmol). After the mixture was stirred for 7 minutes, powdered NaHSO$_3$ (45 mg, ~0.43 mmol, mixture with Na$_2$S$_2$O$_5$) was added, the mixture was stirred another 35 minutes, ~2 M NaHSO$_3$ (35 μL) was added, the mixture was stirred another 5 minutes, and water (600 μL) was added. The mixture was stirred 45 minutes and then partitioned between CH$_2$Cl$_2$ (6 mL) and water (1.5 mL). The aqueous phase was separated and extracted with CH$_2$Cl$_2$. The combined organic phases were washed with brine, dried (Na$_2$SO$_4$), concentrated and chromatographed on silica (2:2:2 to 3:1:2 to 4:0:2 EtOAc/CH$_2$Cl$_2$/hexanes) to give the titled compound. $^1$H NMR (400 MHz, DMSO-d$_6$) δ ppm 1.90-2.19 (2H), 3.26-3.68 (4H), 4.46 (2H), 5.29 (1H), 5.49 (1H), 7.43 (1H), 7.61-7.72 (2H), 7.88-7.90 (1H); MS (ESI+) m/z 452 (M+H)$^+$.

Example 94

N-[4-(difluoromethoxy)benzyl]-N-methyl-N'-[(2Z)-5-methyl-3-(2,2,3,3-tetrafluoro-2,3-dihydro-1,4-benzodioxin-6-yl)-1,3-thiazol-2(3H)-ylidene]urea The titled compound was obtained using the procedure described in Example 81B substituting 1-(4-(difluoromethoxy)phenyl)-N-methylmethanamine for 1-(5-fluoro-2-phenoxyphenyl)-N-methylmethanamine. $^1$H NMR (CD$_3$OD) δ ppm 2.20 (3H), 2.90 (3H), 4.55 (2H), 6.24-7.60 (9H); MS (ESI) m/z 534 (M+H)$^+$.

Example 95

N-[1-(4-ethoxyphenyl)ethyl]-N-methyl-N'-[(2Z)-5-methyl-3-(2,2,3,3-tetrafluoro-2,3-dihydro-1,4-benzodioxin-6-yl)-1,3-thiazol-2(3H)-ylidene]urea The titled compound was obtained using the procedure described in Example 81B substituting 1-(4-ethoxyphenyl)-N-methylethanamine for 1-(5-fluoro-2-phenoxyphenyl)-N-methylmethanamine. $^1$H NMR (CD$_3$OD) δ ppm 1.40 (6H), 2.20 (3H), 2.80 (3H), 4.00 (2H), 5.65 (1H), 6.80-7.60 (8H); MS (ESI) m/z 526 (M+H)$^+$.

Example 96

N-methyl-N-[(6-methylpyridin-2-yl)methyl]-N'-[(2Z)-5-methyl-3-(2,2,3,3-tetrafluoro-2,3-dihydro-1,4-benzodioxin-6-yl)-1,3-thiazol-2(3H)-ylidene]urea The titled compound was obtained using the procedure described in Example 81B substituting N-methyl-1-(6-methylpyridin-2-yl)methanamine for 1-(5-fluoro-2-phenoxyphenyl)-N-methylmethanamine. $^1$H NMR (CD$_3$OD) δ ppm 2.20 (3H), 2.75 (3H), 3.05 (3H), 4.50 (2H), 6.95-7.70 (6H), 8.20 (1H); MS (ESI) m/z 483 (M+H)$^+$.

Example 97

N-benzyl-N-but-2-ynyl-N'-[(2Z)-5-methyl-3-(2,2,3,3-tetrafluoro-2,3-dihydro-1,4-benzodioxin-6-yl)-1,3-thiazol-2(3H)-ylidene]urea A solution of (Z)-3-methyl-1-(5-methyl-3-(2,2,3,3-tetrafluoro-2,3-dihydrobenzo[b][1,4]dioxin-6-yl)thiazol-2(3H)-ylidenecarbamoyl)-1H-imidazol-3-ium iodide (Example 81A, 0.75 mL of 0.14 M in acetonitrile, 58 mg, 0.1 mmol) was added to a 20 mL vial followed by N,N-diisopropylethylamine (0.75 mL of 0.14 M in acetonitrile, 18 mg, 0.13 mmol). Subsequently, N-benzylbut-2-yn-1-amine (0.57 mL of 0.2 M in acetonitrile, 0.11 mmol) was added. The resulting mixture was shaken at room temperature overnight. It was then concentrated in vacuo and the residue was taken up in 1:1 MeOH/DMSO and purified by reverse phase HPLC (acetonitrile/water 0.1% TFA gradient elution method). $^1$H NMR (500 MHz, DMSO-d$_6$/D$_2$O) δ ppm 1.75 (3H) 2.24 (3H) 4.05 (2H) 4.55 (2H) 7.01-7.10 (1H) 7.17-7.29 (4H) 7.29-7.35 (1H) 7.40-7.54 (1H) 7.58-7.63 (1H) 7.66-7.94 (1H); MS (ESI+) m/z 506 (M+H)$^+$.

Example 99

N-(1-methyl-1-phenylethyl)-N'-[(2Z)-5-methyl-3-(2,2,3,3-tetrafluoro-2,3-dihydro-1,4-benzodioxin-6-yl)-1,3-thiazol-2(3H)-ylidene]urea The titled compound was prepared as described in Example 97 substituting 2-phenylpropan-2-amine for N-benzylbut-2-yn-1-amine. $^1$H NMR (300 MHz, DMSO-d$_6$/D$_2$O) δ ppm 1.55-1.63 (6H) 2.19 (3H) 6.95-7.00 (1H) 7.12-7.19 (1H) 7.21-7.29 (2H) 7.30-7.36 (2H) 7.43-7.51 (2H) 7.58-7.63 (1H); MS (ESI+) m/z 482 (M+H)$^+$.

Example 100

N-(2-chlorobenzyl)-N-methyl-N'-[(2Z)-5-methyl-3-(2,2,3,3-tetrafluoro-2,3-dihydro-1,4-benzodioxin-6-yl)-1,3-thiazol-2(3H)-ylidene]urea The titled compound was prepared as described in Example 97 substituting 1-(2-chlorophenyl)-N-methylmethanamine for N-benzylbut-2-yn-1-amine. $^1$H NMR (300 MHz, DMSO-d$_6$/D$_2$O) δ ppm 2.22-2.27 (3H) 2.95 (3H) 4.62 (2H) 7.03-7.08 (1H) 7.09-7.17 (1H) 7.23-7.30 (2H) 7.34-7.44 (3H) 7.51-7.59 (1H); MS (ESI+) m/z 502 (M+H)$^+$.

Example 101

N-methyl-N'-[(2Z)-5-methyl-3-(2,2,3,3-tetrafluoro-2,3-dihydro-1,4-benzodioxin-6-yl)-1,3-thiazol-2(3H)-ylidene]-N-(thien-2-ylmethyl)urea The titled compound was prepared as described in Example 97 substituting N-methyl-1-(thiophen-2-yl)methanamine for N-benzylbut-2-yn-1-amine. $^1$H NMR (300 MHz, DMSO-d$_6$/D$_2$O) δ ppm 2.03-2.09 (3H) 2.71 (3H) 4.47 (2H) 6.64-6.70 (1H) 6.71-6.77 (1H) 6.85-6.93 (1H) 7.04-7.13 (1H) 7.22-7.40 (2H) 7.46-7.54 (1H); MS (ESI-) m/z 472 (M-H)$^-$.

Example 102

N-(4-chlorobenzyl)-N-methyl-N'-[(2Z)-5-methyl-3-(2,2,3,3-tetrafluoro-2,3-dihydro-1,4-benzodioxin-6-yl)-1,3-thiazol-2(3H)-ylidene]urea The titled compound was prepared as described in Example 97 substituting 1-(4-chlorophenyl)-N-methylmethanamine for N-benzylbut-2-yn-1-amine. $^1$H NMR (300 MHz, DMSO-d$_6$/D$_2$O) δ ppm 2.21-2.29 (3H) 2.87 (3H) 4.50 (2H) 7.04-7.09 (1H) 7.10-7.19 (2H) 7.26-7.34 (2H) 7.41-7.52 (2H) 7.61-7.67 (1H); MS (ESI+) m/z 502 (M+H)$^+$.

Example 103

N-(3-chlorobenzyl)-N-methyl-N'-[(2Z)-5-methyl-3-(2,2,3,3-tetrafluoro-2,3-dihydro-1,4-benzodioxin-6-yl)-1,3-thiazol-2(3H)-ylidene]urea The titled compound was prepared as described in Example 97 substituting 1-(3-chlorophenyl)-N-methylmethanamine for N-benzylbut-2-yn-1-amine. $^1$H NMR (300 MHz, DMSO-d$_6$/D$_2$O) δ ppm 2.24-2.28 (3H) 2.91 (3H) 4.50 (2H) 7.05-7.19 (3H) 7.21-7.35 (2H) 7.43-7.51 (2H) 7.61-7.67 (1H); MS (ESI-) m/z 500 (M-H)$^-$.

Example 104

N-[1-(methoxymethyl)propyl]-N'-[(2Z)-5-methyl-3-(2,2,3,3-tetrafluoro-2,3-dihydro-1,4-benzodioxin-6-yl)-1,3-thiazol-2(3H)-ylidene]urea The titled compound was prepared as described in Example 97 substituting 1-methoxybutan-2-amine for N-benzylbut-2-yn-1-amine. $^1$H NMR (300 MHz, DMSO-d$_6$/D$_2$O) δ ppm 0.85 (3H) 1.33-1.61 (2H) 2.20-2.27 (3H) 3.25 (3H) 3.27-3.42 (2H) 3.62-3.75 (1H) 6.99-7.07 (1H) 7.47-7.57 (2H) 7.68-7.74 (1H); MS (ESI+) m/z 450 (M+H)$^+$.

Example 105

N-cyclopentyl-N-(4-fluorobenzyl)-N'-[(2Z)-5-methyl-3-(2,2,3,3-tetrafluoro-2,3-dihydro-1,4-benzodioxin-6-yl)-1,3-thiazol-2(3H)-ylidene]urea The titled compound was prepared as described in Example 97 substituting N-(4-fluorobenzyl)cyclopentanamine for N-benzylbut-2-yn-1-amine. $^1$H NMR (300 MHz, DMSO-d$_6$/D$_2$O) δ ppm 1.35-1.71 (8H) 2.22-2.27 (3H) 4.42-4.51 (3H) 6.94-7.07 (3H) 7.11-7.20 (2H) 7.33-7.44 (2H) 7.55-7.61 (1H); MS (ESI+) m/z 540 (M+H)$^+$.

Example 106

N-[(1S)-2-hydroxy-1-pheniylethyl]-N'-[(2Z)-5-methyl-3-(2,2,3,3-tetrafluoro-2,3-dihydro-1,4-benzodioxin-6-yl)-1,3-thiazol-2(3H)-ylidene]urea The titled compound was prepared as described in Example 97 substituting (S)-2-amino-2-phenylethanol for N-benzylbut-2-yn-1-amine. $^1$H NMR (300 MHz, DMSO-d$_6$/D$_2$O) δ ppm 2.50-2.58 (3H) 3.94-4.01 (2H) 5.09 (1H) 7.31-7.38 (1H) 7.48-7.57 (1H) 7.57-7.66 (4H) 7.77-7.87 (2H) 7.96-8.03 (1H); MS (ESI+) m/z 484 (M+H)$^+$.

Example 107

N-[(2Z)-5-methyl-3-(2,2,3,3-tetrafluoro-2,3-dihydro-1,4-benzodioxin-6-yl)-1,3-thiazol-2(3H)-ylidene]-N'-[(1R)-1-phenylethyl]urea The titled compound was prepared as described in Example 97 substituting (R)-1-phenylethanamine for N-benzylbut-2-yn-1-amine. $^1$H NMR (300 MHz, DMSO-d$_6$/D$_2$O) δ ppm 1.40 (3H) 2.20-2.24 (3H) 4.84 (1H) 6.94-7.04 (1H) 7.15-7.24 (1H) 7.25-7.33 (4H) 7.43-7.56 (2H) 7.65-7.70 (1H); MS (ESI+) m/z 468 (M+H)$^+$.

Example 108

N-[(2Z)-5-methyl-3-(2,2,3,3-tetrafluoro-2,3-dihydro-1,4-benzodioxin-6-yl)-1,3-thiazol-2(3H)-ylidene]-N'-[(1S)-1-phenylethyl]urea The titled compound was prepared as described in Example 97 substituting (S)-1-phenylethanamine for N-benzylbut-2-yn-1-amine. $^1$H NMR (300 MHz, DMSO-d$_6$/D$_2$O) δ ppm 1.39 (3H) 2.19-2.24 (3H) 4.85 (1H) 6.96-7.04 (1H) 7.15-7.24 (1H) 7.24-7.32 (4H) 7.47-7.54 (2H) 7.63-7.71 (1H); MS (ESI+) m/z 468 (M+H)$^+$.

Example 109

(3R)-3-hydroxy-N-[(2Z)-5-methyl-3-(2,2,3,3-tetrafluoro-2,3-dihydro-1,4-benzodioxin-6-yl)-1,3-thiazol-2(3H)-ylidene]pyrrolidine-1-carboxamide The titled compound was prepared as described in Example 97 substituting (R)-pyrrolidin-3-ol for N-benzylbut-2-yn-1-amine. $^1$H NMR (300 MHz, DMSO-d$_6$/D$_2$O) δ ppm 1.70-1.85 (1H) 1.86-2.00 (1H) 2.20-2.26 (3H) 3.20-3.29 (1H) 3.36-3.48 (3H) 4.23-4.32 (1H) 7.05-7.11 (1H) 7.52 (1H) 7.61 (1H) 7.75-7.80 (1H); MS (ESI-) m/z 432 (M-H)$^-$.

Example 110

N-methyl-N-[(1-methyl-1H-pyrazol-4-yl)methyl]-N'-[(2Z)-5-methyl-3-(2,2,3,3-tetrafluoro-2,3-dihydro-1,4-benzodioxin-6-yl)-1,3-thiazol-2(3H)-ylidene]urea The titled compound was prepared as described in Example 97 substituting N-methyl-1-(1-methyl-1H-pyrazol-4-yl)methanamine for N-benzylbut-2-yn-1-amine. $^1$H NMR (300 MHz, DMSO-d$_6$/D$_2$O) δ ppm 2.44-2.55 (3H) 3.06-3.18 (3H) 3.96-4.08 (3H) 4.52-4.65 (2H) 7.26-7.36 (1H) 7.38-7.47 (1H) 7.56-7.64 (1H) 7.69-7.83 (2H) 7.92-8.02 (1H); MS (ESI+) m/z 472 (M+H)$^+$.

Example 111

N-methyl-N'-[(2Z)-5-methyl-3-(2,2,3,3-tetrafluoro-2,3-dihydro-1,4-benzodioxin-6-yl)-1,3-thiazol-2(3H)-ylidene]-N-(pyrazin-2-ylmethyl)urea The titled compound was prepared as described in Example 97 substituting N-methyl-1-(pyrazin-2-yl)methanamine for N-benzylbut-2-yn-1-amine. $^1$H NMR (300 MHz, DMSO-d$_6$/D$_2$O) δ ppm 2.21-2.28 (3H) 3.00 (3H) 4.65 (2H) 7.01-7.11 (1H) 7.39-7.50 (2H) 7.56-7.66 (1H) 8.27-8.39 (1H) 8.42-8.48 (1H) 8.48-8.53 (1H); MS (ESI+) m/z 470 (M+H)$^+$.

Example 112

N-[(2Z)-5-(methoxymethyl)-3-(2,2,3,3-tetrafluoro-2,3-dihydro-1,4-benzodioxin-6-yl)-1,3-thiazol-2(3H)-ylidene]pyrrolidine-1-carboxamide Example 22D (28 mg, 67 μmol) was dissolved into CH$_2$Cl$_2$ (500 μL) and MeCN (1.0 mL), treated with CuBr$_2$ (30 mg, 134 μmol). After stirring for half an hour, more CuBr$_2$ (30 mg) was added. More CuBr$_2$ (30 mg) was also added after 70 minutes. At 90 minutes, DMF (31 μL, 400 μmol) was added, and at 2½ hrs, MeOH (500 μL) was added. After 15 minutes more, the mixture was concentrated and partitioned between CH$_2$Cl$_2$ (10 mL) and concentrated aqueous NH$_4$OH (5 mL). The aqueous phase was separated and extracted with more CH$_2$Cl$_2$, and the combined organic phases were washed with concentrated aqueous NH$_4$OH, dried (Na$_2$SO$_4$), concentrated, and chromatographed on silica (2:1 hexanes/EtOAc) to give the titled compound. $^1$H NMR (400 MHz, CDCl$_3$) δ ppm 1.85 (4H), 3.38 (2H), 3.49 (2H), 4.40 (2H), 7.23 (1H), 7.38 (1H), 7.49 (1H); MS (ESI+) m/z 448 (M+H)$^+$.

Example 113

N-[(2Z)-5-(ethoxymethyl)-3-(2,2,3,3-tetrafluoro-2,3-dihydro-1,4-benzodioxin-6-yl)-1,3-thiazol-2(3H)-ylidene]pyrrolidine-1-carboxamide Example 22D (28 mg, 67 μmol) was dissolved into CH$_2$Cl$_2$ (500 μL) and then diluted with acetonitrile (1.0 mL) and treated with CuBr$_2$ (30 mg, 134 μmol). After 40 minutes, EtOH (200 μL) was added. After 30 minutes more, the mixture was concentrated and partitioned between CH$_2$Cl$_2$ (10 mL) and concentrated aqueous NH$_4$OH (3 mL). The aqueous phase was separated and extracted with more CH$_2$Cl$_2$ (2 mL). The combined organic phases were washed with concentrated aqueous NH$_4$OH (2 mL), dried (Na$_2$SO$_4$), concentrated, and chromatographed on silica (2:1 hexanes/EtOAc) to give the titled compound. $^1$H NMR (500 MHz, CDCl$_3$) δ ppm 1.24 (3H), 1.85 (4H), 3.44 (4H), 3.58 (2H), 4.45 (2H), 6.88 (1H), 7.23 (1H), 7.38 (1H), 7.49 (1H); MS (ESI+) m/z 462 (M+H)$^+$.

Example 114

N-[(2Z)-3-(2,2-difluoro-1,3-benzodioxol-5-yl)-5-methylene-1,3-thiazolidin-2-ylidene]-1H-imidazole-1-carboxamide A mixture of 3-(2,2-difluorobenzo[d][1,3]dioxol-5-yl)5-methylenethiazolidin-2-imine (Example 115, 0.2 g, 0.74 mmol) and carbonyldiimidazole (0.14 g, 0.92 mmol) in dry acetonitrile (5 mL) was stirred at 70° C. for 16 hours. After cooling down, the mixture was diluted with 150 mL of CH$_2$Cl$_2$ and washed successively with saturated sodium bicarbonate (75 mL), water (75 mL) and brine (75 mL). The organic phase was dried over sodium sulfate, filtered and evaporated under reduced pressure. The residue was chromatographed over silica using 100% CH$_2$Cl$_2$ to CH$_2$Cl$_2$:MeOH 95:5 as mobile phase to give the titled compound. $^1$H NMR (CD$_3$OD) δ ppm 5.00 (2H), 5.40 (1H), 5.50 (1H), 6.90 (1H), 7.35 (2H), 7.44 (1H), 7.50 (1H), 8.05 (1H); MS (ESI) m/z 365(M+H)$^+$.

Example 115

3-(2,2-difluoro-1,3-benzodioxol-5-yl)-5-methylene-1,3-thiazolidin-2-imine

The acetyl-imine (Example 5, 9.37 g, 30.0 mmol) and methylboronic acid (1.796 g, 30.0 mmol) were dissolved into acetic acid (75 mL) and treated with NaBO$_3$ (~2.45 g, 30.0 mmol). After 40 minutes, more NaBO$_3$ (~2.45 g, 30.0 mmol) was added while the reaction vessel was in a water bath. More NaBO$_3$ (2.45+g, 30.0 mmol) was added after a total of 80 minutes and again at 120 minutes (600 mg, 7.3 mmol). The mixture was stirred at room temperature overnight, transferred to a larger flask with an EtOAc rinse, and concentrated three times from toluene. The residue was mixed with water and basified with concentrated aqueous NH$_4$OH, and then partitioned into 2:1 EtOAc/hexanes (150 mL). The aqueous phase was separated and extracted three times with more 2:1 EtOAc/hexanes. The combined organic phases were washed with a mixture of water (30 mL), concentrated aqueous NH$_4$OH (5 mL) and brine (5 mL), then dried (Na2SO4), concentrated, and chromatographed on silica (15 to 30 to 50% EtOAc/hexanes) to give the titled compound. $^1$H NMR (400 MHz, CD$_3$OD) δ ppm 4.77 (2H), 5.16 (1H), 5.32 (1H), 7.19 (1H), 7.23 (1H), 7.46 (1H); MS (ESI) 271 (M+H)$^+$.

Example 116

1-({[(2Z)-3-(2,2-difluoro-1,3-benzodioxol-5-yl)-5-methylene-1,3-thiazolidin-2-ylidene]amino}carbonyl)-3-methyl-1H-imidazol-3-ium iodide A solution of N-[(2Z)-3-(2,2-difluoro-1,3-benzodioxol-5-yl)-5-methylene-1,3-thiazolidin-2-ylidene]-1H-imidazole-1-carboxamide (Example 114, 0.5 g, 1.37 mmol) and idomethane (0.97 g, 6.8 mmol) in dry acetonitrile (10 mL) was stirred at room temperature for four days after which the solvent was evaporated leaving a solid residue.

Example 117

N-[(2Z)-3-(2,2-difluoro-1,3-benzodioxol-5-yl)-5-methylene-1,3-thiazolidin-2-ylidene]-2-methylpyrrolidine-1-carboxamide To a solution of 1-({[(2Z)-3-(2,2-difluoro-1,3-benzodioxol-5-yl)-5-methylene-1,3-thiazolidin-2-ylidene]amino}carbonyl)-3-methyl-1H-imidazol-3-ium iodide (Example 116, 0.1 g, 0.19 mmol) and 2-methylpyrrolidine (0.018 g, 0.19 mmol) in anhydrous acetonitrile (5 mL) was added Hunig's base (0.025 g), and then the solution was heated at 60° C. for 3 hours. After cooling to room temperature, the reaction was diluted with 50 mL of CH$_2$Cl$_2$, washed water and brine, dried over sodium sulfate, and evaporated under reduced pressure. The crude residue was choromatographed over silica using CH$_2$Cl$_2$ to give the titled compound. $^1$H NMR (CD$_3$OD) δ ppm 1.00 (3H), 1.60 (1H), 1.90 (3H), 3.40 (2H), 3.90 (1H), 4.80 (2H), 5.20 (1H), 5.35 (1H), 7.30 (2H), 7.50 (1H); MS (ESI) 382(M+H)$^+$.

Example 118

N-[(2Z)-3-(2,2-difluoro-1,3-benzodioxol-5-yl)-5-methylene-1,3-thiazolidin-2-ylidene]pyrrolidine-1-carboxamide Impure Example 115 (5.63 g, ~20.8 mmol) was dissolved into CH$_2$Cl$_2$ (400 mL) and cooled to -~78° C. The solution was treated rapidly (over ~7 seconds) with ~20% phosgene in toluene (16.4 mL, ~31.2 mmol), stirred 5 minutes, and then further treated with diisopropylethylamine (~7.25 mL, 41.6 mmol). The resultant mixture was stirred for about 15 minutes at -~78° C., treated with pyrrolidine (~5.21 mL, 62.4 mmol), and stirred several minutes before the flask was removed from the cold bath and permitted to warm to near room temperature. Then the mixture was quenched with concentrated aqueous NH$_4$OH (40 mL) and stirred well. The aqueous phase was separated and extracted with CH$_2$Cl$_2$, and the combined organic phases were washed with water (40 mL), dried (Na$_2$SO$_4$), and concentrated. The residue was slurried in 2:1 hexanes/CH$_2$Cl$_2$ (100 mL) and sonicated. The solids were collected by filtration and rinsed with more 2:1 solution. The filtrate was concentrated and three additional lots of material were collected in a similar fashion. The lots were dried under vacuum and combined to give the title compound. $^1$H NMR (500 MHz, CD$_2$Cl$_2$) δ ppm 1.82 (4H), 3.36 (4H), 4.65 (2H), 5.24 (1H), 5.30 (1H), 7.11 (1H), 7.13 (1H), 7.52 (1H); MS (ESI+) m/z 368 (M+H)$^+$.

Example 119

N-[(2Z)-4-amino-3-(2,2-difluoro-1,3-benzodioxol-5-yl)-5-methylene-1,3-thiazolidin-2-ylidene]pyrrolidine-1-carboxamide Example 118 (~18.5 mg, 50 μmol) was dissolved into a mixture of CH$_2$Cl$_2$ (400 μL) and MeCN (800 μL), then treated with CuBr$_2$ (17 mg, 76 μmol). The solution was stirred for 5 minutes, then further treated with water (18 μL, 1.0 mmol). After more than 20 minutes, the mixture was quenched with concentrated aqueous NH$_4$OH (2 mL) and diluted with CH$_2$Cl$_2$ (5 mL), then stirred overnight. The aqueous phase was separated and extracted with CH$_2$Cl$_2$. Then the combined organic phases were washed with more concentrated aqueous NH$_4$OH, dried (Na$_2$SO$_4$), and chromatographed on silica (3:1 to 2:1 to 1:1 to 1:2 hexanes/EtOAc) to give the titled compound. $^1$H NMR (400 MHz, CD$_2$Cl$_2$) δ ppm 1.78 (4H), 1.94 (2H), 3.21 (2H), 3.34 (2H), 5.36 (1H), 5.47 (1H), 5.58 (1H), 7.09 (1H), 7.14 (1H), 7.22 (1H); MS (APCI) m/z 383 (M+H)$^+$.

Example 120

N-[(2Z)-3-(2,2-difluoro-1,3-benzodioxol-5-yl)-5-(hydroxymethyl)-1,3-thiazol-2(3H)-ylidene]pyrrolidine-1-carboxamide Example 118 (5.26 g, 14.3 mmol) was suspended into a mixture of anhydrous MeCN (175 mL) and anhydrous DMF (25 mL) and sonicated to get most of the material into solution. While the solution was being well-stirred, benzyltrimethylammonium tribromide (6.71 g, 17.2 mmol) was added over less than a minute. After 5 minutes from the beginning of the tribromide addition, powdered NaHSO$_3$ (1.79 g, ~17.2 mmol, a mixture with Na$_2$S$_2$O$_5$) was added portionwise with swirling, intermittent swirling of the thick suspension was continued for 15 minutes, and the mixture was stirred overnight. Then ~2 M aqueous NaHSO$_3$ (1.4 mL) was added and the suspension was stirred for 21 minutes before water (30 mL) was added dropwise over 15 minutes. The mixture was then stirred for another hour and fifteen minutes and partitioned between 5:1 CH$_2$Cl$_2$/hexanes (300 mL) and water (75 mL). The aqueous phase was separated and extracted with more 5:1 solution. Then the combined organic phases were washed with water, and this aqueous phase was also separated and extracted with 5:1 solution (30 mL). The combined organic phases were washed with 2:1 water/brine, dried (Na$_2$SO$_4$), concentrated, and the residue slurried in 9:1 CH$_2$Cl$_2$/hexanes. The solids were collected by filtration and rinsed with more 9:1 solution. Collection flasks were exchanged and the purified material was slowly rinsed through with 10% MeOH/CH$_2$Cl$_2$. This filtrate was concentrated and dried under high vacuum to give the titled compound. $^1$H NMR (300 MHz, DMSO-d$_6$) δ ppm 1.76 (4H), 3.28 (4H), 4.44 (2H), 5.41 (1H), 7.31 (1H), 7.43 (1H), 7.54 (1H), 7.81 (1H); MS (ESI+) m/z 384 (M+H)+.

Example 121

N-[(2Z)-3-(2,2-difluoro-1,3-benzodioxol-5-yl)-5-(ethoxymethyl)-1,3-thiazol-2(3H)-ylidene]pyrrolidine-1-carboxamide Example 118 (~18.5 mg, 50 µmol) was dissolved into a mixture of $CH_2Cl_2$ (400 µL) and MeCN (800 µL), then treated with $CuBr_2$ (17 mg, 76 µmol). The solution was stirred for 5 minutes, then further treated with ethanol (59 µL, 1.0 mmol). After more than 20 minutes, the mixture was quenched with concentrated aqueous $NH_4OH$ (2 mL) and diluted with $CH_2Cl_2$ (5 mL). The aqueous phase was separated and extracted with $CH_2Cl_2$. Then the combined organic phases were washed with more concentrated aqueous $NH_4OH$, and dried ($Na_2SO_4$), concentrated, and chromatographed on silica (3:1 to 2:1 to 1:1 to 1:2 hexanes/EtOAc) to give the titled compound. $^1$H NMR (400 MHz, $CDCl_3$) δ ppm 1.23 (3H), 1.84 (4H), 3.35 (2H), 3.48 (2H), 3.57 (2H), 4.44 (2H), 6.85 (1H), 7.12 (1H), 7.17 (1H), 7.40 (1H); MS (ESI+) m/z 412 (M+H)+.

Example 122

N-[(2Z)-3-(2,2-difluoro-1,3-benzodioxol-5-yl)-5-{[(4-fluorophenyl)amino]methyl}-1,3-thiazol-2(3H)-ylidene]pyrrolidine-1-carboxamide Example 118 (18 mg, 50 µmol) was dissolved into 2:1 MeCN/$CH_2Cl_2$ (1.0 mL) and treated with $CuBr_2$ (22 mg, 100 µmol). After being stirred for at least 5 minutes at room temperature, the solution was further treated with 4-fluoroaniline (~14.4 µl, 0.15 mmol). The mixture was stirred another 20-25 minutes before being partitioned between concentrated aqueous $NH_4OH$ (3 mL) and $CH_2Cl_2$ (10 mL). The aqueous phase was separated and extracted with $CH_2Cl_2$, and the combined organic phases were washed with concentrated aqueous $NH_4OH$, dried ($Na_2SO_4$), concentrated, and chromatographed on silica (1:3 to 1:2 to 1:1 EtOAc/hexanes) to give the titled compound. $^1$H NMR (400 MHz, $CDCl_3$) δ ppm 1.83 (4H), 3.35 (2H), 3.46 (2H), 4.09 (1H), 4.25 (2H), 6.55-6.60 (2H), 6.80 (1H), 6.84-6.91 (2H), 7.10 (1H), 7.14 (1H), 7.37 (1H); MS (ESI+) m/z 477 (M+H)+.

Example 123

N-[(2Z)-3-(2,2-difluoro-1,3-benzodioxol-5-yl)-5-{[(4-fluorophenyl)(methyl)amino]methyl}-1,3-thiazol-2(3H)-ylidene]pyrrolidine-1-carboxamide Example 118 (18 mg, 50 µmol) was dissolved into 2:1 MeCN/$CH_2Cl_2$ (1.0 mL) and treated with $CuBr_2$ (22 mg, 100 µmol). After being stirred for at least 5 minutes at room temperature, the solution was further treated with 4-fluoro-N-methylaniline (17.0 µl, 0.15 mmol). The mixture was stirred another 20-25 minutes before being partitioned between concentrated aqueous $NH_4OH$ (3 mL) and $CH_2Cl_2$ (10 mL). The aqueous phase was separated and extracted with $CH_2Cl_2$, and the combined organic phases were washed with concentrated aqueous $NH_4OH$, dried ($Na_2SO_4$), concentrated, and chromatographed on silica (1:3 to 1:2 to 1:1 EtOAc/hexanes) to give the titled compound. $^1$H NMR (400 MHz, $CDCl_3$) δ ppm 1.83 (4H), 2.95 (3H), 3.34 (2H), 3.46 (2H), 4.36 (2H), 6.70-6.75 (3H), 6.89-6.96 (2H), 7.10 (1H), 7.13 (1H), 7.38 (1H); MS (ESI+) m/z 491 (M+H)+.

Example 124

N-[(2Z)-3-(2,2-difluoro-1,3-benzodioxol-5-yl)-5-methylene-4-(pyridin-3-ylamino)-1,3-thiazolidin-2-ylidene]pyrrolidine-1-carboxamide Example 118 (18 mg, 50 µmol) was dissolved into 2:1 MeCN/$CH_2Cl_2$ (1.0 mL) and treated with $CuBr_2$ (22 mg, 100 µmol). After being stirred for at least 5 minutes at room temperature, the solution was further treated with 3-aminopyridine (14 mg, 0.15 mmol). The mixture was stirred another 20-25 minutes before being partitioned between concentrated aqueous $NH_4OH$ (3 mL) and $CH_2Cl_2$ (10 mL). The aqueous phase was separated and extracted with $CH_2Cl_2$, and the combined organic phases were washed with concentrated aqueous $NH_4OH$, dried ($Na_2SO_4$), concentrated and chromatographed on silica [0 to 1% EtOH in 1:1 EtOAc/hexanes] to furnish the titled compound. The titled compound was further purified on silica (0 stepwise to 0.8% 2M NH3 in MeOH/50 stepwise to 49.2% MeCN/50% $CH_2Cl_2$). $^1$H NMR (400 MHz, $CD_2Cl_2$) δ ppm 1.77 (4H), 3.17 (2H), 3.35 (2H), 5.04 (1H), 5.37 (1H), 5.50 (1H), 6.08 (1H), 6.92 (1H), 6.99 (1H), 7.01-7.07 (3H), 8.00 (2H); MS (ESI+) m/z 460 (M+H)+.

Example 125

N-[(2Z)-3-(2,2-difluoro-1,3-benzodioxol-5-yl)-5-methyl-1,3-thiazol-2(3H)-ylidene]-N'-2,3-dihydro-1H-inden-2-ylurea The titled compound was prepared as described in Example 40C substituting 2,3-dihydro-1H-inden-2-amine for propan-2-amine. $^1$H NMR (500 MHz, DMSO-$d_6$/$D_2O$) δ ppm 2.21 (3H) 2.72-2.89 (2H) 3.12-3.22 (2H) 4.28-4.46 (1H) 6.95 (1H) 7.05-7.22 (4H) 7.29 (1H) 7.40 (1H) 7.58 (1H); MS (ESI) m/z 430 (M+H)+.

Example 126

N-[(2Z)-5-methyl-3-(2,2,3,3-tetrafluoro-2,3-dihydro-1,4-benzodioxin-6-yl)-1,3-thiazol-2(3H)-ylidene]-1H-imidazole-1-carboxamide Example 26A (6.02 g, 18.8 mmol) and carbonyl diimidazole (3.36 g, 20.7 mmol) were mixed in acetonitrile (60 mL) resulting in rapid precipitation of the desired product. The thick suspension was stirred/swirled for 20 minutes at room temperature, and then the solids were collected by filtration and rinsed with acetonitrile. The filtrate was concentrated, mixed with more acetonitrile (20 mL), and a small second crop collected as before. The two crops were combined and dried under vacuum to give the titled compound. $^1$H NMR (400 MHz, DMSO-$d_6$) δ ppm 2.36 (3H), 6.98 (1H), 7.46 (1H), 7.60 (1H), 7.72-7.76 (2H), 7.94-7.97 (1H), 8.06 (1H); MS (ESI) m/z 415 (M+H)+.

Example 127

N-[(2Z)-3-(2,2-difluoro-1,3-benzodioxol-5-yl)-5-methyl-1,3-thiazol-2(3H)-ylidene]-N'-[1-(methoxymethyl)propyl]urea The titled compound was prepared as described in Example 40C substituting 1-methoxybutan-2-amine for propan-2-amine. $^1$H NMR (500 MHz, DMSO-$d_6$/$D_2O$) δ ppm 0.82 (3H) 1.27-1.62 (2H) 2.20 (3H) 3.21-3.23 (3H) 3.24-3.41 (2H) 3.53-3.76 (1H) 6.97 (1H) 7.31 (1H) 7.44 (1H) 7.61 (1H); MS (ESI) m/z 400 (M+H)⁺.

Example 128

N'-[(2Z)-3-(2,2-difluoro-1,3-benzodioxol-5-yl)-5-methyl-1,3-thiazol-2(3H)-ylidene]-N-isobutyl-N-prop-2-ynylurea The titled compound was prepared as described in Example 40C substituting N-isobutylprop-2-yn-1-amine hydrochloride for propan-2-amine. ¹H NMR (500 MHz, DMSO-d₆/D₂O) δ ppm 0.74 (6H) 2.22 (3H) 2.74 (1H) 3.15 (3H) 4.09 (2H) 7.02 (1H) 7.32 (1H) 7.42 (1H) 7.62 (1H); MS (ESI) m/z 408 (M+H)⁺.

Example 129

N-[(2Z)-3-(2,2-difluoro-1,3-benzodioxol-5-yl)-5-methyl-1,3-thiazol-2(3H)-ylidene]azetidine-1-carboxamide The titled compound was prepared as described in Example 40C substituting azetidine for propan-2-amine. ¹H NMR (500 MHz, DMSO-d₆/D₂O) δ ppm 2.03-2.17 (2H) 2.21 (3H) 3.85 (4H) 7.00 (1H) 7.31-7.43 (2H) 7.64 (1H); MS (ESI) m/z 354 (M+H)⁺.

Example 130

N-[(2Z)-3-(2,2-difluoro-1,3-benzodioxol-5-yl)-5-methyl-1,3-thiazol-2(3H)-ylidene]-N'-(1-methyl-1-phenylethyl)urea The titled compound was prepared as described in Example 40C substituting 2-phenylpropan-2-amine for propan-2-amine. ¹H NMR (500 MHz, DMSO-d₆/D₂O) δ ppm 1.54-1.57 (6H) 2.16 (3H) 6.87-6.94 (1H) 7.06-7.34 (6H) 7.40 (1H) 7.45-7.54 (1H); MS (ESI) m/z 432 (M+H)⁺.

Example 131

N-cyclopropyl-N'-[(2Z)-3-(2,2-difluoro-1,3-benzodioxol-5-yl)-5-methyl-1,3-thiazol-2(3H)-ylidene]-N-(2-fluorobenzyl)urea The titled compound was prepared as described in Example 40C substituting N-(2-fluorobenzyl)cyclopropanamine for propan-2-amine. ¹H NMR (500 MHz, DMSO-d₆/D₂O) δ ppm 0.43-0.67 (4H) 2.22 (3H) 2.54-2.64 (1H) 4.49-4.53 (2H) 6.96-7.14 (4H) 7.16-7.28 (2H) 7.33 (1H) 7.43-7.52 (1H); MS (ESI) m/z 462 (M+H)⁺.

Example 132

N-(2-chlorobenzyl)-N'-[(2Z)-3-(2,2-difluoro-1,3-benzodioxol-5-yl)-5-methyl-1,3-thiazol-2(3H)-ylidene]-N-methylurea The titled compound was prepared as described in Example 40C substituting 1-(2-chlorophenyl)-N-methylmethanamine for propan-2-amine. ¹H NMR (500 MHz, DMSO-d₆/D₂O) δ ppm 2.20 (3H) 2.87-2.95 (3H) 4.52-4.59 (2H) 6.95-7.01 (1H) 7.03-7.48 (7H); MS (ESI) m/z 452 (M+H).

Example 133

N-(4-chlorobenzyl)-N'-[(2Z)-3-(2,2-difluoro-1,3-benzodioxol-5-yl)-5-methyl-1,3-thiazol-2(3H)-ylidene]-N-methylurea The titled compound was prepared as described in Example 40C substituting 1-(4-chlorophenyl)-N-methylmethanamine for propan-2-amine. ¹H NMR (500 MHz, DMSO-d₆/D₂O) δ ppm 2.21 (3H) 2.82-2.87 (3H) 4.43-4.47 (2H) 6.99 (1H) 7.06-7.18 (2H) 7.20-7.33 (3H) 7.37 (1H) 7.46-7.54 (1H); MS (ESI) m/z 452 (M+H)⁺.

Example 134

N'-[(2Z)-3-(2,2-difluoro-1,3-benzodioxol-5-yl)-5-methyl-1,3-thiazol-2(3H)-ylidene]-N-(4-methoxybenzyl)-N-methylurea The titled compound was prepared as described in Example 40C substituting 1-(4-methoxyphenyl)-N-methylmethanamine for propan-2-amine. ¹H NMR (500 MHz, DMSO-d₆/D₂O) δ ppm 2.21 (3H) 2.78-2.85 (3H) 3.70-3.74 (3H) 4.37-4.43 (2H) 6.75-6.85 (2H) 6.95-7.08 (3H) 7.30 (1H) 7.38 (1H) 7.50-7.58 (1H); MS (ESI) m/z 448 (M+H)⁺.

Example 135

N'-[(2Z)-3-(2,2-difluoro-1,3-benzodioxol-5-yl)-5-methyl-1,3-thiazol-2(3H)-ylidene]-N-methyl-N-(pyridin-2-ylmethyl)urea The titled compound was prepared as described in Example 40C substituting N-methyl-1-(pyridin-2-yl)methanamine for propan-2-amine. ¹H NMR (500 MHz, DMSO-d₆/D₂O) δ ppm 2.22 (3H) 2.91-3.00 (3H) 4.56-4.66 (2H) 6.96-7.01 (1H) 7.14-7.56 (5H) 7.90 (1H) 8.49 (1H); MS (ESI) m/z 419 (M+H)⁺.

Example 136

N'-[(2Z)-3-(2,2-difluoro-1,3-benzodioxol-5-yl)-5-methyl-1,3-thiazol-2(3H)-ylidene]-N-methyl-N-(pyridin-3-ylmethyl)urea The titled compound was prepared as described in Example 40C substituting N-methyl-1-(pyridin-3-yl)methanamine for propan-2-amine. ¹H NMR (500 MHz, DMSO-d₆/D₂O) δ ppm 2.20 (3H) 2.83-2.96 (3H) 4.33-4.66 (2H) 6.96-7.07 (1H) 7.26 (1H) 7.36 (1H) 7.47-7.62 (2H) 7.84 (1H) 8.36-8.47 (1H) 8.54 (1H); MS (ESI) m/z 419 (M+H)⁺.

Example 137

N'-[(2Z)-3-(2,2-difluoro-1,3-benzodioxol-5-yl)-5-methyl-1,3-thiazol-2(3H)-ylidene]-N-ethyl-N-(pyridin-3-ylmethyl)urea The titled compound was prepared as described in Example 40C substituting N-(pyridin-3-ylmethyl)ethanamine for propan-2-amine. ¹H NMR (500 MHz, DMSO-d₆/D₂O) δ ppm 0.98 (3H) 2.21 (3H) 3.31 (2H) 4.43-4.56 (2H) 6.93-7.08 (1H) 7.21-7.64 (5H) 8.24-8.50 (2H); MS (ESI) m/z 433 (M+H)⁺.

Example 138

N'-[(2Z)-3-(2,2-difluoro-1,3-benzodioxol-5-yl)-5-methyl-1,3-thiazol-2(3H)-ylidene]-N-methyl-N-(pyridin-4-ylmethyl)urea The titled compound was prepared as described in Example 40C substituting N-methyl-1-(pyridin-4-yl)methanamine for propan-2-amine. ¹H NMR (500 MHz, DMSO-d₆/D₂O) δ ppm 2.21 (3H) 2.90-2.98 (3H) 4.47-4.73 (2H) 6.94-7.06 (1H) 7.19-7.53 (5H) 8.54-8.58 (2H); MS (ESI) m/z 419 (M+H)⁺.

Example 139

N'-[(2Z)-3-(2,2-difluoro-1,3-benzodioxol-5-yl)-5-methyl-1,3-thiazol-2(3H)-ylidene]-N-methyl-N-(pyrazin-2-ylmethyl)urea The titled compound was prepared as described in Example 40C substituting N-methyl-1-(pyrazin-2-yl)methanamine for propan-2-amine. $^1$H NMR (500 MHz, DMSO-d$_6$/D$_2$O) δ ppm 2.21 (3H) 2.94-2.99 (3H) 4.55-4.62 (2H) 6.92-7.02 (1H) 7.19-7.25 (m, 1H) 7.35 (1H) 7.42-7.54 (1H) 8.16-8.33 (1H) 8.37-8.50 (2H); MS (ESI) m/z 420 (M+H)$^+$.

Example 140

N-methyl-N'-[(2Z)-5-methyl-3-(2,2,3,3-tetrafluoro-2,3-dihydro-1,4-benzodioxin-6-yl)-1,3-thiazol-2(3H)-ylidene]-N-(pyridin-3-ylmethyl)urea Crude Example 81A (334 mg, ~0.60 mmol) and methyl-(pyridin-3-ylmethyl)-amine (98 mg, 0.80 mmol) were mixed into CH$_2$Cl$_2$ (6 mL) and treated with diisopropylethylamine (115 µL, 0.66 mmol). After the solution was stirred for 15 minutes at room temperature, it was concentrated to a syrup and chromatographed on silica (33 to 50% EtOAc/50 to 33% CH$_2$Cl$_2$/17% hexanes) to give the titled compound. $^1$H NMR (400 MHz, CD$_2$Cl$_2$) δ ppm 2.25 (3H), 2.90-2.98 (3H), 4.54-4.59 (2H), 6.63-6.69 (1H), 7.10-7.63 (5H), 8.32-8.51 (2H); MS (ESI+) m/z 469 (M+H)$^+$.

Example 141

N-[(2Z)-5-(hydroxymethyl)-3-(2,2,3,3-tetrafluoro-2,3-dihydro-1,4-benzodioxin-6-yl)-1,3-thiazol-2(3H)-ylidene]acetamide Example 22B (544 mg, 1.50 mmol) was dissolved into anhydrous MeCN (15 mL) and treated with benzyltrimethylammonium tribromide (702 mg, 1.80 mmol). The solution was stirred 5 minutes, NaHSO$_3$ (188 mg, ~1.8 mmol, mixture with Na$_2$S$_2$O$_5$) was added, the mixture was stirred 30 minutes, ~2 M aqueous NaHSO$_3$ (150 µL) was added, the mixture was stirred another 5 minutes, and then water (3.0 mL) was added. The mixture was then left to stir at room temperature for three days. It was partitioned between CH$_2$Cl$_2$ (30 mL) and water (7 mL). The aqueous phase was separated and extracted with CH$_2$Cl$_2$. The combined organic phases were washed with a 1:1 mixture of brine and water, and the separated aqueous phase was extracted twice with CH$_2$Cl$_2$. The combined organic phases were dried (Na$_2$SO$_4$) and concentrated. The solid residue was suspended into 4:1 CH$_2$Cl$_2$/hexanes, collected by filtration, and rinsed with more of the 4:1 solution. A small second crop was collected in a similar manner. The solids were dissolved into 10% MeOH/CH$_2$Cl$_2$, filtered, and concentrated to give the titled compound. $^1$H NMR (400 MHz, DMSO-d$_6$) δ ppm 2.06 (3H), 4.52 (2H), 5.60 (1H), 7.53 (1H), 7.60 (1H), 7.68 (1H), 7.86 (1H); MS (ESI+) m/z 379 (M+H)$^-$.

Example 142

N-[(2Z)-3-(2,2-difluoro-1,3-benzodioxol-5-yl)-5-methyl-1,3-thiazol-2(3H)-ylidene]pyrrolidine-1-carbothioamide A solution of the product of Example 12 (40 mg, 0.11 mmol) and [2,4-bis(4-methoxyphenyl)-1,3-dithia-2,4-diphosphetane-2,4-disulfide] (Lawesson's reagent, Aldrich, 44 mg, 0.11 mmol) in anhydrous toluene (0.50 mL) was heated at 100° C. for 2.5 hours. The reaction mixture was cooled and loaded directly onto a silica column. The product was eluted with 0-1% methanol in CH$_2$Cl$_2$ to provide the title compound. $^1$H NMR (300 MHz, CDCl$_3$) δ ppm 1.82-1.94 (4H) 2.28 (3H) 3.40 (2H) 3.77 (2H) 6.69 (1H) 7.11-7.14 (2H) 7.27-7.29 (1H); MS (DCI) m/z 384.0 (M+H)$^+$.

Example 143

2-methyl-N-[(2Z)-5-methyl-3-(2,2,3,3-tetrafluoro-2,3-dihydro-1,4-benzodioxin-6-yl)-1,3-thiazol-2(3H)-ylidene]indoline-1-carboxamide The titled compound was obtained using the procedure described in Example 81B substituting 2-methylindoline for 1-(5-fluoro-2-phenoxyphenyl)-N-methylmethanamine. $^1$H NMR (CD$_3$OD) δ ppm 1.2 (3H), 2.25 (3H), 2.60 (2H), 4.60 (1H), 6.90-7.90 (8H); MS (ESI) m/z 480 (M+H)$^+$.

Example 144

5-bromo-N-[(2Z)-5-methyl-3-(2,2,3,3-tetrafluoro-2,3-dihydro-1,4-benzodioxin-6-yl)-1,3-thiazol-2(3H)-ylidene]indoline-1-carboxamide The titled compound was obtained using the procedure described in Example 81B substituting 5-bromoindoline for 1-(5-fluoro-2-phenoxyphenyl)-N-methylmethanamine. $^1$H NMR (CD$_3$OD) δ ppm 2.30 (3H), 3.05 (2H), 4.0 (2H), 7.0-7.85 (7H); MS (ESI) m/z 545 (M+H)$^+$.

Example 145

N-methyl-N-[(1-methyl-1H-indol-5-yl)methyl]-N'-[(2Z)-5-methyl-3-(2,2,3,3-tetrafluoro-2,3-dihydro-1,4-benzodioxin-6-yl)-1,3-thiazol-2(3H)-ylidene]urea The titled compound was obtained using the procedure described in Example 81B substituting N-methyl-1-(1-methyl-1H-indol-5-yl)methanamine for 1-(5-fluoro-2-phenoxyphenyl)-N-methylmethanamine. $^1$H NMR (CD$_3$OD) δ ppm 2.20 (3H), 2.95 (3H), 3.80 (3H), 4.60 (2H), 6.95-7.85 (9H); MS (ESI) m/z 521 (M+H)$^+$.

Example 146

N-methyl-N'-[(2Z)-5-methyl-3-(2,2,3,3-tetrafluoro-2,3-dihydro-1,4-benzodioxin-6-yl)-1,3-thiazol-2(3H)-ylidene]-N-(4-pyridin-4-ylbenzyl)urea The titled compound was obtained using the procedure described in Example 81B substituting N-methyl-1-(4-(pyridine-4-yl)phenyl)methanamine for 1-(5-fluoro-2-phenoxyphenyl)-N-methylmethanamine. $^1$H NMR (CD$_3$OD) δ ppm 2.30 (3H), 2.95 (3H), 4.65 (2H), 6.95-7.60 (6H), 7.90 (2H), 8.30 (2H), 8.80 (2H); MS (ESI) m/z 546 (M+H)$^+$.

Example 147

N-methyl-N'-[(2Z)-5-methyl-3-(2,2,3,3-tetrafluoro-2,3-dihydro-1,4-benzodioxin-6-y)-1,3-thiazol-2(3H)-ylidene]-N-[(1R)-1-phenylethyl]urea The titled compound was obtained using the procedure described in Example 81B substituting (R)-N-methyl-1-phenylethanamine for 1-(5-fluoro-2-phenoxyphenyl)-N-methylmethanamine. $^1$H NMR (CD$_3$OD) δ ppm 1.40 (3H), 2.25 (3H), 2.65 (3H), 5.75 (1H), 6.95-7.60 (9H); MS (ESI) m/z 482 (M+H)$^-$.

Example 148

2-(4-fluorophenyl)-N-[(2Z)-5-methyl-3-(2,2,3,3-tetrafluoro-2,3-dihydro-1,4-benzodioxin-6-yl)-1,3-thiazol-2(3H)-ylidene]indoline-1-carboxamide The titled compound was obtained using the procedure described in Example 81B substituting 2-(4-fluorophenyl)indoline for 1-(5-fluoro-2-phenoxyphenyl)-N-methylmethanamine. $^1$H NMR (CD$_3$OD) δ ppm 2.25 (3H), 2.80 (1H), 3.60 (1H), 5.55 (1H), 6.85-7.60 (12H); MS (ESI) m/z 560 (M+H)$^+$.

Example 149

N-but-2-ynyl-N'-[(2Z)-5-methyl-3-(2,2,3,3-tetrafluoro-2,3-dihydro-1,4-benzodioxin-6-yl)-1,3-thiazol-2(3H)-ylidene]-N-phenylurea The titled compound was obtained using the procedure described in Example 81B substituting N-(but-2-ynyl)aniline for 1-(5-fluoro-2-phenoxyphenyl)-N-methylmethanamine. $^1$H NMR (CD$_3$OD) δ ppm 2.20 (3H), 2.90 (3H), 3.65 (2H), 6.95-7.60 (9H); MS (ESI) m/z 492 (M+H)$^+$.

Example 150

N-isobutyl-N'-[(2Z)-5-methyl-3-(2,2,3,3-tetrafluoro-2,3-dihydro-1,4-benzodioxin-6-yl)-1,3-thiazol-2(3H)-ylidene]-N-prop-2-ynylurea The titled compound was obtained using the procedure described in Example 81B substituting N-isobutylprop-2-yn-1-amine for 1-(5-fluoro-2-phenoxyphenyl)-N-methylmethanamine. $^1$H NMR (CD$_3$OD) δ ppm 0.70 (3H), 0.95 (3H), 2.00 (1H), 2.20 (3H), 2.50 (1H), 3.25 (2H), 4.05 (2H), 7.00 (1H), 7.20-7.60 (3H); MS (ESI) m/z 458 (M+H)$^+$.

Example 151

N,N-dibut-2-ynyl-N'-[(2Z)-5-methyl-3-(2,2,3,3-tetrafluoro-2,3-dihydro-1,4-benzodioxin-6-yl)-1,3-thiazol-2(3H)-ylidene]urea The titled compound was obtained using the procedure described in Example 81B substituting dibut-2-ynylamine as amine for 1-(5-fluoro-2-phenoxyphenyl)-N-methylmethanamine. $^1$H NMR (CD$_3$OD) δ ppm 1.38 (6H), 2.25 (3H), 4.05 (4H), 7.05 (1H), 7.40 (1H), 7.50 (1H), 7.70 (1H); MS (ESI) m/z 468 (M+H)$^+$.

Example 152

N-ethyl-N'-[(2Z)-5-methyl-3-(2,2,3,3-tetrafluoro-2,3-dihydro-1,4-benzodioxin-6-yl)-1,3-thiazol-2(3H)-ylidene]-N-(thien-2-ylmethyl)urea The titled compound was obtained using the procedure described in Example 81B substituting N-(thiophen-2-ylmethyl)ethanamine for 1-(5-fluoro-2-phenoxyphenyl)-N-methylmethanamine. $^1$H NMR (CD$_3$OD) δ ppm 1.05 (3H), 2.25 (3H), 3.40 (2H), 4.75 (2H), 6.85-7.70 (7H); MS (ESI) m/z 488 (M+H)$^+$.

Example 153

N-methyl-N-[(3-methylpyridin-2-yl)methyl]-N'-[(2Z)-5-methyl-3-(2,2,3,3-tetrafluoro-2,3-dihydro-1,4-benzodioxin-6-yl)-1,3-thiazol-2(3H)-ylidene]urea The titled compound was obtained using the procedure described in Example 81B substituting N-methyl-1-(3-methylpyridin-2-yl)methanamine for 1-(5-fluoro-2-phenoxyphenyl)-N-methylmethanamine. $^1$H NMR (CD$_3$OD) δ ppm 2.20 (3H), 2.32 (3H), 3.00 (3H), 4.55 (2H), 6.95-7.80 (4H), 8.20-8.45 (3H); MS (ESI) m/z 483 (M+H)$^+$.

Example 154

N-methyl-N-[(3-methylpyridin-4-yl)methyl]-N'-[(2Z)-5-methyl-3-(2,2,3,3-tetrafluoro-2,3-dihydro-1,4-benzodioxin-6-yl)-1,3-thiazol-2(3H)-ylidene]urea The titled compound was obtained using the procedure described in Example 81B substituting N-methyl-1-(3-methylpyridin-4-yl)methanamine for 1-(5-fluoro-2-phenoxyphenyl)-N-methylmethanamine. $^1$H NMR (CD$_3$OD) δ ppm 2.25 (3H), 2.35 (3H), 3.05 (3H), 4.60 (2H), 6.95 (1H), 7.05-7.80 (4H), 8.40-8.45 (2H); MS (ESI) m/z 483 (M+H)$^+$.

Example 155

N-[(2Z)-5-methyl-3-(2,2,3,3-tetrafluoro-2,3-dihydro-1,4-benzodioxin-6-yl)-1,3-thiazol-2(3H)-ylidene]-2-pyridin-3-ylpyrrolidine-1-carboxamide A solution of (Z)-3-methyl-1-(5-methyl-3-(2,2,3,3-tetrafluoro-2,3-dihydrobenzo[b][1,4]dioxin-6-yl)thiazol-2(3H)-ylidenecarbamoyl)-1H-imidazol-3-ium iodide core (Example 81A, 0.88 mL of 0.16 M in acetonitrile, 80 mg, 0.1 mmol) was added to a 20 mL vial, followed by N,N-diisopropylethylamine (0.88 mL of 0.2 M in acetonitrile, 24 mg, 0.13 mmol). 3-(Pyrrolidin-2-yl)pyridine (0.79 mL of 0.2 M in acetonitrile, 0.11 mmol) was added last. The resulting mixture was shaken at room temperature overnight. It was then concentrated in vacuo, and the residue was taken up in 1:1 MeOH/DMSO and purified by reverse phase HPLC (acetonitrile/water 0.1% TFA gradient elution method) to give the titled compound. $^1$H NMR (300 MHz, DMSO-d$_6$/D$_2$O) δ ppm 1.74-1.93 (3H) 2.12-2.21 (3H) 2.33-2.44 (1H) 3.50-3.68 (2H) 4.95-5.07 (1H) 6.91-7.06 (1H) 7.21-7.59 (3H) 7.70-7.91 (1H) 8.33-8.42 (1H) 8.44-8.52 (1H); MS (ESI+) m/z 495 (M+H)$^+$.

Example 156

N-(4-ethylbenzyl)-N-methyl-N'-[(2Z)-5-methyl-3-(2,2,3,3-tetrafluoro-2,3-dihydro-1,4-benzodioxin-6-yl)-1,3-thiazol-2(3H)-ylidene]urea The titled compound was prepared using the procedure described in Example 155 substituting 1-(4-ethylphenyl)-N-methylmethanamine for 3-(pyrrolidin-2-yl)pyridine. $^1$H NMR (300 MHz, DMSO-d$_6$/D$_2$O) δ ppm 1.16 (3H) 2.19-2.26 (3H) 2.57 (2H) 2.86 (3H) 4.45 (2H) 6.98-7.15 (5H) 7.38-7.51 (2H) 7.59-7.65 (1H); MS (ESI+) m/z 496 (M+H)$^+$.

Example 157

N-ethyl-N'-[(2Z)-5-methyl-3-(2,2,3,3-tetrafluoro-2,3-dihydro-1,4-benzodioxin-6-yl)-1,3-thiazol-2(3H)-ylidene]-N-(pyridin-4-ylmethyl)urea The titled compound was prepared using the procedure described in Example 155 substituting N-(pyridin-4-ylmethyl)ethanamine for 3-(pyrrolidin-2-yl)pyridine. $^1$H NMR (300 MHz, DMSO-d$_6$/D$_2$O) δ ppm 1.00 (3H) 2.20-2.26 (3H) 3.40 (2H) 4.55-4.64 (2H) 7.00-7.12 (1H) 7.34-7.47 (4H) 7.50-7.63 (1H) 8.49-8.57 (2H); MS (ESI+) m/z 483 (M+H)$^+$.

Example 158

N-(4-ethoxybenzyl)-N-methyl-N'-[(2Z)-5-methyl-3-(2,2,3,3-tetrafluoro-2,3-dihydro-1,4-benzodioxin-6-yl)-1,3-thiazol-2(3H)-ylidene]urea The titled compound was prepared using the procedure described in Example 155 substituting 1-(4-ethoxyphenyl)-

N-methylmethanamine for 3-(pyrrolidin-2-yl)pyridine. $^1$H NMR (300 MHz, DMSO-d$_6$/D$_2$O) δ ppm 1.29 (3H) 2.20-2.26 (3H) 2.84 (3H) 4.00 (2H) 4.45 (2H) 6.76-6.84 (2H) 6.98-7.08 (3H) 7.41-7.52 (2H) 7.62-7.67 (1H); MS (ESI+) m/z 512 (M+H)$^+$.

Example 159

N-methyl-N-(4-methylbenzyl)-N'-[(2Z)-5-methyl-3-(2,2,3,3-tetrafluoro-2,3-dihydro-1,4-benzodioxin-6-yl)-1,3-thiazol-2(3H)-ylidene]urea The titled compound was prepared using the procedure described in Example 155 substituting N-methyl-1-p-tolylmethanamine for 3-(pyrrolidin-2-yl)pyridine. $^1$H NMR (300 MHz, DMSO-d$_6$/D$_2$O) δ ppm 2.21-2.23 (3H) 2.26 (3H) 2.85 (3H) 4.44 (2H) 6.94-7.12 (5H) 7.40-7.51 (2H) 7.60-7.65 (1H); MS (ESI−) m/z 480 (M−H)$^-$.

Example 160

N-(4-bromobenzyl)-N-methyl-N'-[(2Z)-5-methyl-3-(2,2,3,3-tetrafluoro-2,3-dihydro-1,4-benzodioxin-6-yl)-1,3-thiazol-2(3H)-ylidene]urea The titled compound was prepared using the procedure described in Example 155 substituting 1-(4-bromophenyl)-N-methylmethanamine for 3-(pyrrolidin-2-yl)pyridine. $^1$H NMR (300 MHz, DMSO-d$_6$/D$_2$O) δ ppm 2.20-2.26 (3H) 2.87 (3H) 4.45 (2H) 7.02-7.11 (3H) 7.38-7.47 (4H) 7.59-7.65 (1H); MS (ESI−) m/z 544 (M−H)$^-$.

Example 161

N-(4-tert-butylbenzyl)-N-methyl-N'-[(2E)-5-methyl-3-(2,2,3,3-tetrafluoro-2,3-dihydro-1,4-benzodioxin-6-yl)-1,3-thiazol-2(3H)-ylidene]urea The titled compound was prepared using the procedure described in Example 155 substituting 1-(4-tert-butylphenyl)-N-methylmethanamine for 3-(pyrrolidin-2-yl)pyridine. $^1$H NMR (300 MHz, DMSO-d$_6$/D$_2$O) δ ppm 1.28 (9H) 2.17-2.25 (3H) 2.85 (3H) 4.41 (2H) 6.97-7.09 (3H) 7.22-7.30 (2H) 7.37-7.50 (2H) 7.58-7.66 (1H); MS (ESI+) m/z 524 (M+H)$^+$.

Example 162

N-(4-isopropylbenzyl)-N-methyl-N'-[(2Z)-5-methyl-3-(2,2,3,3-tetrafluoro-2,3-dihydro-1,4-benzodioxin-6-yl)-1,3-thiazol-2(3H)-ylidene]urea The titled compound was prepared using the procedure described in Example 155 substituting 1-(4-isopropylphenyl)-N-methylmethanamine for 3-(pyrrolidin-2-yl)pyridine. $^1$H NMR (300 MHz, DMSO-d$_6$/D$_2$O) δ ppm 1.17 (6H) 2.18-2.25 (3H) 2.81-2.84 (1H) 2.87 (3H) 4.44 (2H) 6.95-7.19 (5H) 7.38-7.51 (2H) 7.57-7.66 (1H); MS (ESI+) m/z 510 (M+H)$^+$.

Example 163

N-(3,4-dichlorobenzyl)-N-methyl-N'-[(2Z)-5-methyl-3-(2,2,3,3-tetrafluoro-2,3-dihydro-1,4-benzodioxin-6-yl)-1,3-thiazol-2(3H)-ylidene]urea The titled compound was prepared using the procedure described in Example 155 substituting 1-(3,4-dichlorophenyl)-N-methylmethanamine for 3-(pyrrolidin-2-yl)pyridine. $^1$H NMR (300 MHz, DMSO-d$_6$/D$_2$O) δ ppm 2.21-2.24 (3H) 2.88 (3H) 4.47 (2H) 7.03-7.13 (2H) 7.26-7.30 (1H) 7.41-7.49 (3H) 7.59-7.64 (1H); MS (ESI+) m/z 536 (M+H)$^+$.

Example 164

N-(2,4-dichlorobenzyl)-N-methyl-N'-[(2Z)-5-methyl-3-(2,2,3,3-tetrafluoro-2,3-dihydro-1,4-benzodioxin-6-yl)-1,3-thiazol-2(3H)-ylidene]urea The titled compound was prepared using the procedure described in Example 155 substituting 1-(2,4-dichlorophenyl)-N-methylmethanamine for 3-(pyrrolidin-2-yl)pyridine. $^1$H NMR (300 MHz, DMSO-d$_6$/D$_2$O) δ ppm 2.20-2.24 (3H) 2.92 (3H) 4.55 (2H) 7.02-7.06 (1H) 7.10 (1H) 7.30 (1H) 7.36-7.40 (2H) 7.42 (1H) 7.47-7.53 (1H); MS (ESI+) m/z 536 (M+H)$^-$.

Example 165

N-(4-fluorobenzyl)-N-methyl-N'-[(2Z)-5-methyl-3-(2,2,3,3-tetrafluoro-2,3-dihydro-1,4-benzodioxin-6-yl)-1,3-thiazol-2(3H)-ylidene]urea The titled compound was prepared using the procedure described in Example 155 substituting 1-(4-fluorophenyl)-N-methylmethanamine for 3-(pyrrolidin-2-yl)pyridine. $^1$H NMR (300 MHz, DMSO-d$_6$/D$_2$O) δ ppm 2.21-2.25 (3H) 2.86 (3H) 4.46 (2H) 6.95-7.07 (3H) 7.10-7.19 (2H) 7.42-7.48 (2H) 7.60-7.65 (1H); MS (ESI+) m/z 486 (M+H)$^+$.

Example 166

N-(4-methoxybenzyl)-N-methyl-N'-[(2Z)-5-methyl-3-(2,2,3,3-tetrafluoro-2,3-dihydro-1,4-benzodioxin-6-yl)-1,3-thiazol-2(3H)-ylidene]urea The titled compound was prepared using the procedure described in Example 155 substituting 1-(4-methoxyphenyl)-N-methylmethanamine for 3-(pyrrolidin-2-yl)pyridine. $^1$H NMR (300 MHz, DMSO-d$_6$/D$_2$O) δ ppm 2.20-2.23 (3H) 2.84 (3H) 3.73 (3H) 4.42 (2H) 6.77-6.86 (2H) 6.98-7.09 (3H) 7.40-7.53 (2H) 7.62-7.67 (1H); MS (ESI−) m/z 496 (M−H)$^-$.

Example 167

N-methyl-N'-[(2Z)-5-methyl-3-(2,2,3,3-tetrafluoro-2,3-dihydro-1,4-benzodioxin-6-yl)-1,3-thiazol-2(3H)-ylidene]-N-(quinolin-6-ylmethyl)urea The titled compound was prepared using the procedure described in Example 155 substituting N-methyl-1-(quinolin-6-yl)methanamine for 3 -(pyrrolidin-2-yl)pyridine. $^1$H NMR (300 MHz, DMSO-d$_6$/D$_2$O) δ ppm 2.16-2.27 (3H) 2.95 (3H) 4.72 (2H) 7.01-7.09 (1H) 7.34-7.50 (2H) 7.58-7.68 (3H) 7.72-7.79 (1H) 7.99 (1H) 8.45 (1H) 8.91 (1H); MS (ESI+) m/z 519 (M+H)$^+$.

Example 168

N-(3-bromobenzyl)-N-methyl-N'-[(2Z)-5-methyl-3-(2,2,3,3-tetrafluoro-2,3-dihydro-1,4-benzodioxin-6-yl)-1,3-thiazol-2(3H)-ylidene]urea The titled compound was prepared using the procedure described in Example 155 substituting 1-(3-bromophenyl)-N-methylmethanamine for 3-(pyrrolidin-2-yl)pyridine. $^1$H NMR (300 MHz, DMSO-d$_6$/D$_2$O) δ ppm 2.19-2.26 (3H) 2.88 (3H) 4.48 (2H) 7.03-7.07 (1H) 7.08-7.15 (1H) 7.17-7.25 (1H) 7.25-7.30 (1H) 7.34-7.40 (1H) 7.40-7.50 (2H) 7.61-7.65 (1H); MS (ESI−) m/z 544 (M−H)$^-$.

Example 169

N-(2-bromobenzyl)-N-methyl-N'-[(2Z)-5-methyl-3-(2,2,3,3-tetrafluoro-2,3-dihydro-1,4-benzodioxin-6-yl)-1,3-thiazol-2(3H)-ylidene]urea The titled compound was prepared using the procedure described in Example 155 substituting 1-(2-bromophenyl)-N-methylmethanamine for 3-(pyrrolidin-2-yl)pyridine. $^1$H NMR (300 MHz, DMSO-$d_6$/$D_2$O) δ ppm 2.19-2.25 (3H) 2.92 (3H) 4.56 (2H) 7.01-7.09 (2H) 7.12-7.22 (1H) 7.25-7.33 (1H) 7.33-7.39 (2H) 7.49-7.56 (2H); MS (ESI+) m/z 546 (M+H)$^-$.

Example 170

N-[(2Z)-3-(2,2-difluoro-1,3-benzodioxol-5-yl)-5-[(pyridin-3-ylamino)methyl]-1,3-thiazol-2(3H)-ylidene]pyrrolidine-1-carboxamide The titled compound was a second product prepared with the procedure described in Example 124. The titled product was isolated and purified with a step gradient silica flash chromatography eluting first with 0 to 1% (provides Example 124) to 2 to 5% (provides titled compound) EtOH in 1:1 EtOAc/hexanes. $^1$H NMR (400 MHz, $CD_2Cl_2$) δ ppm 1.81 (4H), 3.33 (2H), 3.39 (2H), 4.32 (2H), 4.68 (1H), 6.87 (1H), 6.96 (1H), 7.07 (1H), 7.13 (1H), 7.18 (1H), 7.42 (1H), 7.95 (1H), 8.08 (1H); MS (ESI+) m/z 460 (M+H)$^-$.

Example 171

N-[(2Z)-3-(2,2-difluoro-1,3-benzodioxol-5-yl)-5-(methoxymethyl)-1,3-thiazol-2(3H)-ylidene]pyrrolidine-1-carboxamide Example 118 (37 mg, 100 μmol) was dissolved into 2:1 MeCN/$CH_2Cl_2$ (2.0 mL) and treated with $CuBr_2$ (45 mg, 200 μmol). After being stirred for at least 5 minutes at room temperature, the solution was further treated with methanol (200 μl, 5 mmol). The mixture was stirred approximately another 25 minutes before being partitioned between concentrated aqueous $NH_4OH$ (5 mL) and $CH_2Cl_2$ (15 mL). The aqueous phase was separated and extracted with $CH_2Cl_2$, and the combined organic phases were washed with concentrated aqueous $NH_4OH$ (1 mL), dried ($Na_2SO_4$), concentrated, and chromatographed on silica (1:3 to 1:2 to 1:1 EtOAc/hexanes) to give the methyl ether. $^1$H NMR (400 MHz, $CDCl_3$) δ ppm 1.84 (4H), 3.36 (2H), 3.48 (2H), 4.40 (2H), 6.87 (1H), 7.13 (1H), 7.18 (1H), 7.41 (1H); MS (ESI+) m/z 398 (M+H)$^+$.

Example 172

N-[(2Z)-3-(2,2-difluoro-1,3-benzodioxol-5-yl)-5-(isopropoxymethyl)-1,3-thiazol-2(3H)-ylidene]pyrrolidine-1-carboxamide Example 118 (37 mg, 100 μmol) was dissolved into 2:1 MeCN/$CH_2Cl_2$ (2.0 mL) and treated with $CuBr_2$ (45 mg, 200 μmol). After being stirred for at least 5 minutes at room temperature, the solution was further treated with isopropanol (380 μl, 5.0 mmol). The mixture was stirred approximately another 25 minutes before being partitioned between concentrated aqueous $NH_4OH$ (5 mL) and $CH_2Cl_2$ (15 mL). The aqueous phase was separated and extracted with $CH_2Cl_2$, and the combined organic phases were washed with concentrated aqueous $NH_4OH$, dried ($Na_2SO_4$), concentrated, and chromatographed on silica (5:1 to 3:1 hexanes/EtOAc) to give the isopropyl ether. $^1$H NMR (400 MHz, $CDCl_3$) δ ppm 1.21 (6H), 1.84 (4H), 3.36 (2H), 3.48 (2H), 3.73 (1H), 4.44 (2H), 6.85 (1H), 7.12 (1H), 7.18 (1H), 7.40 (1H); MS (ESI+) m/z 426 (M+H)$^+$.

Example 173

N-[(2Z)-5-[(benzyloxy)methyl]-3-(2,2-difluoro-1,3-benzodioxol-5-yl)-1,3-thiazol-2(3H)-ylidene]pyrrolidine-1-carboxamide Example 118 (37 mg, 100 μmol) was dissolved into 2:1 MeCN/$CH_2Cl_2$ (2.0 mL) and treated with $CuBr_2$ (45 mg, 200 μmol). After being stirred for at least 5 minutes at room temperature, the solution was further treated with benzyl alcohol (210 μl, 2.0 mmol). The mixture was stirred approximately another 25 minutes before being partitioned between concentrated aqueous $NH_4OH$ (5 mL) and $CH_2Cl_2$ (15 mL). The aqueous phase was separated and extracted with $CH_2Cl_2$, and the combined organic phases were washed with concentrated aqueous $NH_4OH$ (1 mL), dried ($Na_2SO_4$), concentrated, chromatographed on silica (10:1 to 5:1 to 3:1 hexanes/EtOAc), and rechromatographed on silica (0 to 1 to 3 to 5 to 10% EtOAc/$CH_2Cl_2$) to give the titled compound. $^1$H NMR (400 MHz, $CDCl_3$) δ ppm 1.84 (4H), 3.36 (2H), 3.49 (2H), 4.49 (2H), 4.59 (2H), 6.85 (1H), 7.12 (1H), 7.17 (1H), 7.26-7.39 (5H), 7.40 (1H); MS (ESI+) m/z 474 (M+H)$^+$.

Example 174

N-[(2Z)-5-methylene-3-(2,2,3,3-tetrafluoro-2,3-dihydro-1,4-benzodioxin-6-yl)-1,3-thiazolidin-2-ylidene]-1H-imidazole-1-carboxamide The crude imine (Example 22C, 169 mg, <0.52 mmol) was dissolved into acetonitrile (10 mL), treated with diisopropylethylamine (130 μL, 0.75 mmol) and carbonyl diimidazole (94 mg, 0.58 mmol), and then heated near 80° C. overnight. The mixture was concentrated and chromatographed through silica (10/40/50 to 25/25/50% EtOAc/$CH_2Cl_2$/hexanes) to give the titled compound. $^1$H NMR (300 MHz, $CDCl_3$) δ ppm 4.83 (2H), 5.42 (1H), 5.45 (1H), 7.01 (1H), 7.26-7.35 (3H), 7.44 (1H), 8.10 (1H); MS (ESI) m/z 415 (M+H)$^+$.

Example 175

N-[(2Z)-5-methylene-3-(2,2,3,3-tetrafluoro-2,3-dihydro-1,4-benzodioxin-6-yl)-1,3-thiazolidin-2-ylidene]-2,5-dihydro-1H-pyrrole-1-carboxamide Example 90A (116 mg, 0.21 mmol) was mostly dissolved into $CH_2Cl_2$ (2.0 mL) and treated with 3-pyrroline (32 μl, 0.42 mmol) followed by diisopropylethylamine (40 μl, 0.23 mmol). The mixture was stirred at room temperature for approximately 30 minutes. The mixture was concentrated and chromatographed on silica (0 to 2 to 5% EtOAc/$CH_2Cl_2$) to give the titled compound. $^1$H NMR (400 MHz, $CD_2Cl_2$) δ ppm 4.18 (4H), 4.68 (2H), 5.26 (1H), 5.32 (1H), 5.80 (2H), 7.20 (1H), 7.38 (1H), 7.64 (1H); MS (ESI+) m/z 416 (M+H)$^+$.

Example 176

(2S)-2-methyl-N-[(2Z)-5-methylene-3-(2,2,3,3-tetrafluoro-2,3-dihydro-1,4-benzodioxin-6-yl)-1,3-thiazolidin-2-ylidene]pyrrolidine-1-carboxamide Example 90A (35 mg, 63 μmol) was suspended into $CH_2Cl_2$ (600 μL) and treated with 87% ee (S)-2-methylpyrrolidine (L)-tartrate (30 mg, 127 μmol), followed by diisopropylethylamine (22 μl, 126 μmol), and stirred at room temperature for approximately 15 minutes. The mixture was filtered through a glass-fritted funnel with a $CH_2Cl_2$ rinse, and chromatographed on silica (0 to 2 to 5% EtOAc/$CH_2Cl_2$). The appropriate fractions were combined, dissolved into $CH_2Cl_2$, and washed with concentrated $NH_4OH$. The aqueous phase was back-extracted with $CH_2Cl_2$. The combined organic phases were dried ($Na_2SO_4$) and concentrated to give the titled compound. $^1H$ NMR (400 MHz, $CD_2Cl_2$) δ ppm 1.06-1.20 (3H), 1.53-1.60 (1H), 1.72-2.06 (3H), 3.38-3.46 (2H), 3.96-4.05 (1H), 4.59-4.71 (2H), 5.25 (1H), 5.31 (1H), 7.16-7.21 (1H), 7.29-7.40 (1H), 7.60-7.64 (1H); MS (ESI+) m/z 432 (M+H)$^+$.

(S)-2-methylpyrrolidine and its salts are available commercially from a number of sources including; (S)-2-methylpyrrolidine (Chemical abstracts registry number 59335-84-1) from Sigma-Aldrich Chemical Company, P. O. Box 14508 St. Louis, Mo., 63178 USA, and (S)-2-methylpyrrolidine hydrochloride (Chemical abstracts registry number 174500-74-4) from AstaTech, Inc. Keystone Business Park 2525 Pearl Buck Road Bristol, Pa., 19007 USA. Methods of obtaining (S)-2-methylpyrrolidine by enantioselective recrystallization with tartaric acid have been described for example in Sakurai, et al. Crystal Growth & Design (2006) vol. 6(7) pages 1606-1610. (S)-2-Methylpyrrolidine L-tartaric acid salt (313 grams) was recrystallized from a mixture of 4.8 Liters of ethanol and 1.2 liters of methanol heated at 60° C. and allowed to cool to deposit (S)-2-methylpyrrolidine L-tartaric acid salt.

Example 177

N-[(2Z)-5-methyl-3-(2,2,3,3-tetrafluoro-2,3-dihydro-1,4-benzodioxin-6-yl)-1,3-thiazol-2(3H)-ylidene]-2,5-dihydro-1H-pyrrole-1-carboxamide Example 175 (61 mg, 147 μmol) was dissolved into $CH_2Cl_2$ (1.5 mL), treated with TFA (30 μL), and stirred at room temperature for two days. More TFA (30 μL) was added, and the mixture was stirred at room temperature overnight, concentrated, and partitioned between $CH_2Cl_2$ (5 mL) and concentrated $NH_4OH$ (500 μL). The organic phase was washed with water, dried ($Na_2SO_4$), concentrated, and chromatographed on silica (10% EtOAc/40% $CH_2Cl_2$/50% hexanes) to give the titled compound. $^1H$ NMR (400 MHz, $CD_2Cl_2$) δ ppm 2.24 (3H), 4.14 (2H), 4.19 (2H), 5.78 (1H), 5.81 (1H), 6.67 (1H), 7.26 (1H), 7.42 (1H), 7.55 (1H); MS (ESI+) m/z 416 (M+H)$^+$.

Example 178

(2S)-2-methyl-N-[(2Z)-5-methyl-3-(2,2,3,3-tetrafluoro-2,3-dihydro-1,4-benzodioxin-6-yl)-1,3-thiazol-2(3H)-ylidene]pyrrolidine-1-carboxamide Crude Example 176 (13.7 mg, <32 μmol) was dissolved into $CH_2Cl_2$ (300 μL), treated with TFA (15 μL), and stirred at room temperature for one day. Then the mixture was concentrated and partitioned between $CH_2Cl_2$ (2 mL) and concentrated aqueous $NH_4OH$ (200 μL). The organic phase was separated and washed with water (500 μL), and this aqueous phase was separated and extracted once with $CH_2Cl_2$. The combined organic phases were dried ($Na_2SO_4$) and placed directly on a silica column and chromatographed (10% EtOAc/40% $CH_2Cl_2$/50% hexanes) to give the titled compound (88% ee). $^1H$ NMR (400 MHz, $CD_2Cl_2$) δ ppm 1.04-1.21 (3H), 1.51-1.59 (1H), 1.69-2.03 (3H), 2.23 (3H), 3.36-3.45 (2H), 3.89-4.09 (1H), 6.66 (1H), 7.25 (1H), 7.33-7.43 (1H), 7.54-7.56 (1H); MS (ESI+) m/z 432 (M+H)$^+$.

Example 179

N-(1-cyclopropyl-1-methylethyl)-N'-[(2Z)-5-methyl-3-(2,2,3,3-tetrafluoro-2,3-dihydro-1,4-benzodioxin-6-yl)-1,3-thiazol-2(3H)-ylidene]urea The titled compound was prepared as described in Example 97 substituting 2-cyclopropylpropan-2-amine for N-benzylbut-2-yn-1-amine. A second chromatography on silica gel eluting with 0 to 10% EtOAc/$CH_2Cl_2$ was required to supply the titled compound. $^1H$ NMR (300 MHz, $CDCl_3$) δ ppm 0.31 (4H), 1.2-1.3 (7H), 2.23 (3H), 5.23 (1H), 6.55 (1H), 7.23 (1H), 7.29 (1H), 7.37 (1H); MS (ESI+) m/z 446 (M+H)$^+$.

Example 180

N-(1,3-dioxolan-2-ylmethyl)-N-methyl-N'-[(2Z)-5-methyl-3-(2,2,3,3-tetrafluoro-2,3-dihydro-1,4-benzodioxin-6-yl)-1,3-thiazol-2(3H)-ylidene]urea The titled compound was prepared as described in Example 97 substituting 1-(1,3-dioxolan-2-yl)-N-methyl-methanamine for N-benzylbut-2-yn-1-amine. A second chromatography on silica gel eluting with 0 to 10% EtOAc/$CH_2Cl_2$ was required to supply the titled compound. $^1H$ NMR (300 MHz, $CDCl_3$) δ ppm 2.25 (3H), 3.05-3.10 (3H), 3.52-3.60 (2H), 3.79-4.01 (4H), 4.9-5.1 (1H), 6.64 (1H), 7.23 (1H), 7.30-7.39 (1H), 7.45-7.50 (1H); MS (ESI+) m/z 464 (M+H)$^+$.

Example 181

N-methyl-N'-[(2Z)-5-methyl-3-(2,2,3,3-tetrafluoro-2,3-dihydro-1,4-benzodioxin-6-yl)-1,3-thiazol-2(3H)-ylidene]urea The titled compound was prepared as described in Example 97 substituting N-methyl-1-(1,3,5-trimethyl-1H-pyrazol-4-yl)methanamine for N-benzylbut-2-yn-1-amine. A second chromatography on silica gel eluting with 0 to 10% EtOAc/$CH_2Cl_2$ was required to supply the titled compound. $^1H$ NMR (300 MHz, $CDCl_3$) δ ppm 2.25 (3H), 2.86 (3H), 5.10 (1H), 6.57 (1H), 7.22 (1H), 7.27 (1H), 7.38 (1H); MS (ESI+) m/z 378 (M+H)$^+$.

Example 182

N-[(1,3-dimethyl-1H-pyrazol-4-yl)methyl]-N-methyl-N'-[(2Z)-5-methyl-3-(2,2,3,3-tetrafluoro-2,3-dihydro-1,4-benzodioxin-6-yl)-1,3-thiazol-2(3H)-ylidene]urea The titled compound was prepared as described in Example 97 substituting 1-(1,3-dimethyl-1H-pyrazol-4-yl)-N-methanamine for N-benzylbut-2-yn-1-amine. A second chromatography on silica gel eluting with 10 to 40% EtOAc/$CH_2Cl_2$ was required to supply the titled compound. $^1H$ NMR (300 MHz, $CDCl_3$) δ ppm 2.03-2.25 (3H), 2.26 (3H), 2.88-2.95 (3H), 3.73-3.78 (3H), 4.38-4.43 (2H), 6.63 (1H), 6.98-7.35 (3H), 7.35-7.47 (1H); MS (ESI+) m/z 486 (M+H)$^+$.

Example 183

N-[(2Z)-5-cyano-3-(2,2-difluoro-1,3-benzodioxol-5-yl)-1,3-thiazol-2(3H)-ylidene]pyrrolidine-1-carboxamide 2,4,6-Trichlorotriazine (18 mg, 0.1 mmol) was dissolved into anhydrous DMF (600 μL) and left at room temperature for almost two hours. Then the solution was added to crude Example 86 (27 mg, ~68 μmol) with an anhydrous DMF (100 mL) rinse. The mixture was stirred at room temperature for more than 3½ hours, then quenched with water (5 mL) and partitioned into 4:1 EtOAc/hexanes (10 mL). The organic phase was separated and washed with water then brine, passed through a plug of $Na_2SO_4$ with EtOAc rinse, dried further ($Na_2SO_4$), concentrated, and chromatographed on silica (0 to 5 to 10% EtOAc/$CH_2Cl_2$) to give the titled compound. $^1H$ NMR (300 MHz, $CD_3OD/CDCl_3$) δ ppm 1.87 (4H), 3.38 (4H), 7.37 (2H), 7.58 (1H), 8.17 (1H); MS (ESI+) m/z 379 (M+H)$^+$.

Example 184

N'-[(2Z)-3-(2,2-difluoro-1,3-benzodioxol-5-yl)-5-(1-hydroxyethyl)-1,3-thiazol-2(3H)-ylidene]-N,N-dimethylurea

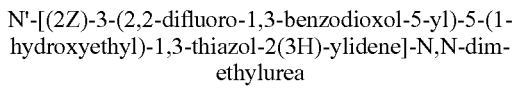

Example 89 (25 mg, 70 μmol) was dissolved into anhydrous THF (3.5 mL), cooled to 0° C., and treated with 3.0 M methylmagnesium chloride in THF (30 μL, 90 μmol). The solution was stirred 10 minutes, the bath was removed, and after 10 more minutes, the reaction was quenched with pH 7 aqueous potassium phosphate buffer (300 μL). Hexanes (500 μL) were added, the mixture was stirred, and the aqueous phase was separated and extracted with 1:1 EtOAc/hexanes. The combined organic phases were dried ($Na_2SO_4$), concentrated, and chromatographed on a C18-silica column (20/60/20% EtOAc/$CH_2Cl_2$/hexanes) to give the titled compound. $^1$H NMR (500 MHz, $CD_2Cl_2$) δ ppm 1.52 (3H), 2.95 (6H), 4.86 (1H), 6.78 (1H), 7.13 (1H), 7.19 (1H), 7.36 (1H); MS (ESI+) m/z 372 (M+H)$^+$.

Example 185

N'-[(2Z)-3-(2,2-difluoro-1,3-benzodioxol-5-yl)-5-(1-hydroxybutyl)-1,3-thiazol-2(3)-ylidene]-N,N-dimethylurea

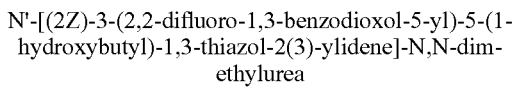

Example 89 (25 mg, 70 μmol) was dissolved into anhydrous THF (3.5 mL), cooled to 0° C., and treated with 2.0 M n-propylmagnesium chloride in $Et_2O$ (45 μL, 90 μmol). The solution was stirred 10 minutes, the bath was removed, and after 10 more minutes, the reaction was quenched with pH 7 aqueous potassium phosphate buffer (300 μL). Hexanes (500 μL) were added, the mixture was stirred, and the aqueous phase was separated and extracted with 1:1 EtOAc/hexanes. The combined organic phases were dried over $Na_2SO_4$, concentrated, and chromatographed on a C18-silica column (10/60/30 to 20/60/20% EtOAc/$CH_2Cl_2$/hexanes) to give the titled compound. $^1$H NMR (500 MHz, $CD_2Cl_2$) δ ppm 0.95 (3H), 1.33-1.53 (2H), 1.69-1.83 (2H), 2.95 (6H), 4.67 (1H), 6.79 (1H), 7.13 (1H), 7.19 (1H), 7.37 (1H); MS (ESI+) m/z 400 (M+H)$^+$.

Example 186

N'-[(2Z)-3-(2,2-difluoro-1,3-benzodioxol-5-yl)-5-(1-hydroxy-2-methylpropyl)-1,3-thiazol-2(3H)-ylidene]-N,N-dimethylurea

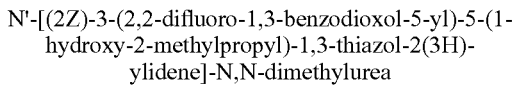

Example 89 (25 mg, 70 μmol) was dissolved into anhydrous THF (3.5 mL), cooled to 0° C., and treated with 2.0 M isopropylmagnesium chloride in THF (45 μL, 90 μmol). The solution was stirred 10 minutes, the bath was removed, and after 35 more minutes, additional isopropylmagnesium chloride (25 μL, 50 μmol) was added. After another 35 minutes, yet more isopropylmagnesium chloride (25 μL, 50 μmol) was added. The mixture was stirred 5 minutes, and then quenched with pH 7 aqueous potassium phosphate buffer (300 μL). Hexanes (500 μL) were added, the mixture was stirred, and the aqueous phase with salts separated was extracted with 1:1 EtOAc/hexanes. The combined organic phases were dried over $Na_2SO_4$, concentrated, and chromatographed on a C18-silica column (10/60/30 to 20/60/20% EtOAc/$CH_2Cl_2$/hexanes) to give the titled compound. $^1$H NMR (500 MHz, $CD_2Cl_2$) δ ppm 0.93 (3H), 1.03 (3H), 1.96 (1H), 2.95 (6H), 4.38 (1H), 6.78 (1H), 7.13 (1H), 7.19 (1H), 7.38 (1H); MS (ESI+) m/z 400 (M+H)$^+$.

Example 187

N'-[(2Z)-3-(2,2-difluoro-1,3-benzodioxol-5-yl)-5-{(E)-[(2-hydroxyethyl)imino]methyl}-1,3-thiazol-2(3H)-ylidene]-N,N-dimethylurea

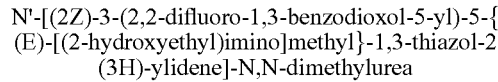

Example 89 (40 mg, 0.11 mmol) and ethanolamine (9 μL, 0.15 mmol) were suspended into MeCN (450 μL) and DMF (50 μL) and stirred at room temperature for three days. Then the suspension was partitioned between $CH_2Cl_2$ and water. The aqueous phase was separated and extracted with $CH_2Cl_2$, and the combined organic phases were washed with water. This aqueous phase was also back-extracted with $CH_2Cl_2$, and the combined organic phases were dried ($Na_2SO_4$), concentrated, chromatographed on silica (0/10 to 0/30 to 1/30 to 2/30 to 4%/30% MeOH/EtOAc in $CH_2Cl_2$), and chromatographed again on silica (10 to 30 to 67% MeCN/$CH_2Cl_2$ then 2 to 5% EtOH/50% MeCN/$CH_2Cl_2$) and concentrated to supply the titled compound. $^1$H NMR (400 MHz, $CD_2Cl_2$) δ ppm 2.93 (3H), 2.95 (3H), 3.68 (2H), 3.83 (2H), 7.20 (2H), 7.26 (1H), 7.39 (1H), 8.24 (1H); MS (ESI+) m/z 399 (M+H)$^+$.

Example 188

N'-[(2Z)-3-(2,2-difluoro-1,3-benzodioxol-5-yl)-5-(hydroxymethyl)-4-pyridin-2-yl-1,3-thiazol-2(3H)-ylidene]-N,N-dimethylurea compound with N'-[(2Z)-3-(2,2-difluoro-1,3-benzodioxol-5-yl)-5-[hydroxy(pyridin-2-yl)methyl]-1,3-thiazol-2(3H)-ylidene]-N,N-dimethylurea

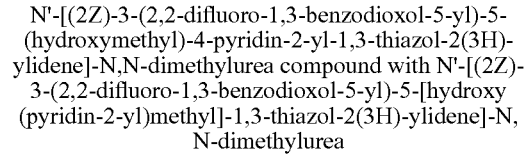

Example 89 (50 mg, 0.14 mmol) was dissolved into anhydrous THF (7.0 mL) and cooled to 0° C. Then 0.25 M 2-pyridylmagnesium bromide in THF (730 μL, 0.18 mmol) was added dropwise. After approximately 10 minutes, the ice bath was removed and the mixture was stirred at room temperature overnight. More Grignard solution (400 μL, 0.10 mmol) was added, and the solution was heated at a gentle reflux for 2 hours before being partially concentrated, mixed into more Grignard solution (5.6 mL, 1.4 mmol), and heated at 65° C. for 30 minutes. The mixture was then removed from the oil bath and quenched with 1 M aqueous $KH_2PO_4$ (5 mL). The aqueous phase was separated and extracted with EtOAc (2 mL). The combined organic phases were washed three times with a 4:1 mixture of water and brine, and each aqueous wash was back extracted with EtOAc (4 mL). The organic phases were combined before the next wash. The organic phases were dried ($Na_2SO_4$), concentrated, chromatographed on silica (MeOH/EtOAc/$CH_2Cl_2$), and rechromatographed on silica (1:1:1 EtOAc/$CH_2Cl_2$/hexanes to 1% MeOH/49% EtOAc/50% $CH_2Cl_2$) to give an inseparable mixture of >3:<1 expected 1,2-addition and 1,4-addition. MS (ESI+) m/z 435 (M+H)$^+$.

Example 189

N'-[(2Z)-3-(2,2-difluoro-1,3-benzodioxol-5-yl)-5-(difluoromethyl)-1,3-thiazol-2(3H)-ylidene]-N,N-dimethylurea

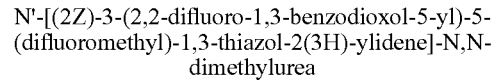

Example 89 (36 mg, 0.10 mmol) was suspended in $CH_2Cl_2$ (500 μL) and treated with bis(2-methoxyethyl)aminosulfur trifluoride (37 μL, 0.20 mmol) followed by a trace of ethanol (half microliter). The mixture was stirred at room temperature for four days, and then it was quenched with saturated aqueous $NaHCO_3$ (400 μL). After the bubbling had ceased, $CH_2Cl_2$ (1 mL) was added. The aqueous phase was separated and extracted with $CH_2Cl_2$. The combined organic phases were again washed with water, and the aqueous phase was separated and back extracted with more $CH_2Cl_2$. Then the combined organic phases were dried (Na$_2$SO$_4$) and placed directly on silica for chromatography (10 to 15% EtOAc/25% CH$_2$Cl$_2$/65 to 60% hexanes) to give the titled compound. $^1$H NMR (400 MHz, CD$_2$Cl$_2$) δ ppm 2.93 (3H), 2.95 (3H), 6.69 (1H), 7.18-7.23 (3H), 7.39 (1H); MS (ESI+) m/z 378 (M+H)$^+$.

Example 190

N-[(2Z)-3-(2,2-difluoro-1,3-benzodioxol-5-yl)-5-(fluoromethyl)-1,3-thiazol-2(3H)-ylidene]pyrrolidine-1-carboxamide The Example 120 (115 mg, 0.30 mmol) was suspended into CH$_2$Cl$_2$ (3.0 mL), cooled to −70° C., and treated with bis(2-methoxyethyl)aminosulfur trifluoride (83 μL, 0.45 mmol). The dry ice was removed from the cold bath to permit it to slowly warm to −5° C. at which point the cold bath was removed and the solution was stirred for 2.5 hours at room temperature. It was then quenched with saturated aqueous NaHCO$_3$ (600 μL). The aqueous phase was separated and extracted with CH$_2$Cl$_2$, and the combined organic phases were washed with water, dried (Na$_2$SO$_4$), placed directly on silica for chromatography (30% EtOAc/hexanes), and then rechromatographed on silica (0.5% EtOH/10% MeCN/89.5% CH$_2$Cl$_2$) to give the titled compound. $^1$H NMR (400 MHz, CD$_2$Cl$_2$) δ ppm 1.83 (4H), 3.33 (2H), 3.41 (2H), 5.30 (2H), 7.05 (1H), 7.19 (2H), 7.44 (1H); MS (ESI+) m/z 386 (M+H)$^+$.

Example 191

N-[(2Z)-3-(2,2-difluoro-1,3-benzodioxol-5-yl)-4-hydroxy-5-methylene-1,3-thiazolidin-2-ylidene]pyrrolidine-1-carboxamide Example 120 (115 mg, 0.30 mmol) was suspended into CH$_2$Cl$_2$ (3.0 mL), cooled to −70° C., and treated with bis(2-methoxyethyl)aminosulfur trifluoride (67 μL, 0.36 mmol). The suspension was stirred for 20 minutes at −70° C., and the dry ice was removed from the bath to permit it to slowly warm up. After 31 minutes, the temperature was at −15° C., the bath was removed, and the cold solution was quenched with saturated aqueous NaHCO$_3$ (600 μL). The aqueous phase was extracted with CH$_2$Cl$_2$, and the combined organic phases were washed with water, dried (Na$_2$SO$_4$), and placed directly on silica for chromatography (30 to 50% EtOAc/hexanes) to give the titled compound. $^1$H NMR (300 MHz, CDCl$_3$) δ ppm 1.80 (4H), 3.25 (2H), 3.40 (2H), 4.90 (1H), 5.36 (1H), 5.55 (1H), 5.72 (1H), 7.09 (1H), 7.24 (1H), 7.33 (1H); MS (ESI+) m/z 384 (M+H)$^+$.

Example 192

(3S)-3-hydroxy-N-[(2Z)-5-methyl-3-(2,2,3,3-tetrafluoro-2,3-dihydro-1,4-benzodioxin-6-yl)-1,3-thiazol-2(3H)-ylidene]pyrrolidine-1-carboxamide A solution of (Z)-3-methyl-1-(5-methyl-3-(2,2,3,3-tetrafluoro-2,3-dihydrobenzo[b][1,4]dioxin-6-yl)thiazol-2(3H)-ylidenecarbamoyl)-1H-imidazol-3-ium iodide (Example 81A, 0.1 g, 0.18 mmol), (S)-pyrrolidin-3-ol (0.016 g, 0.18 mmol) and Hunig's base (0.023 g, 018 mmol) in dry acetonitrile (5 mL) was heated to 60° C. for three hours. After cooling, the mixture was diluted with CH$_2$Cl$_2$ (50 mL) and washed with water and brine. The organic phase was dried over sodium sulfate, filtered and dried. After evaporation under reduced pressure, the residue was chromatographed over silica using CH$_2$Cl$_2$ and then 2% MeOH/CH$_2$Cl$_2$ to give the titled compound. $^1$H NMR (CDCl$_3$) δ ppm 1.99 (2H), 2.20 (3H), 3.40-3.70 (4H), 4.42 (1H), 6.60 (1H), 7.20-7.50 (3H); MS (ESI) m/z 434(M+H).

Example 193

2,2-dimethyl-N-[(2Z)-5-methyl-3-(2,2,3,3-tetrafluoro-2,3-dihydro-1,4-benzodioxin-6-yl)-1,3-thiazol-2(3H)-ylidene]propanamide To a solution of 5-methylene-3-(2,2,3,3-tetrafluoro-2,3-dihydrobenzo[b][1,4]dioxin-6-yl)thiazolidin-2-imine (Example 22C, 0.14 g, 0.44 mmol) in acetonitrile (3 mL) was added Hunig's base (0.062 g, 0.48 mmol) followed by pivaloyl chloride (0.064 g, 0.54 mmol). The mixture was heated for 12 hours at 65° C. The mixture was cooled down and more pivaloyl chloride (0.064 g, 0.54 mmol) was added. The mixture was heated again at 65° C. for 12 hours. After cooling, the reaction mixture was diluted with CH$_2$Cl$_2$ (50 mL) and washed with water and brine. The organic phase was dried over sodium sulfate, filtered and dried. After evaporation under reduced pressure, the residue was chromatographed over silica using CH$_2$Cl$_2$-5%MeOH/CH$_2$Cl$_2$ to supply the titled compound. $^1$H NMR (CDCl$_3$) δ ppm 1.05 (9H), 2.30 (3H), 6.80 (1H), 7.20 (1H), 7.40 (1H), 7.50 (1H); MS (ESI) m/z 405 (M+H)$^+$.

Example 194

3,3-dimethyl-N-[(2Z)-5-methylene-3-(2,2,3,3-tetrafluoro-2,3-dihydro-1,4-benzodioxin-6-yl)-1,3-thiazolidin-2-ylidene]butanamide To a solution of 5-methylene-3-(2,2,3,3-tetrafluoro-2,3-dihydrobenzo[b][1,4]dioxin-6-yl)thiazolidin-2-imine (Example 22C, 0.14 g, 0.44 mmol) in acetonitrile (3 mL) was added Hunig's base (0.062 g, 0.48 mmol) followed by 3,3-dimethylbutanoyl chloride (0.088 g, 0.66 mmol). The mixture was heated for 12 hours at 65° C. The reaction mixture was cooled down, diluted with CH$_2$Cl$_2$ (50 mL), and washed with water and brine. The organic phase was dried over sodium sulfate, filtered and dried. After evaporation under reduced pressure, the residue was chromatographed over silica using CH$_2$Cl$_2$-5%MeOH/CH$_2$Cl$_2$ to supply the titled compound. $^1$H NMR (CDCl$_3$) δ ppm 1.00 (9H), 2.35 (2H), 4.65 (2H), 5.25 (1H), 5.35 (1H), 7.15 (1H), 7.25 (1H), 7.55 (1H); MS (ESI) m/z 419 (M+H)$^+$.

Example 195

3-methyl-N-[(2Z)-5-methyl-3-(2,2,3,3-tetrafluoro-2,3-dihydro-1,4-benzodioxin-6-yl)-1,3-thiazol-2(3H)-ylidene]butanamide To a solution of 5-methylene-3-(2,2,3,3-tetrafluoro-2,3-dihydrobenzo[b][1,4]dioxin-6-yl)thiazolidin-2-imine (Example 22C, 0.14 g, 0.44 mmol) in acetonitrile (3 mL) was added Hunig's base (0.062 g, 0.48 mmol) followed by 3-methylbutanoyl chloride (0.08 g, 0.66 mmol). The mixture was heated for 12 hours at 65° C. The reaction mixture was cooled down and more 3-methylbutanoyl chloride (0.08 g, 0.66 mmol) was added. The mixture was heated again at 65° C. for 12 hours. After cooling off, the mixture was diluted with CH$_2$Cl$_2$ (50 mL) and washed with water and brine. The organic phase was dried over sodium sulfate, filtered and dried. After evaporation under reduced pressure the residue was chromatographed over silica using CH$_2$Cl$_2$ 100%-5%MeOH/CH$_2$Cl$_2$ to supply the titled compound. $^1$H NMR (CDCl$_3$) δ ppm 0.95 (6H), 2.20 (1H), 2.35 (3H), 2.40 (2H), 6.75 (1H), 7.20 (1H), 7.30 (1H), 7.40 (1H); MS (ESI) m/z 405(M+H)$^+$.

Example 196

N-[(2Z)-5-(cyanomethyl)-3-(2,2-difluoro-1,3-benzodioxol-5-yl)-1,3-thiazol-2(3H)-ylidene]pyrrolidine-1-carboxamide

Example 196A

{(2Z)-3-(2,2-difluoro-1,3-benzodioxol-5-yl)-2-[(pyrrolidin-1-ylcarbonyl)imino]-2,3-dihydro-1,3-thiazol-5-yl}methyl methanesulfonate To an ice-cold solution of Example 120 (0.1 g, 0.26 mmol) in dry $CH_2Cl_2$ (5 mL) were added triethylamine (0.28 mmol, 0.029 g) and methanesulfonyl chloride (0.28 mmol, 0.033 g) after which the mixture was stirred at room temperature for 1 hour. The reaction was diluted with $CH_2Cl_2$ (50 mL) and washed twice with water (2×50 mL) and once with brine (50 mL). The organic layers were dried over sodium sulfate, filtered, and evaporated under reduced pressure to give the desired mesylate. $^1H$ NMR (CDCl3) δ ppm 1.80 (4H), 2.90 (3H), 3.25 (4H), 4.40 (2H), 6.85 (1H), 7.23-7.81 (3H); MS (ESI+) m/z 462 $(M+H)^+$.

Example 196B

N-[(2Z)-5-(cyanomethyl)-3-(2,2-difluoro-1,3-benzodioxol-5-yl)-1,3-thiazol-2(3H)-ylidene]pyrrolidine-1-carboxamide Example 196A (100 mg, 0.26 mmol) was suspended into DMSO (2.0 mL), treated with $Et_4N^+CN^-$ (0.12 g, 0.78 mmol), and stirred for one hour before being partitioned between water (10 mL) and 7:3 EtOAc/hexanes (10 mL). The aqueous phase and solids were separated and extracted five times with more 7:3 solution. The organic phases were combined, washed with water then brine, dried ($Na_2SO_4$), concentrated, and chromatographed on silica (10 to 20 to 30% EtOAc/20% $CH_2Cl_2$/hexanes then 50% EtOAc/hexanes) to give the titled compound. $^1H$ NMR (400 MHz, $CD_2Cl_2$) δ ppm 1.83 (4H), 3.37 (4H), 3.68 (2H), 6.96 (1H), 7.18 (1H), 7.20 (1H), 7.44 (1H); MS (ESI+) m/z 393 $(M+H)^+$.

Example 197

(3R)-3-fluoro-N-[(2Z)-5-methyl-3-(2,2,3,3-tetrafluoro-2,3-dihydro-1,4-benzodioxin-6-yl)-1,3-thiazol-2(3H)-ylidene]pyrrolidine-1-carboxamide (Z)-3-Methyl-1-(5-methyl-3-(2,2,3,3-tetrafluoro-2,3-dihydrobenzo[b][1,4]dioxin-6-yl)thiazol-2(3H)-ylidenecarbamoyl)-1H-imidazol-3-ium iodide (Example 81A, 250 mg, 0.45 mmol), (R)-3-fluoropyrrolidine hydrochloride (62 mg, 0.49 mmol) and Hunig's base (0.078 mL, 0.45 mmol) in acetonitrile (5 mL) were stirred at 55° C. for 3 hours. The reaction mixture was then cooled to 30° C. with continued stirring for 12 hours. The mixture was evaporated to dryness and purified by reverse phase HPLC to give the title compound. $^1H$ NMR (CDCl$_3$) δ ppm 2.00 (2H), 2.20 (3H), 3.35-3.85 (4H), 5.10-5.30 (1H), 6.60 (1H), 7.20 (1H), 7.35 (1H), 7.45 (1H); MS (ESI) m/z 436$(M+H)^+$.

Example 198

(3S)-3-fluoro-N-[(2Z)-5-methyl-3-(2,2,3,3-tetrafluoro-2,3-dihydro-1,4-benzodioxin-6-yl)-1,3-thiazol-2(3H)-ylidene]pyrrolidine-1-carboxamide A solution of (3R)-3-hydroxy-N-[(2Z)-5-methyl-3-(2,2,3,3-tetrafluoro-2,3-dihydro-1,4-benzodioxin-6-yl)-1,3-thiazol-2(3H)-ylidene]pyrrolidine-1-carboxamide (Example 109, 0.1 g, 0.23 mmol) in dry $CH_2Cl_2$ (5 mL) was treated with bis(2-methoxyethyl)aminosulfur trifluoride (0.056 g, 0.25 mmol). After 2 hours at room temperature, the mixture was neutralized by dropwise addition of a saturated solution of sodium bicarbonate. The mixture was washed with water and brine, dried over sodium sulfate, filtered, and evaporated under reduced pressure. The residue was purified over silica using $CH_2Cl_2$ as eluant. $^1H$ NMR (CDCl$_3$) δ ppm 2.00 (2H), 2.25 (3H), 3.35-3.85 (4H), 5.15-5.30 (1H), 6.60 (1H), 7.20 (1H), 7.35 (1H), 7.45 (1H); MS (ESI) m/z 436$(M+H)^+$.

Example 199

[2-imino-3-(2,2,3,3-tetrafluoro-2,3-dihydro-1,4-benzodioxin-6-yl)-2,3-dihydro-1,3-thiazol-5-yl]methanol Example 141 (303 mg, 0.80 mmol) was suspended into acetic acid (5.0 mL), 30% aqueous $H_2O_2$ (410 μL, 4.0 mmol) was added dropwise, and the resulting mixture was stirred overnight. It was quenched by the slow addition of sufficient sodium bisulfite to make a peroxide test strip negative to the presence of peroxide, and water (2 mL). The mixture was partially concentrated under vacuum, then reconcentrated from EtOAc. The residue was mixed into EtOAc (15 mL) and water (5 mL), then treated with sufficient saturated aqueous $NaHCO_3$ to bring the aqueous phase to pH=8 with thorough stirring. The aqueous phase was separated and extracted with EtOAc, and the combined organic phases were washed with brine, dried ($Na_2SO_4$), concentrated, and chromatographed on silica (80 to 100% EtOAc/hexanes) to give the titled compound. $^1H$ NMR (400 MHz, DMSO-$d_6$) δ ppm 4.26 (2H), 5.25 (1H), 7.06 (1H), 7.54 (1H), 7.56 (1H), 7.85 (1H), 8.40 (1H); MS (ESI+) m/z 337 $(M+H)^+$.

Example 200

N-[(2Z)-5-(hydroxymethyl)-3-(2,2,3,3-tetrafluoro-2,3-dihydro-1,4-benzodioxin-6-yl)-1,3-thiazol-2(3H)-ylidene]-2,2-dimethylpropanamide Example 199 [54 mg, 0.16 mmol (contains ~0.2 eq AcOH)] was dissolved into MeCN (800 μL) and treated with diisopropylethylamine (35 μL, 0.20 mmol). The orange mixture was then further treated with dropwise addition of pivaloyl chloride (25 μL, 0.20 mmol) over 40 seconds. The resulting suspension was stirred for 10 minutes, diluted with EtOAc (2 mL), and washed with saturated aqueous $NaHCO_3$. The aqueous phase was extracted with EtOAc, and the combined organic phases were washed with brine, dried ($Na_2SO_4$), concentrated and chromatographed on silica (20% EtOAc/40% $CH_2Cl_2$/40% hexanes) to give the titled compound. $^1H$ NMR (300 MHz, DMSO-$d_6$) δ ppm 1.09 (9H), 4.51 (2H), 5.52 (1H), 7.60 (1H), 7.66 (1H), 7.69 (1H), 7.91 (1H); MS (ESI+) m/z 421 $(M+H)^+$.

Example 201

N-[(2Z)-5-(hydroxymethyl)-3-(2,2,3,3-tetrafluoro-2,3-dihydro-1,4-benzodioxin-6-yl)-1,3-thiazol-2(3H)-ylidene]benzamide Example 199 [54 mg, 0.16 mmol (contains ~0.2 eq AcOH)] was dissolved into MeCN (800 μL) and treated with diisopropylethylamine (35 μL, 0.20 mmol). The orange mixture was then further treated with dropwise addition of benzoyl chloride (23 μL, 0.20 mmol) over 40 seconds. The solution was stirred for 10 minutes, diluted with EtOAc (2 mL), and washed with saturated aqueous $NaHCO_3$. The aqueous phase was extracted with EtOAc, and the combined organic phases were washed with brine, dried (Na$_2$SO$_4$), concentrated and chromatographed on silica (20% EtOAc/40% CH$_2$Cl$_2$/40% hexanes) to give the titled compound. $^1$H NMR (300 MHz, CDCl$_3$) δ ppm 4.77 (2H), 7.10 (1H), 7.32-7.52 (6H), 8.16 (2H); MS (ESI+) m/z 441 (M+H)$^+$.

Example 202

N-[(2Z)-5-(hydroxymethyl)-3-(2,2,3,3-tetrafluoro-2,3-dihydro-1,4-benzodioxin-6-yl)-1,3-thiazol-2(3H)-ylidene]-1H-imidazole-1-carboxamide Example 199 (96 mg, 0.28 mmol) was dissolved into anhydrous MeCN (1.4 mL) and treated with carbonyl diimidazole (59 mg, 0.36 mmol). The mixture was stirred for 15 minutes before being diluted with Et$_2$O (2 mL). The solids were collected by filtration and rinsed with more Et$_2$O, then dried under vacuum to give the titled compound. $^1$H NMR (300 MHz, DMSO-d$_6$) δ ppm 4.59 (2H), 5.71 (1H), 6.99 (1H), 7.47 (1H), 7.71-7.79 (3H), 7.96 (1H), 8.07 (1H); MS (ESI+) m/z 453 (M+Na)$^+$.

Example 203

N-benzyl-N-(2-hydroxyethyl)-N'-[(2Z)-5-methyl-3-(2,2,3,3-tetrafluoro-2,3-dihydro-1,4-benzodioxin-6-yl)-1,3-thiazol-2(3H)-ylidene]urea The titled compound was prepared as described in Example 97 substituting 2-(benzylamino)ethanol for N-benzylbut-2-yn-1-amine. $^1$H NMR (300 MHz, DMSO-d$_6$/D$_2$O) δ ppm 2.25 (3H) 3.35-3.46 (2H) 3.47-3.59 (2H) 4.50-4.63 (2H) 7.01-7.09 (1H) 7.10-7.19 (2H) 7.19-7.34 (3H) 7.39-7.50 (2H) 7.56-7.66 (1H); MS (ESI+) m/z 498 (M+H)$^+$.

Example 204

N-[(2Z)-5-methyl-3-(2,2,3,3-tetrafluoro-2,3-dihydro-1,4-benzodioxin-6-yl)-1,3-thiazol-2(3H)-ylidene]indoline-1-carboxamide The titled compound was prepared as described in Example 97 substituting indoline for N-benzylbut-2-yn-1-amine. $^1$H NMR (300 MHz, DMSO-d$_6$/D$_2$O) δ ppm 2.26-2.33 (3H) 3.02 (2H) 3.96 (2H) 6.81-6.89 (1H) 6.89-6.99 (1H) 7.09-7.20 (2H) 7.56-7.63 (2H) 7.63-7.73 (1H) 7.76-7.81 (1H); MS (ESI+) m/z 466 (M+H)$^+$.

Example 205

2-methyl-N-[(2Z)-5-methyl-3-(2,2,3,3-tetrafluoro-2,3-dihydro-1,4-benzodioxin-6-yl)-1,3-thiazol-2(3H)-ylidene]piperidine-1-carboxamide The titled compound was prepared as described in Example 97 substituting 2-methylpiperidine for N-benzylbut-2-yn-1-amine. $^1$H NMR (300 MHz, DMSO-d$_6$/D$_2$O) δ ppm 1.09 (3H) 1.19-1.37 (1H) 1.41-1.70 (5H) 2.17-2.28 (3H) 2.74-2.92 (1H) 4.04-4.16 (1H) 4.48-4.62 (1H) 7.05-7.10 (1H) 7.51-7.55 (2H) 7.71-7.75 (1H); MS (ESI+) m/z 446 (M+H)$^-$.

Example 206

N-(tert-butyl)-N'-[(2Z)-5-methyl-3-(2,2,3,3-tetrafluoro-2,3-dihydro-1,4-benzodioxin-6-yl)-1,3-thiazol-2(3H)-ylidene]urea The titled compound was prepared as described in Example 97 substituting 2-methylpropan-2-amine for N-benzylbut-2-yn-1-amine. $^1$H NMR (300 MHz, DMSO-d$_6$/D$_2$O) δ ppm 1.30 (9H) 2.24 (3H) 7.01-7.07 (1H) 7.50-7.55 (2H), 7.67-7.72 (1H); MS (ESI+) m/z 420 (M+H)$^+$.

Example 207

N-(2-hydroxy-1,1-dimethylethyl)-N'-[(2Z)-5-methyl-3-(2,2,3,3-tetrafluoro-2,3-dihydro-1,4-benzodioxin-6-yl)-1,3-thiazol-2(3H)-ylidene]urea The titled compound was prepared as described in Example 97 substituting 2-amino-2-methylpropan-1-ol for N-benzylbut-2-yn-1-amine. $^1$H NMR (300 MHz, DMSO-d$_6$/D$_2$O) δ ppm 1.18 (6H) 2.15-2.21 (3H) 3.32-3.37 (2H) 6.95-7.00 (1H) 7.45-7.50 (2H) 7.62-7.65 (1H); MS (ESI+) m/z 436 (M+H)$^+$.

Example 208

N-(1,1-dimethylprop-2-ynyl)-N'-[(2Z)-5-methyl-3-(2,2,3,3-tetrafluoro-2,3-dihydro-1,4-benzodioxin-6-yl)-1,3-thiazol-2(3H)-ylidene]urea The titled compound was prepared as described in Example 97 substituting 2-methylbut-3-yn-2-amine for N-benzylbut-2-yn-1-amine. $^1$H NMR (300 MHz, DMSO-d$_6$/D$_2$O) δ ppm 1.53 (6H) 2.22-2.26 (3H) 3.20-3.23 (1H) 7.01-7.06 (1H) 7.52-7.54 (2H) 7.71-7.74 (1H); MS (ESI+) m/z 430 (M+H)$^+$.

Example 209

N-[(2Z)-5-methyl-3-(2,2,3,3-tetrafluoro-2,3-dihydro-1,4-benzodioxin-6-yl)-1,3-thiazol-2(3H)-ylidene]-N'-(1,1,3,3-tetramethylbutyl)urea The titled compound was prepared as described in Example 97 substituting 2,4,4-trimethylpentan-2-amine for N-benzylbut-2-yn-1-amine. $^1$H NMR (300 MHz, DMSO-d$_6$/D$_2$O) δ ppm 0.95 (9H) 1.33 (6H) 1.71 (2H) 2.21-2.25 (3H) 7.00-7.02 (1H) 7.51-7.53 (2H) 7.66-7.69 (1H); MS (ESI+) m/z 476 (M+H)$^+$.

Example 210

N-(1,1-dimethylpropyl)-N'-[(2Z)-5-methyl-3-(2,2,3,3-tetrafluoro-2,3-dihydro-1,4-benzodioxin-6-yl)-1,3-thiazol-2(3H)-ylidene]urea The titled compound was prepared as described in Example 97 substituting 2-methylbutan-2-amine for N-benzylbut-2-yn-1-amine. $^1$H NMR (300 MHz, DMSO-d$_6$/D$_2$O) δ ppm 0.80 (3H) 1.20-1.24 (6H) 1.65 (2H) 2.22-2.26 (3H) 7.00-7.04 (1H) 7.50-7.55 (2H) 7.68-7.70 (1H); MS (ESI+) m/z 434 (M+H)$^+$.

Example 211

N-(1-ethyl-1-methylpropyl)-N'-[(2Z)-5-methyl-3-(2,2,3,3-tetrafluoro-2,3-dihydro-1,4-benzodioxin-6-yl)-1,3-thiazol-2(3H)-ylidene]urea The titled compound was prepared as described in Example 97 substituting 3-methylpentan-3-amine for N-benzylbut-2-yn-1-amine. $^1$H NMR (300 MHz, DMSO-d$_6$/D$_2$O) δ ppm 0.78 (6H) 1.12-1.17 (3H) 1.49-1.63 (2H) 1.64-1.78 (2H) 2.21-2.26 (3H) 6.99-7.02 (1H) 7.50-7.54 (2H) 7.66-7.69 (1H); MS (ESI+) m/z 448 (M+H)$^+$.

Example 212

N-methyl-N'-[(2Z)-5-methyl-3-(2,2,3,3-tetrafluoro-2,
3-dihydro-1,4-benzodioxin-6-yl)-1,3-thiazol-2(3H)-
ylidene]-N-(thieno[2,3-b]pyridin-2-ylmethyl)urea The titled compound was prepared as its trifluoroacetic acid salt as described in Example 97 substituting N-methyl-1-(thieno[2,3-b]pyridin-2-yl)methanamine for N-benzylbut-2-yn-1-amine. $^1$H NMR (300 MHz, DMSO-$d_6$/$D_2$O) δ ppm 2.51-2.57 (3H) 3.24 (3H) 5.05 (2H) 7.34-7.39 (1H) 7.39-7.44 (1H) 7.63 (1H) 7.72-7.83 (2H) 7.96-7.99 (1H) 8.36 (1H) 8.73 (1H); MS (ESI−) m/z 523 (M−H)$^-$.

Example 213

N-[(1R)-2-hydroxy-1-phenylethyl]-N'-[(2Z)-5-methyl-3-(2,2,3,3-tetrafluoro-2,3-dihydro-1,4-benzodioxin-6-yl)-1,3-thiazol-2(3H)-ylidene]urea The titled compound was prepared as described in Example 97 substituting (R)-2-amino-2-phenylethanol for N-benzylbut-2-yn-1-amine. $^1$H NMR (300 MHz, DMSO-$d_6$/$D_2$O) δ ppm 2.19-2.24 (3H) 3.65 (2H) 4.77 (1H) 6.99-7.05 (1H) 7.17-7.26 (1H) 7.26-7.31 (4H) 7.49-7.55 (2H) 7.67-7.70 (1H); MS (ESI−) m/z 482 (M−H)$^-$.

Example 214

N-(1,2-dimethylpropyl)-N'-[(2Z)-5-methyl-3-(2,2,3,3-tetrafluoro-2,3-dihydro-1,4-benzodioxin-6-yl)-1,3-thiazol-2(3H)-ylidene]urea The titled compound was prepared as described in Example 97 substituting 3-methylbutan-2-amine for N-benzylbut-2-yn-1-amine. $^1$H NMR (300 MHz, DMSO-$d_6$/$D_2$O) δ ppm 0.84 (6H) 1.03 (3H) 1.62-1.76 (1H) 2.19-2.28 (3H) 3.48-3.61 (1H) 7.01-7.06 (1H) 7.51-7.57 (2H) 7.68-7.75 (1H); MS (ESI+) m/z 434 (M+H)$^+$.

Example 215

N-isopropyl-N'-[(2Z)-5-methyl-3-(2,2,3,3-tetrafluoro-2,3-dihydro-1,4-benzodioxin-6-yl)-1,3-thiazol-2(3H)-ylidene]urea The titled compound was prepared as described in Example 97 substituting propan-2-amine for N-benzylbut-2-yn-1-amine. $^1$H NMR (300 MHz, DMSO-$d_6$/$D_2$O) δ ppm 1.11 (6H) 2.19-2.27 (3H) 3.71-3.87 (1H) 6.98-7.07 (1H) 7.49-7.59 (2H) 7.70-7.75 (1H); MS (ESI+) m/z 406 (M+H)$^+$.

Example 216

N-(2-methoxy-1-methylethyl)-N'-[(2Z)-5-methyl-3-(2,2,3,3-tetrafluoro-2,3-dihydro-1,4-benzodioxin-6-yl)-1,3-thiazol-2(3H)-ylidene]urea The titled compound was prepared as described in Example 97 substituting 1-methoxypropan-2-amine for N-benzylbut-2-yn-1-amine. $^1$H NMR (300 MHz, DMSO-$d_6$/$D_2$O) δ ppm 1.09 (3H) 2.20-2.26 (3H) 3.26 (3H) 3.29-3.40 (2H) 3.77-3.93 (1H) 6.99-7.09 (1H) 7.49-7.57 (2H) 7.68-7.76 (1H); MS (ESI+) m/z 436 (M+H)$^+$.

Example 217

N-(sec-butyl)-N'-[(2Z)-5-methyl-3-(2,2,3,3-tetrafluoro-2,3-dihydro-1,4-benzodioxin-6-yl)-1,3-thiazol-2(3H)-ylidene]urea The titled compound was prepared as described in Example 97 substituting butan-2-amine for N-benzylbut-2-yn-1-amine. $^1$H NMR (300 MHz, DMSO-$d_6$/$D_2$O) δ ppm 0.84 (3H) 1.06 (3H) 1.33-1.55 (2H) 2.20-2.28 (3H) 3.53-3.67 (1H) 6.96-7.08 (1H) 7.45-7.59 (2H) 7.69-7.77 (1H); MS (ESI+) m/z 420 (M+H)$^+$.

Example 218

N-(1-ethylpropyl)-N'-[(2Z)-5-methyl-3-(2,2,3,3-tetrafluoro-2,3-dihydro-1,4-benzodioxin-6-yl)-1,3-thiazol-2(3H)-ylidene]urea The titled compound was prepared as described in Example 97 substituting pentan-3-amine for N-benzylbut-2-yn-1-amine. $^1$H NMR (300 MHz, DMSO-$d_6$/$D_2$O) δ ppm 0.84 (6H) 1.30-1.59 (4H) 2.20-2.25 (3H) 3.34-3.53 (1H) 6.96-7.07 (1H) 7.48-7.60 (2H) 7.69-7.76 (1H); MS (ESI+) m/z 434 (M+H)$^+$.

Example 219

N-(1-methylbutyl)-N'-[(2Z)-5-methyl-3-(2,2,3,3-tetrafluoro-2,3-dihydro-1,4-benzodioxin-6-yl)-1,3-thiazol-2(3H)-ylidene]urea The titled compound was prepared as described in Example 97 substituting pentan-2-amine for N-benzylbut-2-yn-1-amine. $^1$H NMR (300 MHz, DMSO-$d_6$/$D_2$O) δ ppm 0.87 (3H) 1.07 (3H) 1.20-1.53 (4H) 2.19-2.28 (3H) 3.62-3.76 (1H) 6.97-7.08 (1H) 7.45-7.58 (2H) 7.68-7.76 (1H); MS (ESI+) m/z 434 (M+H)$^+$.

Example 220

N-benzyl-N-methyl-N'-[(2Z)-5-methyl-3-(2,2,3,3-tetrafluoro-2,3-dihydro-1,4-benzodioxin-6-yl)-1,3-thiazol-2(3H)-ylidene]urea The titled compound was prepared as described in Example 97 substituting N-methyl-1-phenylmethanamine for N-benzylbut-2-yn-1-amine. $^1$H NMR (300 MHz, DMSO-$d_6$/$D_2$O) δ ppm 2.22-2.28 (3H) 2.90 (3H) 4.53 (2H) 7.05-7.09 (1H) 7.10-7.18 (2H) 7.19-7.34 (3H) 7.42-7.53 (2H) 7.61-7.69 (1H).

Example 221

N-methyl-N'-[(2Z)-5-methyl-3-(2,2,3,3-tetrafluoro-2,3-dihydro-1,4-benzodioxin-6-yl)-1,3-thiazol-2(3H)-ylidene]-N-prop-2-ynylurea The titled compound was prepared as described in Example 97 substituting N-methylprop-2-yn-1-amine for N-benzylbut-2-yn-1-amine. $^1$H NMR (300 MHz, DMSO-$d_6$/$D_2$O) δ ppm 2.24-2.28 (3H) 2.78-2.82 (1H) 2.92-2.95 (3H) 4.15 (2H) 7.08-7.13 (1H) 7.49-7.55 (1H) 7.56-7.61 (1H) 7.73-7.77 (1H); MS (ESI+) m/z 416 (M+H)$^+$.

Example 222

N-benzyl-N-isopropyl-N'-[(2Z)-5-methyl-3-(2,2,3,3-tetrafluoro-2,3-dihydro-1,4-benzodioxin-6-yl)-1,3-thiazol-2(3H)-ylidene]urea The titled compound was prepared as described in Example 97 substituting N-benzylpropan-2-amine for N-benzylbut-2-yn-1-amine. $^1$H NMR (300 MHz, DMSO-$d_6$/$D_2O$) δ ppm 1.06 (6H) 2.20-2.27 (3H) 4.35-4.45 (1H) 4.48 (2H) 7.01-7.08 (1H) 7.10-7.29 (5H) 7.30-7.43 (2H) 7.49-7.60 (1H); MS (ESI+) m/z 496 (M+H)$^+$.

Example 223

N-ethyl-N-methyl-N'-[(2Z)-5-methyl-3-(2,2,3,3-tetrafluoro-2,3-dihydro-1,4-benzodioxin-6-yl)-1,3-thiazol-2(3H)-ylidene]urea The titled compound was prepared as described in Example 97 substituting N-methylethanamine for N-benzylbut-2-yn-1-amine. $^1$H NMR (300 MHz, DMSO-$d_6$/$D_2O$) δ ppm 1.02 (3H) 2.20-2.26 (3H) 2.86 (3H) 3.34 (2H) 7.04-7.10 (1H) 7.48-7.58 (2H) 7.71-7.76 (1H); MS (ESI+) m/z 406 (M+H)$^+$.

Example 224

N-benzyl-N-ethyl-N'-[(2Z)-5-methyl-3-(2,2,3,3-tetrafluoro-2,3-dihydro-1,4-benzodioxin-6-yl)-1,3-thiazol-2(3H)-ylidene]urea The titled compound was prepared as described in Example 97 substituting N-benzylethanamine for N-benzylbut-2-yn-1-amine. $^1$H NMR (300 MHz, DMSO-$d_6$/$D_2O$) δ ppm 1.00 (3H) 2.20-2.29 (3H) 3.35 (2H) 4.52 (2H) 7.02-7.10 (1H) 7.13-7.20 (2H) 7.19-7.33 (3H) 7.40-7.49 (2H) 7.61-7.68 (1H); MS (ESI+) m/z 482 (M+H)$^+$.

Example 225

N-benzyl-N-butyl-N'-[(2Z)-5-methyl-3-(2,2,3,3-tetrafluoro-2,3-dihydro-1,4-benzodioxin-6-yl)-1,3-thiazol-2(3H)-ylidene]urea The titled compound was prepared as described in Example 97 substituting N-benzylbutane-1-amine for N-benzylbut-2-yn-1-amine. $^1$H NMR (300 MHz, DMSO-$d_6$/$D_2O$) δ ppm 0.77 (3H) 1.08-1.22 (2H) 1.33-1.50 (2H) 2.22-2.27 (3H) 3.22-3.33 (2H) 4.50 (2H) 7.01-7.11 (1H) 7.14-7.21 (2H) 7.21-7.35 (3H) 7.40-7.48 (2H) 7.62-7.69 (1H); MS (ESI−) m/z 508 (M−H)$^-$.

DETERMINATION OF BIOLOGICAL ACTIVITY

To determine the effectiveness of compounds of formula (I) or (II), as allosteric modulators, the compounds of the invention were evaluated according to two high-throughput functional assays using (i) IMR-32 cells endogenous expressing α7 nAChRs and measuring Ca$^{2+}$ flux or membrane potential changes utilizing the fluorescence-imaging plate reader (FLIPR)-based assays and (ii) measurement of phospho-ERK activity using western blot assays. These assays allow for higher throughput screening of positive allosteric modulators using cells or cell lines expressing endogenous α7 nAChRs.

(i) High-throughput Calcium Flux Assays using Cells Expressing Endogenous α7 nAChRs Since allosteric modulators affect the kinetics of channel function and thus affect calcium dynamics, it is demonstrated that novel modulators can be identified when assays are conducted in the presence of a selective agonist, and conversely, novel agonists can be identified when screened or tested in the presence an allosteric modulator. As such, positive allosteric modulators can be identified or nicotinic acetylcholine receptor agonists can be identified by using IMR-32 cells that endogenously express various nicotinic receptors including α7 nAChRs. It is contemplated that such assay can be utilized with a number of cell lines conventionally not amenable to α7 nicotinic compound screening. Accordingly, allosteric modulator compounds described herein can be identified using fluorescence-based throughput functional assay using cell lines such as IMR-32 neuroblastoma or primary dissociated neurons. Although cell types such as IMR-32 neuroblastoma and neurons are known to contain several nicotinic receptor subunits, α7 selective agonists in the present assay selectively stimulate calcium responses only in the presence of positive allosteric modulators. Any suitable selective α7 agonist can be used. Selective α7 agonists from a range of structural types may be used such as those described in the literature including PNU-282987, SSR180711A and AR-R17779 and others described in earlier patent applications, such as 2-methyl-5-(6-phenyl-pyridazin-3-yl)-octahydro-pyrrolo[3,4-c]pyrrole (published in US 20050065178) 5-[6-(5-methyl-hexahydro-pyrrolo[3,4-c]pyrrol-2yl)-pyridazin-3-yl]-1H-indole (published in US 20050065178), 3-[6-(1H-indol-5-yl)-pyradazin-3-yloxy]-1-aza-bicyclo[2.2.2]octane (published in US 2005/0137204 and US 2005/0245531) and 4-(5-phenyl-[1,3,4] oxadiazol-2-yl)-1,4-diaza-bicyclo[3.2.2]nonane (published in WO 2004/029053).

IMR-32 neuroblastoma cells (ATCC) were grown to confluency in 162 cm$^2$ tissue culture flasks in minimum essential media supplemented with 10% FBS and 1 mM sodium pyruvate, 0.1 mM non-essential amino acids and 1% antibiotic-antimycotic. The cells were then dissociated using cell dissociation buffer and 40 μl of 3.5×10$^5$ cells/ml cell suspension was plated (~15,000 cells/well) into black plates with clear bottom and maintained for 48 hours in a tissue culture incubator at 37° C. under an atmosphere of 5% CO$_2$: 95% air. Other clonal cell lines or dissociated primary cortical neurons that express endogenous α7 nicotinic receptors may also be used in this assay. Calcium flux was measured using calcium-3 assay kit (Molecular Devices, Sunnyvale, Calif.) or fluo-4. A stock solution of the dye was prepared by dissolving each vial supplied by the vendor in Hank's balanced salt solution buffer (HBSS) containing 20 mM HEPES. The stock solution was diluted 1:20 using the same buffer before use. The growth media was removed from the cells and loaded with 45 μl of the dye and incubated at room temperature for three hours. Fluorescence measurements were read simultaneously from all the wells by a Fluorometic Imaging Plate Reader (FLIPR) at an excitation wavelength of 480 nm and an emission wavelength of 520 nm. Baseline fluorescence was measured for the first 10 seconds at which 5× concentrations of modulator/test compounds were added to the cell plate and incubated for three minutes. The fluorescence intensity was captured every second for the first 1 minute followed by every 5 seconds for an additional 2 minutes. This procedure was followed by 20 μl of 4× concentration of agonist and readings were taken for a period of three minutes as described above. Data was normalized to maximal responses and plotted as a function of concentration. The concentration dependence of changes fluorescence responses was fitted by nonlinear regression analysis (GraphPad Prism, San Diego, Calif.) to obtain EC$_{50}$ values. Neither agonist alone nor modulator alone evoked responses. However, in the presence of an allosteric modulator, the agonist elicited concentration dependent increase in calcium response and likewise in presence of an α7 selective agonist, modulator responses were revealed. The α7 selective antagonist, methyllycaconitine (MLA), abolishes response demonstrating that the effects are mediated via the α7 receptor.

Positive allosteric modulators were identified by measuring fluorescence changes to intracellular calcium in a fluorimetric plate reader in the presence of selective α7 nAChR agonists using cells natively expressing α7 nAChRs. As shown in FIG. 1, a compound with positive allosteric modulator activity (Example 9) evoked calcium fluorescence response in IMR-32 neuroblastoma cell line, a cell line that expresses endogenous α7 nAChRs. Agonist alone or modulator alone did not evoke a calcium response. However, when the agonist and the modulator were co-applied together, calcium responses were triggered. In the example above, 4-(5-phenyl-[1,3,4]oxadiazol-2-yl)-1,4-diaza-bicyclo[3.2.2]nonane (published in WO 2004/029053) was used as an agonist in the absence or presence of example 9 (10 μM). Other α7 agonists including 2-methyl-5-(6-phenyl-pyridazin-3-yl)-octahydro-pyrrolo[3,4-c]pyrrole (published in US 20050065178), 5-[6-(5-methyl-hexahydro-pyrrolo[3,4-c]pyrrol-2yl)-pyridazin-3-yl]-1H-indole (published in US 20050065178), various quinuclidine derivatives (published in US 2005/0137204 and US 2005/0245531) and PNU-282987 (Hajos et al. J Pharmacol. Exp Ther. 2005; 312: 1213-22) also are suitable for the assay. Likewise, primary neurons and other clonal cell lines that natively express α7 nAChRs may also be utilized. Other fluorescence measurements such as those monitoring changes in membrane potential also are suitable for the assay.

Figure 2:
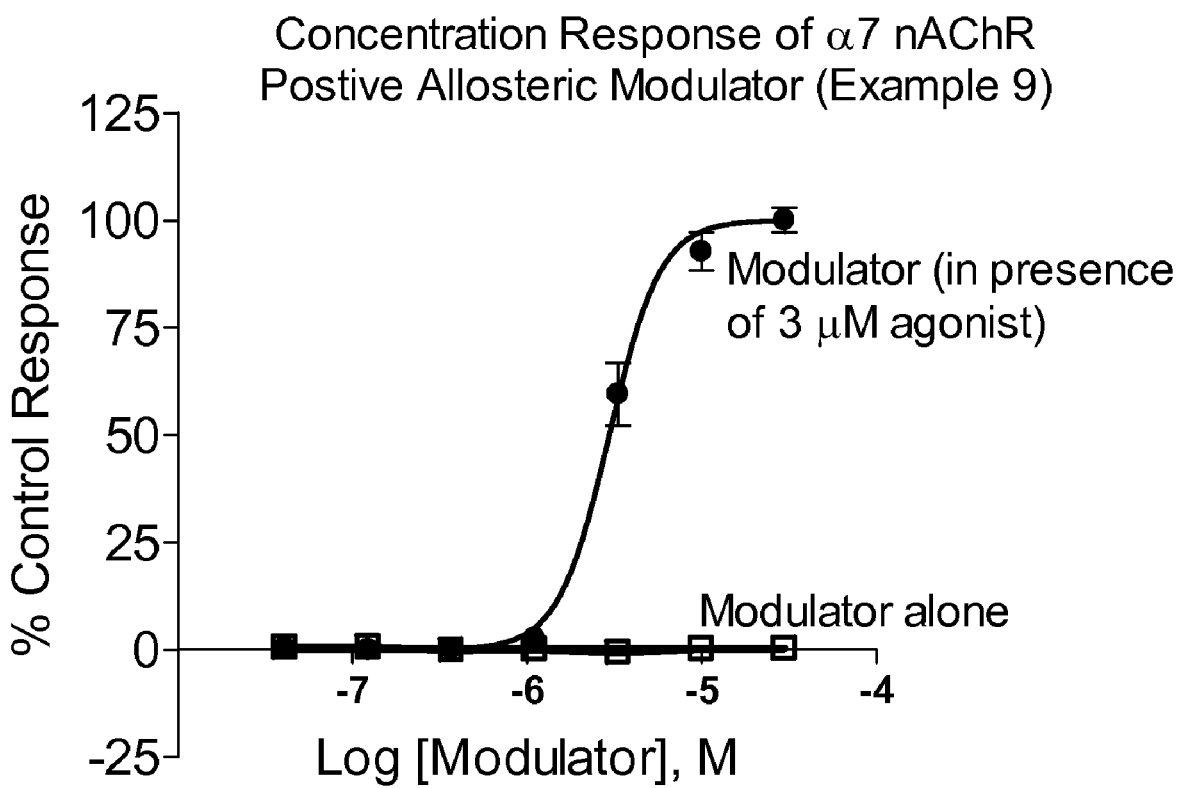
FIG. 2 is a graphical representation of a concentration response curve wherein control response measured in percentages is represented as a function of the log of the concentration of the positive allosteric modulator. The data were obtained by assaying a compound, Example 9, in the presence or absence of selective $\alpha 7$ nAChR agonists in cells natively expressing $\alpha 7$ nAChRs.

The concentration response curve of the α7 nAChR positive allosteric modulator also can be useful for characterizing the activity of a nAChR agonist. As shown in FIG. 2, a compound of the invention, Example 9, was allowed to interact with the IMR-32 neuroblastoma cell line in the presence of a selective α7 nAChR agonist or in its absence. The modulator alone did not trigger calcium responses, but when combined with the selective α7 nAChR agonist, fluorescence responses were evoked in a concentration-dependent manner. In FIG. 2, the Y-axis is the normalized change in fluorescence and the X-axis represents increasing concentrations of the modulator. The $EC_{50}$ value of positive allosteric modulator compounds as determined in this assay typically can range from 10 nM to 30 μM. For the data obtained to provide FIG. 2, 4-(5-phenyl-[1,3,4]oxadiazol-2-yl)-1,4-diaza-bicyclo[3.2.2]nonane (published in WO 2004/029053) was used as the agonist and the $EC_{50}$ value of the modulator (Example 9) was determined to be 3.0 μM. The fixed concentration of the allosteric modulator was 3 μM. Other α7 nicotinic receptor agonists including methyl-5-(6-phenyl-pyridazin-3-yl)-octahydro-pyrrolo[3,4-c]pyrrole (published in US 20050065178), 5-[6-(5-methyl-hexahydro-pyrrolo[3,4-c]pyrrol-2yl)-pyridazin-3-yl]-1H-indole (published in US 20050065178), various quinuclidine derivatives (published in US 2005/0137204 and US 2005/0245531) and PNU-282987 (Hajos et al. J Pharmacol. Exp Ther. 2005; 312: 1213-22) also are suitable for the assay.

Figure 3:
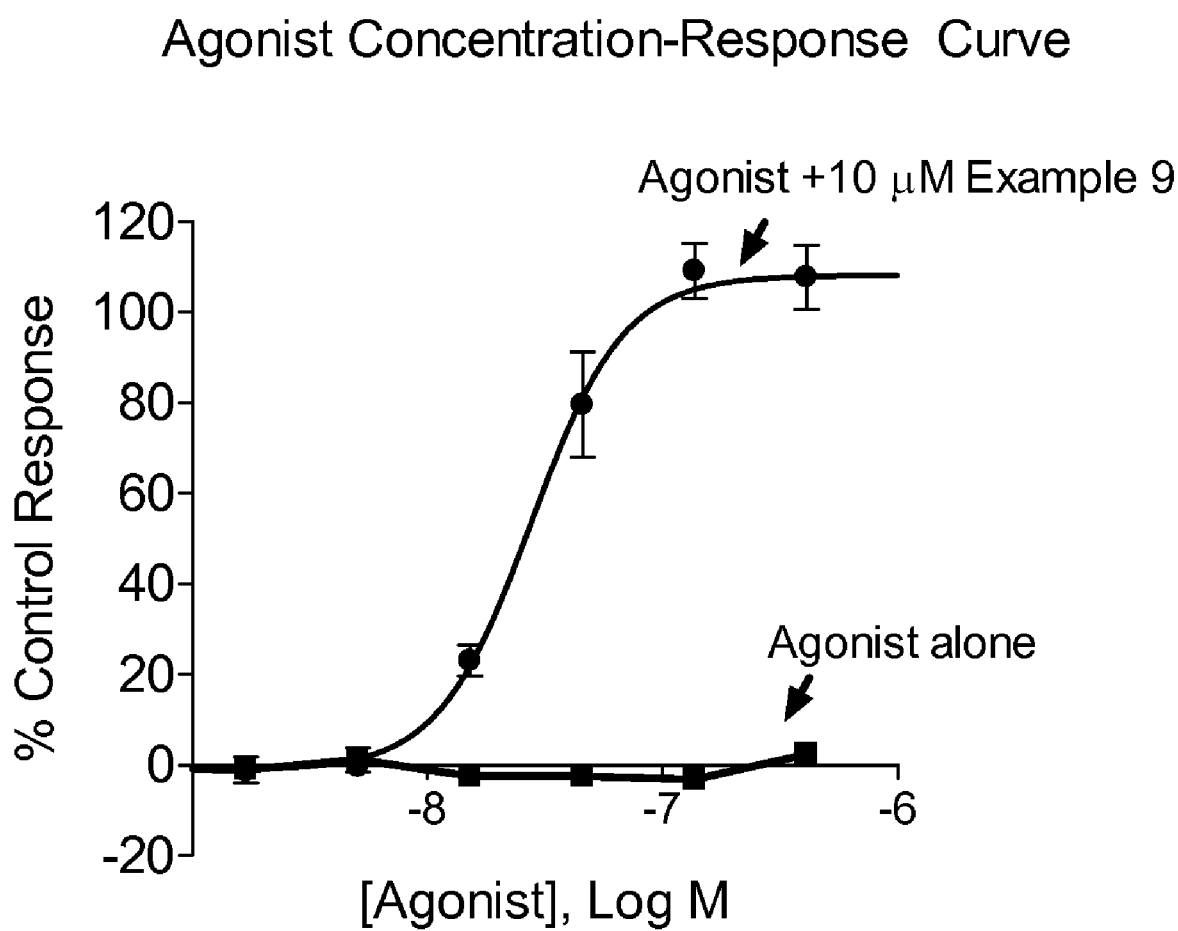
FIG. 3 is a graphical representation of a concentration response curve wherein control response measured in percentages is represented as a function of the log of the concentration of a known agonist. The data were obtained by assaying a known a7 nAChR agonist in the presence or absence of a positive allosteric modulator (Example 9) in cells natively expressing $\alpha 7$ nAChRs, for example the IMR-32 cell line.

The concentration response curve of an α7 nAChR agonist also is useful for characterizing the activity of an allosteric modulator. In FIG. 3, concentration response curves to a α7 nAChR agonist in the presence of allosteric modulator (Example 9) or in its absence are shown. Agonist alone did not trigger calcium responses. However, when combined with a selective α7 nAChR modulator, such as Example 9, fluorescence responses were evoked in a concentration-dependent manner. In FIG. 3, the Y-axis is the normalized fluorescence change and the X-axis represents increasing concentrations of the agonist. 4-(5-Phenyl-[1,3,4]oxadiazol-2-yl)-1,4-diaza-bicyclo[3.2.2]nonane (published in WO 2004/029053) was used as the agonist in the absence or presence of example 9 for the data obtained for FIG. 3. An $EC_{50}$ value of about 27 nM was determined. The fixed concentration of the allosteric modulator was 10 μM. Typical $EC_{50}$ values of agonists identified in this assay could range from 1 nM to 30 μM. Other α7 nicotinic receptor agonists including 5-[6-(5-methyl-hexahydro-pyrrolo[3,4-c]pyrrol-2yl)-pyridazin-3-yl]-1H-indole (published in US 20050065178), 2-methyl-5-(6-phenyl-pyridazin-3-yl)-octahydro-pyrrolo[3,4-c]pyrrole (published in US 20050065178), various quinuclidine derivatives (published in US 2005/0137204 and US 2005/0245531) and PNU-282987 (Hajos et al. J Pharmacol. Exp Ther. 2005; 312: 1213-22) also are suitable for the assay.

(ii) High-throughput Phospho-ERK assays using Cells Expressing Endogenous α7 nAChRs Rat pheochromocytoma (PC-12) cells (ATCC, Manassas, Va.) were cultured and maintained in F-12K media supplemented with 15% horse serum, 2.5% fetal calf serum, and 2 mM L-Glutamine in poly-D lysine coated dishes at 37° C. and 5% $CO_2$. Cells were plated in black-walled clear bottom 96-well Biocoat™ plates coated with poly-D-lysine (BD Biosciences, Bedford, Mass.) and grown for 2-3 days. Afterward, the culture media is replaced with serum-free media to starve cells overnight. On the day of the assay, cell media was removed and cells (60-80% confluent) were treated with agonist and/or modulator in Dulbecco's phosphate buffer saline (D-PBS) (with $Ca^{2+}$, $Mg^{2+}$, and 1 mg/ml D-glucose), as indicated in the result section.

PC-12 cells are treated for 10 minutes at 37° C. with test positive allosteric modulator compounds and then challenged with a selective α7 agonist for 5 minutes at 37° C. in a final volume of 100 μl/well, unless otherwise indicated. After treatment, media was discarded and adherent cells were immediately fixed in the presence of 150 μl/well of 3.7% formaldehyde/phosphate-buffered saline for 30-60 minutes at room temperature. Cells were then washed (4 times/5 minutes) and permeabilized with 200 μl/well of 0.1% Triton X-100/PBS. Permeabilized cells were blocked using the Odyssey blocking buffer (100 μl/well) and plates were rocked overnight at 4° C. Both anti-total ERK (rabbit) and anti-phospho ERK (mouse) antibodies were diluted to 1/1000 and 1/500, respectively, in Odyssey blocking buffer and added together at 50 μl/well for 2-3 hours at room temperature. Polyclonal rabbit anti-ERK1/2 and monoclonal mouse anti-phospho-ERK 1/2 were purchased from Sigma-Aldrich (St. Louis, Mo.). The plates were washed 4 times with 0.1% Tween 20/PBS (200 ul/well), and incubated with secondary antibodies (1/1000 dilution) in blocking buffer supplemented with 0.2% Tween for 1 hour. Alexa Fluor 680-labeled goat anti-rabbit antibodies were added to recognize total ERK labeling (red color) and IRDye800-labeled donkey anti-mouse antibodies were added to recognize phospho-ERK labeling (green color). Alexa Fluor 680-labeled goat-anti-rabbit antibodies were obtained from Molecular Probes (Eugene, Oreg.). IRDye 800CW-labeled Donkey-anti-mouse antibodies were purchased from Rockland (Gilbertsville, Pa.). The plates were washed 4 times with 0.2% Tween and 0.01% SDS/PBS and scanned using the Odyssey infrared scanner. Well intensities were quantitated and phospho-ERK signals were normalized to total ERK signals by the Odyssey software. Data analysis was performed using GraphPad Prism (GraphPad Software, San Diego, Calif.).

Figure 4:
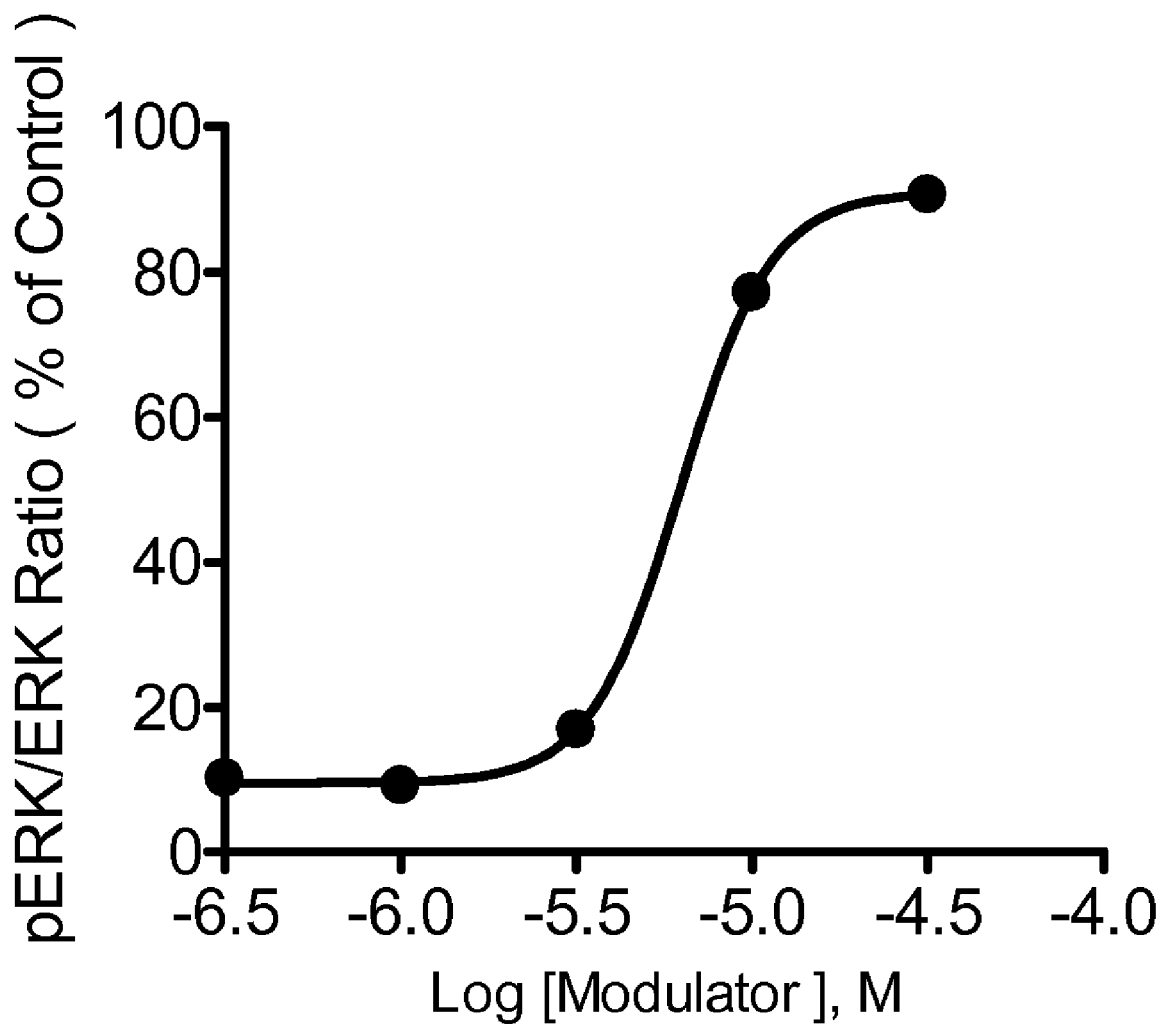
FIG. 4 is a graphical representation of phosphorylation of extracellular receptor kinase (ERK) represented as a function of the log of the concentration of a positive allosteric modulator. The data were obtained by assaying a compound, Example 9, in the presence of selective $\alpha 7$ nAChR agonists in cells natively expressing $\alpha 7$ nAChRs, for example PC-12 cells.

Positive allosteric modulators can be identified by measuring changes in the phosphorylation of ERK (extracellular receptor kinase) by in-cell western analysis. To obtain data represented in FIG. 4, a combination of modulator increases ERK1/2 phosphorylation in rat pheochromocytoma PC-12 cells in presence of selective α7 agonists were used to obtain the data. The assay was utilized to identify positive allosteric modulators in cells expressing endogenous α7 nAChRs without the need for overexpressing recombinant receptors. FIG. 4 represents a concentration-response relationship where the Y-axis is the normalized change in phospho-ERK1/2 to total ERK ratio and the X-axis represents increasing concentrations of the allosteric modulator. Compounds with allosteric modulator activity, such as Example 9 shown above, evoke concentration-dependent increases in ERK phosphorylation. To obtain data for FIG. 4, PNU-282987 (Hajos et al. J Pharmacol. Exp Ther. 2005; 312: 1213-22) was used as the α7 selective agonist. The $EC_{50}$ value of Example 9 was 6 μM. Typical $EC_{50}$ values in this assay range from about 10 nM to about 30 μM. Other α7 nicotinic receptor agonists including 2-methyl-5-(6-phenyl-pyridazin-3-yl)-octahydro-pyrrolo[3,4-c]pyrrole, 5-[6-(5-methyl-hexahydro-pyrrolo[3,4-c]pyrrol-2yl)-pyridazin-3-yl]-1H-indole (published in US 20050065178), various quinuclidine derivatives (published in US 2005/0137204 and US 2005/0245531) and 4-(5-Phenyl-[1,3,4]oxadiazol-2-yl)-1,4-diaza-bicyclo[3.2.2]nonane and related analogs (published in WO 2004/029053) also are suitable for the assay.

Compounds of the invention are positive allosteric modulators of α7 nAChR that can enhance the effects of naturally occurring neurotransmitter, acetylcholine or exogenous administered agonist. Although not being limited by theory, positive allosteric modulators generally amplify agonist (acetylcholine) responses by (i) attenuating receptor desensitization so that the receptor remains open for longer duration and/or (ii) by directly amplifying the efficacy of ACh by enhancing maximal receptor activation. In either case, such compounds typically boost endogenous transmission of acetylcholine, and can do so in a temporally and spatially restricted manner since these effects will be localized to regions where the α7 receptors are expressed. Allosteric modulator compounds can modulate function of α7 nAChRs by enhancing ion channel function as measured by calcium responses or ERK phosphorylation described herein, or other approaches such as current or membrane potential studies. Preferred compounds are those that behave as positive allosteric modulators in these assays between a concentration range of about 0.1 nM to about 30 μM. Allosteric modulation of the α7 receptor can trigger key signaling processes that are important to effects on memory, cytoprotection, gene transcription and disease modification. Therefore, the administration of a therapeutically effective amount of a compound of formula (I) or (II) to a mammal provides a method of selectively modulating the effects of α7 nAChRs.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof.

What is claimed is:

1. A compound of formula (I):

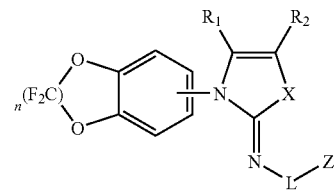

or a pharmaceutically acceptable salt, ester, or amide thereof, wherein n is 1;
$R_1$ is hydrogen or alkyl;
$R_2$ is alkyl, wherein the alkyl group is substituted with 1, 2, or 3 hydroxyl groups;
L is C(O);
X is S; and
Z is heterocycle.

2. The compound of claim 1, wherein
Z is a heterocycle represented by the formula $R_kR_lN$—, wherein $R_k$ and $_l$ taken
together with the nitrogen atom to which each is attached form a monocyclic heterocycle, a bicyclic heterocycle, a monocyclic heteroaryl, or a bicyclic heteroaryl, wherein each group is substituted with 0, 1, 2, or 3 substituents selected from halo, hydroxyl, aryl, and heteroaryl.

3. The compound of claim 2, wherein
Z is unsubstituted pyrrolidine or pyrrolidine substituted with halo.

4. The compound of claim 3, wherein halo is fluoro.

5. The compound of claim 1, or a pharmaceutically acceptable salt thereof, wherein the compound is N-[(2Z)-3-(2,2-difluoro-1,3-benzodioxol-5-yl)-5-(hydroxymethyl)-1,3-thiazol-2(3H)-ylidene]pyrrolidine-1-carboxamide.

6. A pharmaceutical composition comprising a therapeutically effective amount of the compound of claim 1 in combination with a pharmaceutically acceptable carrier.

* * * * *

UNITED STATES PATENT AND TRADEMARK OFFICE
CERTIFICATE OF CORRECTION

PATENT NO. : 7,683,084 B2
APPLICATION NO. : 11/769241
DATED : March 23, 2010
INVENTOR(S) : Faghih et al.

It is certified that error appears in the above-identified patent and that said Letters Patent is hereby corrected as shown below:

Title page
Inventors, "Ramin Faghih, Lake Forest, IL (US); Gregory A. Gfesser, Lindenhurst, IL (US); Christopher L. Lynch, Trevor, WI (US): Murali Gopalakrishnan, Libertyville, IL (US); Sujatha Gopalakrishnan, Libertyville, IL (US); John Malysz, Round Lake, IL (US); Earl J. Gubbins, Libertyville, IL (US); Rachid El Kouhen, Libertyville, IL (US); Jinhe Li, Long Grove, IL (US); Kathy A. Sarris, Deerfield, IL (US); Melissa J. Michmerhuizen, Beach Park, IL (US); Ying Wang, Lake Villa, IL (US)" should read --Ramin Faghih, Lake Forest, IL (US); Gregory A. Gfesser, Lindenhurst, IL (US)--

Column 1, Line 11
delete "1."

Column 1, Line 15
delete "2."

Column 60, Line 54
"23 mg, 55" should read --~23 mg, 55--

Column 64, Line 3
"$(M+H)^-$." should read --$(M+H)^+$.--

Column 64, Line 16
"$(M+H)^-$." should read --$(M+H)^+$.--

Column 73, Line 24
"$(M+H)^-$." should read --$(M+H)^+$.--

Signed and Sealed this
Eighteenth Day of January, 2011

David J. Kappos
*Director of the United States Patent and Trademark Office*